US012173039B1

(12) United States Patent
Lim et al.

(10) Patent No.: US 12,173,039 B1

(45) Date of Patent: Dec. 24, 2024

(54) TPL2 INHIBITING AGENTS, USES THEREOF, AND DETECTION OF TPL2

(71) Applicants: Kian-Huat Lim, St. Louis, MO (US); Paarth B. Dodhiawala, St. Louis, MO (US)

(72) Inventors: Kian-Huat Lim, St. Louis, MO (US); Paarth B. Dodhiawala, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/571,275

(22) Filed: Jan. 7, 2022

Related U.S. Application Data

(60) Provisional application No. 63/135,013, filed on Jan. 8, 2021.

(51) Int. Cl.

| | |
|---|---|
| ***C07K 14/47*** | (2006.01) |
| ***A61K 45/06*** | (2006.01) |
| ***A61P 35/00*** | (2006.01) |
| ***C12Q 1/6886*** | (2018.01) |

(52) U.S. Cl.

CPC .......... *C07K 14/4703* (2013.01); *A61K 45/06* (2013.01); *A61P 35/00* (2018.01); *C12Q 1/6886* (2013.01); *C12Q 2600/156* (2013.01)

(58) Field of Classification Search

None

See application file for complete search history.

(56) References Cited

FOREIGN PATENT DOCUMENTS

| | | | | |
|---|---|---|---|---|
| EP | 2545187 B1 | 9/2018 | | |
| WO | WO-2014204261 A1 * | 12/2014 | ......... | A61K 31/4375 |

OTHER PUBLICATIONS

Dodhiawala PB, Khurana N, Zhang D, Cheng Y, Li L, Wei Q, Seehra K, Jiang H, Grierson PM, Wang-Gillam A, Lim KH. TPL2 enforces RAS-induced inflammatory signaling and is activated by point mutations. J Clin Invest. Sep. 1, 2020;130(9):4771-479 (Year: 2020).*

Cayman Chemical Product information for Tpl2 Kinase Inhibitore, CAS Registry No. 871307-18-5, 1 page. (Year: 2022).*

Karki, et al., Defining "mutation" and "polymorphism" in the era of personal genomics, BMC Medical Genomics (2015) 8:37, pp. 1-7 (Year: 2015).*

Translation of 20150000419 Specification, pp. 1-14, (Year: 2015).*

Adachi et al. (1998). Targeted disruption of the MyD88 gene results in loss of IL-1- and IL-18-mediated function. *Immunity*. vol. 9, No. 1, pp. 143-150.

Adams et al. (2015) IRAK1 is a novel DEK transcriptional target and is essential for head and neck cancer cell survival. *Oncotarget*. vol. 6, No. 41, pp. 43395-43407.

Algul et al. (2002). NF-kappaB/ Rel transcriptional pathway: implications in pancreatic cancer. *Int J Gastrointest Cancer*. vol. 31, No. 1-3, pp. 71-78.

Ancrile et al. (2007). Oncogenic Ras-induced secretion of IL6 is required for tumorigenesis. *Genes Dev*. vol. 21, No. 14, pp. 1714-1719.

Babu et al. (2006) Phosphorylation of NF-kappaB1/ p105 by oncoprotein kinase Tpl2: implicationsfor a novel mechanism of Tpl2 regulation. *Biochim Biophys Acta*. vol. 1763, No. 2, pp. 174-181.

Beinke et al. (2004) Lipopolysaccharide activation of the TPL-2/ MEK/extracellular signal-regulated kinase mitogen-activated protein kinase cascade is regulated by IkappaB kinase-induced proteolysis of NF-kappaB1 p105. *Mol Cell Biol*. vol. 24, No. 21, pp. 9658-9667.

Ben-Addi et al. (2014) IκB kinase-induced interaction of TPL-2 kinase with 14-3-3 is essential for Toll-like receptor activation of ERK-1 and -2 MAP kinases. *Proc Natl Acad Sci U S A*. vol. 111, No. 23, pp. E2394-E2403.

Canon et al. (2019) The clinical KRAS(G12C) inhibitor AMG 510 drives anti-tumour immunity. *Nature*. vol. 575, No. 7781, pp. 217-223.

Ceci et al. (1997) Tpl-2 is an oncogenic kinase that is activated by carboxy-terminal truncation. *Genes Dev*. vol. 11, No. 6, pp. 688-700.

Chien et al. (2006) RalB GTPase-mediated activation of the IkappaB family kinase TBK1 couples innate immune signaling to tumor cell survival. *Cell*. vol. 127, No. 1, pp. 157-170.

Cho et al. (2005) Tpl2 (tumor progression locus 2) phosphorylation at Thr290 is induced by lipopolysaccharide via an Ikappa-B Kinase beta-dependent pathway and is required for Tpl2 activation by external signals. *J Biol Chem*. vol. 280, No. 21, pp. 20442-20448.

Christoforidou et al. (2004) Expression of the Tpl2/Cot oncogene in human T-cell neoplasias. *Mol Cancer*. vol. 3, No. 34, 9 pages.

Chung et al. (2017) Effect of selumetinib and MK-2206 vs oxaliplatin and fluorouracil in patients with metastatic pancreatic cancer after prior therapy: SWOG S1115 study randomized clinical trial. *JAMA* Oncol. vol. 3, No. 4, pp. 516-522.

Clark et al. (2004) Mutational activation of the MAP3K8 protooncogene in lung cancer. *Genes Chromosomes Cancer*. vol. 41, No. 2, pp. 99-108.

Conroy et al. (2011) Folfirinox versus gemcitabine for metastatic pancreatic cancer. *N Engl J Med*. vol. 364, No. 19, pp. 1817-1825.

Dan et al. (2008) Akt-dependent regulation of NF-{kappa}B is controlled by mTOR and Raptor in association with IKK. *Genes Dev*. vol. 22, No. 11, pp. 1490-1500.

Das et al. (2005) Tpl2/cot signals activate ERK, JNK, and NF-kappaB in a cell-type and stimulus-specific manner. *J Biol Chem*. vol. 280, No. 25, pp. 23748-23757.

Dumitru et al. (2000) TNF-alpha induction by LPS is regulated posttranscriptionally via a Tpl2/ERK-dependent pathway. *Cell*. vol. 103, No. 7, pp. 1071-1083.

(Continued)

*Primary Examiner* — Thomas S Heard

(57) ABSTRACT

Among the various aspects of the present disclosure is the provision of targeting TPL2 kinase as a novel strategy to block oncogenic KRAS-driven signaling, detection of TPL2 mutations, and uses of TPL2 inhibiting agents alone or in combination with chemotherapy in subjects having TPL2- or RAS-associated cancer.

21 Claims, 63 Drawing Sheets

Specification includes a Sequence Listing.

(56) References Cited

OTHER PUBLICATIONS

Durkin et al. (2013) Isolation of mouse embryo fibroblasts. *Bio Protoc.* vol. 3, No. 18, e908, 5 pages.
Fujioka et al. (2003) Function of nuclear factor kappaB in pancreatic cancer metastasis. *Clin Cancer Res.* vol. 9, No. 1, pp. 346-354.
Gavrin et al. (2005) Inhibition of Tpl2 kinase and TNF-alpha production with 1,7-naphthyridine-3-carbonitriles: synthesis and structure-activity relationships. *Bioorg Med Chem Lett.* vol. 15, No. 23, pp. 5288-5292.
Ghandi et al. (2019) Next-generation characterization of the Cancer Cell Line Encyclopedia. *Nature.* vol. 569, No. 7757, pp. 503-508.
Gioeli et al. (2011) Compensatory pathways induced by MEK inhibition are effective drug targets for combination therapy against castration-resistant prostate cancer. *Mol Cancer Ther.* vol. 10, No. 9, pp. 1581-1590.
Gruosso et al. (2015) MAP3K8/TPL-2/COT is a potential predictive marker for MEK inhibitor treatment in high-grade serous ovarian carcinomas. *Nat Commun.* vol. 6, No. 8583, 15 pages.
Infante et al. (2014) A randomised, double-blind, placebo-controlled trial of trametinib, an oral MEK inhibitor, in combination with gemcitabine for patients with untreated metastatic adenocarcinoma of the pancreas. *Eur J Cancer.* vol. 50, No. 12, pp. 2072-2081.
Jain et al. (2014) IL-1 receptor-associated kinase signaling and its role in inflammation, cancer progression, and therapy resistance. *Front Immunol.* vol. 5, No. 553, 8 pages.
Jeong et al. (2011) TPL2/COT/MAP3K8 (TPL2) Activation Promotes Androgen Depletion-Independent (ADI) Prostate Cancer Growth. PLOS One. vol. 6, 10 pages.
Jiang et al. (2016) Targeting focal adhesion kinase renders pancreatic cancers responsive to checkpoint immunotherapy. *Nat Med.* vol. 22, No. 8, pp. 851-860.
Johannessen et al. (2010) COT drives resistance to RAF inhibition through MAP kinase pathway reactivation. *Nature.* vol. 468, No. 7326, pp. 968-972.
Jones et al. (2008) Core signaling pathways in human pancreatic cancers revealed by global genomic analyses. *Science.* vol. 321, No. 5897, pp. 1801-1806.
Kim et al. (2009) Generation of orthotopic and heterotopic human pancreatic cancer xenografts in immunodeficient mice. *Nat Protoc.* vol. 4, No. 11, pp. 1670-1680.
Lee et al. (2017) Discovery of clinical candidate 1-{[(2S,3S,4S)-3-ethyl-4-fluoro-5-oxopyrrolidin-2-yl]methoxy}-7-methoxyisoquinoline-6-carboxamide (PF-06650833), a potent, selective inhibitor of interleukin-1 receptor associated kinase 4 (IRAK4), by fragment-based drug design. *J Med Chem.* vol. 60, No. 13, pp. 5521-5542.
Lehmann et al. (2019) Identification of Targetable Recurrent MAP3K8 Rearrangements in Melanomas Lacking Known Driver Mutations. *Mol Cancer Res.* vol. 17, No. 9, pp. 1842-1853.
Li et al. (2019) IRAK4 mediates colitis-induced tumorigenesis and chemoresistance in colorectal cancer. *JCI Insight.* vol. 4, No. 19, 130867, 19 pages.
Liberzon et al. (2015) The Molecular Signatures Database (MSigDB) hallmark gene set collection. *Cell Syst.* vol. 1, No. 6, pp. 417-425.
Lim et al. (2005) Activation of RalA is critical for Ras-induced tumorigenesis of human cells. *Cancer Cell.* vol. 7, No. 6, pp. 533-545.
Lim et al. (2013) Toll-like receptor signaling. *Cold Spring Harb Perspect Biol.* vol. 5, No. 1, a011247, 4 pages.
Lim et al. (2017) A clinically feasible multiplex proteomic immunoassay as a novel functional diagnostic for pancreatic ductal adenocarcinoma. *Oncotarget.* vol. 8, No. 15, pp. 24250-24261.
Lin et al. (2010) Helical assembly in the MyD88-IRAK4-IRAK2 complex in TLR/IL-1R signalling. *Nature.* vol. 465, No. 7300, pp. 885-890.
Ling et al. (2012) KrasG12D-induced IKK2/β/NF-κB activation by IL-1α and p62 feedforward loops is required for development of pancreatic ductal adenocarcinoma. *Cancer Cell.* vol. 21, No. 1, pp. 105-120.
Mielke et al. (2009) Tumor progression locus 2 (Map3k8) is critical for host defense against *Listeria monocytogenes* and IL-1 beta production. *J Immunol.* vol. 183, No. 12, pp. 7984-7993.
Nagathihalli et al. (2015) Signal transducer and activator of transcription 3, mediated remodeling of the tumor microenvironment results in enhanced tumor drug delivery in a mouse model of pancreatic cancer. *Gastroenterology.* vol. 149, No. 7, pp. 1932-1943.e9.
Nagathihalli et al. (2018) Inverse correlation of STAT3 and MEK signaling mediates resistance to RAS pathway inhibition in pancreatic cancer. *Cancer Res.* vol. 78, No. 21, pp. 6235-6246.
National Cancer Institute (2020). Cancer of Any Site—Cancer Stat Facts. SEER. Accessed from https://web.archive.org/web/20200719164714/https://seer.cancer.gov/statfacts/html/all.html on Dec. 12, 2022. 11 pages.
NCI Staff (2019) KRAS Inhibitor Shows Promise in Early Trial. Accessed Dec. 12, 2022 from https://www.cancer.gov/news-events/cancer-currents-blog/2019/kras-inhibitor-amg-510-clinical-trial. 7 pages.
Newman et al. (2019) Clinical genome sequencing uncovers potentially targetable truncations and fusions of MAP3K8 in spitzoid and other melanomas. *Nat Med.* vol. 25, No. 4, pp. 597-602.
Pattison et al. (2016) TLR and TNF-R1 activation of the MKK3/MKK6-p38α axis in macrophages is mediated by TPL-2 kinase. *Biochem J.* vol. 473, No. 18, pp. 2845-2861.
Prabhu et al. (2014) Critical role of NF-κB in pancreatic cancer. *Oncotarget.* vol. 5, No. 22, pp. 10969-10975.
Prescott et al. (2018). Targeting IKKβ in cancer: challenges and opportunities for the therapeutic utilisation of IKKβ inhibitors. *Cells.* vol. 7, 34 pages.
Research and Markets (2019) Global Solid Tumor Cancer Treatment Market Expected to Generate a Value of US$ 424.6 Billion During the Forecast Period, 2019-2027. Accessed on Dec. 12, 2022 from http://www.globenewswire.com/news-release/2019/09/03/1910178/0/en/Global-Solid-Tumor-Cancer-Treatment-Market-Expected-to-Generate-a-Value-of-US-424-6-Billion-During-the-Forecast-Period-2019-2027.html. 6 pages.
Roget et al. (2012) IκB kinase 2 regulates TPL-2 activation of extracellular signal-regulated kinases 1 and 2 by direct phosphorylation of TPL-2 serine 400. *Mol Cell Biol.* vol. 32, No. 22, pp. 4684-4690.
Rosenthal et al. (2019) Phase 1 study of CA-4948, a novel inhibitor of interleukin-1 receptor-associated kinase 4 (IRAK4) in patients (pts) with r/r non-Hodgkin lymphoma. *J Clin Oncol.* vol. 37, No. 15 suppl, e19055, 3 pages.
Salaroglio et al. (2019) ERK is a pivotal player of chemo-immune-resistance in cancer. *Int J Mol Sci.* vol. 20, No. 10, E2505, 31 pages.
Senger et al. (2017) The kinase TPL2 activates ERK and p38 signaling to promote neutrophilic inflammation. *Sci Signal.* vol. 10, No. 475, eaah4273, 16 pages.
Shoemaker (2006) The NCI60 human tumour cell line anticancer drug screen. *Nat Rev Cancer.* vol. 6, No. 10, pp. 813-823.
Sourvinos et al. (1999) Overexpression of the Tpl-2/Cot oncogene in human breast cancer. *Oncogene.* vol. 18, No. 35, pp. 4968-4973.
Srivastava et al. (2012) Augmentation of therapeutic responses in melanoma by inhibition of IRAK-1,-4. *Cancer Res.* vol. 72, No. 23, pp. 6209-6216.
Suzuki et al. (2002) Severe impairment of interleukin-1 and Toll-like receptor signalling in mice lacking IRAK-4. *Nature.* vol. 416, No. 6882, pp. 750-756.
Van Cutsem et al. (2018) Phase I/II trial of pimasertib plus gemcitabine in patients with metastatic pancreatic cancer. *Int J Cancer.* vol. 143, No. 8, pp. 2053-2064.
Von Bernuth H et al. (2012) Experimental and natural infections in MyD88- and IRAK-4-deficient mice and humans. *Eur J Immunol.* vol. 42, No. 12, pp. 3126-3135.
Von Hoff et al. (2013) Increased survival in pancreatic cancer with nab-paclitaxel plus gemcitabine. *N Engl J Med.* vol. 369, No. 18, pp. 1691-1703.
Wang et al. (1999) The nuclear factor-kappa B RelA transcription factor is constitutively activated in human pancreatic adenocarcinoma cells. *Clin Cancer Res.* vol. 5, No. 1, pp. 119-127.
Waters et al. (2018) KRAS: the critical driver and therapeutic target for pancreatic cancer. *Cold Spring Harb Perspect Med.* vol. 8, No. 9, a031435, 18 pages.

(56) References Cited

OTHER PUBLICATIONS

Wee et al. (2015) IRAK1 is a therapeutic target that drives breast cancer metastasis and resistance to paclitaxel. *Nat Commun.* vol. 6, No. 8746, 16 pages.
Weichert et al. (2007) High expression of RelA/p65 is associated with activation of nuclear factor-kappaB-dependent signaling in pancreatic cancer and marks a patient population with poor prognosis. *Br J Cancer.* vol. 97, No. 4, pp. 523-530.
Zhang et al. (2017) Constitutive IRAK4 activation underlies poor prognosis and chemoresistance in pancreatic ductal adenocarcinoma. *Clin Cancer Res.* vol. 23, No. 7, pp. 1748-1759.
Zhang et al. (2018) Tumor-stroma IL1β-IRAK4 feedforward circuitry drives tumor fibrosis, chemoresistance, and poor prognosis in pancreatic cancer. *Cancer Res.* vol. 78, No. 7, pp. 1700-1712.
Zhu et al. (2014) Inhibition of KRAS-driven tumorigenicity by interruption of an autocrine cytokine circuit. *Cancer Discov.* vol. 4, No. 4, pp. 452-465.
Zhuang et al. (2016) IL1 receptor antagonist inhibits pancreatic cancer growth by abrogating NF-κB activation. *Clin Cancer Res.* vol. 22, No. 6, pp. 1432-1444.

* cited by examiner

| TPL2 | $t_{1/2}$ (mins) |
| --- | --- |
| WT | 43.92 |
| E188K | 58.84 |

| TPL2 | $t_{1/2}$ (mins) |
|---|---|
| WT | 43.199 |
| R442H | 61.703 |
| L444V | 50.105 |
| R459W | 50.772 |
| ΔC-term | 64.034 |

| | GI50 (μM) 5 days | GI50 (μM) 7 days |
|---|---|---|
| Pa01C | 14.66 | 9.683 |
| Pa02C | 9.729 | 6.186 |
| Pa03C | 16.63 | 14.34 |
| Pa04C | 57.41 | 27.67 |
| Pa14C | 19.45 | 9.525 |
| Pa16C | 24.52 | 16.57 |
| AsPc-1 | 10.52 | 13.49 |
| BxPC- 3 | 14.81 | 12.02 |
| CF PAC- 1 | 12.00 | 7.649 |
| MIA PaCa-2 | 3.693 | 2.648 |
| PANC- 1 | 27.65 | 8.956 |
| HPNE -*KRAS*$^{G12D}$ | 4.848 | 14.26 |

TPL2 drives *RAS*-induced inflammatory signaling and promotes survival under genotoxic stress

TPL2 INHIBITING AGENTS, USES THEREOF, AND DETECTION OF TPL2

CROSS-REFERENCE TO RELATED APPLICATIONS

This application claims priority from U.S. Provisional Application Ser. No. 63/135,013 filed on 8 Jan. 2021, which is incorporated herein by reference in its entirety.

STATEMENT REGARDING FEDERALLY SPONSORED RESEARCH OR DEVELOPMENT

This invention was made with government support under CA196510 and CA219697 awarded by the National Institutes of Health. The government has certain rights in the invention.

MATERIAL INCORPORATED-BY-REFERENCE

The Sequence Listing, which is a part of the present disclosure, includes a computer-readable form comprising nucleotide and/or amino acid sequences of the present invention (file name "019493-US-NP_Sequence_Listing_ST25.txt" created on 7 Jan. 2022; 17,827 bytes). The subject matter of the Sequence Listing is incorporated herein by reference in its entirety.

FIELD OF THE INVENTION

The present disclosure generally relates to cancer treatment and prognostics.

SUMMARY OF THE INVENTION

Among the various aspects of the present disclosure is the provision of targeting TPL2 kinase as a novel strategy to block oncogenic KRAS-driven signaling, detection of TPL2 mutations, and uses of TPL2 inhibiting agents alone or in combination with chemotherapy. An aspect of the present disclosure provides for a method of suppressing tumor proliferation or cell growth in a subject having cancer or in cancer cells comprising administering a pharmaceutical composition comprising a TPL2 inhibiting agent, wherein the TPL2 inhibiting agent has anti-tumor activity. In some embodiments, the subject has, or the cancer cells are from, a RAS-mutant cancer or a TPL2-mutant cancer. In some embodiments, the TPL2-mutant cancer or cancer cells have at least one TPL2 mutation or at least one TPL2 point mutation. In some embodiments, the TPL2-mutant cancer or cancer cells comprise at least one gain-of-function TPL2 mutation. In some embodiments, the cancer or the cancer cells comprise mutations that reduce polyubiquitination of TPL2. In some embodiments, the cancer or the cancer cells comprise TPL2 summoned by oncogenic RAS or genotoxic stress or spontaneously activated by genetic mutations. In some embodiments, the at least one TPL2 mutation renders TPL2 more stable than wild type TPL2. In some embodiments, at least one TPL2 mutation comprises one or more gain-of-function TPL2 mutations that hyperactivate MAPK and NF-κB pathways. In some embodiments, at least one TPL2 mutation comprises one or more of TPL2 point mutations selected from E188K, R397H, R442H, R442 frame shift, L444V, and R459W. In some embodiments, the cancer or the cancer cells further comprise $BRAF^{V600E}$ mutation. In some embodiments, the cancer is KRAS mutant cancer, optionally $KRAS^{G12C}$, $KRAS^{G12D}$, $KRAS^{G12R}$, or $KRAS^{G12V}$. In some embodiments, the cancer is refractory or treatment-resistant cancer. In some embodiments, the cancer comprises TPL2 mutations associated with RAF inhibitor resistance. In some embodiments, the cancer is a RAF inhibitor-resistant cancer. In some embodiments, the cancer is not responsive to MEK inhibitors. In some embodiments, the cancer comprises TPL2 mutations that cause overexpression, C-terminal truncations, or fusions of TPL2. In some embodiments, the cancer comprises TPL2 mutations comprises TPL2 mutations that have increased stability compared to wild type and capable of hyperactivating both MAPK and NF-kB cascades. In some embodiments, the cancer comprises cells having $TPL2^{E188K}$ or $TPL2^{R442}$ mutations. In some embodiments, the cancer is a RAS-mutant cancer and MAP3K8-mutant cancer. In some embodiments, the cancer comprises cells having $RAF^{V600E}$/$MAP3K8^{E188K}$ double mutations. In some embodiments, the cancer is: breast cancer, bladder, colon cancer, rectal cancer, small bowel cancer, endometrial cancer, gastric carcinoma, gastrointestinal carcinoid tumor, gastrointestinal stromal tumor, oligodendroglioma, urothelial carcinoma, head and neck cancer, head and neck squamous cell carcinomas (HNSCC), glioblastoma, hepatocellular carcinoma, lung cancer, lung adenocarcinoma (LAC), small cell lung cancer, non-small lung cancer (NSCLC), melanoma, ovarian cancer, cervical cancer, pancreatic cancer, pancreatic ductal adenocarcinoma (PDAC), biliary tract cancers, prostate carcinoma, acute myelogenous leukemia (AML), non-Hodgkin's lymphoma, T-cell neoplasms, or thyroid carcinoma. In some embodiments, the TPL2 inhibiting agent is a broader-spectrum therapeutic agent than a MEK inhibiting agent or ERK inhibiting agent. In some embodiments, the TPL2 inhibiting agent is administered in an amount effective to reduce, block, or inhibit: RAS-induced oncogenic transformation and tumorigenicity; MAPK and NF-κB signaling; chemotherapy-induced MAPK and NF-κB activation, resulting in increased apoptosis and increased tumor suppression; KRAS-induced MAPK activity; p-MEK, p-ERK, or p-RSK levels; or crosstalk between IRAK4 and MAPK pathway, compared to the cancer cells not being treated with the TPL2 inhibiting agent. In some embodiments, the TPL2 inhibiting agent is administered in an amount effective to suppress MAPK activity and proliferation of the cancer or the cancer cells. In some embodiments, the TPL2 inhibiting agent is administered in an amount effective to sensitize the cancer or the cancer cells to chemotherapy; suppress tumor proliferation or cell growth; increase apoptosis; or increases tumor suppression compared to the cancer cells not being treated with the TPL2 inhibiting agent. In some embodiments, the TPL2 inhibiting agent targets MEK/ERK or targets cascades implicated in chemoresistance selected from one or more of, NF-κB, JNK, and p38. In some embodiments, the TPL2 inhibiting agent is an IRAK4 inhibiting agent. In some embodiments, the TPL2 inhibiting agent is 4-[(3-chloro-4-fluorophenyl)amino]-6-[(3-pyridinylmethyl)amino]-1,7-naphthyridine-3-carbonitrile; Tilpisertib; Emavusertib; Zimlovisertib; a 8-halo-4-(3-chloro-4-fluoro-phenylamino)-6-[(1H-[1,2,3]triazol-4-ylmethyl)-amino]-quinoline-3-carbonitrile, optionally, 8-chloro-4-(3-chloro-4-fluorophenylamino)-6-((1-(1-ethylpiperidin-4-yl)-1H-1,2,3-triazol-4-yl)methylamino) quinoline-3-carbonitrile; Cot inhibitor-1; or a pharmaceutically acceptable salt thereof, including all tautomers and stereoisomers, and substituted analogs thereof. In some embodiments, the method further comprises administering a chemotherapeutic agent or regimen. In some embodiments, the combination of administering a TPL2 inhibiting agent and a chemotherapeutic agent:

synergistically sensitizes the cancer or the cancer cells to chemotherapy; reduces chemotherapy-induced survival signaling; suppresses tumor proliferation or cell growth; increases apoptosis; reduces clonogenicity (resistant clones); reduces genotoxic stress-induced survival signaling; or enhances chemotherapy efficacy, compared to either treatment alone. In some embodiments, the chemotherapeutic agent is selected from one or more of: gemcitabine; a taxane, optionally paclitaxel or docetaxel; irinotecan or metabolite thereof, optionally, irinotecan hydrochloride, irinotecan hydrochloride liposome, or SN-38; 5-fluorouracil [5-FU]; and oxaliplatin. In some embodiments, the chemotherapeutic agent is selected from a metabolite of irinotecan, SN-38. In some embodiments, the chemotherapeutic agent is selected from gemcitabine/paclitaxel or FIRINOX (5-FU/SN-38/oxaliplatin). In some embodiments, the method further comprises administering: an IRAK4 inhibiting agent, optionally, PF06650833/Zimlovisertib or Emavusertib/CA-4948; an IKK inhibiting agent, optionally, IMD-0354; a BRAF inhibiting agent, optionally, PLX-4720, dabrafenib, or PLX-4032); a MEK inhibiting agent, optionally, trametinib; an ERK inhibiting agent, optionally, BVD-523 or ulixertinib; a KRAS inhibiting agent specifically for a $KRAS^{G12C}$ mutation, optionally, AMG 510 or sotorasib; or a PI3K inhibiting agent, optionally, GDC-0941. In some embodiments, the method further comprises detecting a gain-of-function TPL2 mutation in a subject. Another aspect of the present disclosure provides for a method of diagnosing and treating cancer in patients having or developing resistance to a first cancer therapy comprising detecting a gain of function TPL2 mutation and/or administering a TPL2 inhibiting agent. Yet another aspect of the present disclosure provides for a method of identifying a subject having cancer who is likely to benefit from treatment with a combination therapy with a chemotherapeutic agent or a chemotherapeutic regimen and a TPL2 inhibitor, the method comprising: detecting activity, expression level, a gene copy number, a mRNA, or a protein level or phosphorylation of one or more kinase targets selected from the group consisting of MAP3K8 (TPL2) in a cancer or cancer cells obtained from the subject and comparing the activity, expression level, gene copy number, the mRNA or the protein level or the phosphorylation with a gene copy number, an mRNA or a protein level or phosphorylation MAP3K8 (TPL2) in cells obtained from a subject without the cancer, wherein if the subject has elevated levels of MAP3K8 (TPL2) compared to a subject not having cancer, the subject is determined to benefit from TPL2 inhibiting agent or TPL2 inhibiting agent and chemotherapeutic agent combination treatment. In some embodiments, the subject has a TPL2 mutation or elevated TPL2 protein level, wherein detection of a TPL2 mutation or an elevated TPL2 protein level is associated with poor prognosis.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1A:
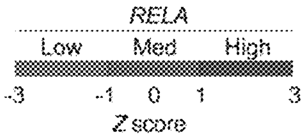
FIG. 1A-FIG. 1M. IRAK signaling dictates NF-κB activity in PDAC and is essential for RAS oncogenesis. (A) Classification of patients with low, medium, and high RELA expression based on mRNA Z score from TCGA. (B) Progression-free survival (PFS) and overall survival (OS) of PDAC patients with high versus low RELA expression. (C) Heatmap comparing mRNA expression of NF-κB signature genes from the Broad Institute Molecular Signatures Database (gene sets are listed in TABLE 2) in $RELA^{High}$ vs. $RELA^{Low}$ patients. (D and E) PFS and disease-free status, respectively, of PDAC patients with high MYD88 and/or high IRAK1 expression ("$MYD88^{High}$, $IRAK1^{High}$") versus low MYD88 and/or low IRAK1 expression ("$MYD88^{Low}$, $IRAK1^{Low}$"). Eight patients overlapping between 2 groups were excluded. (F and G) OS and vital status of patients as in D and E. (H) Graph of IRAK4 expression in normal human pancreas versus PDAC. Data for normal tissue is from the Genotype-Tissue Expression (GTEx) project and PDAC expression from TCGA PanCancer Atlas. P values are from unpaired 2-sided t test. (I) Soft-agar colonies formed by Irak4-KO and rescue (KO+Irak4WT) MEF cells transformed with 3 pairs of oncogenes. Data show 9 replicates from 3 independent experiments. (J) Number of tumors formed in nude mice from subcutaneous implantation of WT and IRAK4-KO human and murine RAS-mutant and/or PDAC cell lines. n=8 tumors per condition. (K) Quantification of soft-agar colonies formed by WT versus Irak4-KO KP2 cells. Data show 6 replicates from 2 independent experiments. (L) Soft-agar colonies formed by KP2 cells treated with IRAK4i or vehicle (V). (M) Soft-agar colonies formed by WT and $KRAS^{G12D}$ HPNE cells ectopically expressing WT IRAK4 and treated with IRAK4i. For L and M, 3 independent experiments were performed, each in technical triplicate, and one set of data is shown. All error bars indicate mean±SEM. **P<0.0001; *P<0.0002; **P<0.0021; *P<0.0332.

The present disclosure is based, at least in part, on the discovery that TPL2 can be a therapeutic target in RAS- and TPL2-mutant cancers.

Targeting the oncogene RAS remains largely challenging in the clinic for cancer patients. This is the most commonly mutated cancer-driving gene that accounts for one third of all human cancers and 95% of pancreatic cancer.

Here it was discovered that TPL2 (or MAP3K8) is an important signaling kinase that RAS protein relies on to fully exert its signaling function. In addition, gain-of-function point mutations in TPL2 were discovered in various cancer types.

Overall the present disclosure provides evidence that TPL2 is a promising new therapeutic target for RAS-mutated cancers and cancers bearing TPL2 point mutations, such as gain-of-function TPL2 mutations that hyperactivate the MAPK and NF-kB pathways.

Targeting RAS signaling pathway has been largely unsuccessful in the clinic except for those with $KRAS^{G12C}$ mutation where a drug is now available. IT is presently believed that there is also no dedicated TPL2 inhibitor that has been developed for clinical trials. The present disclosure shows that a dedicated TPL2 inhibitor can be used as a therapeutic.

TPL2 Inhibiting Agent

One aspect of the present disclosure provides for targeting of TPL2, its receptor, its upstream activator (e.g., IRAK4, IL-1B) or its downstream signaling (e.g., MEK). The present disclosure provides methods of treating or preventing cancer based on the discovery that removing TPL2 signals via knockout or small molecule inhibition reduces reduce RAS-induced oncogenic transformation and tumorigenicity. The small molecule TPL2 inhibitor, 4-[(3-Chloro-4-fluorophenyl)amino]-6-[(3-pyridinylmethyl)amino]-1,7-naphthyridine-3-carbonitrile, was tested and described in Example 1. Other TPL2 inhibitors known in the art can be utilized in the methods described herein, such as TPL2 inhibitors: Tilpisertib (formerly GS-4875) (6-{[(S)-[1-(bicyclo[1.1.1]pentan-1-yl)-1H-1,2,3-triazol-4-yl](2-methyl-1-oxo-1,2-dihydroisoquinolin-5-yl)methyl]amino}-8-chloro-4-[(2,2-dimethylpropyl)amino]quinoline-3-carbonitrile); Emavusertib/CA-4948 (N-[5-[(3R)-3-hydroxypyrrolidin-1-yl]-2-morpholin-4-yl-[1,3]oxazolo[4,5-b]pyridin-6-yl]-2-(2-methylpyridin-4-yl)-1,3-oxazole-4-carboxamide); Zimlovisertib (1-(((2S,3S,4S)-3-ethyl-4-fluoro-5-oxopyrrolidin-2-yl) methoxy)-7-methoxyisoquinoline-6-carboxamide); 8-halo-4-(3-chloro-4-fluoro-phenylamino)-6-[(1H-[1,2,3] triazol-4-ylmethyl)-amino]-quinoline-3-carbonitriles, such as 8-chloro-4-(3-chloro-4-fluorophenylamino)-6-((1-(1-ethylpiperidin-4-yl)-1H-1,2,3-triazol-4-yl)methylamino) quinoline-3-carbonitrile (Wu et al. Bioorg Med Chem Lett. 2009 Jul. 1; 19 (13): 3485-8); or Cot inhibitor-1 (6-(((1-(2-(azepan-1-yl)ethyl)-1H-1,2,3-triazol-4-yl)methyl)amino)-8-chloro-4-((3-chloro-4-fluorophenyl)amino) quinoline-3-carbonitrile).

Because IRAK4 is an upstream activator of TPL2, this IRAK4i, and other IRAK4 inhibitors, can be used as a TPL2 inhibitor to block the TPL2 activation.

The combination of IRAK4 inhibitor (which is upstream of TPL2) with immunotherapy is extremely effective in preclinical pancreatic cancer mouse model. Incorporation of TPL2 inhibitor into an immunotherapy regimen is developing and is believed to also be effective.

As described herein, inhibitors of TPL2 (e.g., antibodies, recombinant or fusion proteins or peptides, small molecules) can reduce or prevent TPL2 expression, activity, or signaling. A TPL2 inhibiting agent can be any agent that can inhibit TPL2 activity, downregulate TPL2 protein level, or knockdown TPL2 gene expression.

For example, the TPL2 inhibiting agent can be an anti-TPL2 antibody. As another example, the TPL2 inhibiting agent can be a fusion protein. For example, the fusion protein can be a decoy receptor for TPL2.

As another example, a TPL2 inhibiting agent can be 4-[(3-Chloro-4-fluorophenyl)amino]-6-[(3-pyridinylmethyl)amino]-1,7-naphthyridine-3-carbonitrile, which has been shown to be a selective ATP competitive small molecule TPL2 inhibitor (TPL2i) that can suppress LPS-induced TNFα production in human monocytes.

As another example, a TPL2 inhibiting agent can be a short hairpin RNA (shRNA, such as shMAP3K8) or a short interfering RNA (siRNA) targeting TPL2. As another example, a TPL2 inhibiting agent can be a sgRNA targeting TPL2.

Inhibiting TPL2 can be performed by genetically modifying TPL2 in a subject or genetically modifying a subject to reduce or prevent expression of the TPL2 gene, such as through the use of CRISPR-Cas9 or analogous technologies, wherein, such modification reduces or prevents TPL2 expression, signaling, or activity.

Inhibiting TPL2 can be in combination with other kinase inhibitors such as those described in PCT/US2011/027689, incorporated herein by reference.

TPL2- or RAS-Associated Cancer

Methods and compositions as described herein can be used for the prevention, treatment, or slowing the progression of cancer or tumor growth. The cancer can be a TPL2- or RAS-associated cancer.

The present disclosure provides for targeting TPL2 (MAP3K8) in various cancer types, such as solid tumors. As shown herein, TPL2 is a promising therapeutic target for RAS-mutated cancers and cancer bearing TPL2 point mutations. The disclosed technology can also provide for a companion diagnostic to identify patients that would respond to TPL2 inhibitor therapy.

TPL2 (MAP3K8) is a protooncogene that activates the MAP kinase, SAP kinase, and NF-kB signaling pathways. MAP3K8 mutations have been found in 1.7% of melanoma patients, ovarian cancer, and prostate cancer patients.

E188K, R397H, R442H, L444V, and R459W mutations in TPL2 were discovered herein. All these mutations reduce polyubiquitination of TPL2 and render TPL2 to be more stable than the WT form.

1 meymstgsdn keeidllikh lnvsdvidim enlyaseepa vyepslmtmc qdsnqnders
61 kslllsgqev pwlssvrygt vedllafanh isntakhfyg qrpqesgill nmvitpqngr
121 yqidsdvlli pwkltyrnig sdfiprgafg kvylaqdikt kkrmacklip vdqfkpsdve
181 iqacfrheni aelygavlwg etvhlfmeag eggsvlekle scgpmrefei iwvtkhvlkg
241 ldflhskkvi hhdikpsniv fmstkavlvd fglsvqmted vyfpkdirgt eiymspevil
301 crghstkadi yslgatlihm qtgtppwvkr yprsaypsyl yiihkqappl ediaddcspg
361 mrelieasle mpnhrpraa dllkhealnp predqprcqs ldsallerkr llsrkelelp
421 eniadssctg steesemlkr qrslyidlga lagyfnlvrg pptleyg (SEQ ID NO: 39)

The three human RAS genes (NRAS, KRAS, and HRAS) encode four highly related RAS small GTPases (NRAS, KRAS4A, KRAS4B, and HRAS). RAS proteins operate as GDP-GTP regulated binary on-off switches which modulate a heterogeneous network of cytoplasmic signaling networks. Among cancer and developmental disorders (RASopathies), mutationally activated RAS proteins are the driving force behind abnormal signal transduction.

RAS genes constitute the most regularly mutated oncogene family in cancer. As such, RAS genes constituted the most regularly mutated oncogenes in the top three causes of cancer deaths in the US in 2016 (colorectal, lung, and pancreatic cancers). As a result, there has been an intensity of effort and interest focused on targeting RAS for cancer treatment.

While NRAS is the principal isoform mutated in melanoma and acute myelogenous leukemia (AML), KRAS is the principal RAS isoform mutated in PDAC, colorectal (CRC), and lung adenocarcinoma (LAC). KRAS mutations are found in 13% of people with lung cancer, 3% of colorectal, and 1-3% of people with other solid tumors. While generally rare, HRAS mutations are principal in bladder and head and neck squamous cell carcinomas (HNSCC). RAS mutations play well-defined parts in the development of divergent cancers. A KRAS inhibitor specifically for the G12C mutation is showing promise in clinical stage trials. KRAS mutant cancer can be, for example, $KRAS^{G12C}$, $KRAS^{G12D}$, $KRAS^{G12R}$, or $KRAS^{G12V}$.

As another example, the cancer can be Acute Lymphoblastic Leukemia (ALL); Acute Myeloid Leukemia (AML); Adrenocortical Carcinoma; AIDS-Related Cancers; Biliary Tract Cancer, Kaposi Sarcoma (Soft Tissue Sarcoma); AIDS-Related Lymphoma (Lymphoma); Primary CNS Lymphoma (Lymphoma); Anal Cancer; Appendix Cancer; Gastrointestinal Carcinoid Tumors; Astrocytomas; Atypical Teratoid/Rhabdoid Tumor, Childhood, Central Nervous System (Brain Cancer); Basal Cell Carcinoma of the Skin; Bile Duct Cancer; Bladder Cancer; Bone Cancer (including Ewing Sarcoma and Osteosarcoma and Malignant Fibrous Histiocytoma); Brain Tumors; Breast Cancer; Bronchial Tumors; Burkitt Lymphoma; Carcinoid Tumor (Gastrointestinal); Childhood Carcinoid Tumors; Cardiac (Heart) Tumors; Central Nervous System cancer; Atypical Teratoid/Rhabdoid Tumor, Childhood (Brain Cancer); Embryonal Tumors, Childhood (Brain Cancer); Germ Cell Tumor, Childhood (Brain Cancer); Primary CNS Lymphoma; Cervical Cancer; Cholangiocarcinoma; Bile Duct Cancer Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell; Ductal Carcinoma In Situ (DCIS); Embryonal Tumors, Central Nervous System, Childhood (Brain Cancer); Endometrial Cancer (Uterine Cancer); Ependymoma, Childhood (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Intraocular Melanoma; Retinoblastoma; Fallopian Tube Cancer; Fibrous Histiocytoma of Bone, Malignant, or Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors; Hepatocellular (Liver) Cancer; Histiocytosis, Langerhans Cell; Hodgkin Lymphoma; Hypopharyngeal Cancer; Intraocular Melanoma; Islet Cell Tumors; Pancreatic Neuroendocrine Tumors; Kaposi Sarcoma (Soft Tissue Sarcoma); Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Lymphoma; Male Breast Cancer; Malignant Fibrous Histiocytoma of Bone or Osteosarcoma; Melanoma; Melanoma, Intraocular (Eye); Merkel Cell Carcinoma (Skin Cancer); Mesothelioma, Malignant; Metastatic Cancer; Metastatic Squamous Neck Cancer with Occult Primary; Midline Tract Carcinoma Involving NUT Gene; Mouth Cancer; Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip or Oral Cavity Cancer; Oropharyngeal Cancer; Osteosarcoma and Malignant Fibrous Histiocytoma of Bone; Ovarian Cancer Pancreatic Cancer; Pancreatic Neuroendocrine Tumors (Islet Cell Tumors); Papillomatosis; Paraganglioma; Paranasal Sinus and Nasal Cavity Cancer; Parathyroid Cancer; Penile Cancer; Pharyngeal Cancer; Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Small Bowel Cancer; Recurrent Cancer Renal Cell (Kidney) Cancer; Retinoblastoma; Rhabdomyosarcoma, Childhood (Soft Tissue Sarcoma); Salivary Gland Cancer; Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Uterine Sarcoma; Sézary Syndrome (Lymphoma); Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; T-Cell Lymphoma, Cutaneous; Lymphoma; Mycosis Fungoides and Sezary Syndrome; Testicular Cancer; Throat Cancer; Nasopharyngeal Cancer; Oropharyngeal Cancer; Hypopharyngeal Cancer; Thymoma and Thymic Carcinoma; Thyroid Cancer; Thyroid Tumors; Transitional Cell Cancer of the Renal Pelvis and Ureter (Kidney (Renal Cell) Cancer); Ureter and Renal Pelvis; Transitional Cell Cancer (Kidney (Renal Cell) Cancer; Urethral Cancer; Uterine Cancer, Endometrial; Uterine Sarcoma; Vaginal Cancer; Vascular Tumors (Soft Tissue Sarcoma); Vulvar Cancer; or Wilms Tumor.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment", or "heterologous nucleic acid," as used herein, each refers to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into an RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10:0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal, or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

"Point mutation" refers to when a single base pair is altered. A point mutation (or substitution) is a genetic mutation where a single nucleotide base is changed, inserted or deleted from a DNA or RNA sequence of an organism's genome. Point mutations have a variety of effects on the downstream protein product—consequences that can be predictable based upon the specifics of the mutation. These consequences can range from no effect (e.g., synonymous mutations) to deleterious effects (e.g., frameshift mutations), with regard to protein production, composition, and function. For example, point mutations can have one of three effects. First, the base substitution can be a silent mutation where the altered codon corresponds to the same amino acid. Second, the base substitution can be a missense mutation where the altered codon corresponds to a different amino acid. Or third, the base substitution can be a nonsense mutation where the altered codon corresponds to a stop signal. Silent mutations can result in a new codon (a triplet nucleotide sequence in RNA) that codes for the same amino acid as the wild type codon in that position. In some silent mutations the codon codes for a different amino acid that happens to have the same properties as the amino acid produced by the wild type codon. Missense mutations can involve substitutions that result in functionally different amino acids; these can lead to alteration or loss of protein function. Nonsense mutations, which are a severe type of base substitution, result in a stop codon in a position where there was not one before, which causes the premature termination of protein synthesis and, more than likely, a complete loss of function in the finished protein.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5 (9), 680-688; Sanger et al. (1991) Gene 97 (1), 119-123; Ghadessy et al. (2001) Proc Natl Acad Sci USA 98 (8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2, or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example, the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. An amino acid sequence can be modulated with the help of art-known computer simulation programs that can produce a polypeptide with, for example, improved activity or altered regulation. On the basis of these artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA: DNA sequence can be determined using the following formula: $T_m$=81.5° C.+16.6 (log 10 [$Na^+$])+0.41 (fraction G/C content)-0.63 (% formamide)-(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10:0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Conservative Substitutions I

| Side Chain Characteristic | Amino Acid |
|---|---|
| Aliphatic Non-polar | G A P I L V |
| Polar-uncharged | C S T M N Q |
| Polar-charged | D E K R |
| Aromatic | H F W Y |
| Other | N Q D E |

Conservative Substitutions II

| Side Chain Characteristic | Amino Acid |
|---|---|
| Non-polar (hydrophobic) | |
| A. Aliphatic: | A L I V P |
| B. Aromatic: | F W |
| C. Sulfur-containing: | M |
| D. Borderline: | G |

-continued

Conservative Substitutions II

| Side Chain Characteristic | Amino Acid |
|---|---|
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14 (12): 807-15, describing targeting deoxyribonucleotide sequences; Lee et al. (2006) Curr Opin Chem Biol. 10, 1-8, describing aptamers; Reynolds et al. (2004) Nature Biotechnology 22 (3), 326-330, describing RNAi; Pushparaj and Melendez (2006) Clinical and Experimental Pharmacology and Physiology 33 (5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Genome Editing

As described herein, TPL2 signals can be modulated (e.g., reduced, eliminated, or enhanced) using genome editing. Processes for genome editing are well known; see e.g., Aldi 2018 Nature Communications 9 (1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of TPL2 expression or activity by genome editing can result in reduced proliferation or prevention or treatment of cancer.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for cancer to target cells by the removal of TPL2 signals (e.g., downregulate TPL2).

For example, the methods as described herein can comprise a method for altering a target polynucleotide sequence in a cell comprising contacting the polynucleotide sequence with a clustered regularly interspaced short palindromic repeats-associated (Cas) protein.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing tumor proliferation, cancer, such as RAS- or TPL2-associated cancers, or refractory or treatment-resistant cancer in a subject in need of administration of a therapeutically effective amount of a TPL2 inhibiting agent, so as to reduce RAS-induced oncogenic transformation and tumorigenicity in a subject; reduce crosstalk between IRAK4 and the MAPK pathway; reduce or block chemotherapy-induced MAPK and NF-kB activation; or increase apoptosis and suppress tumor growth.

Methods described herein are generally performed on a subject in need thereof. A subject in need of the therapeutic methods described herein can be a subject having, diagnosed with, suspected of having, or at risk for developing cancer. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a TPL2 inhibiting agent is, for example, an amount that would cause the desired therapeutic effect in a subject while minimizing undesired side effects. In various embodiments, an effective amount of a TPL2 inhibiting agent described herein can substantially inhibit tumor growth, slow the progress of cancer, or limit the development of cancer.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a TPL2 inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reduce RAS-induced oncogenic transformation and tumorigenicity in a subject; reduce crosstalk between IRAK4 and the MAPK pathway; reduce or block chemotherapy-induced MAPK and NF-kB activation; or increase apoptosis and suppress tumor growth.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

Inhibition of agents as described herein can be determined by standard pharmaceutical procedures in assays or cell cultures for determining the $IC_{50}$. The half maximal inhibitory concentration ($IC_{50}$) is a measure of the potency of a substance in inhibiting a specific biological or biochemical function. The $IC_{50}$ is a quantitative measure that indicates how much of a particular inhibitory substance (e.g., pharmaceutical agent or drug) is needed to inhibit, in vitro, a given biological process or biological component by 50%. The biological component could be an enzyme, cell, cell receptor, or microorganism, for example. $IC_{50}$ values are typically expressed as molar concentration. $IC_{50}$ is generally used as a measure of antagonist drug potency in pharmacological research. $IC_{50}$ is comparable to other measures of potency, such as $EC_{50}$ for excitatory drugs. $EC_{50}$ represents the dose or plasma concentration required for obtaining 50% of a maximum effect in vivo. $IC_{50}$ can be determined with functional assays or with competition binding assays.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a TPL2 inhibiting agent can occur as a single event or over a time course of treatment. For example, a TPL2 inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for cancer.

A TPL2 inhibiting agent can be administered simultaneously or sequentially with another agent, such as an antibiotic, an anti-inflammatory, or another agent or anti-cancer therapy (e.g., chemotherapy). For example, a TPL2 inhibiting agent can be administered simultaneously with another agent, such as a cancer therapy, an anti-cancer agent, antibiotic, or an anti-inflammatory. Simultaneous administration can occur through administration of separate compositions. Simultaneous administration can occur through administration of one composition containing two or more agents. A TPL2 inhibiting agent can be administered sequentially with a cancer therapy, an anti-cancer agent, an antibiotic, an anti-inflammatory, or another agent. For example, a TPL2 inhibiting agent can be administered before or after administration of a cancer therapy, an anti-cancer agent, an antibiotic, an anti-inflammatory, or another agent.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general, a human equivalent dose (HED) in mg/kg can be calculated in accordance with the following formula (see e.g., Reagan-Shaw et al., *FASEB J.,* 22(3): 659-661, 2008, which is incorporated herein by reference):

$$\text{HED (mg/kg)}=\text{Animal dose (mg/kg)}\times(\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment, and the potency, stability, and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the TPL2 inhibiting agent may be administered in an amount from about 1 mg/kg to about 100 mg/kg, or about 1 mg/kg to about 50 mg/kg, or about 1 mg/kg to about 25 mg/kg, or about 1 mg/kg to about 15 mg/kg, or about 1 mg/kg to about 10 mg/kg, or about 1 mg/kg to about 5 mg/kg, or about 3 mg/kg. In some embodiments, a TPL2 inhibiting agent may be administered in a range of about 1 mg/kg to about 200 mg/kg, or about 50 mg/kg to about 200 mg/kg, or about 50 mg/kg to about 100 mg/kg, or about 75 mg/kg to about 100 mg/kg, or about 100 mg/kg.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above.

Combination Therapies

The present disclosure may relate to one or more agents used in combination with an agent as described herein. The present disclosure describes combinations of TPL2 inhibiting agents with other therapeutic modalities as combination therapies to increase the efficacy of anti-cancer therapies or as a stand alone cancer treatment. For example, the agents described herein can be used with currently available treatments for cancer, such as chemotherapy.

To treat cancers using the methods and compositions of the present disclosure, one would generally administer to the subject a TPL2 inhibiting agent and optionally at least one other therapy. These therapies would be provided in a combined amount effective to achieve an increased activity, efficacy, cytotoxicity, or decrease off-target effects or dosage. This process may involve contacting the cells/subjects with both agents/therapies at the same time, e.g., using a single composition or pharmacological formulation that includes both agents, or by contacting the cell/subject with two distinct compositions or formulations, at the same time, wherein one composition includes the TPL2 inhibiting agent and the other includes the other agent.

Alternatively, the individual compounds in the compositions described herein may precede or follow the other compound treatment by time intervals ranging from seconds to days. One would generally ensure that a significant period of time did not expire between the time of each delivery, such that the therapies would still be able to exert an advantageously combined effect on the cell/subject. In such instances, it is contemplated that one would administer both modalities within about 12-24 hours of each other, within about 6-12 hours of each other, with a delay time of only about 1-2 hours, or less than 1 hour. Additionally, the TPL2 inhibiting agents may be administered about 10-15 minutes, about 5-10 minutes, or about 0-5 minutes prior to administration of the anti-cancer agent. For example, TPL2 inhibiting agents may be administered from about 15 minutes, about 14 minutes, about 13 minutes, about 12 minutes, about 11 minutes, about 10 minutes, about 9 minutes, about 8 minutes, about 7 minutes, about 6 minutes, about 5 minutes, about 4 minutes, about 3 minutes, about 2 minutes, to about 1 minute, or any range derivable therein before the anti-cancer agent. Alternatively, the components may be administered at the same time.

The compositions and combination of agents used in the methods described herein may be administered as a single bolus dose, a dose over time such as an infusion, as in intravenous, subcutaneous, or transdermal administration, or in multiple dosages. If infusion is used, the combination may be infused for about 15 minutes to about 6 hours. In one embodiment, the infusion may occur for the duration of length of the apheresis. Additionally, the compositions or combinations may be administered once daily for multiple days including from 1 to 4 days.

It also is conceivable that more than one administration of either the compound or the other therapy will be desired. Various combinations may be employed, where a compound of the present disclosure is "A," and the other compound or therapy is "B," as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

In other embodiments, the compositions or methods used herein may be administered with an anti-cancer therapy such as those described below. The methods or compositions described herein may be used in conjunction with standard methods or variations as practiced by a person of ordinary skill in the art. These anti-cancer agents may be administered prior to and/or concomitant with the compositions or methods described herein. Some non-limiting examples of anti-cancer therapies which may be used herein include carmustine, etoposide, cytarabine, melphalan, cyclophosphamide, busulfan, thiotepa, bleomycin, platinum (cisplatin), cytarabine, cyclophosphamide, buside, daunorubicin, doxorubicin, agent ara-C, cyclosporin; Rituxan®; thalidomide; clofarabine; Velcade®; Antegren®; Ontak®; Revlimid® (thalidomide analog); Prochymal®; Genasense® (oblimersen sodium); Gleevec®; Glivec® (imatinib); tamibarotene; nelarabine; gallium nitrate; PT-100; Bexxar®; Zevalin®; pixantrone; Onco-TCS; and agents that are topoisomerase inhibitors, or another specific anti-cancer therapy.

Chemotherapeutic Agents

Chemotherapy can be used in combination with the TPL2 inhibitor. Example 1 shows TPL2 inhibitor synergizes with chemotherapy regimens, such as FIRINOX, to suppress human and murine in vivo PDAC growth.

In some embodiments, the agents described herein can be used in combination with chemotherapeutic agents or used to sensitize a tumor, subject, or cancer to a chemotherapeutic agent. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents can include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma 1$ and calicheamicin $\omega 1$; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-l-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichloro-triethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; toxoids or taxanes, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; mitoxantrone; teniposide; edatrexate; daunomycin; aminopterin; capecitabine; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicomycin, mitomycin, etoposide (VP16), tamoxifen, raloxifene, estrogen receptor binding agents, paclitaxel, docetaxel, gemcitabine, vinorelbine, farnesyl-protein transferase inhibitors, transplatinum, 5-fluorouracil, vincristine, vinblastine, or methotrexate or pharmaceutically acceptable salts, acids or derivatives of any of the above.

Other examples of chemotherapeutic agents can be Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alkeran (Melphalan Hydrochloride), Alkeran (Melphalan), Alimta (Pemetrexed Disodium), Aloxi (Palonosetron Hydrochloride), Ambochlorin/Amboclorin (Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar (Irinotecan Hydrochloride), Capecitabine, CAPOX, Carac (Fluorouracil-Topical), Carboplatin, Carboplatin-Taxol, Carfilzomib, Carmubris (Carmustine), Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, Chlorambucil-prednisone, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-bevacizumab, FOLFIRI-Cetuximab, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), IL-2 (Aldesleukin), Imatinib Mesylate, Imbruvica (Ibrutinib), Imiquimod, Imlygic (Talimogene Laherparepvec), Inlyta (Axitinib), Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituximab, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tolak (Fluorouracil-Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), or Zytiga (Abiraterone Acetate) or pharmaceutically acceptable salts, acids or derivatives of any of the above.

Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter can repair themselves and function properly.

Radiation therapy used according to the present disclosure may include, but is not limited to, the use of y-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer or tumor. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8, and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides, et al., 1998), cytokine therapy, e.g., interferons α, β, and γ; IL-1, GM-CSF and TNF (Bukowski, et al., 1998; Davidson, et al., 1998; Hellstrand, et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras, et al., 1998; Hanibuchi, et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton, et al., 1992; Mitchell, et al., 1990; Mitchell, et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg, et al., 1988; 1989).

Administration

Agents and compositions described herein can be administered according to methods described herein in a variety of means known to the art.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve taste of the product; or improve shelf life of the product.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Figure 23:
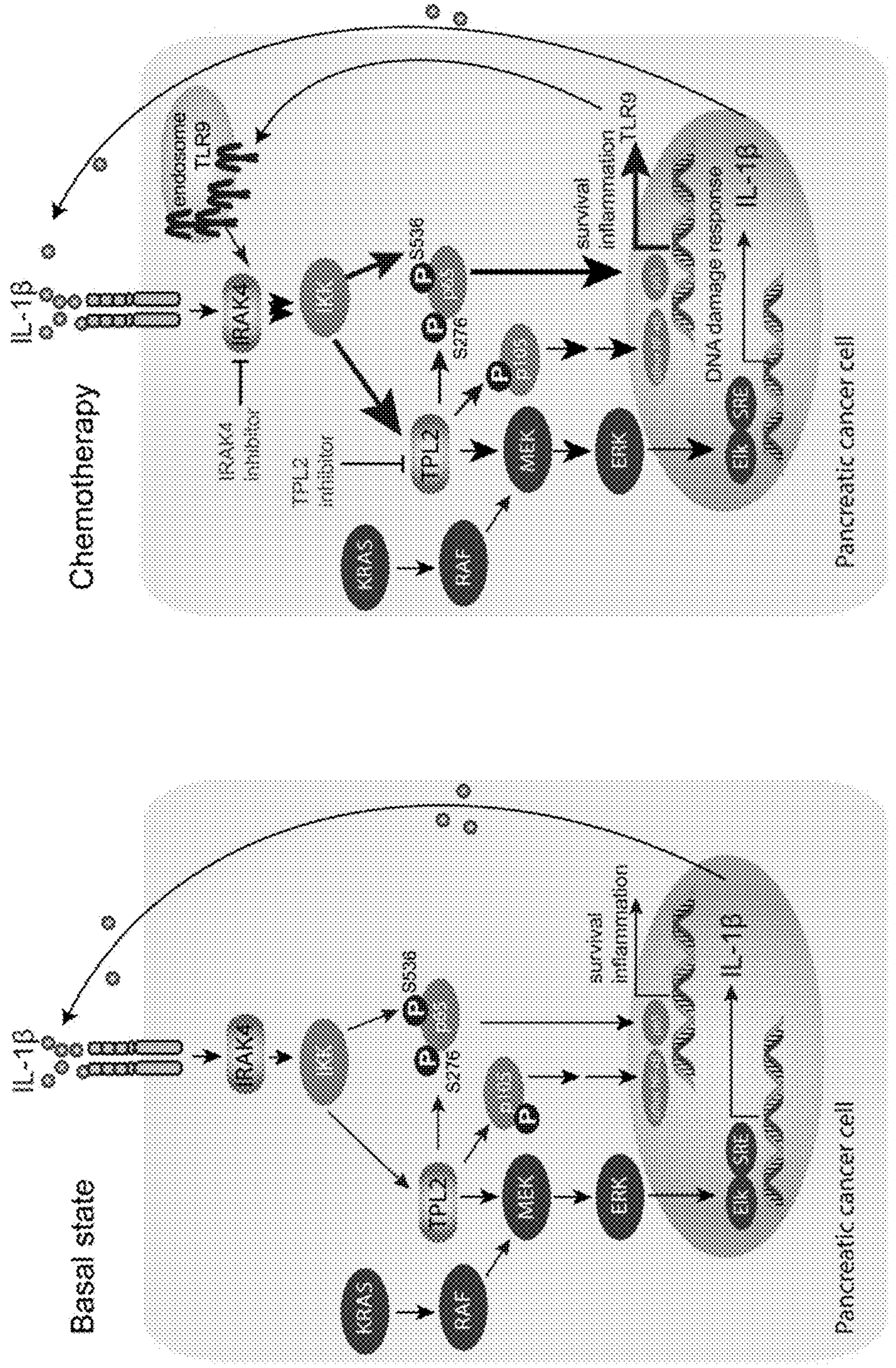
FIG. 23. Schematic illustrating the proposed mechanism that leads to activation of p-IRAK4 and TPL2 signaling in basal state and in context of chemotherapy-induced genotoxic stress.

Example 1: TPL2 Enforces RAS-Induced Inflammatory Signaling and is Activated by Point Mutations This example describes the discovery that TPL2 drives RAS-induced inflammatory signaling and promotes survival under genotoxic stress (see e.g., FIG. 23). Demonstrated herein is the in vivo antitumor efficacy of tumor progression loci-2 kinase inhibitor (TPL2i) as a single agent and in combination with chemotherapy.

Abstract

NF-κB transcription factors, driven by the IRAK-IKK cascade, confer treatment resistance in pancreatic ductal adenocarcinoma (PDAC), a cancer characterized by near-universal KRAS mutation. Through reverse-phase protein array and RNAseq, it was discovered that IRAK4 also contributes substantially to MAPK activation in KRAS-mutant PDAC. IRAK4 ablation completely blocked RAS-induced transformation of human and murine cells. Mechanistically, expression of mutant KRAS stimulated an inflammatory, autocrine IL-1B signaling loop that activated IRAK4 and the MAPK pathway. Downstream of IRAK4, TPL2/MAP3K8 was uncovered as the essential kinase that propels both MAPK and NF-κB cascades. Inhibition of TPL2 blocked both MAPK and NF-κB signaling, and suppressed KRAS-mutant cell growth. To counter chemotherapy-induced genotoxic stress, PDAC cells upregulated TLR9, which activated pro-survival IRAK4-TPL2 signaling. Accordingly, TPL2 inhibitor synergized with chemotherapy to curb PDAC growth in vivo. Finally, from TCGA two MAP3K8 point mutations were characterized that hyperactivate MAPK and NF-κB cascades by impeding TPL2 protein degradation. Cancer cell lines naturally harboring these MAP3K8 mutations are strikingly sensitive to TPL2 inhibition, underscoring the need to identify these potentially targetable mutations in patients. Overall, this study establishes TPL2 as a promising therapeutic target in RAS- and MAP3K8-mutant cancers and strongly prompts development of TPL2 inhibitors for pre-clinical and clinical studies.

For example, a TPL2 kinase inhibitor (TPL2i) can be:

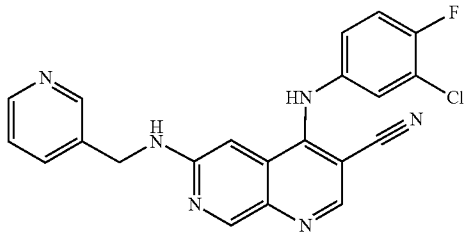 [SMILES: N#Cc1cnc2cnc(NCc3cccnc3)cc2c1Nc1ccc(F)c(Cl)c1]

4-[(3-Chloro-4-fluorophenyl)amino]-6-[(3-pyridinylmethyl)amino]-1,7-naphthyridine-3-carbonitrile or a functional analog thereof or analog having TPL2 inhibiting activity.

Introduction

Targeting the RAS oncoproteins remains unfulfilled in the clinic. Although a newly developed KRAS$^{G12C}$ inhibitor (e.g., AMG 510, sotorasib) has achieved considerable success in lung cancer, it is ineffective in other KRAS$^{G12C}$-mutant cancer types such as colon cancer. In addition, HRAS, NRAS, and non-G12C KRAS oncoproteins remain undruggable. In pancreatic ductal adenocarcinoma (PDAC), though KRAS mutations are virtually universal, the G12C mutation is rare. Strategies to target KRAS effectors including the mitogen-activated protein kinase (MAPK) and phosphoinositide 3-kinase (PI3K) cascades are unsuccessful and multiple resistance mechanisms have been described explaining their failures. Aberrant activation of the NF-κB transcription factors, especially the RELA (or p65) family member, occurs in approximately two-thirds of PDAC and is a major mechanism that underlies the aggressive nature of PDAC. In a genetically-engineered mouse model (GEMM), ablation of IKKB kinase, which activates the NF-κB members, completely abolished $KRAS^{G12D}$ induced PDAC development. However, development of IKK inhibitors is hampered by clinical toxicities and off-target effects. PDAC cells and the surrounding stromal fibroblasts secrete IL-1β that engages interleukin-1 receptor-associated kinase 4 (IRAK4) to drive IKKB and the NF-κB pathway, indicating that IRAK4 is a promising therapeutic target. IRAK4 is a critical signal transducer downstream of the innate immune receptors including the Toll-like (TLR) and IL-1 (IL-1R) receptors. When engaged, these receptors recruit MYD88 and IRAK1 as adaptors, forming a platform that recruits IRAK4. IRAK4 then activates the IKK complex, allowing cytoplasmic NF-κB subunits such as RELA/p65 and p50 to enter the nucleus and transactivate inflammatory and survival genes. The protumorigenic role of this pathway has been described in melanoma, breast, head and neck, colon, and pancreatic cancers. However, these studies do not describe the genetic context in which IRAK4 inhibition is most likely to succeed, nor do they provide insights into the crosstalk of IRAK4 signaling with other oncogenic events besides the NF-κB pathway.

In this study, The Cancer Genome Atlas (TCGA) database was interrogated and MYD88, IRAK1, and IRAK4 were found to be associated with RELA expression and poor prognosis in PDAC. IRAK4 was also found to be essential for RAS-induced oncogenic transformation. Interestingly, by unbiased reverse-phase protein array (RPPA) and RNA sequencing, signaling crosstalk was discovered between IRAK4 and the MAPK pathway in KRAS-mutant PDAC cells. The mechanism of how oncogenic KRAS activates IRAK4 was elucidated, and tumor progression locus 2 (TPL2, also known as MAP3K8 or COT) was uncovered as the essential kinase that controls both MAPK and NF-κB cascades downstream of IRAK4 and effectively KRAS. In addition, the role of TPL2 under genotoxic stress was interrogated and a TPL2 inhibitor (TPL2i) was shown to synergize with the FIRINOX chemotherapy regimen to suppress human and murine in vivo PDAC growth. Last, recurrent MAP3K8 mutations were screened from TCGA and 2 gain-of-function point mutants were discovered, which naturally exist in ovarian cancer and melanoma cell lines, and are highly sensitive to TPL2 blockade.

Results

IRAK signaling dictates NF-κB activity in PDAC and is essential for RAS oncogenesis.

Figure 1B:
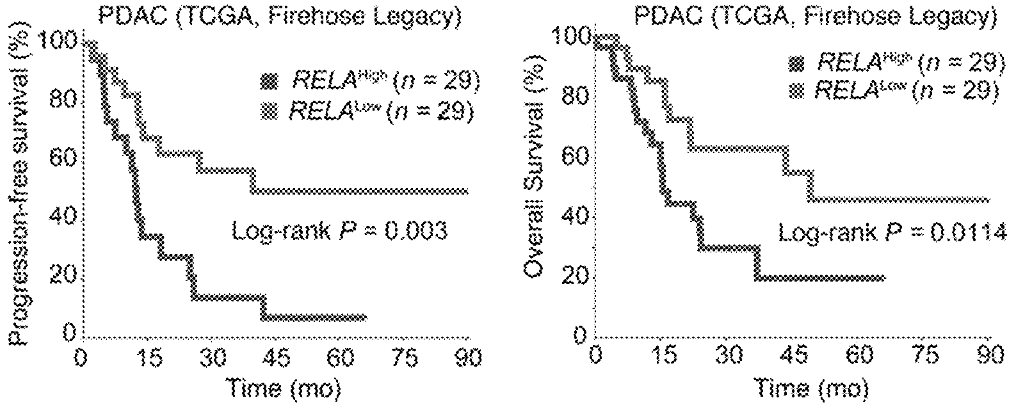
Figure 1C:
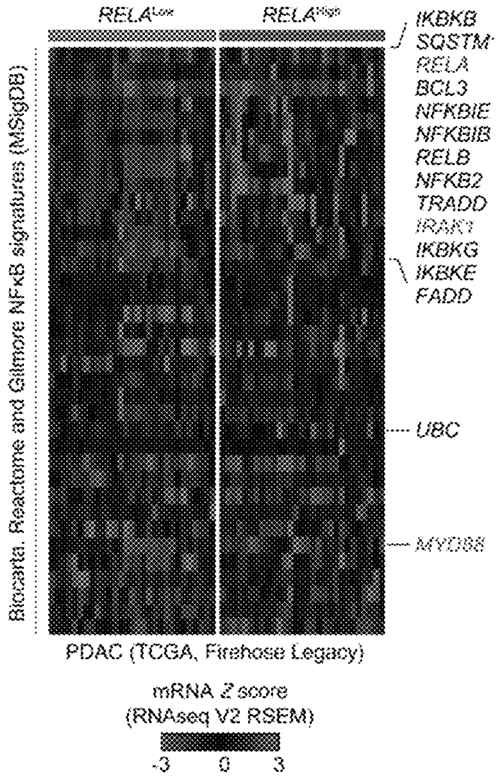
Figure 1D:
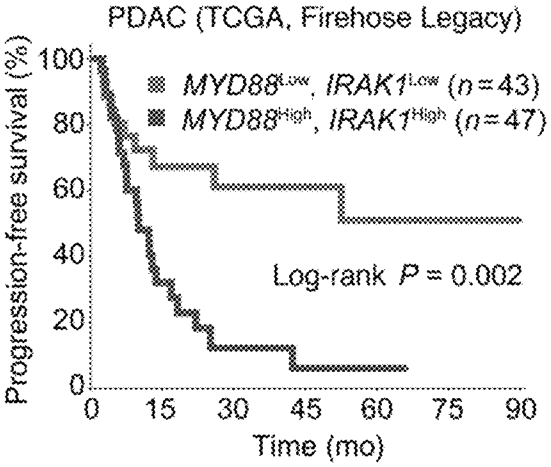
Figure 1E:
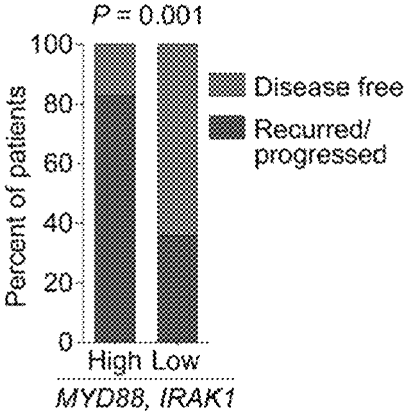
Figure 1F:
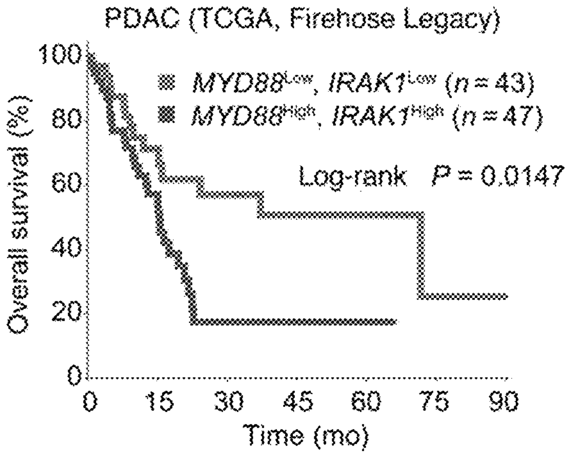
Figure 1G:
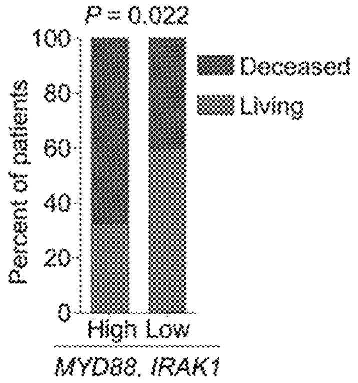
Figure 11A:
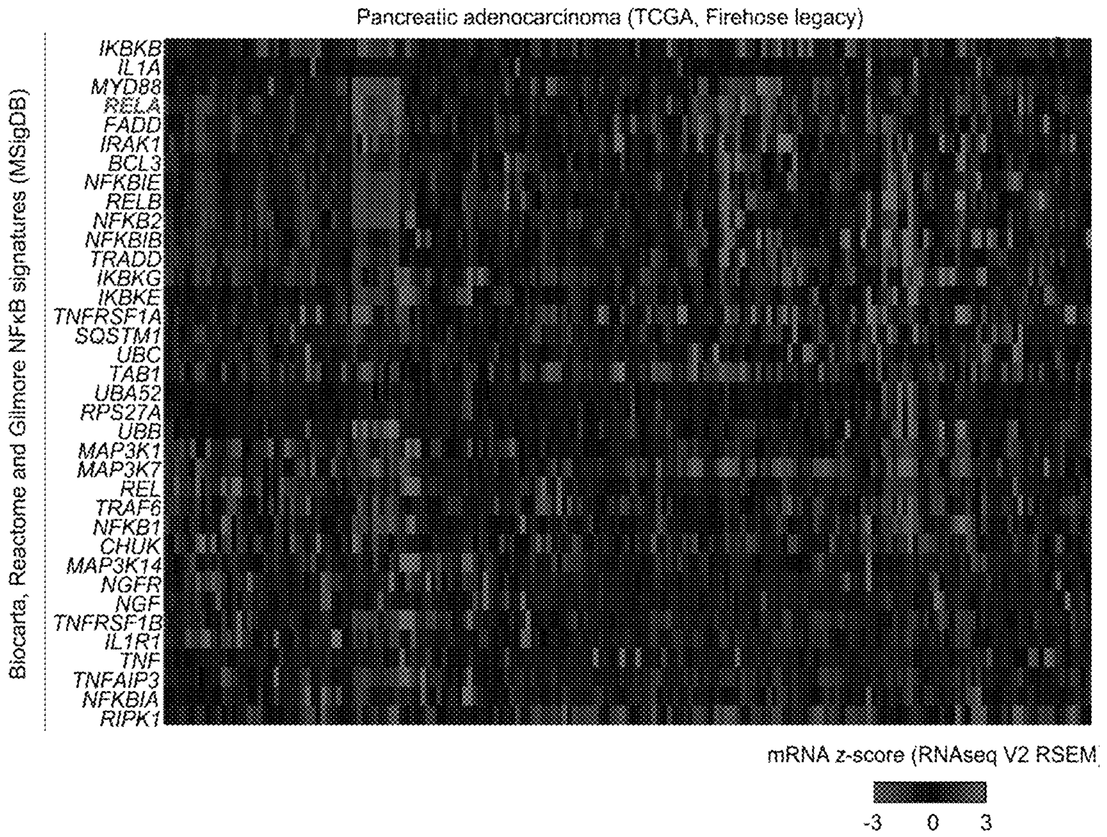
FIG. 11A-FIG. 11F. (A) Heatmap of mRNA RNAseq z-scores for NFkB related genes from the Broad Institute Molecular Signatures Database evaluated in PDAC patient samples in the TCGA Firehose Legacy project. Gene-set lists are provided in TABLE 2. (B) Progression-free and overall survival of patients with high (z-score>1), medium (z-score-1 to 1) and low (z-score<−1) mRNA expression of RELA. (C) Scatter plot showing correlation (Pearson r) between MYD88 and IRAK1 RNA expression. (D) Scatter plot showing correlation (Pearson r) between RELA and IRAK1 (left) or RELA and MYD88 RNA expression. For (B-D) expression was analyzed in samples in the PDAC TCGA Firehose Legacy study. (E) Graph depicting IRAK4 RNA expression in multiple cancers in the TCGA PanCancer Atlas project. Data are arranged by increasing median expression, from left to right. Disease of interest, PDAC, is in red color. P values are from one-way ANOVA with Dunnett's multiple comparison test and are listed for each comparison in TABLE 1. (F) Relative viability of KP2 cells after Irak4 knockout. Data shows average of four replicates, P values from one-way ANOVA with Dunnett's multiple comparison test and error bars indicate mean±SEM. **P<0.0001, *P<0.0002, **P<0.0021, *P<0.0332.
Figure 11B:
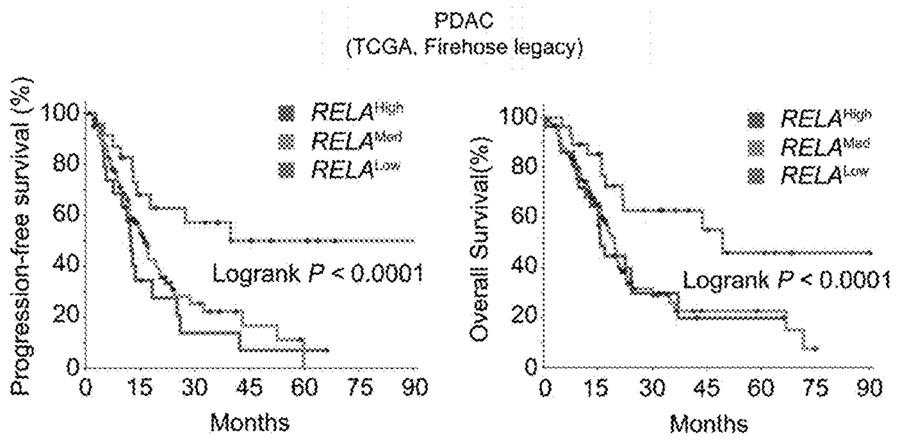
Figure 11C:
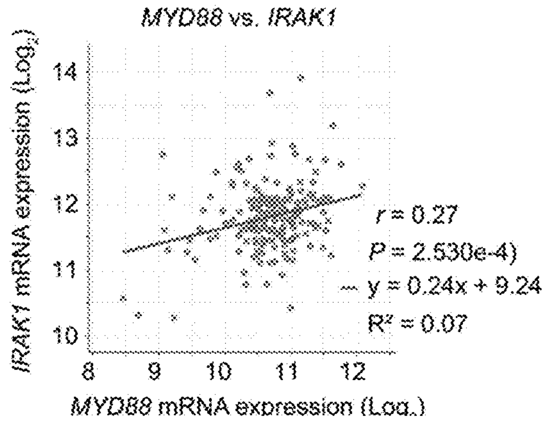
Figure 11D:
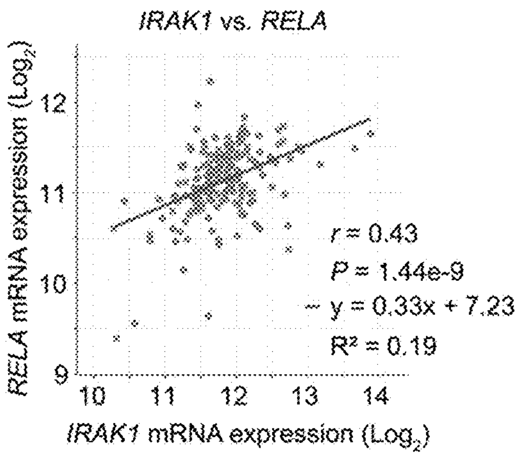

Aberrant NF-κB activation is conventionally defined by increased RELA (or p65 NF-κB family member) expression or nuclear translocation by immunohistochemistry (IHC) in tumor samples. To more comprehensively understand the NF-κB-associated transcriptomes in PDAC, the expression pattern of 37 core NF-κB genes, which include RELA as defined by the Molecular Signatures Database (MSigDB), was evaluated in PDAC samples from TCGA (Firehose Legacy, n=185). By unsupervised clustering heterogeneous expression of these 37 genes was observed across all samples, reflecting the complexity of mechanisms that activate NF-κB and presence of different categories of NF-κB signatures in PDAC (see e.g., FIG. 11A). Because RELA expression is the single, most established NF-κB marker associated with poor prognosis in PDAC, these samples were divided into 3 groups based on RELA mRNA level: $RELA^{High}$ (Z score>1.0, n=29), RELAMed (Z score between −1.0 and 1.0, n=129), and $RELA^{Low}$ (Z score<−1.0, n=29) (see e.g., FIG. 1A). Compared with the $RELA^{Low}$ group, patients in the $RELA^{High}$ and RELAMed groups had significantly worse progression-free and overall survival (see e.g., FIG. 1B and FIG. 11B). The analysis was focused on $RELA^{High}$ and $RELA^{Low}$ cohorts in order to discern the remaining NF-κB genes that cluster with RELA expression. Notably, many genes in the canonical NF-κB pathway were upregulated in the $RELA^{High}$ group (see e.g., FIG. 1C), such as the IKK isoform genes (IKBKB, IKBKE, and IKBKG), inhibitory IκB genes (NFKBIE and NFKBIB), RELB, NFKB2, IRAK1, and MYD88. Of these, MYD88 and IRAK1 stood out because these are known upstream activators of the IKK kinases. MYD88 and IRAK1 expression positively correlated with each other (see e.g., FIG. 11C) and RELA (see e.g., FIG. 11D). Notably, patients with high (Z score>1.0) MYD88 and/or IRAK1 expression (termed "$MYD88^{High}$, $IRAK1^{High}$") had significantly worse progression-free survival (log-rank P=0.0020, see e.g., FIG. 1D), disease-free status (see e.g., FIG. 1E), overall survival (log-rank P=0.0147, see e.g., FIG. 1F), and vital status at the time of data cutoff (see e.g., FIG. 1G), compared with patients with low (Z score<1.0) MYD88 and/or IRAK1 expression (termed "$MYD88^{Low}$, $IRAK1^{Low}$"). Together, these results demonstrate positive correlation between MYD88-IRAK and RELA expression, and further support the TLR/IL-1R canonical pathway as the main driving mechanism of NF-κB activity in PDAC that translates into clinical aggressiveness, congruent with published studies.

Figure 1H:
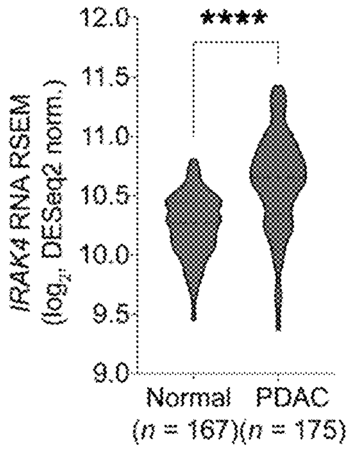
Figure 11E:
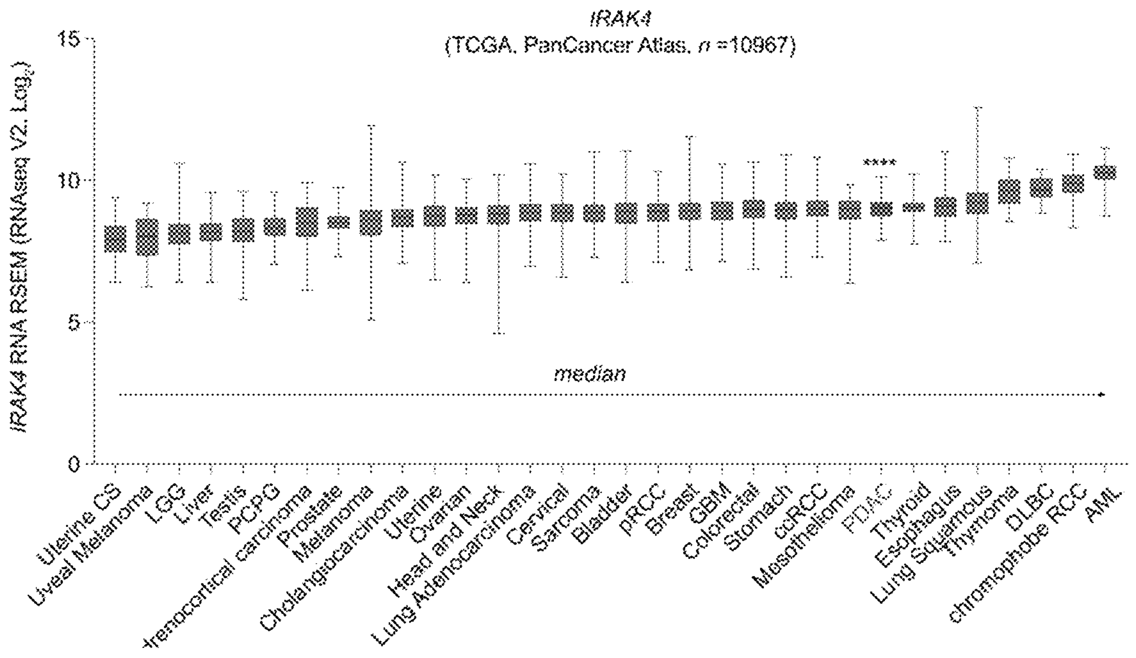

Unlike MYD88 and IRAK1, which function as adaptor proteins, IRAK4 is the bone fide kinase that initiates NF-κB signaling and can be targeted. Phosphoactivation of IRAK4 is associated with higher RELA activity and poor survival of PDAC patients. IRAK4, though not included in the pre-defined 37-gene MSigDB NF-κB signature, was significantly overexpressed in PDAC compared with normal pancreas (see e.g., FIG. 1H). Analysis of the whole TCGA data showed significantly higher IRAK4 expression in PDAC compared with majority of other cancers (see e.g., FIG. 11E and TABLE 1), supporting a pathogenic role of IRAK4 in PDAC.

TABLE 1

IRAK4 pan-cancer mRNA expression P-values.

| Dunnett's multiple comparisons test | Mean Diff. | 95.00% CI of diff. | Significant? | Summary | Adjusted P Value |
|---|---|---|---|---|---|
| PDAC vs. Adrenocortical carcinoma | 0.4806 | 0.2721 to 0.6890 | Yes | **** | <0.0001 |

TABLE 1-continued

IRAK4 pan-cancer mRNA expression P-values.

| Dunnett's multiple comparisons test | Mean Diff. | 95.00% CI of diff. | Significant? | Summary | Adjusted P Value |
|---|---|---|---|---|---|
| PDAC vs. Bladder | 0.1298 | −0.008270 to 0.2679 | No | ns | 0.0815 |
| PDAC vs. Breast | 0.08398 | −0.04037 to 0.2083 | No | ns | 0.4463 |
| PDAC vs. Cervical | 0.1362 | −0.009685 to 0.2821 | No | ns | 0.0858 |
| PDAC vs. Cholangiocarcinoma | 0.3248 | 0.04444 to 0.6053 | Yes | * | 0.0115 |
| PDAC vs. Colorectal | 0.03366 | −0.09773 to 0.1650 | No | ns | 0.9988 |
| PDAC vs. DLBC | −0.6839 | −0.9335 to −0.4343 | Yes | **** | <0.0001 |
| PDAC vs. Esophagus | −0.09136 | −0.2535 to 0.07076 | No | ns | 0.7085 |
| PDAC vs. GBM | 0.05462 | −0.1127 to 0.2219 | No | ns | 0.9936 |
| PDAC vs. Head and Neck | 0.2036 | 0.06997 to 0.3372 | Yes | *** | 0.0002 |
| PDAC vs. chromophobe RCC | −0.8905 | −1.113 to −0.6681 | Yes | | <0.0001 |
| PDAC vs. ccRCC | −0.04327 | −0.1771 to 0.09053 | No | ns | 0.9938 |
| PDAC vs. pRCC | 0.1246 | −0.02233 to 0.2716 | No | ns | 0.1607 |
| PDAC vs. AML | −1.277 | −1.441 to −1.113 | Yes | **** | <0.0001 |
| PDAC vs. LGG | 0.8688 | 0.7351 to 1.002 | Yes | **** | <0.0001 |
| PDAC vs. Liver | 0.8025 | 0.6621 to 0.9429 | Yes | **** | <0.0001 |
| PDAC vs. Lung Adenocarcinoma | 0.1298 | −0.004041 to 0.2636 | No | ns | 0.0643 |
| PDAC vs. Lung Squamous | −0.2042 | −0.3390 to −0.06951 | Yes | *** | 0.0002 |
| PDAC vs. Mesothelioma | 0.0478 | −0.1530 to 0.2486 | No | ns | 0.9989 |
| PDAC vs. Ovarian | 0.2411 | 0.09569 to 0.3864 | Yes | **** | <0.0001 |
| PDAC vs. PCPG | 0.6489 | 0.4861 to 0.8117 | Yes | **** | <0.0001 |
| PDAC vs. Prostate | 0.4648 | 0.3304 to 0.5992 | Yes | **** | <0.0001 |
| PDAC vs. Sarcoma | 0.1332 | −0.01707 to 0.2835 | No | ns | 0.1224 |
| PDAC vs. Melanoma | 0.5222 | 0.3858 to 0.6586 | Yes | **** | <0.0001 |
| PDAC vs. Stomach | 0.04626 | −0.09158 to 0.1841 | No | ns | 0.9933 |
| PDAC vs. Testis | 0.7555 | 0.5850 to 0.9261 | Yes | **** | <0.0001 |
| PDAC vs. Thyroid | −0.06449 | −0.1987 to 0.06973 | No | ns | 0.8805 |
| PDAC vs. Thymoma | −0.6417 | −0.8235 to −0.4599 | Yes | **** | <0.0001 |
| PDAC vs. Uterine | 0.2865 | 0.1532 to 0.4197 | Yes | **** | <0.0001 |
| PDAC vs. Uterine CS | 1.067 | 0.8338 to 1.301 | Yes | **** | <0.0001 |
| PDAC vs. Uveal Melanoma | 1.032 | 0.8251 to 1.238 | Yes | **** | <0.0001 |

Figure 1I:
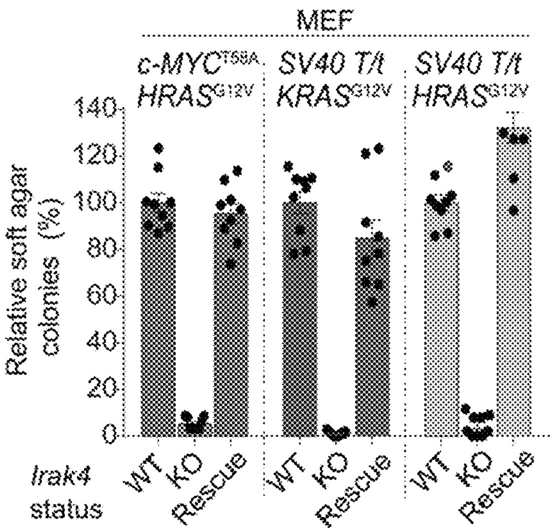
Figure 1J:
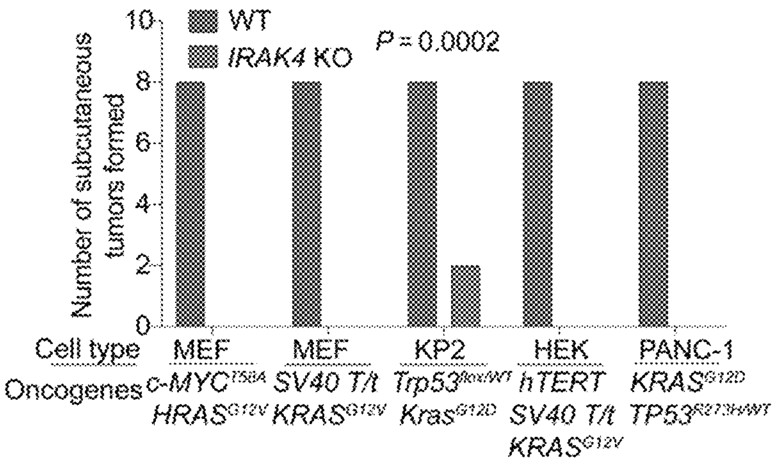
Figure 1K:
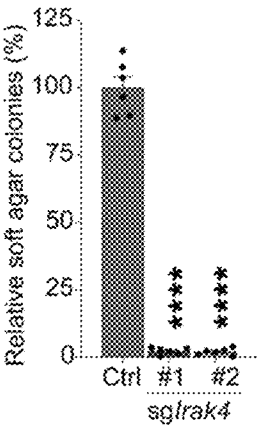
Figure 1L:
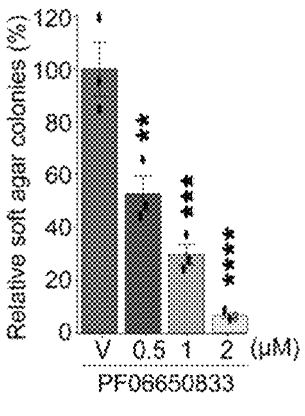
Figure 1M:
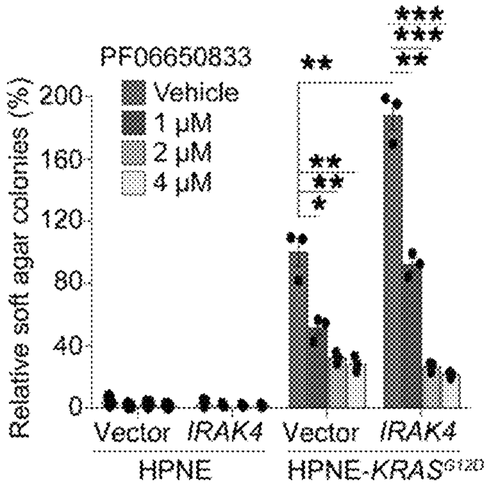
Figure 11F:
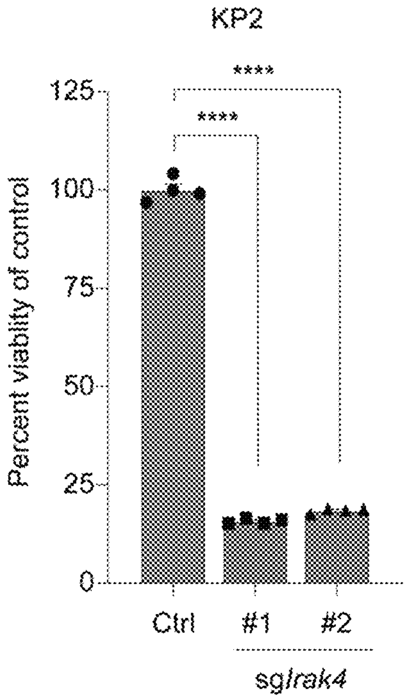

Both IRAK4 and KRAS can drive NF-κB signaling in PDAC, but their crosstalk has not been investigated. While KRAS oncoprotein can stimulate the noncanonical IKK through the RalGEF/RalB/TBK1 effector and the canonical IKK a/B through the PI3K/AKT/mTOR effectors, IRAK4 uses TAK1 kinase to activate IKKB. Therefore, IRAK4 should not be required for KRAS-induced oncogenesis per se. Yet, to test this, pairs of oncogenes were stably expressed including c-MYCT58A and HRASG12V, SV-40 T/t antigens and HRASG12V, or SV-40 T/t and $KRAS^{G12V}$ in WT and $Irak4^{-/-}$ murine embryonic fibroblasts (MEFs). Surprisingly, anchorage-independent (AI) growth in soft agar, a classical assay for transformation, is completely abrogated in $IRAK4^{-/-}$ MEFs, but this could be fully rescued with reexpression of murine Irak4 cDNA (see e.g., FIG. 1I). Consistently, $Irak4^{-/-}$ MEFs expressing oncogenic HRAS or KRAS failed to form tumors in nude mice (see e.g., FIG. 1J). As further confirmation, the CRISPR/Cas9 technique was employed to ablate IRAK4 in 3 KRAS-transformed cell lines: KP2 (a murine PDAC line originating from a p48-Cre; $Tp53^{fl/WT}$; $LSLKras^{G12D}$, or KPC mouse), a human embryonic kidney (HEK T/tH) line transformed with hTERT, SV-40 T/t, and KRAS$^{G12V}$, and the KRAS$^{G12D}$-mutant PANC-1 line. Again, loss of IRAK4 completely abrogated tumorigenic growth of these lines in nude mice (see e.g., FIG. 1J). KP2 cells expressing single guide RNAs against Irak4 (sg/rak4) were severely impaired not only in AI growth, but also 2-dimensional (2D) proliferation (see e.g., FIG. 1K and FIG. 11F), revealing a role of IRAK4 in cell fitness. Similarly, AI growth of KP2 cells was dose-dependently suppressed by PF06650833, a selective IRAK4 inhibitor (IRAK4i) (see e.g., FIG. 1L). To dissect the role of IRAK4 in KRAS-mutant human PDAC, the HPNE model, an artificial pancreatic ductal epithelial line immortalized with hTERT and HPV E6/E7 was used. Stable expression of KRAS$^{G12D}$ in this line (named HPNE-KRAS$^{G12D}$) completes the malignant transformation, enabling AI growth. Ectopic expression of IRAK4 was found to double the AI growth of HPNE-KRAS$^{G12D}$ cells but had no effect on the untransformed HPNE cells (see e.g., FIG. 1M). Notably, treatment with PF06650833 not only reversed the effect of IRAK4 overexpression, but also crippled the AI growth of HPNE-KRAS$^{G12D}$. Together, these studies showed IRAK4 is essential for and cooperates with mutant RAS in oncogenic transformation.

IRAK4 is Crucial for Oncogenic RAS-Driven MAPK Signaling.

Figure 2A:
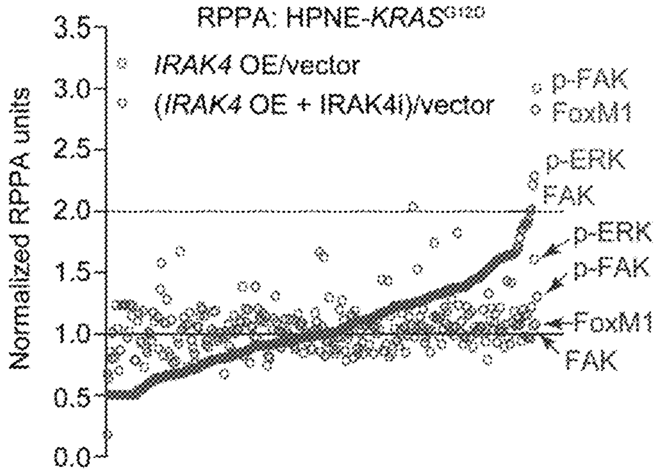
FIG. 2A-FIG. 2K. IRAK4 is crucial for oncogenic RAS-driven MAPK signaling. (A) Linear fold-change for all targets evaluated by reverse-phase protein array (RPPA) performed on HPNE-$KRAS^{G12D}$ overexpressing (OE) IRAK4 and treated with IRAK4i. Targets with fold-change >2 upon IRAK4 overexpression are identified. (B) Heatmap showing relative expression of ERK-regulated targets in RPPA shown in A. (C) Immunoblots of 293T cells transfected with AU1 epitope-tagged WT or kinase-dead IRAK4. (D) Heatmap depicting fold-change for MAPK-, RAS-, and cell growth-related Gene Ontology (GO) signatures upon Irak4 knockout (KO) and rescue (KO+Irak4WT) in murine KP2 cells. Comparisons are KO vs. WT and rescue vs. KO. Signatures significantly (P<0.05) depleted (blue) or enriched (red) are marked with an asterisk (*). (E) Immunoblots of WT and Irak4-KO KP2 cells. (F and G) Gene set enrichment plot and normalized enrichment scores (NES), respectively, for signatures associated with oncogenic KRAS in WT, Irak4-KO, and rescue KP2 cells, compared as in D. "Hallmark" and "C6: Oncogenic Signature" databases were used. Negative NES indicates downregulation and signatures significantly (P<0.05) depleted (blue) or enriched (red) are marked with an asterisk (*). (H) Gene set enrichment plot for PDAC signature in Irak4-KO and -rescue KP2 cells. PDAC signature gene list is provided in TABLE 5. Barcode plots under curves in F and H depict the enrichment clustering for individual genes in the respective gene signatures interrogated for KO vs. WT (top barcode) and rescue vs. KO (bottom barcode) cells. (I) Immunoblots of KP2 and KI cells treated with IRAK4i (PF06650833) or vehicle (V) for 24 hours in serum-free condition. (J) Immunoblots of PDAC cells treated with IRAK4i for 16 hours. (K) Immunoblots of HPNE-$KRAS^{G12D}$ and 293T-$KRAS^{G12V}$ cells treated with IRAK4i for 24 hours in serum-free media. For D and F-H, RNA sequencing was performed on n=2 independent samples for each condition.
Figure 2B:
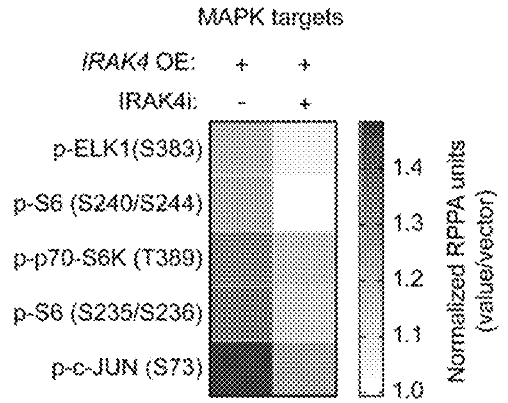
Figure 2C:
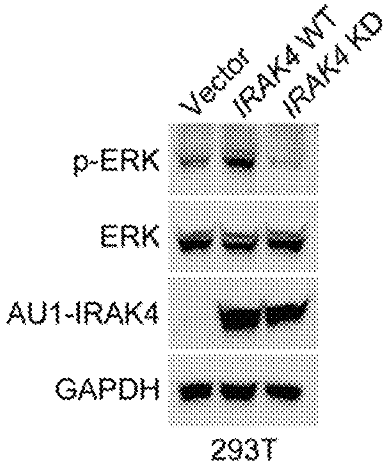
Figure 2D:
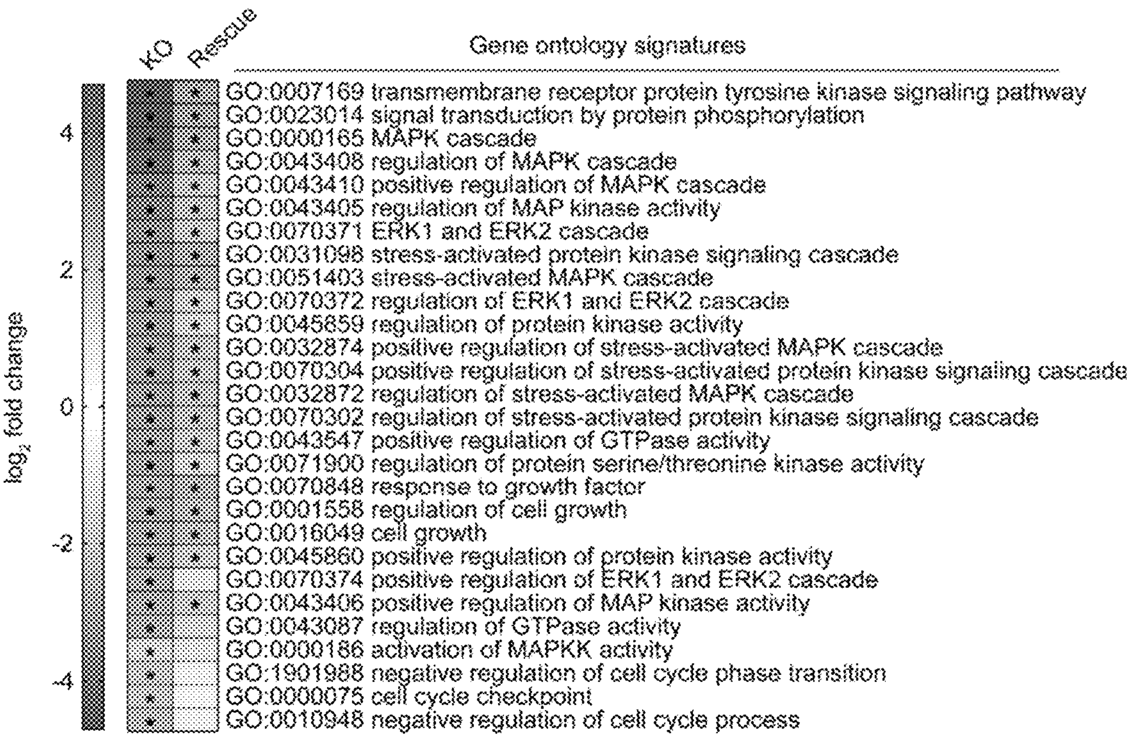
Figure 2E:
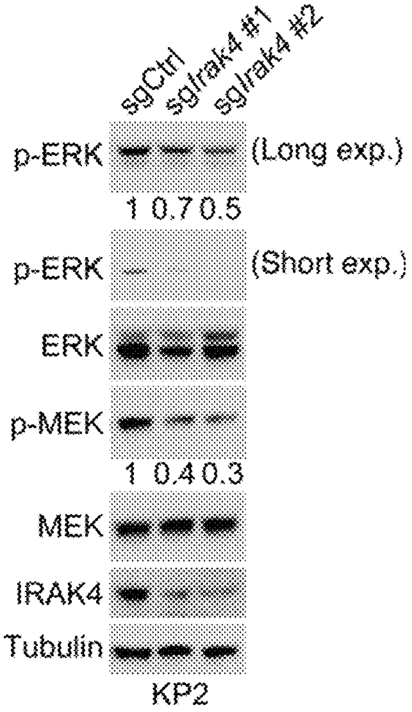
Figure 2F:
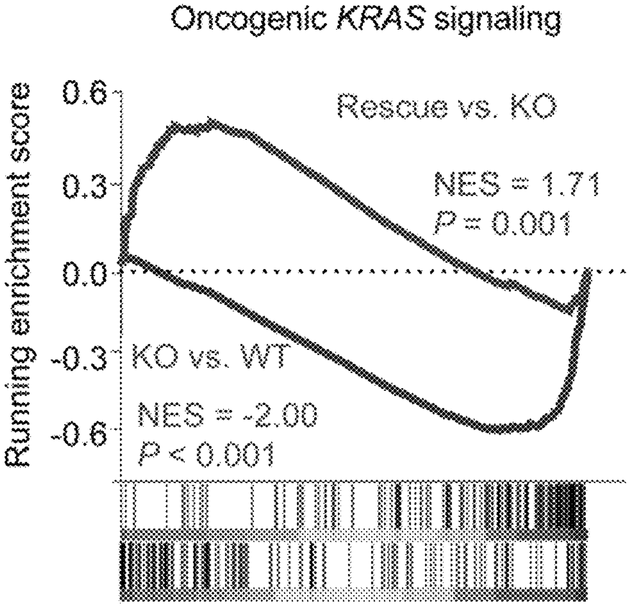
Figure 2G:
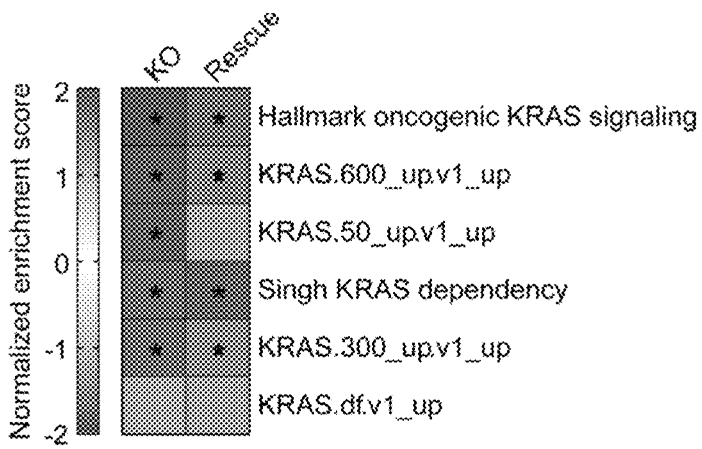
Figure 2H:
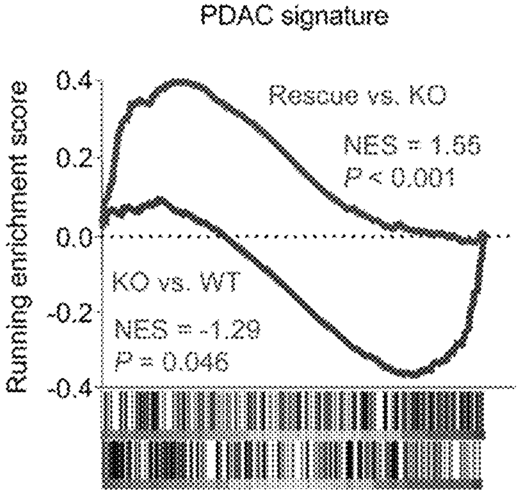
Figure 2I:
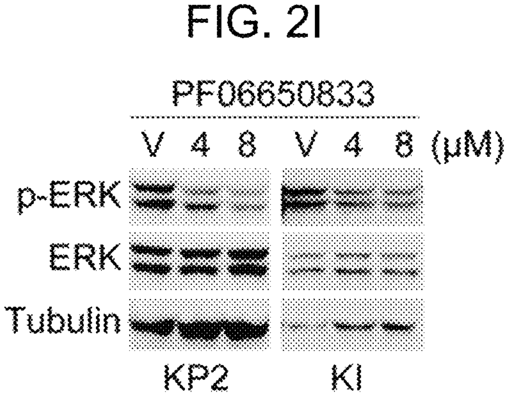
Figure 2J:
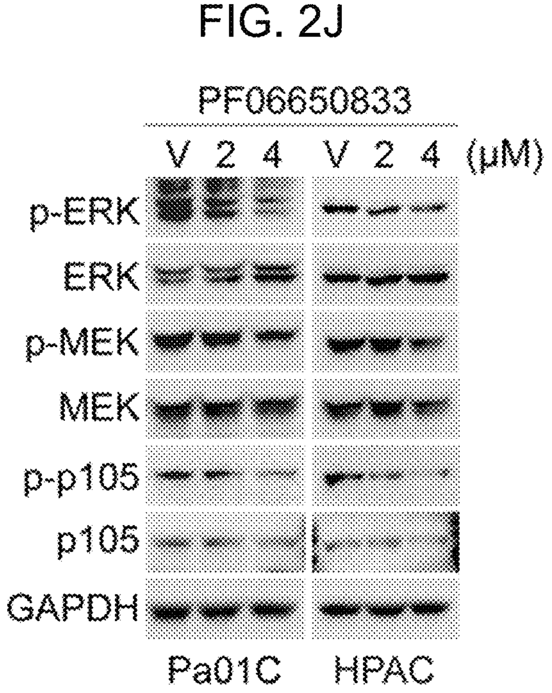
Figure 2K:
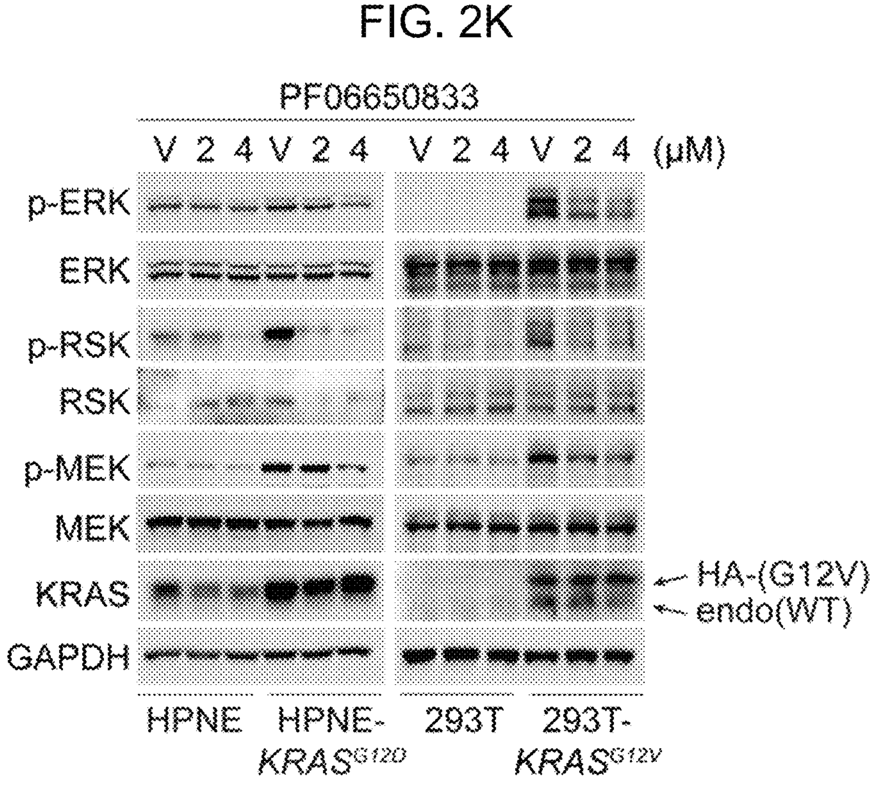
Figure 12A:
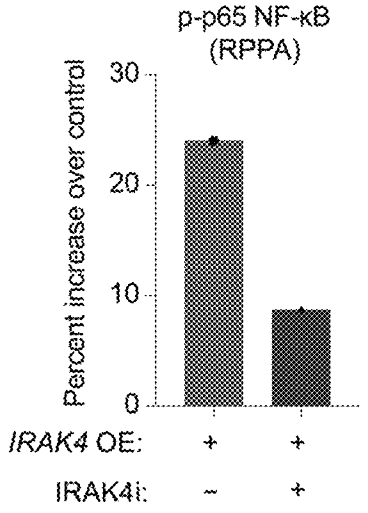
FIG. 12A-FIG. 12G. (A) Graph depicting percent change (compared to vector control) in p-p65 levels from RPPA on HPNE-KRAS$^{G12V}$ cells, as in FIG. 2A. (B) Immunoblots of WT, Irak4-KO, and m/rak4 rescued (KO+m/rak4) KP2 cells. (C) Heat map showing fold change in NF-kB associated GO gene signatures in Irak4-KO and rescue KP2 cells. Signatures significantly (P<0.05) depleted (blue) or enriched (red) are marked with an asterisk (*). (D) Immunoblots of three human PDAC cell lines treated with IRAK4i as in FIG. 2J. (E) Relative SRE activity of HPAC cells treated with IRAK4i (PF06650833), IKKi (IMD-0354), BRAFi (PLX-4720), MEKi (trametinib) and ERKi (BVD-523). Data represents three or more independent experiments, each with technical replicates. P values from two-way ANOVA with Dunnett's multiple comparison test. (F) Viability of 12 human PDAC cell lines after treatment with IRAK4i for 5 days (left) and 7 days (middle). $GI_{50}$ values for each cell line are listed on right. (G) Viability of HEK-KRAS$^{G12V}$ cells with or without ectopic MEK1-$5^{DD}$ expression treated with IRAK4i (PF06650833) for 96 hours. Data represents 12 replicates from 4 independent experiments. Graph on right shows $GI_{50}$ with P value from two-sided paired t-test. All error bars indicate mean±SEM; **P<0.0001, *P<0.0002, **P<0.0021, *P<0.0332
Figure 12B:
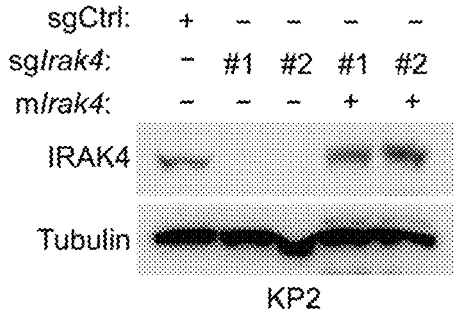
Figure 12C:
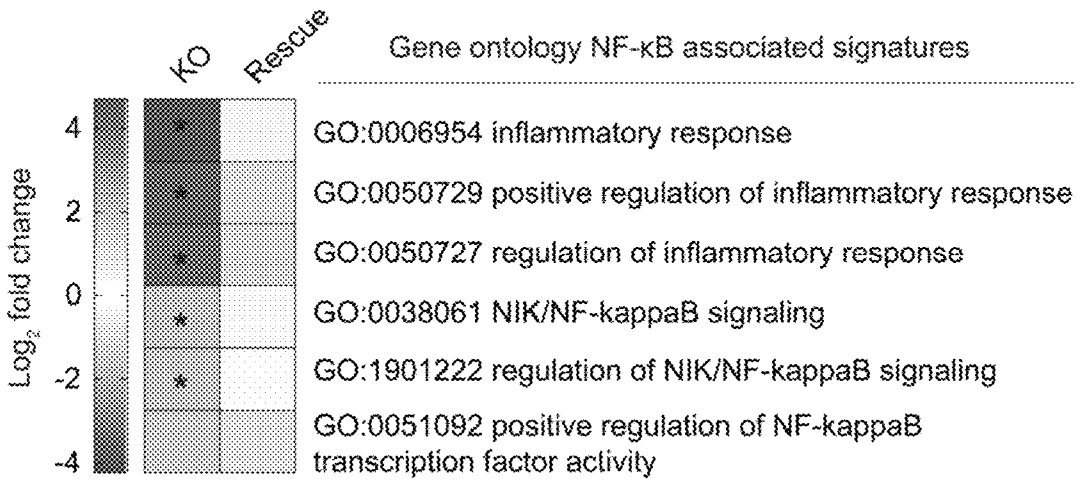
Figure 12D:
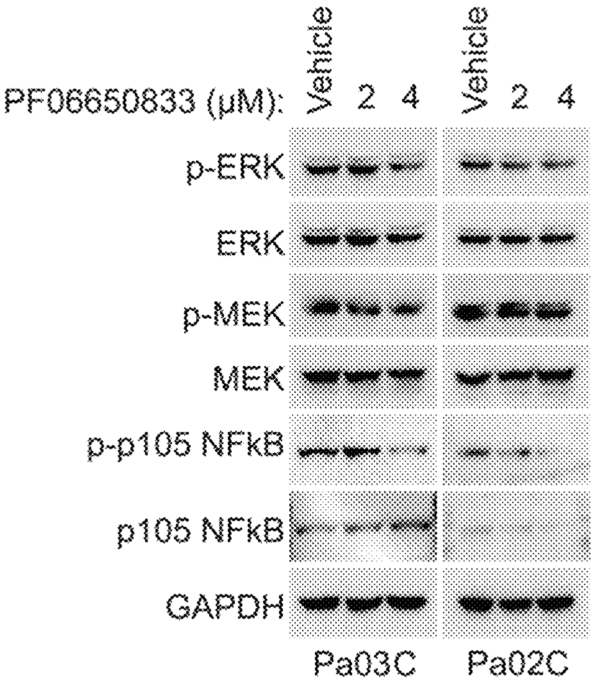
Figure 12E:
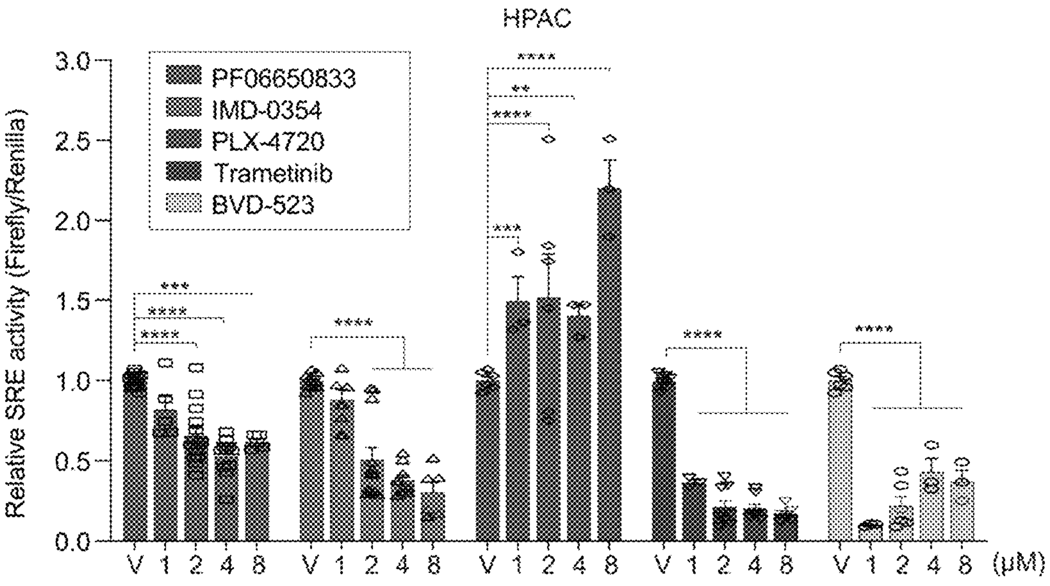
Figure 12F:
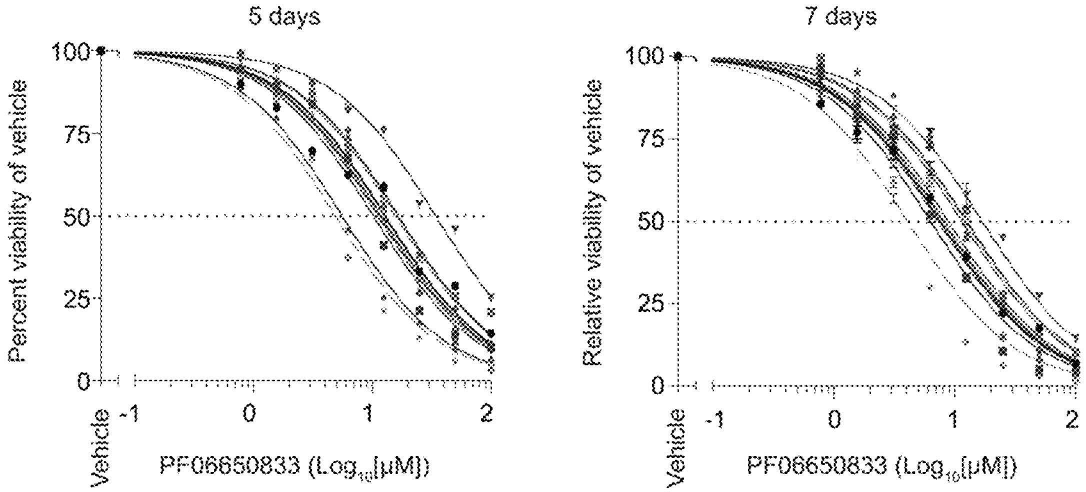
Figure 12G:
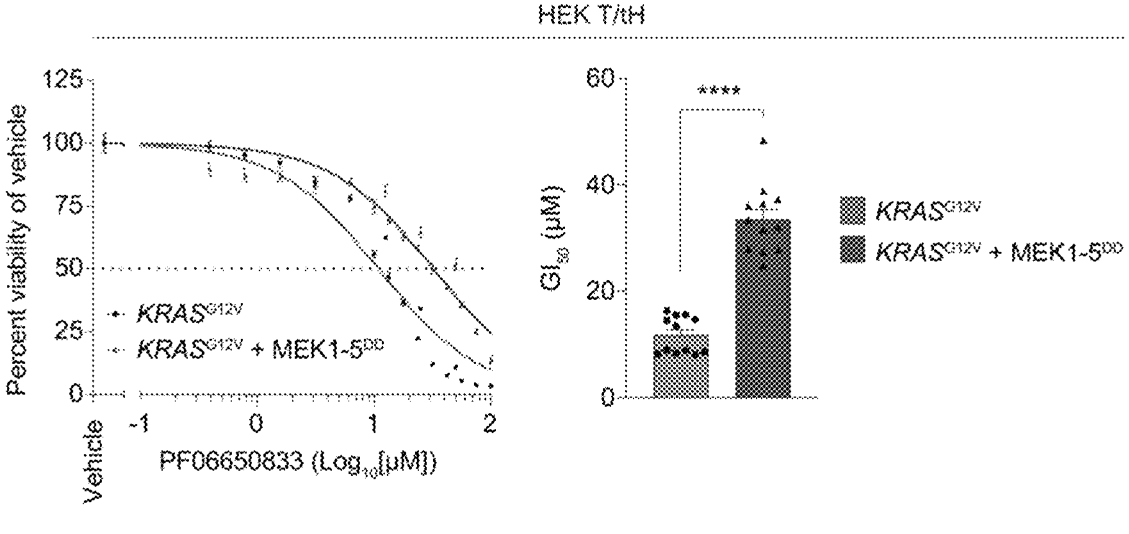

To understand the mechanism by which IRAK4 promotes RAS-induced transformation, an unbiased RPPA was performed on HPNE-KRAS$^{G12D}$ cells stably expressing IRAK4 or empty vector. Compared with vector-expressing cells, IRAK4-overexpressing cells exhibited a greater than 2-fold increase in phosphorylated FAK (p-FAK), p-ERK, total FAK, and FoxM1, which was reversed by IRAK4i treatment (see e.g., FIG. 2A). Indeed, various MAPK target proteins were activated by IRAK4 overexpression and conversely suppressed by IRAK4i (see e.g., FIG. 2B). Similar changes were observed with p-p65/RELA (see e.g., FIG. 12A), resonating with previous studies (see e.g., Zhang et al. (2017) Clin Cancer Res. 23 (7): 1748-1759 and Zhang et al. (2018) Cancer Res. 78 (7): 1700-1712). As confirmation, overexpression of WT, but not kinase-dead IRAK4, enhanced p-ERK in 293T cells, as determined by Western blotting (see e.g., FIG. 2C). Next, RNA sequencing analysis was performed on KP2 cells expressing vector, 2 different sglrak4, or sglrak4 followed by rescue with a murine Irak4 cDNA (termed “rescue”; see e.g., FIG. 12B). Consistent with the RPPA results, MAPK, ERK, and progrowth gene ontology (GO) signatures were significantly suppressed in Irak4-depleted KP2 cells and restored in Irak4-rescued cells (see e.g., FIG. 2D). As confirmation, Western blots showed reduced p-MEK and p-ERK levels in IRAK4-ablated KP2 cells (see e.g., FIG. 2E). Various NF-κB signatures were also similarly affected (see e.g., FIG. 12C). Gene set enrichment analysis (GSEA) showed oncogenic KRAS signaling and PDAC signatures to be significantly downregulated following Irak4 ablation and restored in Irak4-rescued cells (see e.g., FIG. 2F-FIG. 2H). In accordance, IRAK4i dose-dependently suppressed MAPK activity in 2 murine PDAC lines, KP2 and KI (derived from a PDX1-Cre; INK4a$^{fl/fl}$); LSL-KRAS$^{G12D}$ mouse), as well as KRAS-mutant PDAC patient-derived cell lines (PDCLs) Pa01C, Pa02C, and Pa03C, and a conventional human pancreatic adenocarcinoma cell line, HPAC (see e.g., FIG. 2I, FIG. 2J, and FIG. 12D). As further confirmation, IRAK4i dose-dependently reduced serum-response element-driven (SRE-driven) luciferase reporter activity in HPAC cells (see e.g., FIG. 12E) and viability of various KRAS-mutant PDAC lines in vitro (see e.g., FIG. 12F). To clearly establish the role of IRAK4 in KRAS-induced MAPK signaling, 2 isogenic pairs of cell lines expressing empty vector, KRAS$^{G12D}$ (for HPNE), or KRAS$^{G12V}$ (for 293T) were used. As expected, expression of KRAS mutants clearly upregulated p-MEK, p-ERK, and p-RSK levels, but all these were dose-dependently blocked by IRAK4i (see e.g., FIG. 2K). Importantly, expression of an activated MEK mutant (MEK1-5DD) rendered HEK T/tH-KRAS$^{G12V}$ cells approximately 3-fold less sensitive to growth inhibition by IRAK4i (see e.g., FIG. 12G), positioning IRAK4 upstream of MEK. Besides the MAPK pathway, IRAK4i also suppresses p-p105 levels in Pa01C, Pa02C, Pa03C, and HPAC cells (see e.g., FIG. 2J and FIG. 12D), resonating with previous findings that IRAK4 is a driver of the NF-κB pathway. Intriguingly, dose-dependent suppression of SRE activity by IKK inhibitor IMD-0354 was also observed in HPAC, suggesting a contribution of IKK to MAPK activity in PDAC cells (see e.g., FIG. 12E). Together, these results establish IRAK4 as a significant contributor to KRAS-induced MAPK signaling.

TPL2 Mediates Signaling Between IRAK4 and the MAPK Pathway.

Figure 3A:
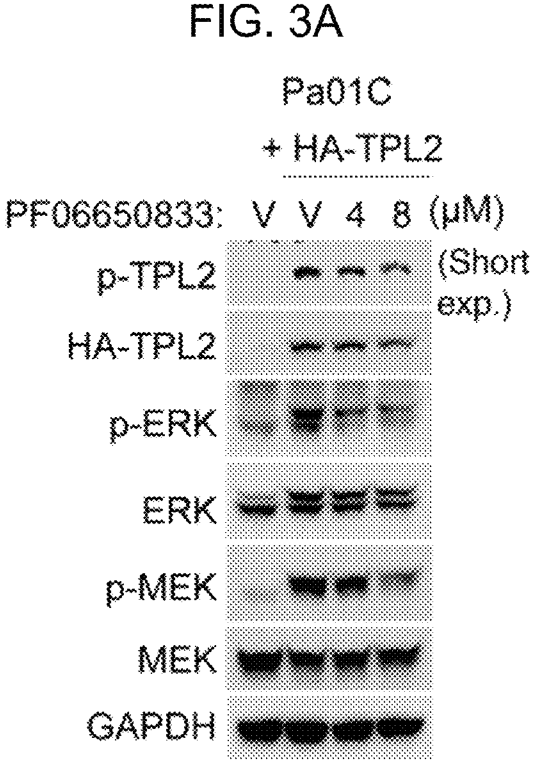
FIG. 3A-FIG. 3F. TPL2 mediates signaling between IRAK4 and the MAPK pathway. (A) Immunoblot of Pa01C cells overexpressing HA epitope-tagged TPL2 WT that were treated with IRAK4i or vehicle (V) for 6 hours in serum-free condition. (B) Immunoblots of 293T cells transfected with WT IRAK4 for 48 hours. (C) Leading-edge analysis performed using data generated by gene set enrichment analysis in order to identify alterations in individual genes within each gene set tested. Significantly downregulated (P<0.05) gene signatures were analyzed and a clustered heatmap was generated. Section of heatmap depicting change in MAP3K8 (TPL2) and MAP2K1 (MEK1) expression is shown with original clustering preserved. TPL2-associated gene set list is provided in TABLE 3. (D) Immunoblot of various commercially available and patient-derived (Pa01C-Pa16C) human PDAC cell lines and 1 normal human pancreatic cell line (HPNE). (E) Correlation plot of p-ERK and TPL2 intensities for PDAC cell lines in D. Two-tailed Pearson correlation (r) analysis was performed. (F) Representative H&E and IHC images of human and murine normal pancreas and PDAC tissue for p-ERK, TPL2, and p-IRAK4. n=6 sections per stain. Scale bars: 50 μm (for full image [×400 magnification]) and 10 μm (insets).
Figure 3B:
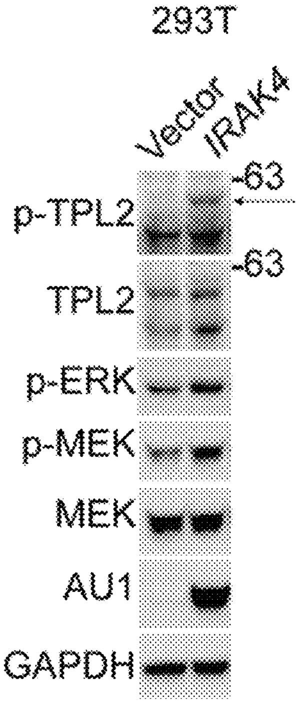
Figure 13A:
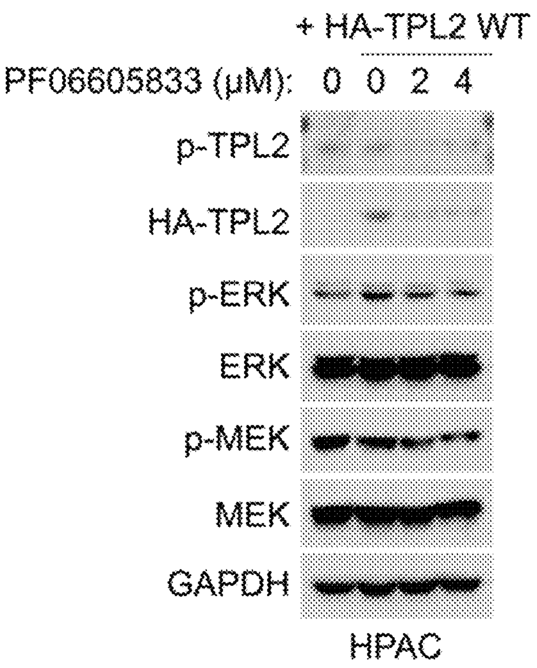
FIG. 13A-FIG. 13B. (A) Immunoblot of HPAC cells ectopically expressing HA epitope-tagged TPL2 WT and treated with IRAK4i (PF06650833) for 24 hours in serum-free media. (B) Heat-map of normalized enrichment scores (NES) for TPL2 associated gene signatures from gene set enrichment analysis of RNAseq differential expression in KP2 IRAK4 knockout and rescue cells. Significantly (P<0.05) depleted (blue) or enriched (red) signatures are marked with an asterisk (*). TPL2 associated gene set lists are provided in TABLE 3.

Next, the mechanistic link between IRAK4 and MEK was investigated. In myeloid cells, IL-1, TNF, or LPS activates MEK and ERK through engaging TPL2 kinase (or COT/MAP3K8). It was therefore hypothesized that IRAK4 engages TPL2 to activate MEK and ERK. Indeed, ectopic expression of TPL2 in Pa01C and HPAC cells enhanced p-MEK and p-ERK levels, but this effect was blocked by IRAK4i. Notably, the ectopically expressed TPL2 protein existed in an activated state, as determined by an anti-p-TPL2 antibody, and was dose-dependently deactivated by IRAK4i, confirming IRAK4 as the upstream activator of TPL2 (see e.g., FIG. 3A and FIG. 13A). In support, ectopic expression of IRAK4 upregulated p-TPL2, p-MEK, and p-ERK in 293T cells (see e.g., FIG. 3B). To strengthen the link between IRAK4, TPL2, and MEK, leading-edge analysis was performed using 15 published TPL2-associated gene signatures from the Broad Institute MSigDB, including significantly downregulated MAPK-related GO 5 signatures identified in Irak4-ablated KP2 cells (see e.g., TABLE 2-TABLE 5).

TABLE 2

NFkB gene set list.

| | |
|---|---|
| BIOCARTA NFKB PATHWAY<br>NF-KB Signaling Pathway | CHUK, FADD, IKBKB, IKBKG, IL1A, IL1R1, MAP3K1, MAP3K14, MAP3K7, MYD88, NFKB1, NFKBIA, RELA, RIPK1, TAB1, TNF, TNFAIP3, TNFRSF1A, TNFRSF1B, TRADD, TRAF6 |
| REACTOME NF KB IS ACTIVATED AND SIGNALS SURVIVAL<br>NF-KB is activated and signals survival | IKBKB, IRAK1, NFKB1, NFKBIA, NGF, NGFR, RELA, RPS27A, SQSTM1, TRAF6, UBA52, UBB, UBC |

TABLE 2-continued

| NFkB gene set list. | |
|---|---|
| GILMORE CORE NFKB PATHWAY Genes encoding the NF-KB core signaling proteins. | BCL3, CHUK, IKBKB, IKBKE, IKBKG, NFKB1, NFKB2, NFKBIA, NFKBIB, NFKBIE, REL, RELA, RELB |
| REACTOME NFKB IS ACTIVATED AND SIGNALS SURVIVAL Genes involved in NF-KB is activated and signals survival | IKBKB, IRAK1, NFKBIA, NGF, NGFR, RELA, RPS27A, RPS27AP11, SQSTM1, TRAF6, UBA52 |

TABLE 3

| TPL2 associated gene sets list. | |
|---|---|
| GO POSITIVE REGULATION OF MAPK CASCADE Any process that activates or increases the frequency, rate or extent of signal transduction mediated by the MAPK cascade. [GOC:go_curators] | ABCA7, ABL1, AC005840.1, AC020613.1, AC139530.1, ACKR3, ADAM8, ADAM9, ADCYAP1, ADORA1, ADORA2B, ADRA1A, ADRA1B, ADRA2A, ADRA2B, ADRA2C, ADRB2, ADRB3, AGER, AJUBA, AKAP13, ALK, ALKAL1, ALKAL2, ALOX12B, ALOX15, ANGPT1, ANKRD6, APELA, APOE, APP, AR, ARHGAP8, ARHGEF5, ARL6IP5, ARRB1, ARRB2, ATP6AP1, AVPI1, AXIN1, BANK1, BIRC7, BMP2, BMP4, BMPER, BRAF, C1QTNF1, C1QTNF2, C5, C5AR1, C5AR2, CALCR, CARD9, CARTPT, CASR, CAV2, CAVIN3, CCL1, CCL11, CCL13, CCL14, CCL15, CCL16, CCL17, CCL18, CCL19, CCL2, CCL20, CCL21, CCL22, CCL23, CCL24, CCL25, CCL26, CCL3, CCL3L1, CCL3L3, CCL4, CCL5, CCL7, CCL8, CCN2, CCR1, CCR7, CD24, CD27, CD36, CD4, CD40, CD40LG, CD44, CD74, CD81, CDH2, CDK1, CDK10, CDON, CFLAR, CHI3L1, CHRNA7, CIB1, CRK, CRKL, CSF1R, CSK, CSPG4, CTNNB1, CX3CL1, CXCL17, CXCR4, DAB2IP, DAXX, DBNL, DDT, DHX33, DKK1, DNAJC27, DOK5, DRD2, DRD4, DSTYK, DUSP15, DUSP19, DUSP22, DUSP5, DUSP6, DUSP7, DUSP9, DVL2, DVL3, EDA2R, EDAR, EDN1, EDN3, EFNA1, EGF, EGFR, EIF2AK2, ELANE, EMC10, EPGN, EPHA4, EPHA8, EPO, ERBB2, ERBB4, ERCC6, ERN1, ERN2, ERP29, EZH2, F2R, F2RL1, FBXW7, FCGR2B, FCRL3, FFAR4, FGA, FGB, FGD2, FGF1, FGF10, FGF18, FGF19, FGF2, FGF20, FGF21, FGF23, FGF4, FGF8, FGF9, FGFR1, FGFR2, FGFR3, FGFR4, FGG, FLT1, FLT3, FLT4, FPR1, FPR2, FRS2, FSHR, FZD10, FZD4, FZD5, FZD7, FZD8, GADD45A, GADD45B, GADD45G, GAREM1, GAS6, GCG, GCNT2, GDF15, GDF6, GFRAL, GH1, GHR, GHRL, GLIPR2, GNAI2, GNG3, GPER1, GPNMB, GPR183, GPR37, GPR37L1, GPR55, GRM1, GRM4, GSDME, HACD3, HAND2, HAVCR2, HCRTR1, HGF, HIPK2, HMGB1, HMGB4, HMGCR, HRAS, HTR2A, HTR2B, HTR2C, IAPP, ICAM1, IGF1, IGF1R, IGF2, IGFBP3, IGFBP4, IKBKG, IL11, IL1B, IL1F10, IL1RN, IL26, IL36A, IL36B, IL36G, IL36RN, IL37, IL6, ILK, INAVA, INS, INSR, IQGAP1, IQGAP3, IRAK1, IRAK2, ITGA1, JAK2, JCAD, JUN, KARS, KDR, KIDINS220, KISS1, KIT, KITLG, KL, KLB, KLHDC10, KRAS, KSR1, LAMTOR1, LAMTOR2, LAMTOR3, LEP, LGALS9, LIF, LILRA5, LPAR1, LPAR3, LRP1, LRRK2, MADD, MAGED1, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K5, MAPK1, MAPK10, MAPK11, MAPK14, MAPK3, MAPK8IP1, MAPK8IP2, MAPK8IP3, MAPKAPK2, MAPKAPK3, MAPKAPK5, MARCO, MDFIC, MFHAS1, MID1, MIF, MINK1, MIR126, MIR181A1, MIR181A2, MIR181B1, MIR181B2, MIR181D, MIR21, MIR221, MIR222, MIR23A, MIR23B, MIR24-1, MIR24-2, MIR27A, MIR27B, MIR92A1, MIR92A2, MIRLET7B, MLKL, MMP8, MOS, MST1R, MT3, MUC20, MUL1, MYDGF, NCF1, NDRG4, NDST1, NECAB2, NEK10, NELFE, NENF, NGF, NMNAT1, NOD1, NOD2, NODAL, NOTCH1, NOTCH2, NOX1, NOX4, NPNT, NPTN, NPY5R, NQO2, NRG1, |

TABLE 3-continued

| TPL2 associated gene sets list. | |
|---|---|
| | NRK, NRP1, NTF3, NTRK1, NTRK2, NTRK3, OPRK1, OPRM1, OSM, P2RX7, P2RY1, P2RY6, PAK1, PAK3, PDCD10, PDE5A, PDE8A, PDGFA, PDGFB, PDGFC, PDGFD, PDGFRA, PDGFRB, PEA15, PELI2, PHB, PHB2, PIK3CB, PIK3CG, PIK3R5, PIK3R6, PJA2, PKN1, PLA2G1B, PLA2G2A, PLA2G5, PLCB1, PLCE1, PRDX2, PRKAA1, PRKCA, PRKCE, PRKCZ, PRKD2, PRMT1, PROK1, PROK2, PRXL2C, PSAP, PSEN1, PTEN, PTK2B, PTPN1, PTPN11, PTPN22, PTPRC, PTPRJ, PYCARD, RAF1, RAMP3, RAP1A, RAP1B, RAPGEF1, RAPGEF2, RASGRP1, RASSF2, RB1CC1, RELL1, RELL2, RET, RIPK1, RIPK2, RIT2, ROBO1, ROCK1, ROCK2, ROR2, RPS27A, RPS3, RYK, S100A12, S100A7, S1PR2, SAA1, SAMD5, SASH1, SCIMP, SDCBP, SEMA3A, SEMA4C, SEMA7A, SERPINF2, SH3RF1, SH3RF2, SH3RF3, SHC1, SHC2, SLAMF1, SLC30A10, SOD1, SORBS3, SOX2, SPAG9, SPRY2, SRC, SSTR4, STK25, STK3, STK39, SYK, SYT14P1, TAB1, TAB2, TAB3, TAOK1, TAOK2, TAOK3, TBX1, TDGF1, TEK, TENM1, TGFA, TGFB1, TGFB2, TGFB3, TGFBR1, THBS1, THPO, TIAM1, TIMP2, TIRAP, TLR3, TLR4, TLR6, TLR9, TNF, TNFAIP8L3, TNFRSF11A, TNFRSF19, TNFSF11, TNIK, TP73, TPD52L1, TRAF2, TRAF4, TRAF6, TRAF7, TREM2, TRIM5, TRPV4, UBA52, UBB, UBC, UBE2N, UBE2V1, UNC5CL, VANGL2, VEGFA, WNT16, WNT5A, WNT7A, WNT7B, WWC1, XCL1, XCL2, XDH, ZC3H12A, ZEB2, ZNF622 |
| GO REGULATION OF MAP KINASE ACTIVITY Any process that modulates the frequency, rate or extent of MAP kinase activity. [GOC:dph, GOC:go_curators] | AC020613.1, AC139530.1, ADAM8, ADAM9, ADIPOQ, ADORA1, ADORA2B, ADRA2A, ADRA2B, AGER, AIDA, AJUBA, AKAP13, ALK, APOE, ARHGEF5, ARRB1, AVPI1, BIRC7, BMP2, BMP4, BMP7, BRAF, C1QTNF2, C5, C5AR1, CARTPT, CAV1, CAV3, CBLC, CCL19, CD24, CD300A, CD40, CD40LG, CD74, CD81, CDK1, CDK12, CDK5RAP3, CHRNA7, CRK, CRKL, CSK, CSPG4, CXCL17, CXCR4, DAB2IP, DAXX, DBNL, DEFB114, DKK1, DNAJA1, DRD4, DTNBP1, DUSP1, DUSP10, DUSP14, DUSP16, DUSP18, DUSP19, DUSP2, DUSP21, DUSP22, DUSP3, DUSP4, DUSP5, DUSP6, DUSP7, DUSP8, DUSP9, DVL2, DVL3, EDN1, EDN3, EGF, EGFR, EIF2AK2, ELANE, EPGN, EPHA4, EPHB2, ERBB2, ERCC6, ERN1, ERN2, ERP29, EZH2, F2R, FGD2, FGF1, FGF10, FGF18, FGF2, FGFR1, FLT1, FLT3, FPR1, FRS2, FZD10, FZD4, FZD5, FZD8, GADD45A, GADD45B, GADD45G, GBA, GDF15, GFRAL, GH1, GHR, GHRL, GNG3, GPS1, GPS2, GRM1, GRM4, GSTP1, HACD3, HGF, HGS, HIPK3, HMGCR, HRAS, HTR2A, HTR2B, HYAL2, IGF1, IGF1R, IKBKG, IL1B, ILK, INAVA, INPP5K, INSR, IQGAP1, IQGAP3, IRAK1, IRAK2, IRAK3, ITGA1, JAK2, KARS, KIDINS220, KIT, KITLG, KRAS, KSR1, LAMTOR2, LAMTOR3, LAX1, LIME1, LPAR1, LPAR3, LRRK2, LYN, MADD, MAGED1, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K5, MAPK1, MAPK10, MAPK11, MAPK14, MAPK3, MAPK8IP1, MAPK8IP3, MAPKAPK2, MAPKAPK3, MAPKAPK5, MBIP, MDFIC, MIF, MIR218-1, MIR218-2, MIR92A1, MIR92A2, MLKL, MOS, MST1R, MUC20, MUL1, NEK10, NF1, NGF, NOD1, NOD2, NOX4, NRG1, NRK, NTF3, NTRK1, NTRK3, NUP62, P2RX7, PAK1, PAK3, PAQR3, PDCD10, PDCD4, PDE5A, PDGFA, PDGFB, PDGFC, PDGFD, PDGFRB, PEA15, PIK3CB, PIK3CG, PIK3R5, PIK3R6, PKN1, PLA2G1B, PLCE1, PP2D1, PPEF2, PPP2CA, PPP2R1A, PRDX2, PRKAA1, PRKCD, PROK1, PROK2, PSEN1, PTK2B, PTPN1, PTPN11, PTPN22, PTPN6, PTPRC, PTPRJ, RAF1, RAPGEF1, RASGRP1, RET, RGS14, RGS2, RGS3, RGS4, RIPK1, RIPK2, ROBO1, ROR2, RPS27A, RPS3, S100A12, S1PR2, SAA1, SAMD5, SASH1, SERPINB3, SFRP1, SFRP2, SHC1, SHC2, SMPD1, SOD1, SORL1, SPAG9, SPRED1, SPRED2, SPRY1, SPRY2, SPRY3, SPRY4, SRC, STK38, STK39, SYK, TAB1, TAB2, TAB3, TAOK1, TAOK2, TAOK3, TDGF1, TENM1, TGFA, TGFB1, TGFB3, TGFBR1, THBS1, TIAM1, TLR4, TLR6, TLR9, TNF, TNFRSF11A, TNFSF11, TNIK, TP73, TPD52L1, |

TABLE 3-continued

| TPL2 associated gene sets list. | |
|---|---|
| | TRAF2, TRAF6, TRAF7, TRIB1, TRIB2, TRIB3, TSG101, UBA52, UBB, UBC, UBE2N, UBE2V1, UCHL1, VANGL2, VEGFA, WNT5A, WNT7B, ZEB2, ZNF675 |
| GO REGULATION OF MAPK CASCADE Any process that modulates the frequency, rate or extent of signal transduction mediated by the MAP kinase (MAPK) cascade. [GOC:go_curators] | ABCA7, ABL1, AC005840.1, AC020613.1, AC129492.1, AC139530.1, ACKR3, ADAM8, ADAM9, ADCYAP1, ADIPOQ, ADORA1, ADORA2B, ADRA1A, ADRA1B, ADRA2A, ADRA2B, ADRA2C, ADRB2, ADRB3, AGER, AIDA, AJUBA, AKAP13, AKT1, ALK, ALKAL1, ALKAL2, ALOX12B, ALOX15, AMBP, ANGPT1, ANKRD6, APELA, APIP, APOE, APP, AR, ARHGAP8, ARHGEF5, ARL6IP5, ARRB1, ARRB2, ASH1L, ATF3, ATP6AP1, ATP6AP2, AVPI1, AXIN1, BANK1, BIRC7, BMP10, BMP15, BMP2, BMP3, BMP4, BMP5, BMP6, BMP7, BMP8A, BMP8B, BMPER, BRAF, BTN2A2, C1QL4, C1QTNF1, C1QTNF2, C3orf33, C5, C5AR1, C5AR2, CALCR, CAMK2N1, CARD9, CARTPT, CASC2, CASR, CAV1, CAV2, CAV3, CAVIN3, CBLC, CCL1, CCL11, CCL13, CCL14, CCL15, CCL16, CCL17, CCL18, CCL19, CCL2, CCL20, CCL21, CCL22, CCL23, CCL24, CCL25, CCL26, CCL3, CCL3L1, CCL3L3, CCL4, CCL5, CCL7, CCL8, CCN1, CCN2, CCR1, CCR7, CD24, CD27, CD300A, CD36, CD4, CD40, CD40LG, CD44, CD74, CD81, CDH2, CDK1, CDK10, CDK12, CDK5RAP3, CDON, CEACAM1, CFLAR, CHI3L1, CHRNA10, CHRNA7, CHRNA9, CIB1, CNKSR3, COPS5, CRK, CRKL, CRYBA1, CSF1R, CSK, CSPG4, CTNNB1, CX3CL1, CXCL17, CXCR4, CYLD, DAB2IP, DACT1, DAG1, DAXX, DBNL, DDT, DEFB114, DHX33, DKK1, DLG1, DNAJA1, DNAJC27, DOK5, DRD2, DRD4, DSTYK, DTNBP1, DUSP1, DUSP10, DUSP14, DUSP15, DUSP16, DUSP18, DUSP19, DUSP2, DUSP21, DUSP22, DUSP26, DUSP3, DUSP4, DUSP5, DUSP6, DUSP7, DUSP8, DUSP9, DVL2, DVL3, EDA2R, EDAR, EDN1, EDN3, EFNA1, EGF, EGFR, EIF2AK2, EIF3A, ELANE, EMC10, EMILIN1, EPGN, EPHA2, EPHA4, EPHA7, EPHA8, EPHB1, EPHB2, EPO, ERBB2, ERBB4, ERCC6, ERN1, ERN2, ERP29, ERRFI1, EZH2, EZR, F2R, F2RL1, FAM83D, FAS, FBLN1, FBXW7, FCGR2B, FCRL3, FFAR4, FGA, FGB, FGD2, FGF1, FGF10, FGF18, FGF19, FGF2, FGF20, FGF21, FGF23, FGF4, FGF8, FGF9, FGFR1, FGFR2, FGFR3, FGFR4, FGG, FKTN, FLCN, FLT1, FLT3, FLT4, FN1, FOXM1, FOXO1, FPR1, FPR2, FRS2, FSHR, FZD10, FZD4, FZD5, FZD7, FZD8, GADD45A, GADD45B, GADD45G, GAREM1, GAS6, GBA, GBP1, GCG, GCNT2, GDF1, GDF10, GDF11, GDF15, GDF2, GDF3, GDF5, GDF6, GDF7, GDF9, GFRAL, GH1, GHR, GHRL, GLIPR2, GNAI2, GNG3, GPER1, GPNMB, GPR183, GPR37, GPR37L1, GPR55, GPS1, GPS2, GRB2, GRIK2, GRM1, GRM4, GSDME, GSTP1, HACD3, HAND2, HAVCR2, HCRTR1, HDAC3, HGF, HGS, HIPK2, HIPK3, HMGB1, HMGB4, HMGCR, HRAS, HRH4, HTR2A, HTR2B, HTR2C, HYAL2, IAPP, ICAM1, ID1, IGBP1, IGF1, IGF1R, IGF2, IGFBP3, IGFBP4, IKBKG, IL11, IL1B, IL1F10, IL1RN, IL26, IL36A, IL36B, IL36G, IL36RN, IL37, IL6, ILK, INAVA, INHA, INHBA, INHBB, INHBC, INHBE, INPP5K, INS, INSR, IQGAP1, IQGAP3, IRAK1, IRAK2, IRAK3, ITCH, ITGA1, ITGB1BP1, JAK2, JCAD, JUN, KARS, KDR, KIDINS220, KISS1, KIT, KITLG, KL, KLB, KLF4, KLHDC10, KRAS, KSR1, LAMTOR1, LAMTOR2, LAMTOR3, LAX1, LEFTY1, LEFTY2, LEMD2, LEP, LGALS9, LIF, LILRA5, LIME1, LMO3, LPAR1, LPAR3, LRP1, LRRK2, LYN, MADD, MAGED1, MAGI3, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K4, MAP4K5, MAPK1, MAPK10, MAPK11, MAPK14, MAPK3, MAPK8IP1, MAPK8IP2, MAPK8IP3, MAPKAPK2, MAPKAPK3, MAPKAPK5, MARCO, MARVELD3, MBIP, MDFIC, MECOM, MEN1, MFHAS1, MID1, MIF, MINK1, MIR126, MIR133A1, MIR133A2, MIR133B, MIR138-1, MIR138-2, MIR145, MIR181A1, MIR181A2, MIR181B1, MIR181B2, MIR181D, MIR185, MIR20A, MIR21, MIR218-1, MIR218-2, MIR221, MIR222, MIR23A, MIR23B, MIR24-1, MIR24-2, MIR26A1, MIR26A2, MIR27A, MIR27B, MIR29B1, MIR29B2, MIR424, MIR503, MIR92A1, MIR92A2, MIRLET7B, |

TABLE 3-continued

| TPL2 associated gene sets list. | |
|---|---|
| | MLKL, MMP8, MOS, MST1R, MSTN, MT3, MUC20, MUL1, MYC, MYDGF, MYOC, NBR1, NCF1, NCOR1, NDRG2, NDRG4, NDST1, NECAB2, NEK10, NELFE, NENF, NF1, NF2, NGF, NLRP12, NLRP6, NMNAT1, NOD1, NOD2, NODAL, NOTCH1, NOTCH2, NOX1, NOX4, NPFFR2, NPNT, NPTN, NPY5R, NQO2, NRG1, NRK, NRP1, NTF3, NTRK1, NTRK2, NTRK3, NUP62, OPRK1, OPRM1, OSM, P2RX7, P2RY1, P2RY6, PAFAH1B1, PAK1, PAK2, PAK3, PAK4, PAK5, PAK6, PAQR3, PBK, PDCD10, PDCD4, PDE5A, PDE8A, PDGFA, PDGFB, PDGFC, PDGFD, PDGFRA, PDGFRB, PEA15, PEBP1, PELI2, PHB, PHB2, PHLPP1, PIK3CB, PIK3CG, PIK3R2, PIK3R5, PIK3R6, PIN1, PINK1, PJA2, PKHD1, PKN1, PLA2G1B, PLA2G2A, PLA2G5, PLCB1, PLCE1, PP2D1, PPEF2, PPP2CA, PPP2R1A, PRDM11, PRDM15, PRDX1, PRDX2, PRKAA1, PRKCA, PRKCD, PRKCE, PRKCZ, PRKD2, PRKN, PRMT1, PRMT5, PROK1, PROK2, PRXL2C, PSAP, PSCA, PSEN1, PSMD10, PTEN, PTK2B, PTPN1, PTPN11, PTPN2, PTPN22, PTPN6, PTPRC, PTPRJ, PTPRR, PYCARD, QARS, RAF1, RAMP3, RANBP9, RAP1A, RAP1B, RAP2A, RAPGEF1, RAPGEF2, RASGRP1, RASSF2, RB1CC1, RELL1, RELL2, REN, RET, RGS14, RGS2, RGS3, RGS4, RIPK1, RIPK2, RIT2, RNF149, RNF41, ROBO1, ROCK1, ROCK2, ROR2, ROS1, RPS27A, RPS3, RPS6KA6, RRAS, RYK, S100A12, S100A7, S1PR2, SAA1, SAMD5, SASH1, SBK2, SCIMP, SDCBP, SEMA3A, SEMA4C, SEMA6A, SEMA7A, SERPINB3, SERPINF2, SFRP1, SFRP2, SH3RF1, SH3RF2, SH3RF3, SHC1, SHC2, SIRPA, SIRT3, SLAMF1, SLC30A10, SLC9A3R1, SMAD4, SMPD1, SOD1, SORBS3, SORL1, SOX2, SPAG9, SPRED1, SPRED2, SPRY1, SPRY2, SPRY3, SPRY4, SRC, SSTR4, STK25, STK3, STK38, STK39, STK40, STYX, SYK, SYNGAP1, SYNJ2BP, SYT14P1, TAB1, TAB2, TAB3, TAOK1, TAOK2, TAOK3, TBC1D10C, TBX1, TDGF1, TEK, TENM1, TGFA, TGFB1, TGFB2, TGFB3, TGFBR1, THBS1, THPO, TIAM1, TIMP2, TIMP3, TIRAP, TLR3, TLR4, TLR6, TLR9, TNF, TNFAIP8L3, TNFRSF11A, TNFRSF19, TNFSF11, TNIK, TNIP1, TP73, TPD52L1, TRAF2, TRAF4, TRAF6, TRAF7, TREM2, TRIB1, TRIB2, TRIB3, TRIM5, TRPV4, TSG101, UBA52, UBB, UBC, UBE2N, UBE2V1, UCHL1, ULK4, UNC5CL, VANGL2, VEGFA, VRK2, VRK3, WNK2, WNT16, WNT5A, WNT7A, WNT7B, WWC1, XCL1, XCL2, XDH, ZC3H12A, ZEB2, ZMYND11, ZNF622, ZNF675 |
| GO REGULATION OF PROTEIN SERINE THREONINE KINASE ACTIVITY<br>Any process that modulates the rate, frequency, or extent of protein serine/threonine kinase activity. [GOC:mah] | ABL1, AC020613.1, AC139530.1, ACSL1, ACTB, ADAM17, ADAM8, ADAM9, ADIPOQ, ADORA1, ADORA2B, ADRA2A, ADRA2B, ADRB2, AGER, AIDA, AJUBA, AKAP13, AKT1, ALK, ALS2, APC, APOE, ARHGEF5, ARRB1, ATP2B4, AVPI1, BCCIP, BIRC7, BLM, BMP2, BMP4, BMP7, BRAF, C1QTNF2, C5, C5AR1, CAB39, CALM1, CALM2, CALM3, CAMK1, CARTPT, CASP3, CAV1, CAV3, CBLC, CCL19, CCNA1, CCNA2, CCNB1, CCNB2, CCNB3, CCNC, CCND1, CCND2, CCND3, CCNE1, CCNE2, CCNF, CCNG1, CCNG2, CCNH, CCNI, CCNI2, CCNJ, CCNJL, CONK, CCNL1, CCNL2, CCNO, CCNQ, CCNT1, CCNT2, CCNY, CCNYL1, CCNYL2, CCNYL3, CD24, CD300A, CD40, CD40LG, CD74, CD81, CDC25A, CDC25C, CDC37, CDC6, CDK1, CDK12, CDK4, CDK5R1, CDK5R2, CDK5RAP1, CDK5RAP3, CDK7, CDKN1A, CDKN1B, CDKN1C, CDKN2A, CDKN2B, CDKN2C, CDKN2D, CDKN3, CEBPA, CEMIP, CHORDC1, CHRNA7, CIB1, CKS1B, CKS2, CNPPD1, CNTD2, CRK, CRKL, CSF1R, CSK, CSPG4, CXCL17, CXCR4, DAB2IP, DAXX, DAZAP2, DBF4, DBF4B, DBNL, DDX3X, DEFB114, DIRAS3, DKK1, DNAJA1, DRD4, DTNBP1, DUSP1, DUSP10, DUSP14, DUSP16, DUSP18, DUSP19, DUSP2, DUSP21, DUSP22, DUSP3, DUSP4, DUSP5, DUSP6, DUSP7, DUSP8, DUSP9, DVL2, DVL3, EDN1, EDN3, EGF, EGFR, EIF2AK2, ELANE, EPGN, EPHA4, EPHB2, ERBB2, ERCC6, ERN1, ERN2, ERP29, ETAA1, EZH2, F2R, FAM20A, FBXO7, FGD2, FGF1, FGF10, FGF18, FGF2, FGFR1, FLT1, FLT3, FPR1, FRS2, FZD10, FZD4, FZD5, FZD8, GADD45A, GADD45B, GADD45G, GBA, GDF15, GFRAL, GH1, GHR, GHRL, GNG3, GPS1, GPS2, GRM1, GRM4, GSTP1, GTF2H1, |

TABLE 3-continued

| TPL2 associated gene sets list. | |
|---|---|
| | GTPBP4, H2AFY, HACD3, HEG1, HERC5, HEXIM1, HEXIM2, HGF, HGS, HHEX, HIGD1A, HIPK3, HMGA2, HMGCR, HRAS, HSPB1, HTR2A, HTR2B, HTT, HYAL2, IFNG, IGF1, IGF1R, IGF2, IKBKG, IL1B, ILK, INAVA, INCA1, INKA1, INKA2, INPP5K, INSR, IPO5, IPO7, IQGAP1, IQGAP3, IRAK1, IRAK2, IRAK3, IRGM, ITGA1, JAK2, KARS, KAT2B, KIDINS220, KIT, KITLG, KRAS, KSR1, LAMTOR2, LAMTOR3, LATS1, LATS2, LAX1, LIME1, LPAR1, LPAR3, LRP5, LRP6, LRRK2, LTF, LYN, MADD, MAGED1, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K5, MAPK1, MAPK10, MAPK11, MAPK14, MAPK3, MAPK8IP1, MAPK8IP3, MAPKAPK2, MAPKAPK3, MAPKAPK5, MAPRE3, MBIP, MDFIC, MEN1, MIF, MIR103A1, MIR103A2, MIR133A1, MIR133A2, MIR15A, MIR20A, MIR218-1, MIR218-2, MIR24-1, MIR24-2, MIR711, MIR92A1, MIR92A2, MLKL, MLST8, MNAT1, MOS, MST1, MST1R, MTCP1, MUC20, MUL1, MYOCD, NEK10, NF1, NGF, NOD1, NOD2, NOX4, NPFFR2, NR2F2, NRG1, NRK, NTF3, NTRK1, NTRK3, NUP62, P2RX7, PAK1, PAK3, PAQR3, PARP16, PDCD10, PDCD4, PDE5A, PDGFA, PDGFB, PDGFC, PDGFD, PDGFRB, PEA15, PIH1D1, PIK3CB, PIK3CG, PIK3R5, PIK3R6, PKD1, PKD2, PKIA, PKIB, PKIG, PKMYT1, PKN1, PLA2G1B, PLCE1, PLK1, PP2D1, PPEF2, PPP2CA, PPP2R1A, PRDX2, PRKAA1, PRKAG1, PRKAG2, PRKAG3, PRKAR1A, PRKAR1B, PRKAR2A, PRKAR2B, PRKCD, PROK1, PROK2, PROX1, PSEN1, PSMD10, PSRC1, PTEN, PTK2B, PTPN1, PTPN11, PTPN22, PTPN6, PTPRC, PTPRJ, PYCARD, RAF1, RALB, RAPGEF1, RAPGEF2, RASGRP1, RASIP1, RET, RGCC, RGS14, RGS2, RGS3, RGS4, RHOA, RIPK1, RIPK2, ROBO1, ROR2, RPS27A, RPS3, RPTOR, S100A12, S1PR2, SAA1, SAMD5, SASH1, SERPINB3, SERTAD1, SESN2, SFN, SFRP1, SFRP2, SHC1, SHC2, SIRT1, SLC27A1, SMPD1, SNCA, SOD1, SORL1, SPAG9, SPDYA, SPRED1, SPRED2, SPRY1, SPRY2, SPRY3, SPRY4, SRC, STK3, STK38, STK39, STK4, STRADA, SYAP1, SYK, TAB1, TAB2, TAB3, TAOK1, TAOK2, TAOK3, TCIM, TCL1A, TCL1B, TDGF1, TELO2, TENM1, TESK1, TFAP4, TGFA, TGFB1, TGFB3, TGFBR1, THBS1, THY1, TIAM1, TLR4, TLR6, TLR9, TNF, TNFAIP3, TNFRSF11A, TNFSF11, TNIK, TP73, TPD52L1, TRAF2, TRAF6, TRAF7, TRIB1, TRIB2, TRIB3, TSG101, UBA52, UBB, UBC, UBE2N, UBE2V1, UCHL1, UVRAG, VANGL2, VEGFA, WEE2, WNK1, WNT5A, WNT7B, YWHAG, ZEB2, ZNF675 |
| GO SIGNAL TRANSDUCTION BY PROTEIN PHOSPHORYLATION A process in which the transfer of one or more phosphate groups to a substrate transmits a signal to the phosphorylated substrate. [GOC:mtg_signal, GOC:signaling] | ABCA7, ABL1, AC005840.1, AC020613.1, AC129492.1, AC139530.1, ACKR3, ACTN2, ADAM8, ADAM9, ADCYAP1, ADIPOQ, ADORA1, ADORA2B, ADRA1A, ADRA1B, ADRA2A, ADRA2B, ADRA2C, ADRB2, ADRB3, AGER, AGT, AIDA, AJUBA, AKAP13, AKT1, ALK, ALKAL1, ALKAL2, ALOX12B, ALOX15, AMBP, ANGPT1, ANKRD6, APELA, APIP, APOE, APP, AR, ARAF, AREG, ARHGAP8, ARHGEF5, ARHGEF6, ARL6IP5, ARRB1, ARRB2, ARTN, ASH1L, ATF3, ATP6AP1, ATP6AP2, AVP, AVPI1, AXIN1, BANK1, BIRC7, BMP10, BMP15, BMP2, BMP3, BMP4, BMP5, BMP6, BMP7, BMP8A, BMP8B, BMPER, BRAF, BRAP, BTC, BTN2A2, BTRC, C1QL4, C1QTNF1, C1QTNF2, C3orf33, C5, C5AR1, C5AR2, CAB39, CAB39L, CALCR, CALM1, CAMK2N1, CAMKK2, CARD9, CARTPT, CASC2, CASR, CAV1, CAV2, CAV3, CAVIN3, CBLC, CCL1, CCL11, CCL13, CCL14, CCL15, CCL16, CCL17, CCL18, CCL19, CCL2, CCL20, CCL21, CCL22, CCL23, CCL24, CCL25, CCL26, CCL3, CCL3L1, CCL3L3, CCL4, CCL5, CCL7, CCL8, CCM2, CCN1, CCN2, CCR1, CCR5, CCR7, CD24, CD27, CD300A, CD36, CD4, CD40, CD40LG, CD44, CD74, CD81, CDC42EP5, CDH2, CDK1, CDK10, CDK12, CDK5RAP3, CDON, CEACAM1, CFLAR, CHI3L1, CHRNA10, CHRNA7, CHRNA9, CHUK, CIB1, CLEC1B, CNKSR3, COPS5, CRK, CRKL, CRYAB, CRYBA1, CSF1R, CSF2, CSF2RA, CSF2RB, CSK, CSPG4, CTNNB1, CTSH, CUL1, CUL3, CX3CL1, CXCL17, |

TABLE 3-continued

| TPL2 associated gene sets list. |
|---|
| CXCR4, CYLD, DAB2IP, DACT1, DAG1, DAXX, DBNL, DDT, DEFB114, DHX33, DKK1, DLG1, DLG2, DLG3, DLG4, DNAJA1, DNAJC27, DOK5, DRD2, DRD4, DSTYK, DTNBP1, DUSP1, DUSP10, DUSP14, DUSP15, DUSP16, DUSP18, DUSP19, DUSP2, DUSP21, DUSP22, DUSP26, DUSP3, DUSP4, DUSP5, DUSP6, DUSP7, DUSP8, DUSP9, DVL2, DVL3, EDA2R, EDAR, EDN1, EDN3, EFNA1, EGF, EGFR, EIF2AK2, EIF3A, ELANE, EMC10, EMILIN1, EPGN, EPHA2, EPHA4, EPHA7, EPHA8, EPHB1, EPHB2, EPO, ERBB2, ERBB3, ERBB4, ERCC6, EREG, ERN1, ERN2, ERP29, ERRFI1, EZH2, EZR, F2R, F2RL1, FAM83D, FAS, FBLN1, FBXW11, FBXW7, FCGR2B, FCRL3, FFAR4, FGA, FGB, FGD2, FGF1, FGF10, FGF13, FGF 16, FGF17, FGF18, FGF19, FGF2, FGF20, FGF21, FGF22, FGF23, FGF3, FGF4, FGF5, FGF6, FGF7, FGF8, FGF9, FGFR1, FGFR2, FGFR3, FGFR4, FGG, FKTN, FLCN, FLT1, FLT3, FLT3LG, FLT4, FN1, FOXM1, FOXO1, FPR1, FPR2, FRS2, FRS3, FSHR, FYN, FZD10, FZD4, FZD5, FZD7, FZD8, GADD45A, GADD45B, GADD45G, GAREM1, GAS6, GBA, GBP1, GCG, GCNT2, GDF1, GDF10, GDF11, GDF15, GDF2, GDF3, GDF5, GDF6, GDF7, GDF9, GDNF, GFRA1, GFRA2, GFRA3, GFRA4, GFRAL, GH1, GHR, GHRL, GLIPR2, GNAI2, GNG3, GPER1, GPNMB, GPR183, GPR37, GPR37L1, GPR55, GPS1, GPS2, GRB2, GRIK2, GRIN1, GRIN2B, GRM1, GRM4, GSDME, GSTP1, HACD3, HAND2, HAVCR2, HBEGF, HCRTR1, HDAC3, HGF, HGS, HIPK2, HIPK3, HMGB1, HMGB4, HMGCR, HRAS, HRH4, HSF1, HTR2A, HTR2B, HTR2C, HYAL2, IAPP, ICAM1, ID1, IGBP1, IGF1, IGF1R, IGF2, IGFBP3, IGFBP4, IKBKB, IKBKG, IL11, IL17RD, IL18, IL1B, IL1F10, IL1RN, IL2, IL26, IL2RA, IL2RB, IL2RG, IL3, IL31RA, IL36A, IL36B, IL36G, IL36RN, IL37, IL3RA, IL5, IL5RA, IL6, ILK, INAVA, INHA, INHBA, INHBB, INHBC, INHBE, INPP5K, INS, INSR, IQGAP1, IQGAP3, IRAK1, IRAK2, IRAK3, IRAK4, IRS1, IRS2, ITCH, ITGA1, ITGAV, ITGB1BP1, ITPKB, JAK1, JAK2, JAK3, JCAD, JUN, KARS, KBTBD7, KDR, KIDINS220, KISS1, KIT, KITLG, KL, KLB, KLF4, KLHDC10, KRAS, KSR1, LAMTOR1, LAMTOR2, LAMTOR3, LAT, LAX1, LEFTY1, LEFTY2, LEMD2, LEP, LGALS9, LIF, LILRA5, LIME1, LMO3, LPAR1, LPAR3, LRP1, LRRC7, LRRK2, LYN, MADD, MAGED1, MAGI3, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K4, MAP4K5, MAPK1, MAPK10, MAPK11, MAPK12, MAPK13, MAPK14, MAPK15, MAPK3, MAPK4, MAPK6, MAPK7, MAPK8, MAPK8IP1, MAPK8IP2, MAPK8IP3, MAPK9, MAPKAPK2, MAPKAPK3, MAPKAPK5, MARCO, MARK3, MARVELD3, MBIP, MBP, MDFIC, MECOM, MED1, MEF2A, MEF2C, MEN1, MET, MFHAS1, MID1, MIF, MINK1, MIR126, MIR133A1, MIR133A2, MIR133B, MIR138-1, MIR138-2, MIR145, MIR181A1, MIR181A2, MIR181B1, MIR181B2, MIR181D, MIR185, MIR20A, MIR21, MIR218-1, MIR218-2, MIR221, MIR222, MIR23A, MIR23B, MIR24-1, MIR24-2, MIR26A1, MIR26A2, MIR27A, MIR27B, MIR29B1, MIR29B2, MIR424, MIR503, MIR92A1, MIR92A2, MIRLET7B, MLKL, MMP8, MOS, MST1R, MSTN, MT3, MUC20, MUL1, MYC, MYDGF, MYOC, NBR1, NCAM1, NCF1, NCOR1, NDRG2, NDRG4, NDST1, NECAB2, NEFL, NEK1, NEK10, NEK4, NELFE, NENF, NF1, NF2, NFKB1, NGF, NLK, NLRP12, NLRP6, NMNAT1, NOD1, NOD2, NODAL, NOTCH1, NOTCH2, NOX1, NOX4, NPFFR2, NPHS1, NPNT, NPTN, NPY5R, NQO2, NRAS, NRG1, NRG2, NRG4, NRK, NRP1, NRTN, NTF3, NTRK1, NTRK2, NTRK3, NUP62, OPRK1, OPRM1, OSM, OXSR1, OXTR, P2RX7, P2RY1, P2RY6, PABPN1, PAFAH1B1, PAK1, PAK2, PAK3, PAK4, PAK5, PAK6, PAQR3, PBK, PDCD10, PDCD4, PDE5A, PDE8A, PDGFA, PDGFB, PDGFC, PDGFD, PDGFRA, PDGFRB, PEA15, PEBP1, PELI2, PHB, PHB2, PHLPP1, PIK3CB, PIK3CG, PIK3R2, PIK3R5, PIK3R6, PIN1, PINK1, PJA2, PKHD1, PKN1, PLA2G1B, PLA2G2A, PLA2G5, PLCB1, PLCE1, PLVAP, |

TABLE 3-continued

| TPL2 associated gene sets list. | |
|---|---|
| | POU4F2, PP2D1, PPEF2, PPM1L, PPP2CA, PPP2R1A, PPP5C, PRDM11, PRDM15, PRDX1, PRDX2, PRKAA1, PRKCA, PRKCD, PRKCE, PRKCZ, PRKD2, PRKN, PRMT1, PRMT5, PROK1, PROK2, PRXL2C, PSAP, PSCA, PSEN1, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PSPN, PTEN, PTGER4, PTK2, PTK2B, PTPN1, PTPN11, PTPN2, PTPN22, PTPN6, PTPRA, PTPRC, PTPRJ, PTPRR, PYCARD, QARS, RAF1, RAMP3, RANBP9, RAP1A, RAP1B, RAP2A, RAPGEF1, RAPGEF2, RASA1, RASA2, RASA3, RASA4, RASAL1, RASAL2, RASAL3, RASGEF1A, RASGRF1, RASGRF2, RASGRP1, RASGRP3, RASGRP4, RASSF2, RB1CC1, RBX1, RELL1, RELL2, REN, RET, RGS14, RGS2, RGS3, RGS4, RHBDD3, RIPK1, RIPK2, RIT2, RNF149, RNF41, ROBO1, ROCK1, ROCK2, ROR2, ROS1, RPS27A, RPS3, RPS6KA6, RRAS, RYK, S100A12, S100A7, S1PR2, SAA1, SAMD5, SASH1, SBK2, SCG2, SCIMP, SDCBP, SEMA3A, SEMA4C, SEMA6A, SEMA7A, SERPINB3, SERPINF2, SETX, SFRP1, SFRP2, SH2D3A, SH2D3C, SH3RF1, SH3RF2, SH3RF3, SHANK3, SHC1, SHC2, SHC3, SIRPA, SIRT3, SKP1, SLAMF1, SLC30A10, SLC9A3R1, SLK, SMAD1, SMAD4, SMPD1, SOD1, SORBS3, SORL1, SOS1, SOX2, SOX9, SPAG9, SPRED1, SPRED2, SPRY1, SPRY2, SPRY3, SPRY4, SPTA1, SPTAN1, SPTB, SPTBN1, SPTBN2, SPTBN4, SPTBN5, SRC, SSTR4, STK10, STK24, STK25, STK26, STK3, STK38, STK39, STK4, STK40, STRADA, STRADB, STYX, SULT1A3, SYK, SYNGAP1, SYNJ2BP, SYT14P1, TAB1, TAB2, TAB3, TAOK1, TAOK2, TAOK3, TBC1D10C, TBX1, TDGF1, TEK, TENM1, TGFA, TGFB1, TGFB2, TGFB3, TGFBR1, THBS1, THPO, TIAM1, TIMP2, TIMP3, TIRAP, TLR3, TLR4, TLR6, TLR9, TNF, TNFAIP8L3, TNFRSF11A, TNFRSF19, TNFSF11, TNIK, TNIP1, TNIP2, TP73, TPD52L1, TRAF2, TRAF4, TRAF6, TRAF7, TREM2, TRIB1, TRIB2, TRIB3, TRIM5, TRPV4, TSG101, UBA52, UBB, UBC, UBE2N, UBE2V1, UCHL1, ULK4, UNC5CL, VANGL2, VEGFA, VRK2, VRK3, WDR83, WNK1, WNK2, WNT16, WNT5A, WNT7A, WNT7B, WWC1, XCL1, XCL2, XDH, YWHAB, YWHAE, ZC3H12A, ZEB2, ZFP36, ZFP36L1, ZFP36L2, ZMYND11, ZNF622, ZNF675 |
| GO STRESS ACTIVATED PROTEIN KINASE SIGNALING CASCADE<br>A series of molecular signals in which a stress-activated protein kinase (SAPK) cascade relays one or more of the signals. [GOC:mah] | AC005840.1, AC129492.1, ADORA2B, AGER, AGT, AIDA, AKR1B1, AKT1, AMBP, ANKRD6, APP, ARHGEF5, ARHGEF6, ARL6IP5, AXIN1, BIRC7, BMP2, BTRC, CARD9, CASR, CAV3, CCDC88C, CCL19, CCL21, CCM2, CCN2, CCR7, CD27, CD40LG, CDC42EP5, CHUK, COPS5, CRKL, CRYAB, CUL1, CYLD, DAB2IP, DACT1, DAXX, DBNL, DKK1, DLG1, DNAJA1, DTNBP1, DUSP1, DUSP10, DUSP15, DUSP19, DUSP22, DUSP3, DUSP9, DVL2, DVL3, EDA2R, EDAR, EDN1, EGFR, EIF2AK2, EMC10, EPHA4, EPHB1, ERCC6, ERN1, ERN2, EZR, F2RL1, FAS, FBXW11, FCGR2B, FGD2, FGF19, FKTN, FLT4, FOXM1, FOXO1, FZD10, FZD4, FZD5, FZD7, FZD8, GADD45A, GADD45B, GADD45G, GDF6, GFRAL, GPS1, GPS2, GRIK2, GSTP1, HACD3, HAND2, HDAC3, HGF, HIPK2, HIPK3, HMGB1, HMGCR, HRAS, IGBP1, IGF1R, IKBKB, IKBKG, IL1B, IL1F10, IL1RN, IL26, IL36A, IL36B, IL36G, IL36RN, IL37, INAVA, IRAK1, IRAK2, IRAK4, ITCH, KARS, KAT7, KLHDC10, LEP, LGALS9, LYN, MAGI3, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K19, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K4, MAP4K5, MAPK1, MAPK10, MAPK11, MAPK13, MAPK14, MAPK3, MAPK8, MAPK8IP1, MAPK8IP2, MAPK8IP3, MAPK9, MAPKAPK2, MARVELD3, MDFIC, MECOM, MEN1, MFHAS1, MID1, MINK1, MIR138-1, MIR138-2, MIR181A1, MIR181A2, MIR181B1, MIR181B2, MIR181D, |

TABLE 3-continued

| TPL2 associated gene sets list. | |
|---|---|
| | MIR20A, MIR92A1, MIR92A2, MLKL, MMP8, MUL1, MYC, NBR1, NCF1, NCOR1, NEK1, NEK4, NFKB1, NOD1, NOD2, NOX1, NPHS1, NRK, OPRK1, OXSR1, PAFAH1B1, PAK1, PAK2, PAK3, PAK4, PAK5, PAK6, PBK, PDCD10, PDCD4, PHLPP1, PINK1, PJA2, PKN1, PLCB1, PPEF2, PRDX1, PRKN, PRMT1, PTGER4, PTK2B, PTPN1, PTPN22, PYCARD, QARS, RAP2A, RAPGEF1, RASGRP1, RASSF2, RB1CC1, RELL1, RELL2, RHOA, RIPK1, RIPK2, ROR2, RPS27A, RPS3, SAMD5, SASH1, SBK2, SDCBP, SEMA3A, SEMA4C, SERPINB3, SERPINF2, SFRP1, SFRP2, SH2D3A, SH2D3C, SH3RF1, SH3RF2, SH3RF3, SIRPA, SKP1, SLAMF1, SLK, SPAG9, STK10, STK24, STK25, STK26, STK3, STK39, STK4, STRADA, STRADB, SYK, TAB1, TAB2, TAB3, TAOK1, TAOK2, TAOK3, TGFB2, TIAM1, TIRAP, TLR3, TLR4, TLR6, TLR9, TNF, TNFRSF11A, TNFRSF19, TNFSF11, TNIK, TNIP2, TPD52L1, TRAF2, TRAF4, TRAF6, TRIB1, TRPV4, UBA52, UBB, UBC, UBE2N, UBE2V1, ULK4, UNC5CL, VANGL2, VEGFA, WNT16, WNT5A, WNT7A, WNT7B, XDH, ZC3H12A, ZEB2, ZFP36, ZFP36L1, ZMPSTE24, ZMYND11, ZNF622, ZNF675 |
| GO MAP KINASE KINASE KINASE ACTIVITY Catalysis of the phosphorylation and activation of a MAP kinase kinase; each MAP kinase kinase can be phosphorylated by any of several MAP kinase kinase kinases. [PMID:9561267] | BRAF, EGFR, MAP3K1, MAP3K10, MAP3K11, MAP3K12, MAP3K13, MAP3K14, MAP3K15, MAP3K2, MAP3K20, MAP3K21, MAP3K3, MAP3K4, MAP3K5, MAP3K6, MAP3K7, MAP3K8, MAP3K9, MLKL, MOS, RAF1, RIPK1, RIPK2, TAOK1, TAOK2, TAOK3 |
| GO POSITIVE REGULATION OF PROTEIN SERINE THREONINE KINASE ACTIVITY Any process that increases the rate, frequency, or extent of protein serine/threonine kinase activity. [GOC:mah] | AC020613.1, AC139530.1, ACSL1, ADAM17, ADAM8, ADAM9, ADIPOQ, ADORA1, ADORA2B, ADRA2A, ADRA2B, ADRB2, AGER, AJUBA, AKAP13, AKT1, ALK, ALS2, ARHGEF5, ARRB1, ATP2B4, AVPI1, BIRC7, BMP2, BMP4, BRAF, C1QTNF2, C5, C5AR1, CAB39, CALM1, CALM2, CALM3, CAMK1, CARTPT, CCL19, CCNB1, CCND1, CCND2, CCND3, CCNK, CCNT1, CCNT2, CCNY, CCNYL1, CCNYL2, CCNYL3, CD24, CD40, CD40LG, CD74, CD81, CDC6, CDK1, CDK5R1, CDK5R2, CDKN1B, CEMIP, CHRNA7, CIB1, CKS1B, CKS2, CRK, CRKL, CSF1R, CSK, CSPG4, CXCL17, CXCR4, DAB2IP, DAXX, DAZAP2, DBF4, DBF4B, DBNL, DDX3X, DKK1, DRD4, DUSP19, DUSP5, DUSP6, DUSP7, DUSP9, DVL2, DVL3, EDN1, EDN3, EGF, EGFR, EIF2AK2, ELANE, EPGN, EPHA4, ERBB2, ERCC6, ERN1, ERN2, ERP29, ETAA1, EZH2, F2R, FAM20A, FGD2, FGF1, FGF10, FGF18, FGF2, FGFR1, FLT1, FLT3, FPR1, FRS2, FZD10, FZD4, FZD5, FZD8, GADD45A, GADD45B, GADD45G, GDF15, GFRAL, GH1, GHR, GHRL, GNG3, GRM1, GRM4, HACD3, HGF, HIGD1A, HMGA2, HRAS, HTR2A, HTR2B, IFNG, IGF1, IGF2, IKBKG, IL1B, ILK, INAVA, INSR, IQGAP1, IQGAP3, IRAK1, IRAK2, IRGM, ITGA1, JAK2, KARS, KIDINS220, KIT, KITLG, KRAS, LAMTOR2, LAMTOR3, LPAR1, LPAR3, LRRK2, LTF, MADD, MAGED1, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K5, MAPK1, MAPK10, MAPK11, MAPK14, MAPK3, MAPK8IP3, MAPKAPK2, MAPKAPK3, MAPKAPK5, MAPRE3, MDFIC, MIF, MIR92A1, MIR92A2, MLKL, MLST8, MNAT1, MOS, MST1R, MTCP1, MUC20, MUL1, NEK10, NGF, NOD1, NOD2, NOX4, NRG1, NRK, NTF3, NTRK1, NTRK3, P2RX7, PAK1, PAK3, PARP16, PDCD10, PDE5A, PDGFA, PDGFB, PDGFC, PDGFD, PDGFRB, PEA15, PIH1D1, PIK3CB, PIK3CG, PIK3R5, PIK3R6, PKD1, PKD2, PKN1, PLA2G1B, PLCE1, PPP2CA, PRDX2, PRKAA1, PROK1, PROK2, PROX1, PSEN1, PSMD10, PSRC1, PTK2B, PTPN1, PTPN11, PTPRC, RAF1, RALB, RAPGEF1, RAPGEF2, RASGRP1, RET, RGCC, RHOA, RIPK1, RIPK2, ROBO1, ROR2, RPS27A, RPS3, RPTOR, |

TABLE 3-continued

| TPL2 associated gene sets list. | |
|---|---|
| | S100A12, S1PR2, SAA1, SAMD5, SASH1, SHC1, SHC2, SIRT1, SLC27A1, SNCA, SOD1, SPAG9, SPDYA, SPRY2, SRC, STK3, STK39, STK4, STRADA, SYAP1, SYK, TAB1, TAB2, TAB3, TAOK1, TAOK2, TAOK3, TCIM, TCL1A, TCL1B, TDGF1, TELO2, TENM1, TGFA, TGFB1, TGFB3, TGFBR1, THBS1, TIAM1, TLR4, TLR6, TLR9, TNF, TNFRSF11A, TNFSF11, TNIK, TP73, TPD52L1, TRAF2, TRAF6, TRAF7, UBA52, UBB, UBC, UBE2N, UBE2V1, VANGL2, VEGFA, WNT5A, WNT7B, ZEB2 |
| GO PROTEIN SERINE THREONINE KINASE ACTIVITY Catalysis of the reactions: ATP + protein serine = ADP + protein serine phosphate, and ATP + protein threonine = ADP + protein threonine phosphate. [GOC:bf] | AAK1, AATK, AC010761.1, ACVR1, ACVR1B, ACVR1C, ACVR2A, ACVR2B, ACVRL1, ADCK1, ADCK2, ADCK5, AKAP13, AKT1, AKT2, AKT3, ALPK1, ALPK2, ALPK3, AMHR2, ANKK1, ARAF, ATM, ATP23, ATR, AURKA, AURKB, AURKC, BCKDK, BCR, BMP2K, BMPR1A, BMPR1B, BMPR2, BRAF, BRD4, BRSK1, BRSK2, BUB1, BUB1B, CAB39, CAB39L, CAMK1, CAMK1D, CAMK1G, CAMK2A, CAMK2B, CAMK2D, CAMK2G, CAMK4, CAMKK1, CAMKK2, CAMKV, CASK, CCL3, CCND3, CCNH, CCNK, CDC42BPA, CDC42BPB, CDC42BPG, CDC7, CDK1, CDK10, CDK11A, CDK11B, CDK12, CDK13, CDK14, CDK15, CDK16, CDK17, CDK18, CDK19, CDK2, CDK20, CDK3, CDK4, CDK5, CDK6, CDK7, CDK8, CDK9, CDKL1, CDKL2, CDKL3, CDKL4, CDKL5, CHEK1, CHEK2, CHUK, CIT, CLK1, CLK2, CLK3, CLK4, CPNE3, CSNK1A1, CSNK1A1L, CSNK1D, CSNK1E, CSNK1G1, CSNK1G2, CSNK1G3, CSNK2A1, CSNK2A2, CSNK2B, DAPK1, DAPK2, DAPK3, DCAF1, DCLK1, DCLK2, DCLK3, DMPK, DSTYK, DYRK1A, DYRK1B, DYRK2, DYRK3, DYRK4, EEF2K, EGFR, EIF2AK1, EIF2AK2, EIF2AK3, EIF2AK4, ERCC2, ERCC3, ERN1, ERN2, FAM20C, FASTK, GAK, GRK1, GRK2, GRK3, GRK4, GRK5, GRK6, GRK7, GSK3A, GSK3B, GTF2H1, GTF2H2, GTF2H3, GTF2H4, HASPIN, HIPK1, HIPK2, HIPK3, HIPK4, HJV, HUNK, ICK, IKBKB, IKBKE, ILK, IRAK1, IRAK2, IRAK3, IRAK4, ITPKA, KALRN, KSR2, LATS1, LATS2, LIMK1, LIMK2, LMTK2, LMTK3, LRRK1, LRRK2, LTBP1, LTBP4, MAK, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K4, MAP4K5, MAPK1, MAPK10, MAPK11, MAPK12, MAPK13, MAPK14, MAPK15, MAPK3, MAPK4, MAPK6, MAPK7, MAPK8, MAPK9, MAPKAPK2, MAPKAPK3, MAPKAPK5, MARK1, MARK2, MARK3, MARK4, MAST1, MAST2, MAST3, MAST4, MASTL, MELK, MINK1, MKNK1, MKNK2, MLKL, MNAT1, MOK, MOS, MTOR, MYLK, MYLK2, MYLK3, MYLK4, MYO3A, MYO3B, NEK1, NEK10, NEK11, NEK2, NEK3, NEK4, NEK5, NEK6, NEK7, NEK9, NIM1K, NLK, NME2, NRBP2, NRK, NUAK1, NUAK2, OBSCN, OXSR1, PAK1, PAK2, PAK3, PAK4, PAK5, PAK6, PASK, PBK, PDIK1L, PDK3, PDPK1, PHKA1, PHKA2, PHKB, PHKG1, PHKG2, PIK3CA, PIK3CG, PIK3R4, PIM1, PIM2, PIM3, PINK1, PKMYT1, PKN1, PKN2, PKN3, PLK1, PLK2, PLK3, PLK4, PNCK, PPM1D, PRKAA1, PRKAA2, PRKAB1, PRKAB2, PRKACA, PRKACB, PRKACG, PRKAG1, PRKAG2, PRKAG3, PRKCA, PRKCB, PRKCD, PRKCE, PRKCG, PRKCH, PRKCI, PRKCQ, PRKCZ, PRKD1, PRKD2, PRKD3, PRKDC, PRKG1, PRKG2, PRKX, PRKY, PRPF4B, PSKH1, PSKH2, PTK2B, RAF1, RIOK1, RIOK2, RIOK3, RIPK1, RIPK2, RIPK3, RIPK4, ROCK1, ROCK2, RPS6KA1, RPS6KA2, RPS6KA3, RPS6KA4, RPS6KA5, RPS6KA6, RPS6KB1, RPS6KB2, RPS6KC1, RPS6KL1, RSKR, SBK1, SBK2, SBK3, SGK1, SGK2, SGK3, SIK1, SIK1B, SIK2, SIK3, SLK, SMG1, SNRK, SOSTDC1, SPEG, SQSTM1, SRPK1, SRPK2, SRPK3, STK10, STK11, STK16, STK17A, STK17B, STK19, STK24, STK25, STK26, STK3, STK31, STK32A, STK32B, STK32C, STK33, STK35, STK36, STK38, STK38L, STK39, STK4, STK40, STKLD1, STRADA, STRADB, SYK, TAF1, TAF1L, TAOK1, TAOK2, TAOK3, TBK1, TESK1, TESK2, TGFBR1, TGFBR2, TGFBR3, TLK1, TLK2, TNIK, TNK2, TNNI3K, TOP1, TP53RK, TRIO, TRPM6, TRPM7, TSSK1B, TSSK2, TSSK3, TSSK4, TSSK6, TTBK1, TTBK2, TTK, TTN, UHMK1, |

TABLE 3-continued

| TPL2 associated gene sets list. | |
|---|---|
| | ULK1, ULK2, ULK3, ULK4, VRK1, VRK2, VRK3, WNK1, WNK2, WNK3, WNK4 |
| GO REGULATION OF KINASE ACTIVITY Any process that modulates the frequency, rate or extent of kinase activity, the catalysis of the transfer of a phosphate group, usually from ATP, to a substrate molecule. [GOC:bf] | ABI1, ABL1, AC020613.1, AC139530.1, ACE, ACP4, ACSL1, ACTB, ACVR2B, ADAM17, ADAM8, ADAM9, ADAR, ADARB1, ADCY1, ADCY2, ADCY3, ADCY4, ADCY5, ADCY6, ADCY7, ADCY8, ADCY9, ADCYAP1, ADIPOQ, ADNP, ADORA1, ADORA2A, ADORA2B, ADRA1A, ADRA2A, ADRA2B, ADRA2C, ADRB2, AFAP1L2, AGAP2, AGER, AGT, AHSG, AIDA, AJUBA, AKAP13, AKT1, AKT1S1, ALK, ALKAL1, ALKAL2, ALS2, AMBRA1, ANG, ANGPT1, ANGPT4, ANKRD54, APC, APOE, APP, ARHGEF5, ARRB1, ATG13, ATG14, ATP2B4, AVPI1, AXIN1, AZU1, BAD, BCCIP, BCL10, BDNF, BIRC7, BLM, BMP2, BMP4, BMP7, BRAF, C1QTNF2, C5, C5AR1, CAB39, CACUL1, CALCA, CALM1, CALM2, CALM3, CAMK1, CAMK2N1, CAMK2N2, CAMKK1, CAMKK2, CARD10, CARD14, CARTPT, CASP3, CASS4, CAV1, CAV3, CBL, CBLB, CBLC, CCDC88A, CCKBR, CCL19, CCL21, CCL5, CCN1, CCNA1, CCNA2, CCNB1, CCNB2, CCNB3, CCNC, CCND1, CCND2, CCND3, CCNE1, CCNE2, CCNF, CCNG1, CCNG2, CCNH, CCNI, CCNI2, CCNJ, CCNJL, CONK, CCNL1, CCNL2, CCNO, CCNQ, CCNT1, CCNT2, CCNY, CCNYL1, CCNYL2, CCNYL3, CCR7, CD19, CD24, CD300A, CD4, CD40, CD40LG, CD74, CD81, CDC25A, CDC25B, CDC25C, CDC37, CDC6, CDK1, CDK12, CDK4, CDK5, CDK5R1, CDK5R2, CDK5RAP1, CDK5RAP3, CDK7, CDKN1A, CDKN1B, CDKN1C, CDKN2A, CDKN2B, CDKN2C, CDKN2D, CDKN3, CEACAM1, CEBPA, CEMIP, CENPE, CEP85, CHI3L1, CHMP6, CHORDC1, CHP1, CHRNA3, CHRNA7, CIB1, CISH, CKS1B, CKS2, CLSPN, CLU, CNPPD1, CNTD2, COPS8, CORO1C, COX11, CRK, CRKL, CSF1, CSF1R, CSK, CSNK2B, CSPG4, CXCL10, CXCL17, CXCR4, DAB1, DAB2IP, DAG1, DAXX, DAZAP2, DBF4, DBF4B, DBNDD2, DBNL, DDR2, DDX3X, DEFB114, DEPTOR, DGKQ, DGKZ, DIRAS3, DKK1, DLG1, DLG3, DLG4, DNAJA1, DNAJC3, DOCK3, DOK7, DRD2, DRD4, DSTYK, DTNBP1, DUS2, DUSP1, DUSP10, DUSP12, DUSP14, DUSP16, DUSP18, DUSP19, DUSP2, DUSP21, DUSP22, DUSP26, DUSP3, DUSP4, DUSP5, DUSP6, DUSP7, DUSP8, DUSP9, DVL1, DVL2, DVL3, DYNAP, ECT2, EDN1, EDN3, EEF1A2, EFNA1, EFNA5, EGF, EGFR, EGR1, EIF2AK2, ELANE, ELP1, ELP3, ELP4, EMP2, EPGN, EPHA1, EPHA4, EPHA8, EPHB2, EPO, ERBB2, ERBB3, ERCC6, EREG, ERN1, ERN2, ERP29, ERRFI1, ETAA1, EZH2, F2, F2R, FABP4, FAF1, FAM20A, FBXO7, FBXW7, FGD2, FGF1, FGF10, FGF13, FGF18, FGF2, FGFR1, FGFR1OP, FGFR3, FGR, FLT1, FLT3, FOXA2, FPR1, FPR2, FRS2, FYN, FZD10, FZD4, FZD5, FZD8, GADD45A, GADD45B, GADD45G, GAS6, GBA, GCG, GCKR, GCN1, GDF15, GFRAL, GGNBP2, GH1, GHR, GHRL, GMFB, GMFG, GNAQ, GNG3, GPRC5A, GPRC5B, GPRC5C, GPRC5D, GPS1, GPS2, GREM1, GRM1, GRM4, GRM5, GSKIP, GSTP1, GTF2H1, GTPBP4, H2AFY, HACD3, HEG1, HERC5, HEXIM1, HEXIM2, HGF, HGS, HHEX, HIGD1A, HIPK3, HMGA2, HMGCR, HNRNPU, HRAS, HSP90AA1, HSP90AB1, HSPB1, HTR2A, HTR2B, HTT, HYAL2, IBTK, IFNG, IGF1, IGF1R, IGF2, IKBKG, IL12B, IL18, IL1B, IL2, IL23A, IL23R, IL4, IL6R, ILK, INAVA, INCA1, INKA1, INKA2, INPP5K, INS, INSR, IPO5, IPO7, IQGAP1, IQGAP3, IRAK1, IRAK2, IRAK3, IRGM, IRS1, IRS2, ITGA1, ITGB1BP1, ITGB3, ITSN1, JAK2, JTB, KARS, KAT2B, KIDINS220, KIF14, KIT, KITLG, KLF4, KRAS, KSR1, LAMTOR2, LAMTOR3, LAT, LATS1, LATS2, LAX1, LCP2, LDB1, LDB2, LEP, LILRA5, LIME1, LMO4, LPAR1, LPAR3, LRP5, LRP6, LRP8, LRRK2, LTF, LYN, MADD, MAGED1, MALT1, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K20, MAP3K21, MAP3K3, MAP3K4, MAP3K5, MAP3K6, MAP3K7, MAP3K8, MAP3K9, MAP4K1, MAP4K2, MAP4K3, MAP4K4, MAP4K5, MAPK1, MAPK10, MAPK11, MAPK14, MAPK3, MAPK8IP1, MAPK8IP3, MAPKAP1, MAPKAPK2, MAPKAPK3, MAPKAPK5, MAPRE3, MAPT, MARK2, MAS1, MBIP, MCPH1, MDFIC, |

TABLE 3-continued

| TPL2 associated gene sets list. | |
|---|---|
| | MEN1, MIDN, MIF, MINK1, MIR103A1, MIR103A2, MIR125B1, MIR133A1, MIR133A2, MIR138-1, MIR138-2, MIR143, MIR15A, MIR20A, MIR21, MIR218-1, MIR218-2, MIR24-1, MIR24-2, MIR711, MIR92A1, MIR92A2, MLKL, MLLT1, MLST8, MMD, MMD2, MNAT1, MOB1B, MOS, MRE11, MRNIP, MST1, MST1R, MSTN, MT3, MTCP1, MTOR, MUC20, MUL1, MVP, MYCNOS, MYOCD, NAB2, NBN, NCAPG2, NCF1, NCK1, NCK2, NCKAP1L, NEDD9, NEK1, NEK10, NEK4, NEURL1, NF1, NF2, NGF, NLRC5, NOD1, NOD2, NOX4, NPFFR2, NPM1, NPRL2, NR2F2, NRBF2, NRG1, NRG3, NRK, NTF3, NTRK1, NTRK2, NTRK3, NUP62, OSBPL8, OXSR1, P2RX7, P2RY12, PAK1, PAK2, PAK3, PAK4, PAK5, PAK6, PAQR3, PARK7, PARP16, PDCD10, PDCD4, PDE5A, PDGFA, PDGFB, PDGFC, PDGFD, PDGFRA, PDGFRB, PDPK1, PEA15, PFKFB1, PFKFB2, PIBF1, PIFO, PIH1D1, PIK3CA, PIK3CB, PIK3CG, PIK3IP1, PIK3R1, PIK3R2, PIK3R3, PIK3R4, PIK3R5, PIK3R6, PILRB, PINK1, PKD1, PKD2, PKIA, PKIB, PKIG, PKMYT1, PKN1, PLA2G1B, PLCE1, PLK1, PP2D1, PPEF2, PPM1E, PPM1F, PPP1R1B, PPP1R9A, PPP2CA, PPP2R1A, PPP2R3C, PPP2R5A, PRDX2, PRDX3, PRKAA1, PRKACA, PRKACB, PRKACG, PRKAG1, PRKAG2, PRKAG3, PRKAR1A, PRKAR1B, PRKAR2A, PRKAR2B, PRKCD, PRKCZ, PRKD1, PRKN, PRKRIP1, PRLR, PRNP, PROK1, PROK2, PROX1, PRR5, PRRC1, PSEN1, PSMD10, PSRC1, PTEN, PTK2, PTK2B, PTK6, PTPN1, PTPN11, PTPN2, PTPN22, PTPN6, PTPRC, PTPRJ, PTPRT, PYCARD, PYDC1, QARS, RAC2, RACK1, RAD50, RAF1, RALB, RANBP2, RAP1A, RAP2B, RAP2C, RAPGEF1, RAPGEF2, RASGRP1, RASIP1, RASSF2, RB1, RBL1, RBL2, RELN, RET, RGCC, RGN, RGS14, RGS2, RGS3, RGS4, RHOA, RHOH, RICTOR, RIPK1, RIPK2, RIPK3, ROBO1, ROR2, RPLP1, RPS27A, RPS3, RPTOR, RTRAF, RUBCN, S100A12, S1PR2, SAA1, SAMD5, SASH1, SBK2, SDC4, SERPINB3, SERTAD1, SESN2, SFN, SFRP1, SFRP2, SH3BP5, SH3BP5L, SHC1, SHC2, SIRT1, SLA2, SLAMF8, SLC11A1, SLC27A1, SLC9A3R1, SLK, SMCR8, SMG8, SMPD1, SMYD3, SNCA, SNX6, SNX9, SOCS1, SOCS2, SOCS3, SOCS4, SOCS5, SOCS6, SOCS7, SOD1, SORL1, SPAG9, SPDYA, SPRED1, SPRED2, SPRY1, SPRY2, SPRY3, SPRY4, SRC, SRCIN1, STAP1, STK10, STK11, STK24, STK25, STK26, STK3, STK38, STK39, STK4, STOX1, STRADA, STRADB, SYAP1, SYK, TAB1, TAB2, TAB3, TAF7, TAL1, TAOK1, TAOK2, TAOK3, TARBP2, TCIM, TCL1A, TCL1B, TDGF1, TEK, TELO2, TENM1, TESC, TESK1, TFAP4, TGFA, TGFB1, TGFB2, TGFB3, TGFBR1, TGFBR2, THBS1, THY1, TIAM1, TIGAR, TIRAP, TLR3, TLR4, TLR6, TLR9, TNF, TNFAIP3, TNFAIP8L3, TNFRSF10A, TNFRSF10B, TNFRSF11A, TNFRSF4, TNFSF11, TNFSF15, TNIK, TOM1L1, TP73, TPD52L1, TPX2, TRAF2, TRAF4, TRAF6, TRAF7, TRIB1, TRIB2, TRIB3, TRIM27, TRPT1, TSC1, TSC2, TSG101, TSPYL2, TTBK1, TTN, TXN, UBA52, UBASH3B, UBB, UBC, UBE2N, UBE2V1, UCHL1, UCN, UNC119, UVRAG, VANGL2, VAV2, VAV3, VEGFA, VLDLR, VPS25, WARS, WASHC1, WDR81, WDR91, WEE2, WNK1, WNT11, WNT3A, WNT5A, WNT7B, WWTR1, XRCC5, XRCC6, YWHAG, ZEB2, ZFP91, ZFYVE28, ZGPAT, ZNF 16, ZNF622, ZNF675 |
| BIOCARTA MAPK PATHWAY MAPKinase Signaling Pathway | ATF2, CEBPA, CHUK, CREB1, DAXX, ELK1, FOS, GRB2, HRAS, IKBKB, JUN, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K2, MAP3K3, MAP3K4, MAP3K5, MAP3K6, MAP3K7, MAP3K8, MAP3K9, MAP4K1, MAP4K2, MAP4K3, MAP4K4, MAP4K5, MAPK1, MAPK10, MAPK11, MAPK12, MAPK13, MAPK14, MAPK3, MAPK4, MAPK6, MAPK7, MAPK8, MAPK9, MAPKAPK2, MAPKAPK3, MAPKAPK5, MAX, MKNK1, MKNK2, MYC, NFKB1, NFKBIA, PAK1, PAK2, RAC1, RAF1, RAPGEF2, RELA, RIPK1, RPS6KA1, RPS6KA2, RPS6KA3, RPS6KA4, RPS6KA5, RPS6KB1, RPS6KB2, SHC1, SP1, STAT1, TGFB1, TGFB2, TGFB3, TGFBR1, TRADD, TRAF2 |

TABLE 3-continued

| TPL2 associated gene sets list. | |
|---|---|
| KEGG MAPK SIGNALING PATHWAY MAPK signaling pathway | AKT1, AKT2, AKT3, ARRB1, ARRB2, ATF2, ATF4, BDNF, BRAF, CACNA1A, CACNA1B, CACNA1C, CACNA1D, CACNA1E, CACNA1F, CACNA1G, CACNA1H, CACNA11, CACNA1S, CACNA2D1, CACNA2D2, CACNA2D3, CACNA2D4, CACNB1, CACNB2, CACNB3, CACNB4, CACNG1, CACNG2, CACNG3, CACNG4, CACNG5, CACNG6, CACNG7, CACNG8, CASP3, CD14, CDC25B, CDC42, CHP1, CHP2, CHUK, CRK, CRKL, DAXX, DDIT3, DUSP1, DUSP10, DUSP14, DUSP16, DUSP2, DUSP3, DUSP4, DUSP5, DUSP6, DUSP7, DUSP8, DUSP9, ECSIT, EGF, EGFR, ELK1, ELK4, FAS, FASLG, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFR1, FGFR2, FGFR3, FGFR4, FLNA, FLNB, FLNC, FOS, GADD45A, GADD45B, GADD45G, GNA12, GNG12, GRB2, HRAS, HSPA1A, HSPA1B, HSPA1L, HSPA2, HSPA6, HSPA8, HSPB1, IKBKB, IKBKG, IL1A, IL1B, IL1R1, IL1R2, JMJD7-PLA2G4B, JUN, JUND, KRAS, LAMTOR3, MAP2K1, MAP2K2, MAP2K3, MAP2K4, MAP2K5, MAP2K6, MAP2K7, MAP3K1, MAP3K11, MAP3K12, MAP3K13, MAP3K14, MAP3K2, MAP3K20, MAP3K3, MAP3K4, MAP3K5, MAP3K6, MAP3K7, MAP3K8, MAP4K1, MAP4K2, MAP4K3, MAP4K4, MAPK1, MAPK10, MAPK11, MAPK12, MAPK13, MAPK14, MAPK3, MAPK7, MAPK8, MAPK8IP1, MAPK8IP2, MAPK8IP3, MAPK9, MAPKAPK2, MAPKAPK3, MAPKAPK5, MAPT, MAX, MECOM, MEF2C, MKNK1, MKNK2, MOS, MRAS, MYC, NF1, NFATC2, NFATC4, NFKB1, NFKB2, NGF, NLK, NR4A1, NRAS, NTF3, NTF4, NTRK1, NTRK2, PAK1, PAK2, PDGFA, PDGFB, PDGFRA, PDGFRB, PLA2G10, PLA2G12A, PLA2G12B, PLA2G1B, PLA2G2A, PLA2G2C, PLA2G2D, PLA2G2E, PLA2G2F, PLA2G3, PLA2G4A, PLA2G4B, PLA2G4E, PLA2G5, PLA2G6, PPM1A, PPM1B, PPP3CA, PPP3CB, PPP3CC, PPP3R1, PPP3R2, PPP5C, PRKACA, PRKACB, PRKACG, PRKCA, PRKCB, PRKCG, PRKX, PTPN5, PTPN7, PTPRR, RAC1, RAC2, RAC3, RAF1, RAP1A, RAP1B, RAPGEF2, RASA1, RASA2, RASGRF1, RASGRF2, RASGRP1, RASGRP2, RASGRP3, RASGRP4, RELA, RELB, RPS6KA1, RPS6KA2, RPS6KA3, RPS6KA4, RPS6KA5, RPS6KA6, RRAS, RRAS2, SOS1, SOS2, SRF, STK3, STK4, STMN1, TAB1, TAB2, TAOK1, TAOK2, TAOK3, TGFB1, TGFB2, TGFB3, TGFBR1, TGFBR2, TNF, TNFRSF1A, TP53, TRAF2, TRAF6 |
| REACTOME MAP3K8 TPL2 DEPENDENT MAPK1 3 ACTIVATION MAP3K8 (TPL2)-dependent MAPK1/3 activation | BTRC, CHUK, CUL1, FBXW11, IKBKB, IKBKG, MAP2K1, MAP2K4, MAP3K8, NFKB1, RPS27A, SKP1, TNIP2, UBA52, UBB, UBC |
| ST ERK1 ERK2 MAPK PATHWAY RK1/ERK2 MAPK Pathway | ARAF, ATF1, BAD, BRAF, CREB1, CREB3, CREB5, DUSP4, DUSP6, DUSP9, EEF2K, EIF4E, GRB2, KAT5, KLF6, MAP2K1, MAP2K2, MAP3K8, MAPK1, MAPK3, MKNK1, MKNK2, MOS, NFKB1, RAP1A, RPS6KA1, RPS6KA2, RPS6KA3, SHC1, SOS1, SOS2, TRAF3 |

TABLE 4

| Interleukin-1 associated gene sets list. | |
|---|---|
| GO INTERLEUKIN 1 MEDIATED SIGNALING PATHWAY > A series of molecular signals initiated by the binding of interleukin-1 to a receptor on the surface of a cell, and ending with regulation of a downstream cellular process, e.g. transcription. [GOC:BHF, | BTRC, CHUK, CUL1, EGR1, FBXW11, IKBKB, IKBKG, IL1A, IL1B, IL1R1, IL1R2, IL1RAP, IL1RL2, IL1RN, IL6, IRAK1, IRAK2, IRAK3, IRAK4, MAP3K3, MAP3K7, MAP3K8, MAPK3, MIR146A, MIR155, MYD88, NFKB1, NFKBIA, NOD1, NOD2, OTUD4, PELI1, PELI2, PELI3, PLCB1, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, |

TABLE 4-continued

| Interleukin-1 associated gene sets list. | |
|---|---|
| GOC:mah, GOC:signaling] | PSME3, PSME4, PSMF1, RBX1, RELA, RIPK2, RPS27A, RPS6KA4, RPS6KA5, SKP1, SQSTM1, ST18, TAB1, TAB2, TAB3, TNIP2, TOLLIP, TRAF6, UBA52, UBB, UBC, UBE2N, UBE2V1, VRK2, ZNF675 |
| GO RESPONSE TO INTERLEUKIN 1 > Any process that results in a change in state or activity of a cell or an organism (in terms of movement, secretion, enzyme production, gene expression, etc.) as a result of an interleukin-1 stimulus. [GOC:BHF, GOC: mah] | ACOD1, ADAMTS12, ADAMTS7, ANKRD1, ANXA1, BTRC, CACTIN, CCL1, CCL11, CCL13, CCL14, CCL15, CCL16, CCL17, CCL18, CCL19, CCL2, CCL20, CCL21, CCL22, CCL23, CCL24, CCL25, CCL26, CCL3, CCL3L1, CCL3L3, CCL4, CCL5, CCL7, CCL8, CD38, CD40, CD47, CEBPB, CHI3L1, CHUK, CITED1, CUL1, CX3CL1, CXCL8, CYBA, DAB2IP, EDN1, EGR1, EPO, ETS1, FBXW11, FGB, FGG, GBP1, GBP2, GBP3, GCLC, HAS2, HDAC4, HIF1A, HNMT, HYAL1, HYAL2, HYAL3, ICAM1, IGBP1, IKBKB, IKBKG, IL1A, IL1B, IL1R1, IL1R2, IL1RAP, IL1RL2, IL1RN, IL6, IRAK1, IRAK2, IRAK3, IRAK4, KLF2, KMO, LCN2, LGALS9, MAP3K3, MAP3K7, MAP3K8, MAPK11, MAPK13, MAPK3, MIR146A, MIR155, MTHFR, MYD88, MYLK3, NFKB1, NFKBIA, NKX3-1, NLRP7, NOD1, NOD2, OTUB1, OTUD4, PCK1, PELI1, PELI2, PELI3, PLCB1, PRKCA, PRKCI, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PTGIS, PYCARD, RBMX, RBX1, RC3H1, RELA, RIPK2, RORA, RPS27A, RPS6KA4, RPS6KA5, SELE, SFRP1, SIRPA, SKP1, SLC30A8, SNCA, SOX9, SQSTM1, SRC, ST18, TAB1, TAB2, TAB3, TAF9, TANK, TFPI, TLE5, TNFRSF11A, TNIP2, TOLLIP, TRAF6, TRIM63, UBA52, UBB, UBC, UBE2N, UBE2V1, UPF1, USP10, VRK2, XCL1, XCL2, YTHDC2, YY1, ZC3H12A, ZNF675 |
| REACTOME IL1 SIGNALING Genes involved in >Interleukin-1 signaling | BTRC, CHUK, CUL1, IKBKB, IKBKG, IL1A, IL1B, IL1R1, IL1R2, IL1RAP, IL1RN, IRAK1, IRAK2, IRAK3, IRAK4, MAP2K1, MAP2K4, MAP2K6, MAP3K3, MAP3K7, MAP3K8, MYD88, NOD1, NOD2, PELI1, PELI2, PELI3, RBX1, RIPK2, SKP1, SQSTM1, TAB1, TAB2, TAB3, TMEM189-UBE2V1, TNIP2, TOLLIP, TRAF6, UBE2N |
| REACTOME INTERLEUKIN 1 FAMILY SIGNALING >Interleukin-1 family signaling | AGER, ALOX5, APP, BTRC, CASP1, CHUK, CTSG, CUL1, FBXW11, HMGB1, IKBKB, IKBKG, IL13, IL18, IL18BP, IL18R1, IL18RAP, IL1A, IL1B, IL1F10, IL1R1, IL1R2, IL1RAP, IL1RAPL1, IL1RL1, IL1RL2, IL1RN, IL33, IL36A, IL36B, IL36G, IL36RN, IL37, IL4, IRAK1, IRAK2, IRAK3, IRAK4, MAP2K1, MAP2K4, MAP2K6, MAP3K3, MAP3K7, MAP3K8, MAPK8, MYD88, NFKB1, NFKB2, NFKBIA, NFKBIB, NKIRAS1, NKIRAS2, NOD1, NOD2, PELI1, PELI2, PELI3, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PTPN11, PTPN12, PTPN13, PTPN14, PTPN18, PTPN2, PTPN20, PTPN23, PTPN4, PTPN5, PTPN6, PTPN7, PTPN9, RBX1, RELA, RIPK2, RPS27A, S100A12, S100B, SAA1, SEM1, SIGIRR, SKP1, SMAD3, SQSTM1, STAT3, TAB1, TAB2, TAB3, TBK1, TNIP2, TOLLIP, TRAF6, UBA52, UBB, UBC, UBE2N, UBE2V1 |
| REACTOME INTERLEUKIN 1 SIGNALING >Interleukin-1 signaling | AGER, APP, BTRC, CHUK, CUL1, FBXW11, HMGB1, IKBKB, IKBKG, IL1A, IL1B, IL1R1, IL1R2, IL1RAP, IL1RN, IRAK1, IRAK2, IRAK3, IRAK4, MAP2K1, MAP2K4, MAP2K6, MAP3K3, MAP3K7, MAP3K8, MYD88, NFKB1, NFKB2, NFKBIA, NFKBIB, NKIRAS1, NKIRAS2, NOD1, NOD2, PELI1, PELI2, PELI3, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, RBX1, RELA, RIPK2, RPS27A, S100A12, S100B, SAA1, SEM1, SKP1, SQSTM1, TAB1, |

TABLE 4-continued

| Interleukin-1 associated gene sets list. | |
|---|---|
| | TAB2, TAB3, TNIP2, TOLLIP, TRAF6, UBA52, UBB, UBC, UBE2N, UBE2V1 |
| BIOCARTA IL1R PATHWAY > Signal transduction through IL1R | CHUK, IFNA1, IFNB1, IKBKB, IL1A, IL1B, IL1R1, IL1RAP, IL1RN, IL6, IRAK1, IRAK2, IRAK3, JUN, MAP2K3, MAP2K6, MAP3K1, MAP3K14, MAP3K7, MAPK14, MAPK8, MYD88, NFKB1, NFKBIA, RELA, TAB1, TGFB1, TGFB2, TGFB3, TNF, TRAF6 |
| GO INTERLEUKIN 1 RECEPTOR ACTIVITY > Combining with interleukin-1 to initiate a change in cell activity. Interleukin-1 is produced mainly by activated macrophages and is involved in the inflammatory response. [GOC:jl] | IL18R1, IL1R1, IL1R2, IL1RAP, IL1RAPL2, IL1RL1, IL1RL2 |
| GO CYTOKINE MEDIATED SIGNALING PATHWAY >A series of molecular signals initiated by the binding of a cytokine to a receptor on the surface of a cell, and ending with regulation of a downstream cellular process, e.g. transcription. [GOC:mah, GOC:signaling, PMID: 19295629] | ABCE1, AC004551.1, AC005840.1, AC074143.1, ACKR1, ACKR2, ACKR3, ACKR4, ACSL1, ACTN4, ADAM17, ADAR, ADIPOQ, ADIPOR1, ADIPOR2, AGPAT1, AGPAT2, AIM2, AIP, AKT1, ALOX15, ALOX5, ANGPT1, ANXA1, ANXA2, APOA1, APPL1, APPL2, ARF1, ARG1, AXL, B2M, BAD, BAG4, BATF, BBS2, BBS4, BCL2, BCL2L1, BCL6, BIRC2, BIRC3, BIRC5, BOLA2, BOLA2B, BRWD1, BST2, BTRC, C1QTNF4, CA1, CACTIN, CAMK2A, CAMK2B, CAMK2D, CAMK2G, CANX, CAPZA1, CARD14, CARD16, CARD8, CASP1, CASP3, CASP4, CASP8, CAV1, CBFB, CBL, CCDC3, CCL1, CCL11, CCL13, CCL14, CCL15, CCL16, CCL17, CCL18, CCL19, CCL2, CCL20, CCL21, CCL22, CCL23, CCL24, CCL25, CCL26, CCL3, CCL3L1, CCL3L3, CCL4, CCL5, CCL7, CCL8, CCND1, CCR1, CCR10, CCR2, CCR3, CCR4, CCR5, CCR6, CCR7, CCR8, CCR9, CCRL2, CD24, CD27, CD300LF, CD36, CD4, CD40, CD40LG, CD44, CD70, CD74, CD80, CD86, CDC37, CDC42, CDIP1, CDKN1A, CEACAM1, CEBPA, CEBPD, CFL1, CHUK, CIB1, CIITA, CISH, CLCF1, CLDN18, CLIP3, CMKLR1, CNN2, CNOT7, CNOT9, CNTF, CNTFR, COL1A2, COMMD7, CPNE1, CREBRF, CRK, CRKL, CRLF1, CRLF2, CSF1, CSF1R, CSF2, CSF2RA, CSF2RB, CSF3, CSF3R, CSNK2B, CTF1, CTR9, CUL1, CX3CL1, CX3CR1, CXCL1, CXCL10, CXCL11, CXCL12, CXCL13, CXCL2, CXCL3, CXCL5, CXCL6, CXCL8, CXCL9, CXCR1, CXCR2, CXCR3, CXCR4, CXCR5, CXCR6, CYLD, DCST1, DOK1, DUOX1, DUOX2, EBI3, ECM1, EDA, EDA2R, EDAR, EDARADD, EDN1, EDN2, EGR1, ELF1, EPO, EPOR, EREG, F13A1, F2RL1, F3, FADD, FASLG, FBXW11, FCER1G, FCER2, FCGR1A, FCGR1B, FER, FGF2, FLT3, FLT3LG, FN1, FOS, FOXC1, FOXO1, FOXO3, FPR1, FSCN1, FYN, GAB2, GAS6, GATA3, GBP1, GBP2, GFI1, GHR, GPR17, GPR35, GPR75, GPS2, GRB2, GREM2, GSTA2, GSTO1, GSTP1, HCK, HGF, HIF1A, HIPK1, HIST1H2BJ, HIST1H3A, HIST1H3B, HIST1H3C, HIST1H3D, HIST1H3E, HIST1H3F, HIST1H3G, HIST1H3H, HIST1H3I, HIST1H3J, HIST2H3A, HIST2H3C, HIST2H3D, HLA-A, HLA-B, HLA-C, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, HLA-E, HLA-F, HLA-G, HLA-H, HMOX1, HNRNPA2B1, HNRNPDL, HNRNPF, HPX, HSP90AA1, HSP90AB1, HSP90B1, HSPA1A, HSPA1B, HSPA8, HSPA9, ICAM1, IFI27, IFI30, IFI35, IFI6, IFIT1, IFIT2, IFIT3, IFITM1, IFITM2, IFITM3, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNE, IFNG, IFNGR1, IFNGR2, IFNK, IFNL1, IFNL2, IFNL3, IFNLR1, IFNW1, IGHE, IGHG1, IGHG4, IKBKB, IKBKE, IKBKG, IL10, IL10RA, IL10RB, IL11, IL11RA, IL12A, IL12B, IL12RB1, IL12RB2, IL13, IL13RA1, IL13RA2, IL15, IL15RA, IL16, IL17A, IL17C, IL17F, IL17RA, IL17RB, IL17RC, IL17RD, IL17RE, IL17REL, IL18, IL18BP, IL18R1, IL18RAP, IL19, IL1A, IL1B, IL1F10, IL1R1, IL1R2, IL1RAP, IL1RAPL2, IL1RL1, IL1RL2, IL1RN, IL2, IL20, IL20RA, IL20RB, IL21, IL21R, IL22, IL22RA1, IL22RA2, IL23A, IL23R, IL24, IL25, IL26, IL27, IL27RA, IL2RA, IL2RB, IL2RG, IL3, IL31, IL31RA, IL32, IL33, IL34, |

TABLE 4-continued

| Interleukin-1 associated gene sets list. | |
|---|---|
| | IL36A, IL36B, IL36G, IL36RN, IL37, IL3RA, IL4, IL4R, IL5, IL5RA, IL6, IL6R, IL6ST, IL7, IL7R, IL9, IL9R, ILK, INPP5D, INPPL1, IP6K2, IRAK1, IRAK2, IRAK3, IRAK4, IRF1, IRF2, IRF3, IRF4, IRF5, IRF6, IRF7, IRF8, IRF9, IRGM, IRS1, IRS2, ISG15, ISG20, ITGAM, ITGAX, ITGB1, ITGB2, JAGN1, JAK1, JAK2, JAK3, JUNB, KARS, KIT, KLF6, KRAS, KRT18, KRT8, LAMA5, LBP, LCN2, LCP1, LEP, LEPR, LIF, LIFR, LIMS1, LMNB1, LRP8, LSM14A, LTA, LTB, MADD, MAOA, MAP3K14, MAP3K3, MAP3K7, MAP3K8, MAPK3, MAVS, MCL1, MED1, MID1, MIF, MIR146A, MIR152, MIR155, MIR21, MIR24-1, MIR24-2, MIR26A1, MIR26A2, MIR34A, MIR98, MIRLET7A1, MIRLET7A2, MIRLET7A3, MKKS, MMP1, MMP12, MMP2, MMP3, MMP9, MPL, MSN, MST1R, MT2A, MT3, MTAP, MUC1, MUL1, MX1, MX2, MYC, MYD88, NANOG, NCAM1, NDN, NFKB1, NFKBIA, NLRC5, NLRP2B, NMI, NOD1, NOD2, NOS2, NR1H2, NR1H3, NR1H4, NUMBL, OAS2, OAS3, OASL, OPRD1, OPRM1, OSM, OSMR, OTOP1, OTUD4, OTULIN, OXSR1, P4HB, PADI2, PAFAH1B1, PAK2, PALM3, PARP14, PARP9, PDCD4, PDGFB, PELI1, PELI2, PELI3, PF4, PF4V1, PIAS1, PIAS3, PIAS4, PIK3CA, PIK3CB, PIK3CD, PIK3R1, PIM1, PITPNA, PLCB1, PLP2, PLVAP, PML, POMC, POU2F1, PPARG, PPBP, PPIA, PRKACA, PRKCD, PRKN, PRLR, PRTN3, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PTAFR, PTGS2, PTK2B, PTPN1, PTPN11, PTPN2, PTPN6, PTPRC, PTPRN, PTPRZ1, PXDN, PYCARD, PYDC1, PYDC2, RACK1, RALA, RAP1B, RAPGEF1, RBCK1, RBM15, RBX1, RELA, RFFL, RHEX, RHOU, RIPK1, RIPK2, RNASEL, RNF113A, RNF31, ROBO1, RORA, RORC, RPLPO, RPS27A, RPS6KA4, RPS6KA5, RSAD2, RUNX1, S1PR1, SAA1, SAMHD1, SCRIB, SDC1, SERPINB2, SH2B2, SHARPIN, SHC1, SIGIRR, SIRT1, SKP1, SLC27A1, SLIT2, SLIT3, SMAD4, SMARCA4, SNRPA1, SOCS1, SOCS2, SOCS3, SOCS5, SOD1, SOD2, SOS1, SOX2, SP100, SPATA2, SPHK1, SPI1, SPPL2A, SPPL2B, SQSTM1, ST18, STAP1, STAT1, STAT2, STAT3, STAT4, STAT5A, STAT5B, STAT6, STK39, STX1A, STX3, STX4, SUMO1, SYK, TAB1, TAB2, TAB3, TALDO1, TAX1BP1, TBK1, TCP1, TEC, TFF2, TGFB1, THPO, TICAM2, TIMP1, TMSB4X, TNF, TNFAIP3, TNFRSF11A, TNFRSF11B, TNFRSF12A, TNFRSF13B, TNFRSF13C, TNFRSF14, TNFRSF 17, TNFRSF18, TNFRSF19, TNFRSF1A, TNFRSF1B, TNFRSF25, TNFRSF4, TNFRSF6B, TNFRSF8, TNFRSF9, TNFSF11, TNFSF12, TNFSF13, TNFSF13B, TNFSF14, TNFSF15, TNFSF18, TNFSF4, TNFSF8, TNFSF9, TNIP2, TOLLIP, TP53, TRADD, TRAF1, TRAF2, TRAF3, TRAF6, TRAIP, TREM2, TREX1, TRIM21, TRIM22, TRIM25, TRIM26, TRIM31, TRIM32, TRIM34, TRIM38, TRIM44, TRIM5, TRIM6, TRIM62, TRIM68, TRIM8, TSLP, TWIST1, TXK, TXLNA, TXNDC17, TYK2, UBA52, UBB, UBC, UBE2K, UBE2N, UBE2V1, USP18, VAV1, VCAM1, VEGFA, VIM, VRK2, WNK1, WNT5A, XAF1, XCL1, XCL2, XCR1, YWHAZ, ZBP1, ZC3H15, ZEB1, ZNF675 |
| GO RESPONSE TO CYTOKINE Any process that results in a change in state or activity of a cell or an organism (in terms of movement, secretion, enzyme production, gene expression, etc.) as a result of a cytokine stimulus. [GOC:si] | AANAT, ABCD4, ABCE1, ABCG4, AC004551.1, AC005840.1, AC074143.1, ACKR1, ACKR2, ACKR3, ACKR4, ACOD1, ACP5, ACSL1, ACSL4, ACTG1, ACTN4, ACTR2, ACTR3, ADAM10, ADAM17, ADAM23, ADAM9, ADAMTS12, ADAMTS13, ADAMTS7, ADAR, ADIPOQ, ADIPOR1, ADIPOR2, AFF3, AGPAT1, AGPAT2, AIF1, AIM2, AIP, AKAP6, AKT1, ALAD, ALDH1A2, ALOX15, ALOX5, ANGPT1, ANKRD1, ANXA1, ANXA2, APOA1, APOB, APPL1, APPL2, AQP4, ARF1, ARG1, ARHGEF2, ARID5B, ASAH1, ASAH2, ASS1, ATIC, ATP5F1B, AVPR2, AXL, B2M, B3GNT2, BAD, BAG4, BATF, BBS2, BBS4, BCAT2, BCL2, BCL2L1, BCL6, BCLAF1, BIRC2, BIRC3, BIRC5, BOLA2, BOLA2B, BRCA1, BRWD1, BSPRY, BST2, BTK, BTRC, C19orf66, C1QTNF4, CA1, CACTIN, CACYBP, CALCA, |

TABLE 4-continued

| Interleukin-1 associated gene sets list. |
|---|
| CALCOCO2, CAMK2A, CAMK2B, CAMK2D, CAMK2G, CANX, CAPN2, CAPZA1, CARD14, CARD16, CARD8, CASP1, CASP3, CASP4, CASP8, CAV1, CBFB, CBL, CCDC3, CCL1, CCL11, CCL13, CCL14, CCL15, CCL16, CCL17, CCL18, CCL19, CCL2, CCL20, CCL21, CCL22, CCL23, CCL24, CCL25, CCL26, CCL3, CCL3L1, CCL3L3, CCL4, CCL5, CCL7, CCL8, CCND1, CCR1, CCR10, CCR2, CCR3, CCR4, CCR5, CCR6, CCR7, CCR8, CCR9, CCRL2, CD14, CD24, CD27, CD274, CD300LF, CD36, CD38, CD4, CD40, CD40LG, CD44, CD47, CD58, CD70, CD74, CD80, CD86, CDC34, CDC37, CDC42, CDC42EP2, CDC42EP4, CDC5L, CDIP1, CDK4, CDK9, CDKN1A, CEACAM1, CEBPA, CEBPB, CEBPD, CFL1, CHCHD4, CHI3L1, CHUK, CIB1, CIITA, CISH, CITED1, CLCF1, CLDN1, CLDN18, CLIP3, CMKLR1, CNN2, CNOT7, CNOT9, CNTF, CNTFR, COL1A1, COL1A2, COL3A1, COMMD7, CORO1A, CPNE1, CREB1, CREBRF, CRHBP, CRK, CRKL, CRLF1, CRLF2, CSF1, CSF1R, CSF2, CSF2RA, CSF2RB, CSF3, CSF3R, CSNK2B, CTBP2, CTF1, CTH, CTR9, CUL1, CX3CL1, CX3CR1, CXCL1, CXCL10, CXCL11, CXCL12, CXCL13, CXCL16, CXCL2, CXCL3, CXCL5, CXCL6, CXCL8, CXCL9, CXCR1, CXCR2, CXCR3, CXCR4, CXCR5, CXCR6, CYBA, CYLD, CYP27B1, DAB2IP, DAPK1, DAPK3, DCST1, DCSTAMP, DDOST, DDX41, DDX58, DHX9, DOCK8, DOK1, DPYSL3, DTX1, DUOX1, DUOX2, DUSP1, EBI3, ECM1, EDA, EDA2R, EDAR, EDARADD, EDN1, EDN2, EED, EFHC2, EGR1, EIF2AK2, EIF4A2, ELF1, ENDOG, EPO, EPOR, EPRS, EPS8, ERBIN, EREG, ETS1, ETV3, EVL, F13A1, F2RL1, F3, FABP4, FADD, FASLG, FASN, FBXW11, FCER1G, FCER2, FCGR1A, FCGR1B, FER, FGB, FGF2, FGF23, FGF4, FGG, FLNB, FLT3, FLT3LG, FN1, FOS, FOSL1, FOXA2, FOXC1, FOXF1, FOXH1, FOXO1, FOXO3, FPR1, FSCN1, FYN, FZD4, GAB2, GAPDH, GAS6, GATA3, GBA, GBP1, GBP2, GBP3, GBP4, GBP5, GBP6, GCH1, GCLC, GCLM, GFI1, GFPT2, GGT1, GGT2, GGT3P, GHR, GIPC1, GLDC, GNAO1, GNPNAT1, GPD1, GPER1, GPR17, GPR35, GPR75, GPS2, GRB2, GREM2, GSDME, GSK3A, GSK3B, GSN, GSS, GSTA2, GSTO1, GSTP1, HAMP, HAS2, HAX1, HCK, HCLS1, HDAC4, HDGF, HGF, HIF1A, HIPK1, HIST1H2BJ, HIST1H3A, HIST1H3B, HIST1H3C, HIST1H3D, HIST1H3E, HIST1H3F, HIST1H3G, HIST1H3H, HIST1H31, HIST1H3J, HIST2H3A, HIST2H3C, HIST2H3D, HK2, HLA-A, HLA-B, HLA-C, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, HLA-E, HLA-F, HLA-G, HLA-H, HMHB1, HMOX1, HNMT, HNRNPA2B1, HNRNPDL, HNRNPF, HNRNPU, HPX, HSP90AA1, HSP90AB1, HSP90B1, HSPA1A, HSPA1B, HSPA5, HSPA8, HSPA9, HTRA2, HYAL1, HYAL2, HYAL3, ICAM1, IFI16, IFI27, IFI30, IFI35, IFI6, IFIH1, IFIT1, IFIT2, IFIT3, IFITM1, IFITM2, IFITM3, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNE, IFNG, IFNGR1, IFNGR2, IFNK, IFNL1, IFNL2, IFNL3, IFNLR1, IFNW1, IGBP1, IGHE, IGHG1, IGHG4, IKBKB, IKBKE, IKBKG, IL10, IL10RA, IL10RB, IL11, IL11RA, IL12A, IL12B, IL12RB1, IL12RB2, IL13, IL13RA1, IL13RA2, IL15, IL15RA, IL16, IL17A, IL17C, IL17F, IL17RA, IL17RB, IL17RC, IL17RD, IL17RE, IL17REL, IL18, IL18BP, IL18R1, IL18RAP, IL19, IL1A, IL1B, IL1F10, IL1R1, IL1R2, IL1RAP, IL1RAPL1, IL1RAPL2, IL1RL1, IL1RL2, IL1RN, IL2, IL20, IL20RA, IL20RB, IL21, IL21R, IL22, IL22RA1, IL22RA2, IL23A, IL23R, IL24, IL25, IL26, IL27, IL27RA, IL2RA, IL2RB, IL2RG, IL3, IL31, IL31RA, IL32, IL33, IL34, IL36A, IL36B, IL36G, IL36RN, IL37, IL3RA, IL4, IL4R, IL5, IL5RA, IL6, IL6R, IL6ST, IL7, IL7R, IL9, IL9R, ILDR1, ILK, IMPDH2, INA, INPP5D, INPP5K, INPPL1, IP6K2, IRAK1, IRAK2, IRAK3, IRAK4, IRF1, IRF2, IRF3, IRF4, IRF5, IRF6, IRF7, IRF8, IRF9, IRGM, IRS1, IRS2, ISG15, ISG20, ITGA4, ITGAM, ITGAX, ITGB1, ITGB2, ITIH4, JAGN1, JAK1, JAK2, JAK3, JARID2, JUN, JUNB, JUND, KARS, KAT2A, KAT6B, KCNJ11, KDM3A, KDM5B, KEAP1, KHSRP, KIF 16B, KIF5B, KIT, KLF2, KLF4, KLF5, KLF6, KLHL20, KMO, |

TABLE 4-continued

| Interleukin-1 associated gene sets list. |
|---|
| KRAS, KRT18, KRT8, KYNU, LAMA5, LAMP3, LAPTM5, LBP, LCN2, LCP1, LDLRAP1, LEF1, LEP, LEPR, LGALS9, LIF, LIFR, LIMS1, LMNB1, LOX, LRAT, LRCH1, LRP8, LSM14A, LTA, LTB, MADD, MAOA, MAP2K5, MAP2K7, MAP3K14, MAP3K3, MAP3K5, MAP3K7, MAP3K8, MAP4K3, MAPK1, MAPK11, MAPK13, MAPK14, MAPK3, MAPK7, MAPK8, MAPKAPK2, MAPKAPK3, MAT2A, MAVS, MCF2, MCL1, MCM2, MED1, MEFV, MID1, MIF, MIR125B1, MIR 125B2, MIR133A1, MIR133A2, MIR146A, MIR149, MIR152, MIR155, MIR181B1, MIR181B2, MIR20B, MIR21, MIR24-1, MIR24-2, MIR26A1, MIR26A2, MIR30C2, MIR31, MIR34A, MIR98, MIRLET7A1, MIRLET7A2, MIRLET7A3, MKKS, MME, MMP1, MMP12, MMP2, MMP3, MMP9, MNDA, MPC1, MPL, MRAS, MRC1, MRPL15, MSC, MSN, MST1R, MT1X, MT2A, MT3, MTAP, MTF2, MTHFR, MUC1, MUL1, MX1, MX2, MYBL2, MYC, MYD88, MYLK3, MYNN, MYO1C, MYOD1, MYOG, NANOG, NCAM1, NCL, NDN, NDUFA13, NEFH, NFAT5, NFE2L2, NFIL3, NFKB1, NFKB2, NFKBIA, NFYB, NKX3-1, NKX6-1, NLRC5, NLRP12, NLRP2B, NLRP7, NMI, NMNAT3, NOD1, NOD2, NOS2, NPNT, NPR2, NR1H2, NR1H3, NR1H4, NR5A2, NRP2, NUB1, NUMBL, OAS2, OAS3, OASL, OCLN, OCSTAMP, OPRD1, OPRM1, OSM, OSMR, OTOP1, OTUB1, OTUD4, OTULIN, OXSR1, OXTR, P4HB, PADI2, PAFAH1B1, PAK2, PALM3, PARP14, PARP16, PARP9, PAX6, PCK1, PCOLCE, PCOLCE2, PDCD10, PDCD4, PDE12, PDE1B, PDE2A, PDGFB, PDIA3, PDX1, PELI1, PELI2, PELI3, PF4, PF4V1, PFKP, PGGT1B, PHB, PIAS1, PIAS3, PIAS4, PID1, PIGA, PIK3CA, PIK3CB, PIK3CD, PIK3R1, PIM1, PITPNA, PLA2G10, PLA2G5, PLCB1, PLP2, PLSCR1, PLVAP, PML, PMM1, PNPT1, POMC, POSTN, POU2F1, POU4F1, POU4F2, PPARG, PPARGC1A, PPBP, PPIA, PPP3CB, PRDM5, PRKACA, PRKCA, PRKCD, PRKCI, PRKN, PRLR, PRPF8, PRTN3, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PTAFR, PTGES, PTGIS, PTGS2, PTK2B, PTP4A3, PTPN1, PTPN11, PTPN12, PTPN13, PTPN14, PTPN18, PTPN2, PTPN20, PTPN23, PTPN4, PTPN5, PTPN6, PTPN7, PTPN9, PTPRC, PTPRN, PTPRT, PTPRZ1, PXDN, PYCARD, PYDC1, PYDC2, PYHIN1, RAB12, RAB20, RAB43, RAB7B, RACK1, RAD23B, RALA, RAP1B, RAPGEF1, RARA, RARG, RBCK1, RBM15, RBMX, RBX1, RC3H1, REG1A, REL, RELA, RELB, RFFL, RFX2, RHEX, RHOA, RHOU, RIF1, RIPK1, RIPK2, RIPOR2, RNASEL, RNF113A, RNF31, RNMT, ROBO1, RORA, RORC, RPL13A, RPL3, RPLPO, RPS16, RPS27A, RPS3, RPS6KA4, RPS6KA5, RPS6KB1, RSAD2, RUFY4, RUNX1, S1PR1, SAA1, SAMHD1, SBNO2, SCGB1A1, SCRIB, SDC1, SEC61A1, SELE, SELPLG, SERPINB2, SETD2, SFRP1, SGMS1, SH2B2, SHARPIN, SHC1, SHMT1, SHMT2, SHPK, SIGIRR, SIRPA, SIRT1, SKIL, SKP1, SLC11A1, SLC12A2, SLC25A5, SLC26A6, SLC27A1, SLC2A4, SLC30A8, SLIT2, SLIT3, SMAD3, SMAD4, SMAD7, SMARCA4, SMARCA5, SMPD3, SMPD4, SNCA, SNRPA1, SNX10, SOCS1, SOCS2, SOCS3, SOCS5, SOD1, SOD2, SOS1, SOX1, SOX17, SOX2, SOX9, SP100, SPARC, SPATA2, SPHK1, SPI1, SPOCK2, SPPL2A, SPPL2B, SPRY2, SQSTM1, SRC, SRF, SRM, SRSF7, SSTR1, ST18, ST3GAL6, STAP1, STAR, STAT1, STAT2, STAT3, STAT4, STAT5A, STAT5B, STAT6, STIP1, STK39, STX1A, STX3, STX4, STX8, STXBP1, STXBP2, STXBP3, STXBP4, SUMO1, SYK, SYNCRIP, SYNGR1, TAB1, TAB2, TAB3, TAF9, TALDO1, TANK, TAX1BP1, TBK1, TCF7, TCL1A, TCP1, TDGF1, TEC, TEX14, TFF2, TFPI, TFRC, TGFB1, THBS1, THPO, TICAM2, TIMP1, TIMP2, TIMP3, TIMP4, TLE4, TLE5, TLR2, TLR3, TLR4, TMEM102, TMEM173, TMSB4X, TNF, TNFAIP3, TNFRSF11A, TNFRSF11B, TNFRSF12A, TNFRSF13B, TNFRSF13C, TNFRSF14, TNFRSF17, |

TABLE 4-continued

| Interleukin-1 associated gene sets list. | |
|---|---|
| | TNFRSF18, TNFRSF19, TNFRSF1A, TNFRSF1B, TNFRSF21, TNFRSF25, TNFRSF4, TNFRSF6B, TNFRSF8, TNFRSF9, TNFSF11, TNFSF12, TNFSF13, TNFSF13B, TNFSF14, TNFSF15, TNFSF18, TNFSF4, TNFSF8, TNFSF9, TNIP2, TOLLIP, TP53, TPR, TRADD, TRAF1, TRAF2, TRAF3, TRAF6, TRAIP, TREM2, TREX1, TRIM21, TRIM22, TRIM25, TRIM26, TRIM31, TRIM32, TRIM34, TRIM38, TRIM44, TRIM5, TRIM56, TRIM6, TRIM62, TRIM63, TRIM68, TRIM8, TRPV1, TSLP, TUBA1B, TWIST1, TWISTNB, TXK, TXLNA, TXNDC17, TYK2, TYMS, UBA52, UBB, UBC, UBD, UBE2G2, UBE2K, UBE2N, UBE2V1, UBXN2A, UPF1, USP10, USP18, VAMP3, VAV1, VCAM1, VEGFA, VEGFC, VIM, VPS26B, VRK2, WAS, WDR35, WNK1, WNT5A, XAF1, XBP1, XCL1, XCL2, XCR1, XRCC5, YBX3, YTHDC2, YWHAZ, YY1, ZBP1, ZC3H12A, ZC3H15, ZEB1, ZFAND6, ZFP36, ZFP36L1, ZFP36L2, ZNF675, ZYX |
| REACTOME SIGNALING BY ILS Genes involved in Signaling by Interleukins | BLNK, BTRC, CASP1, CBL, CDK1, CHUK, CRK, CRKL, CSF2, CSF2RA, CSF2RB, CUL1, FYN, GAB2, GRB2, HCK, HGF, HRAS, IKBKB, IKBKG, IL18, IL1A, IL1B, IL1R1, IL1R2, IL1RAP, IL1RN, IL2, IL2RA, IL2RB, IL2RG, IL3, IL3RA, IL5, IL5RA, IL6, IL6R, IL6ST, IL7, IL7R, INPPL1, IRAK1, IRAK2, IRAK3, IRAK4, JAK1, JAK2, JAK3, KRAS, LCK, LYN, MAP2K1, MAP2K2, MAP2K4, MAP2K6, MAP3K3, MAP3K7, MAP3K8, MAPK1, MAPK3, MYD88, NFKB2, NOD1, NOD2, NRAS, PELI1, PELI2, PELI3, PIK3CA, PIK3CB, PIK3CD, PIK3R1, PIK3R2, PIK3R3, PRKACB, PTK2B, PTPN6, RAF1, RAPGEF1, RBX1, RELA, RIPK2, SHC1, SKP1, SOCS3, SOS1, SQSTM1, STAT1, STAT3, STAT5A, STAT5B, SYK, TAB1, TAB2, TAB3, TEC, TMEM189-UBE2V1, TNIP2, TOLLIP, TRAF6, TYK2, UBE2N, VAV1, YES1, YWHAB, YWHAZ |
| REACTOME SIGNALING BY INTERLEUKINS Signaling by Interleukins | ACTB, ACTG1, ACTN2, AGER, AIP, AKT1, AKT2, ALOX15, ALOX5, ANGPT1, ANXA1, ANXA2, APBB1IP, APP, ARAF, AREG, ARF1, ARRB1, ARRB2, ARTN, ATF1, ATF2, BATF, BCL2, BCL2L1, BCL6, BIRC5, BLNK, BOLA2, BOLA2B, BRAF, BRAP, BRWD1, BTC, BTRC, CA1, CALM1, CAMK2A, CAMK2B, CAMK2D, CAMK2G, CANX, CAPZA1, CASP1, CASP3, CBL, CCL11, CCL19, CCL2, CCL20, CCL22, CCL3, CCL3L1, CCL3L3, CCL4, CCL5, CCND1, CCR1, CCR2, CCR5, CD36, CD4, CD80, CD86, CDC42, CDKN1A, CEBPD, CFL1, CHUK, CISH, CLCF1, CNKSR1, CNKSR2, CNN2, CNTF, CNTFR, COL1A2, CREB1, CRK, CRKL, CRLF1, CRLF2, CSF1, CSF1R, CSF2, CSF2RA, CSF2RB, CSF3, CSF3R, CSK, CTF1, CTSG, CUL1, CUL3, CXCL1, CXCL10, CXCL2, CXCL8, DAB2IP, DLG1, DLG2, DLG3, DLG4, DUSP1, DUSP10, DUSP16, DUSP2, DUSP3, DUSP4, DUSP5, DUSP6, DUSP7, DUSP8, DUSP9, EBI3, EGF, EGFR, ELK1, EPGN, ERBB2, ERBB3, ERBB4, EREG, F13A1, FASLG, FBXW11, FCER2, FGA, FGB, FGF1, FGF10, FGF16, FGF17, FGF18, FGF19, FGF2, FGF20, FGF22, FGF23, FGF3, FGF4, FGF5, FGF6, FGF7, FGF8, FGF9, FGFR1, FGFR2, FGFR3, FGFR4, FGG, FLT3, FLT3LG, FN1, FOS, FOXO1, FOXO3, FPR1, FRS2, FRS3, FSCN1, FYN, GAB1, GAB2, GATA3, GDNF, GFRA1, GFRA2, GFRA3, GFRA4, GRB2, GRIN1, GRIN2B, GRIN2D, GSTA2, GSTO1, HAVCR2, HBEGF, HCK, HGF, HIF1A, HIST1H3A, HIST1H3D, HIST1H3E, HIST1H3F, HIST1H3G, HIST1H3H, HIST1H31, HIST1H3J, HIST2H3A, HIST2H3C, HIST2H3D, HMGB1, HMOX1, HNRNPA2B1, HNRNPDL, HNRNPF, HRAS, HSP90AA1, HSP90B1, HSPA8, HSPA9, ICAM1, IFNG, IFNL1, IFNL2, IFNL3, IFNLR1, IGHE, IGHG1, IGHG4, IKBKB, IKBKG, IL10, IL10RA, IL10RB, IL11, IL11RA, IL12A, IL12B, IL12RB1, IL12RB2, IL13, IL13RA1, IL13RA2, IL15, IL15RA, IL16, IL17A, IL17C, IL17F, IL17RA, IL17RB, IL17RC, IL17RD, IL17RE, IL18, IL18BP, IL18R1, IL18RAP, IL19, IL1A, IL1B, IL1F10, IL1R1, IL1R2, IL1RAP, IL1RAPL1, IL1RL1, IL1RL2, IL1RN, IL2, IL20, IL20RA, IL20RB, IL21, IL21R, IL22, IL22RA1, IL22RA2, IL23A, IL23R, IL24, IL25, IL26, IL27, IL27RA, IL2RA, IL2RB, IL2RG, IL3, IL31, IL31RA, IL32, IL33, IL34, IL36A, IL36B, IL36G, IL36RN, IL37, IL3RA, IL4, IL4R, IL5, IL5RA, IL6, IL6R, IL6ST, IL7, IL7R, IL9, IL9R, INPP5D, INPPL1, IQGAP1, IRAK1, IRAK2, IRAK3, IRAK4, IRF4, |

TABLE 4-continued

| Interleukin-1 associated gene sets list. | |
|---|---|
| | IRS1, IRS2, ITGA2B, ITGAM, ITGAX, ITGB1, ITGB2, ITGB3, JAK1, JAK2, JAK3, JUN, JUNB, KBTBD7, KIT, KITLG, KL, KLB, KRAS, KSR1, KSR2, LAMA5, LAMTOR2, LAMTOR3, LAT, LBP, LCK, LCN2, LCP1, LGALS9, LIF, LIFR, LMNB1, LRRC7, LYN, MAOA, MAP2K1, MAP2K2, MAP2K3, MAP2K4, MAP2K6, MAP2K7, MAP3K11, MAP3K3, MAP3K7, MAP3K8, MAPK1, MAPK10, MAPK11, MAPK14, MAPK3, MAPK7, MAPK8, MAPK9, MAPKAPK2, MAPKAPK3, MARK3, MCL1, MEF2A, MEF2C, MET, MIF, MMP1, MMP2, MMP3, MMP9, MSN, MTAP, MUC1, MYC, MYD88, NANOG, NCAM1, NDN, NEFL, NF1, NFKB1, NFKB2, NFKBIA, NFKBIB, NKIRAS1, NKIRAS2, NOD1, NOD2, NOS2, NRAS, NRG1, NRG2, NRG3, NRG4, NRTN, OPRD1, OPRM1, OSM, OSMR, P4HB, PAK2, PAQR3, PDCD4, PDE3B, PDGFA, PDGFB, PDGFRA, PDGFRB, PDPK1, PEA15, PEBP1, PELI1, PELI2, PELI3, PHB, PIK3C3, PIK3CA, PIK3CB, PIK3CD, PIK3R1, PIK3R2, PIK3R3, PIK3R4, PIM1, PITPNA, POMC, POU2F1, PPIA, PPP2CA, PPP2CB, PPP2R1A, PPP2R1B, PPP2R5A, PPP2R5B, PPP2R5C, PPP2R5D, PPP2R5E, PPP5C, PRKACA, PRTN3, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PSPN, PTAFR, PTGS2, PTK2, PTK2B, PTPN11, PTPN12, PTPN13, PTPN14, PTPN18, PTPN2, PTPN20, PTPN23, PTPN4, PTPN5, PTPN6, PTPN7, PTPN9, PTPRA, PTPRZ1, RAF1, RAG1, RAG2, RALA, RANBP9, RAP1A, RAP1B, RAPGEF1, RAPGEF2, RASA1, RASA2, RASA3, RASA4, RASAL1, RASAL2, RASAL3, RASGEF1A, RASGRF1, RASGRF2, RASGRP1, RASGRP3, RASGRP4, RBX1, RELA, RET, RHOU, RIPK2, RORA, RORC, RPLPO, RPS27A, RPS6KA1, RPS6KA2, RPS6KA3, RPS6KA5, S100A12, S100B, S1PR1, SAA1, SDC1, SEM1, SERPINB2, SHC1, SHC2, SHC3, SIGIRR, SKP1, SMAD3, SMARCA4, SNAP25, SNRPA1, SOCS1, SOCS2, SOCS3, SOCS5, SOD1, SOD2, SOS1, SOS2, SOX2, SPRED1, SPRED2, SPRED3, SPTA1, SPTAN1, SPTB, SPTBN1, SPTBN2, SPTBN4, SPTBN5, SQSTM1, SRC, STAT1, STAT2, STAT3, STAT4, STAT5A, STAT5B, STAT6, STX1A, STX3, STX4, STXBP2, SYK, SYNGAP1, TAB1, TAB2, TAB3, TALDO1, TBK1, TCP1, TEC, TEK, TGFA, TGFB1, THEM4, TIMP1, TLN1, TLR9, TNF, TNFRSF1A, TNFRSF1B, TNIP2, TOLLIP, TP53, TRAF6, TRIB3, TSLP, TWIST1, TXLNA, TYK2, UBA52, UBB, UBC, UBE2N, UBE2V1, VAMP2, VAMP7, VAV1, VCAM1, VCL, VEGFA, VIM, VRK3, VWF, WDR83, YES1, YWHAB, YWHAZ, ZEB1 |
| PID IL1 PATHWAY > IL1-mediated signaling events | CASP1, CHUK, ERC1, IKBKB, IKBKG, IL1A, IL1B, IL1R1, IL1R2, IL1RAP, IL1RN, IRAK1, IRAK3, IRAK4, JUN, MAP2K6, MAP3K3, MAP3K7, MAPK8, MYD88, NFKB1, PIK3CA, PIK3R1, PRKCI, PRKCZ, RELA, SQSTM1, TAB1, TAB2, TICAM2, TOLLIP, TRAF6, UBE2N, UBE2V1 |

TABLE 5

| PDAC associated gene sets list. | |
|---|---|
| GRUETZMANN PANCREATIC CANCER UP >Genes up-regulated in pancreatic ductal adenocarcinoma (PDAC) identified in a meta analysis across four independent studies. | ABCG1, AC004551.1, AC034102.1, ACVR1, ACYP1, ADAM10, ADAM9, ADSS, AKAP12, ALDOC, ALOX5, AMPD3, ANXA1, ANXA5, ANXA8, APLP2, APOC1, AREG, ARHGAP1, ARHGDIA, ARHGEF2, ARL4A, ARL6IP1, ASNA1, ATP1B3, ATP6AP1, BIRC3, BPTF, BST1, BST2, BZW1, C2, CALD1, CASP1, CASP4, CAV1, CAV2, CBFB, CBR1, CBX3, CCNA2, CCNG2, CD1C, CD47, CD53, CD55, CD86, CD9, CDK7, CELF2, CENPF, CETN2, CFLAR, CHMP1A, CKS1B, CKS2, CLIC1, CLOCK, CNN1, COL1A1, COL5A2, COPS8, CRABP2, CRIP2, CSE1L, CSK, CSNK1A1, CSTB, CTPS1, CTSC, CTSK, CTSL, CXCR4, CYFIP1, |

TABLE 5-continued

| | PDAC associated gene sets list. |
|---|---|
| | CYTH1, DGKA, DGKD, DHX8, DHX9, DLAT, DLST, DNAJA1, DNMT1, DOCK2, DPYD, DPYSL3, DUSP5, DUSP6, DYNLT3, DYRK2, ECM1, EIF2AK2, EIF4G3, ELF4, EMP2, EMP3, ENO1, ENTPD1, EPS8, ETFB, EVPL, EXOSC7, FABP5, FAP, FBLN2, FBN1, FCGR3A, FLAD1, FLOT2, FN1, FOXF1, FYB1, FYN, G3BP1, GADD45A, GBP1, GBP2, GDI1, GEM, GGT5, GK, GLUD1, GM2A, GNPDA1, GOLIM4, GPC1, GPI, GPX1, GPX4, GRB2, GRN, GUSBP11, HBA2, HCCS, HIST2H2AA3, HIST2H2BE, HLA-DRA, HMGB2, HMGN4, HNRNPU, HPGD, IFI30, IFI44L, IFITM2, IGFBP5, IL1RN, IL4R, INPP1, IQGAP1, IRS1, ISG20, ITGA2, ITGA3, ITGB1BP1, ITGB2, ITGB4, ITGB5, ITPR3, KCNK1, KDSR, KLF4, KLF5, KRT13, KYNU, LAD1, LAMA3, LAMA4, LAMP2, LAPTM5, LCN2, LCP1, LCP2, LDHA, LGMN, LMO4, LOXL2, LTBP1, LUM, MAP4, MBOAT7, MCM3, MCM6, MELK, MFSD10, MGP, MKI67, MMD, MMP11, MMP2, MMP9, MPHOSPH6, MPP3, MRPS12, MSMO1, MSN, MX2, MYH10, MYH9, MYL12A, MYL6B, MYL9, MYLK, NBL1, NCBP2, NDRG1, NDUFA9, NDUFB7, NID1, NMT1, NNMT, NR1D1, NREP, NSDHL, NUP93, P4HA1, PAK2, PARP4, PCLAF, PCOLCE, PDE1A, PDGFRB, PDIA2, PFN1, PGK1, PHB, PIK3R4, PIP4K2B, PKM, PLAT, PLAU, PLAUR, PLCG2, PLEC, PLN, PLOD2, PMP22, PNP, POLB, POSTN, PPIG, PPP1R8, PPP2R1A, PPP3CA, PRDX1, PRKACB, PRKDC, PRNP, PRR13, PSG11, PSMA3, PSMA5, PSMB3, PSMC6, PSMD14, PSME3, PTGS1, PTGS2, PTPN12, PTPN9, PTPRC, PUF60, PXDN, PYGB, PYGL, R3HDM1, RAB2A, RAB31, RALB, RALBP1, RAP1GAP, RCN1, RFC4, RGS16, RHOA, RHOG, RIN1, S100A10, S100A11, S100P, SCNN1A, SDC1, SEC23A, SELENOW, SEM1, SEP8, SERPINA1, SERPINE1, SERPINH1, SFN, SHC1, SLBP, SLC1A3, SLC2A1, SLPI, SMAD3, SNRPA, SNRPB2, SOD1, SORL1, SPARC, SPINT2, SPTA1, SRGN, SRI, STAT1, STMN1, STOM, SULT1C2, SUMO1, SUSD6, TANK, TAP1, TBCB, TFCP2, TFF1, TFF3, THBS2, TIMP3, TM9SF4, TMSB10, TNFAIP3, TNFAIP6, TOP1, TOP2A, TRIM29, TRIP10, TSC22D1, TSN, TSPO, TUBA1A, TUBB, TUSC3, TXNRD1, UGCG, USP14, VCAN, VDAC1, WASHC5, WNK1, WNT2, WNT5A, XPO1, XRCC4, YWHAH, YWHAZ, ZMYND8 |
| GRUETZMANN PANCREATIC CANCER DN >Genes down-regulated in pancreatic ductal adenocarcinoma (PDAC) identified in a meta analysis across four independent studies. | ABCA3, AC139530.1, ACADM, ACO1, ACOX1, ACRV1, ACSM3, AEBP1, ALDH1A1, AMD1, ANXA4, AP1B1, APLP1, ARSA, BCAT1, BCAT2, BTG1, C5, C6, CACNA2D1, CCL7, CCND2, CDO1, CELA2A, CHRNA7, CLDN10, CLU, CPA3, CRAT, CRYAB, CRYZ, CTAG1B, CTNND2, CXCL12, CXCL2, CYB5A, CYBA, DANCR, DAP, DDT, DENND4A, DMAC2L, DMD, DMPK, DPEP1, DPP6, DRD2, DSTN, EEF2, EIF3A, EPHX2, ETV5, EVX1, F11, F12, FGL1, FKBP2, FLT3LG, FXYD2, GAMT, GATD3A, GATM, GJB1, GOLGA4, GPC3, GPX3, GRB14, GRB7, GSTZ1, GTF3C1, GYPC, H19, HDLBP, HERPUD1, HHEX, HSD17B4, HTT, HYOU1, ICA1, IGBP1, IL6ST, IMPDH2, INSR, ISG15, ITPRID2, ITSN2, JUN, KANK1, KAT2B, KCNAB1, KCNJ15, KCNJ4, KRAS, LAMP1, LGALS2, LGALS8, LMAN1, LMF2, LOXL1, LSP1, LSS, MAOA, MAPK8IP2, MAPK9, MAT1A, MAT2A, MEST, MKNK1, MST1, MT1B, MT1X, MXI1, MYC, MYO1F, NCOA1, NFIB, NFKBIL1, NPY1R, NR5A2, NRCAM, NTRK2, NUCB1, NUCB2, ONECUT1, P4HB, PABPC4, PAX6, PBX3, PCBD1, PCK2, PDIA5, PEBP1, PEPD, PEX1, PEX6, PHOX2B, PPIF, PPOX, PPP2R1B, PRDX4, PRKAR2B, PRPSAP1, PSEN2, PTH1R, PTP4A1, PTPRN, PTPRN2, PWP1, RAF1, RARRES2, RBP1, RDX, REG3A, RFC1, RGN, RNASE1, ROM1, RPL13, RPL17, RPL32, RPL7A, RPS10, RPS24, RPS7, RPS9, SEC61B, SEC62, SEL1L, SERPINA5, SERPINA6, SGK1, SHC3, SLC1A4, SLC20A2, SLC25A3, SLC25A5, SLC33A1, SMAD4, SMPD1, SMPDL3A, SNHG14, SRP54, SRPX, SSR1, SSR4, TAF1, TMED10, TOB1, TOMM20, TRPV6, UBXN8, UGT2B15, WWP2, XBP1, YBX3, ZNF22, ZNF32 |

TABLE 5-continued

| | PDAC associated gene sets list. |
|---|---|
| AGUIRRE PANCREATIC CANCER COPY NUMBER UP >Up-regulated genes whose expression correlates with copy number gains in pancreatic adenocarcinoma cell lines and primary tumor specimens. | AARSD1, AC005261.1, ACLY, ACSF2, ACTR10, ADGRA2, ANKRD40, ANXA13, AOC2, AP2S1, AP4M1, AP4S1, AP5M1, ARFRP1, ARHGAP35, ARHGAP5, ARL17A, ARPC1A, ARPC1B, ASH2L, ASL, ASNS, ATP5F1E, ATP5MC1, ATP6VOA1, ATXN7L1, BAG4, BAX, BECN1, BET1, BMP4, BRD9, BRF2, C5AR1, CABYR, CASD1, CASKIN2, CBLL1, CBX1, CD3EAP, CDC27, CDKN2A, CELA2B, CEP72, CLTA, CMAS, CNOT3, CNPY3, COA3, COX11, CPSF1, CRCP, CREB3, CYC1, CYHR1, CYP3A5, DBP, DDHD2, DDT, DERL1, DGAT1, DKKL1, DLD, DLGAP5, DMPK, DOCK4, DPF1, DUSP3, EAPP, EEF1D, EHD2, EIF3K, EML2, EPN1, EPN3, EXOC3, EXOC5, EXOSC4, EZH1, FAM117A, FAM49B, FBXO17, FBXO34, FCF1, FIS1, FUT1, G6PC3, GARS, GID8, GIPR, GNB2, GPAA1, GPATCH8, GPER1, GRN, GRWD1, GSDMD, GSTT1, GYS1, HAS2, HGH1, HIF1A, HLF, HNRNPL, ICE1, ID1, INTS1, IRF3, KAT7, KCTD7, KDELR1, KLK13, KPNB1, KRT10, KTN1, LAMA5, LHB, LIG1, LMTK2, LPCAT1, LRRC37A, LRRC37A4P, LRRC59, LSM1, LUC7L3, MAD1L1, MAFK, MAP4K1, MAPK1IP1L, MBOAT7, MICALL2, MLX, MPP2, MPP3, MRPL13, MRPS12, MTAP, MTMR6, MYC, MYL10, MYL6, NAPA, NBR1, NDRG1, NDUFS6, NFKBIB, NKIRAS2, NME1, NME2, NMT1, NOSIP, NPAS3, NPC1, NPEPPS, NPR2, NR1H2, NSD3, NSF, NUBPL, NUCB1, NUDC, NUP62, OPA3, OPLAH, OR7E12P, ORAI2, OSBPL1A, OSBPL2, PAF1, PAK4, PARP4, PCNX4, PCTP, PDCD6, PDK2, PDK4, PHB, PLEKHA4, PLEKHG3, PLOD3, PMS2P1, PNPO, PON2, PON3, PPP1R13L, PPP1R3D, PPP2R5D, PQLC3, PRELID3B, PRKCH, PRKD2, PRMT1, PRPF6, PSMA7, PSMC3IP, PSMD8, PSME3, PTK2, PTOV1-AS2, PVT1, RAB5C, RABGEF1, RASA4, RCN3, RETREG3, RGP1, RIOK3, RMC1, RNF139, RNF38, RNF6, RPL13A, RPL18, RPL27, RPS21, RPS9, RSAD1, RUVBL2, SAMD4A, SARS2, SCFD1, SCRIB, SDHA, SDHAF3, SEM1, SHARPIN, SIRT2, SLC12A9, SLC1A5, SLC25A13, SLC26A4, SLC35B1, SLC39A4, SLC52A2, SMARCE1, SMURF1, SNAPC1, SNF8, SNRNP70, SNRPD2, SNX11, SNX6, SPAG8, SPAG9, SPATA20, SPOP, SS18L1, STAT5B, STRN4, SYPL1, SYT5, TAF2, TAF4, TAF6, TBC1D31, TCFL5, THEM6, TLN1, TMEM248, TMEM8B, TMEM94, TMUB2, TNXA, TPD52L2, TPM2, TRRAP, TSEN34, TSTA3, TTF2, TUG1, U2AF2, UBE2Z, UCKL1, UPF3A, UTP18, VPS28, WASHC5, WDHD1, WDR3, WDYHV1, XYLT2, YTHDF1, ZBTB1, ZC3H3, ZDHHC24, ZGPAT, ZKSCAN5, ZNF134, ZNF146, ZNF211, ZNF264, ZNF331, ZNF419, ZNF444, ZNF460, ZNF573, ZNF580, ZNF623, ZNF652, ZNF787, ZNHIT1 |
| HEIDENBLAD AMPLIFIED IN PANCREATIC CANCER >Genes amplified and up-regulated more than twofold in at least two out of 10 pancreatic cancer cell lines studied. | AKAP9, AKT2, ATAT1, ATF6B, BCAT1, BET1, BHLHE41, C2CD5, CAPN12, CBLL1, CCDC91, CCN3, CMAS, COMMD5, CYC1, DLD, DLL3, DSCC1, ECH1, EID2, ERGIC2, ETNK1, FAM49B, FAR2, FBL, FGFR1OP2, HBS1L, HCG4, ITPR2, KLHL42, LRATD2, MAF1, MAL2, MDFIC, MED21, METTL2A, MRPS12, PAF1, PAK4, PON2, PPFIBP1, PSMC4, PTK2, RASSF8, REP15, SMURF1, SSPN, ST8SIA1, SUPT5H, TBC1D31, TLK2, TM7SF3, TMEM65, TMTC1, TRIM26, TSPAN12, ZNF780A |
| PDAC ENRICHED SIG >Reference PMID: 25557080 | 0610010K14RIK, 1110034A24RIK, 1110049F12RIK, 1500001M20RIK, 1700029F09RIK, 1700040103RIK, 1700066M21RIK, 2010317E24RIK, 2010321M09RIK, 2610002D18RIK, 2610318N02RIK, 2700099C18RIK, 2810025M15RIK, 2810417H13RIK, 2810429104RIK, 4930422G04RIK, 4930503L19RIK, 4930579G24RIK, 5730590G19RIK, 6430548M08RIK, 6720463M24RIK, 8430406107RIK, 8430410A17RIK, 9430015G10RIK, 9430020K01RIK, A330049M08RIK, AARS, AATF, AB033524, ACAT2, ACTL6A, ACY1, ADCY3, ADD3, AGPAT2, AGR2, AHCTF1, AIMP2, AK011460, AK011479, AK013046, AK031561, AK079263, AK088959, AK132898, AK133925, AK2, ALDH18A1, ALG13, ALMS1, AMMECR1, ANKRD13A, ANP32B, ANP32E, ANXA10, APEX1, API5, APITD1, ARCN1, |

TABLE 5-continued

| PDAC associated gene sets list. |
|---|
| ARHGAP19, ARHGAP42, ARID5A, ARL6IP6, ARRB2, ASCC3, ASF1B, ASNS, ASP, ASRGL1, ATAD2, ATAD5, ATF1, ATF4, ATF5, ATP10B, AZIN1, B4GALT4, BANF1, BARD1, BAZ1B, BC048355, BC079836, BCCIP, BCL7C, BLM, BPGM, CABLES1, CAND1, CASC5, CASP8AP2, CAT60, CBS, CBX3, CCDC101, CCDC115, CCNA2, CCNE1, CCNE2, CCNYL1, CCT6A, CD59B, CDC26, CDC45, CDC6, CDC6, CDC7, CDCA5, CDCA7, CDCA7L, CDCA8, CDK14, CDK2, CDK5RAP2, CDKN2D, CDR2L, CDV3, CDX2, CENPA, CENPI, CENPL, CEP192, CEP57, CFTR, CHAF1A, CHCHD7, CHEK1, CINP, CKAP4, CKAP5, CKS1B, CKS2, CLSPN, COL4A3BP, CPSF3, CPSF4, CPSF7, CRTAP, CRYBG3, CSE1L, CTNNAL1, CTSC, CTU2, CUL4B, CWF19L1, CWH43, D230037D09RIK, DCK, DCTPP1, DDB2, DDX39, DEGS1, DENND4A, DENND5B, DEPDC5, DHFR, DHRS13, DIS3, DKC1, DLEU2, DNA2, DNMT1, DONSON, DPH2, DPY19L1, DQ716436, DSC2, DSN1, DTL, DTWD2, DUS1L, E2F1, E2F4, ECD, EEA1, EFTUD2, EIF1AD, EIF1AX, EIF2B1, EIF2S2, EIF3C, EIF4E, EIF5A, EMG1, ENDOG, EPRS, ERCC6L, ERH, ERI1, ERLIN1, ESF1, ESPL1, ETAA1, ETV5, EXO1, EXOSC1, EXOSC2, EXOSC7, EXOSC8, EZH2, FAM101B, FAM126A, FAM46A, FAM46C, FAM54A, FAM69B, FANCA, FANCD2, FANCM, FASTKD2, FBXO45, FBXO5, FEN1, FKBP4, FNDC4, FNIP2, FSCN1, FST, FTSJ3, FUT8, FUT9, FYN, GABPA, GABPB2, GCSH, GDAP2, GGA2, GINS1, GLCE, GLS2, GLTPD1, GM129, GMNN, GNMT, GPC1, GPN1, GPSM2, GRHL1, GSG2, GTF2A2, GTF2H2, H2AFZ, HARS, HAT1, HAUS6, HAUS8, HEATR3, HELB, HELLS, HINFP, HIRIP3, HIST1H1A, HIST1H2BC, HIST1H2BF, HIST1H2BH, HIST1H2BJ, HIST1H2BM, HIST1H2BP, HIST2H2BB, HIST3H2A, HIST3H2BA, HIST4H4, HMGB1, HMGB2, HNRNPA2B1, HOMER2, HOOK1, HSPA5, HSPB6, HSPD1, HSPE1, HTATSF1, IBTK, IFRD2, ILF3, IMPDH1, IMPDH2, INCENP, INTS6, INTS7, INTS9, IPO11, IPO5, ISG20L2, ISY1, ITPK1, IVNS1ABP, KHDRBS3, KIAA1440, KIF14, KIF15, KIF22, KPNB1, LAP3, LARP1B, LARP4, LARP7, LBR, LCMT2, LGR5, LIFR, LIG1, LIN54, LIPT2, LMAN2, LMNB2, LRP8, LSM3, LSM5, LSM7, LUC7L2, LYAR, LYPD6B, MANF, MAOA, MAPK14, MARS, MBD3, MCM10, MCM2, MCM3, MCM5, MCM6, MCM7, MCMBP, MECOM, MED4, MED6, MEPCE, METTL1, METTL2, MFSD2A, MFSD5, MIF4GD, MIS12, MKI67, MKIAA0259, MKIAA0377, MLF1IP, MND1, MPHOSPH9, MPP6, MPV17L, MREG, MRPL17, MRPL18, MRPL46, MRPS14, MRTO4, MTBP, MTDH, MTHFD2, MUM1, MUTYH, MYB, MYBL2, MYO19, MYO5A, MYO9A, MYST3, NAA15, NAA16, NAA50, NARS, NASP, NBN, NCAPD3, NCAPG2, NCL, NCOA7, NETO2, NFX1, NFYC, NGDN, NKRF, NME6, NOLC1, NOP14, NOP16, NOP56, NOP58, NPAT, NPM1, NPM3, NSL1, NSMCE4A, NSUN5, NT5C3L, NT5DC2, NUP107, NUP133, NUP160, NUP205, NUP210, NUP37, NUP43, NUP54, NUP62, NUP85, NUP98, NXT1, OAT, ORC6, OSGEPL1, PAIP2B, PALB2, PAXIP1, PBK, PCNA, PDE4D, PDS5A, PDSS1, PGM2L1, PGP, PHF16, PHF19, PHLPP2, PHTF2, PLAGL2, PLEKHF1, PLK4, PMS1, PMS2, PNN, POLA1, POLA2, POLD2, POLE, POLQ, POLR2D, POLR3G, POP4, PPA1, PPIF, PPIH, PPIL5, PPM1G, PPP1R1B, PPPDE1, PPWD1, PRIM2, PRMT7, PRPF3, PRPF31, PRPF4, PSD4, PSIP1, PSMB2, PSMC1, PSMC2, PSMC5, PSPH, PSTK, PTCD3, QDPR, RAB33B, RACGAP1, RAD18, RAD21, RAD51AP1, RAD54L, RAD9, RALY, RAN, RANGRF, RARS, RBBP7, RBM10, RBM15, RBM27, RCC1, RDBP, RECQL4, REEP4, RFC1, RFC4, RFWD3, RIPPLY3, RNASEH2B, RNF26, RPA1, RPA2, RPL13A-PS1, RPL34, RPP25, RPP30, RPS6KA6, RQCD1, RRM1, RRP15, RRP8, RTEL1, RTTN, SAAL1, SAE1, SAG, SAMHD1, SAP30, SART3, SDAD1, SEC61A1, SEH1L, SENP1, SERPINI1, SET, SF3A3, SFXN5, SGCB, SGOL1, SHCBP1, SHMT2, SIP1, SKA1, |

TABLE 5-continued

| PDAC associated gene sets list. |
|---|
| SKIV2L2, SKP2, SLBP, SLC16A1, SLC20A1, SLC25A15, SLC29A1, SLC29A2, SLC2A3, SLC35A4, SLC39A8, SLC7A5, SLFN9, SMARCA5, SMC1A, SMC3, SMC4, SMC6, SMCHD1, SMPD4, SNRNP40, SNRPA1, SNRPB, SNRPC, SNRPD1, SNRPF, SOX11, SPAG5, SPDEF, SPIRE1, SRP19, SRPR, SSR1, SSRP1, STARD4, STARD7, STC2, STK39, STOML2, STRAP, STXBP5, STYX, SUPT16H, SUPV3L1, SUV39H1, SUV39H2, SUZ12, SWAP70, SYT16, TAF15, TAF5, TAF6L, TAPBPL, TARS, TBC1D4, TCERG1, TCF19, TCF7, TERF1, TESK2, TGS1, THOC3, THOC4, TIAM1, TIMM50, TIPIN, TLCD1, TLN2, TMCO7, TMED1, TMEM158, TMEM170B, TMEM188, TMEM39B, TMEM56, TMEM79, TMEM97, TMX1, TMX2, TOMM5, TOP2A, TOPBP1, TOR1AIP1, TPST1, TRAIP, TRIM59, TRIP13, TRMT61A, TRPM6, TSPAN12, TSPAN13, TSR2, TSSC4, TUBA1B, TUBA4A, TXNDC5, TYMS, U2AF1, UBA2, UBR7, UBTF, UCHL5, UHRF1, UNG, USP1, USP37, USP39, USP7, UTP15, VAMP1, WBSCR16, WDR33, WDR76, WDR82, WHSC1, X95399, XAF1, XPO1, XPO4, XPO7, XPOT, XRCC3, XRCC6BP1, YARS, ZFP106, ZFP367, ZMYM1, ZMYND19, ZNHIT3 |

Figure 3C:
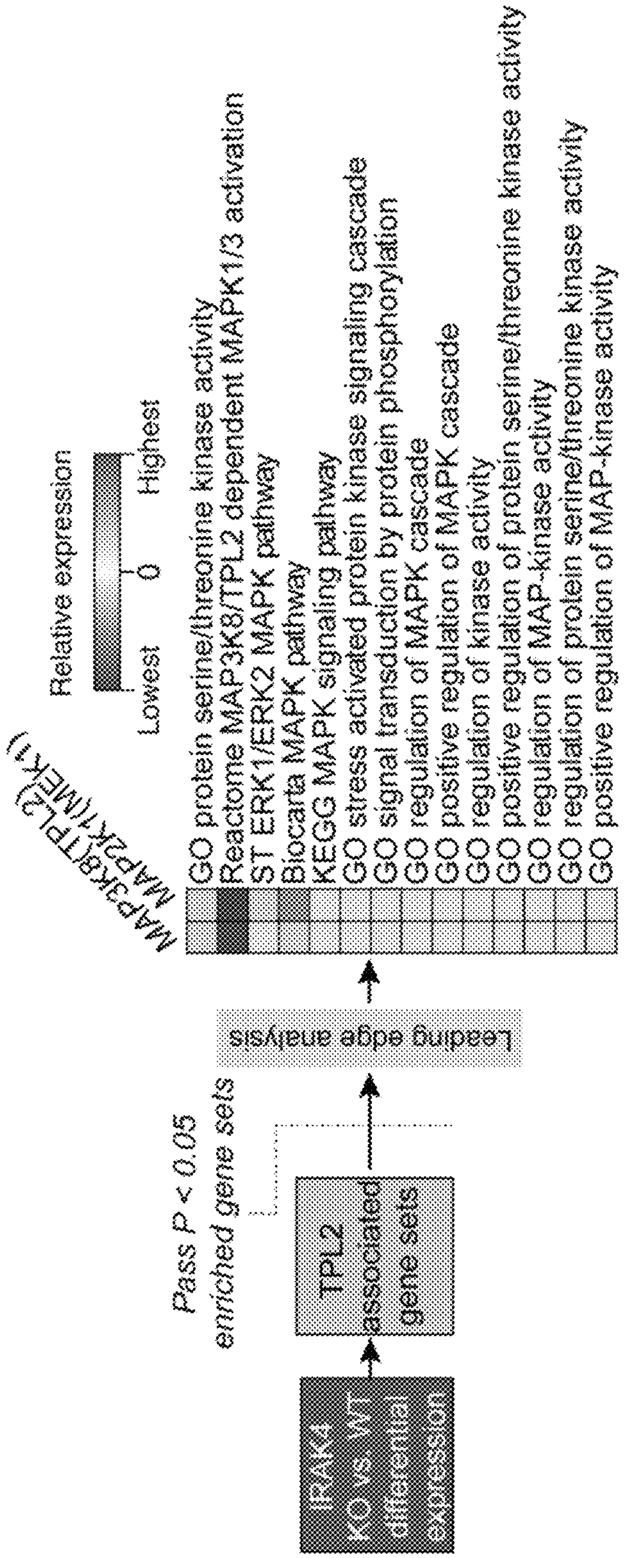
Figure 3D:
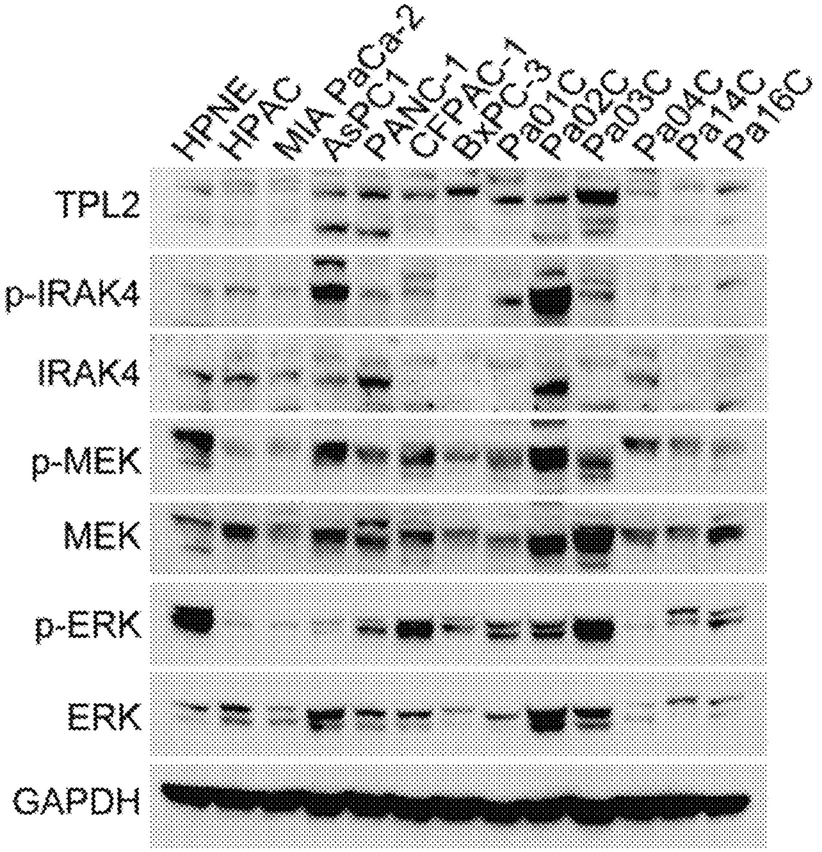
Figure 3E:
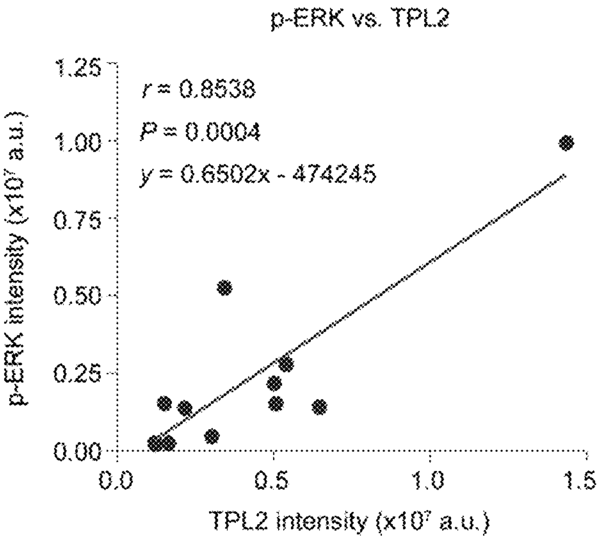
Figure 3F:
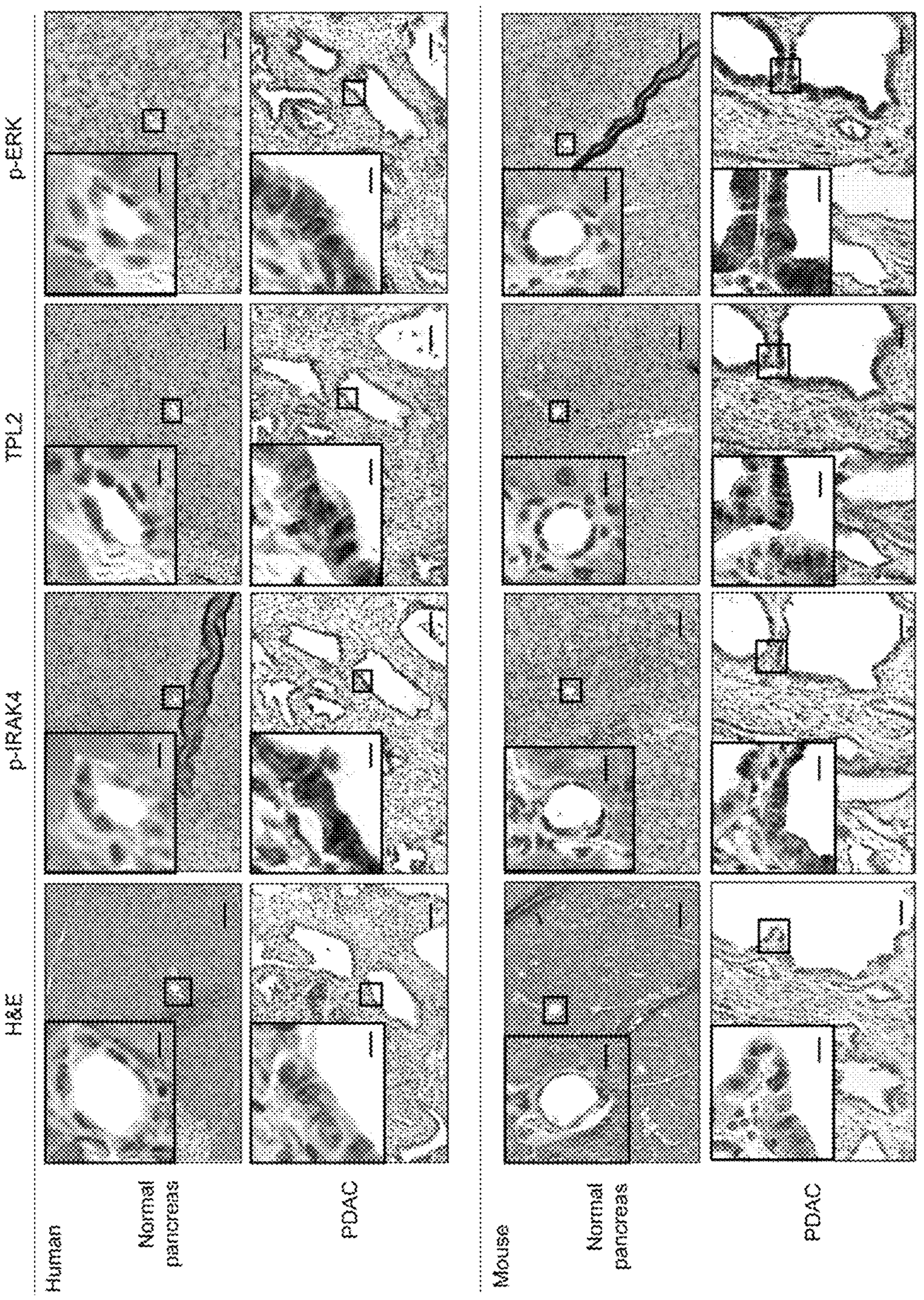
Figure 13B:
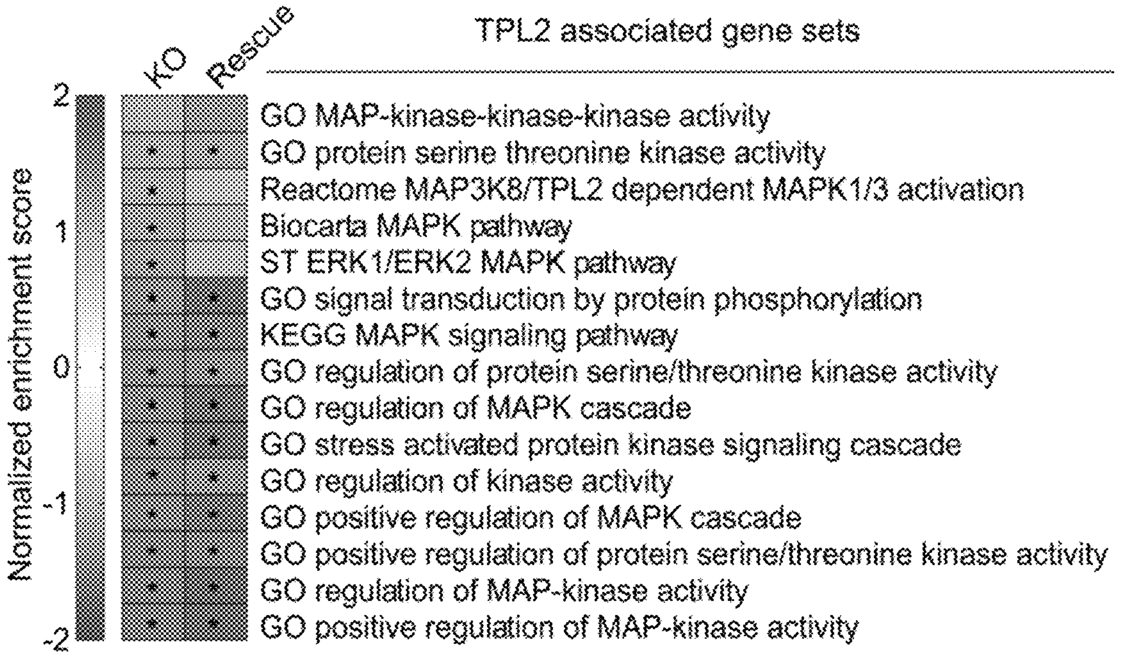
Figure 14A:
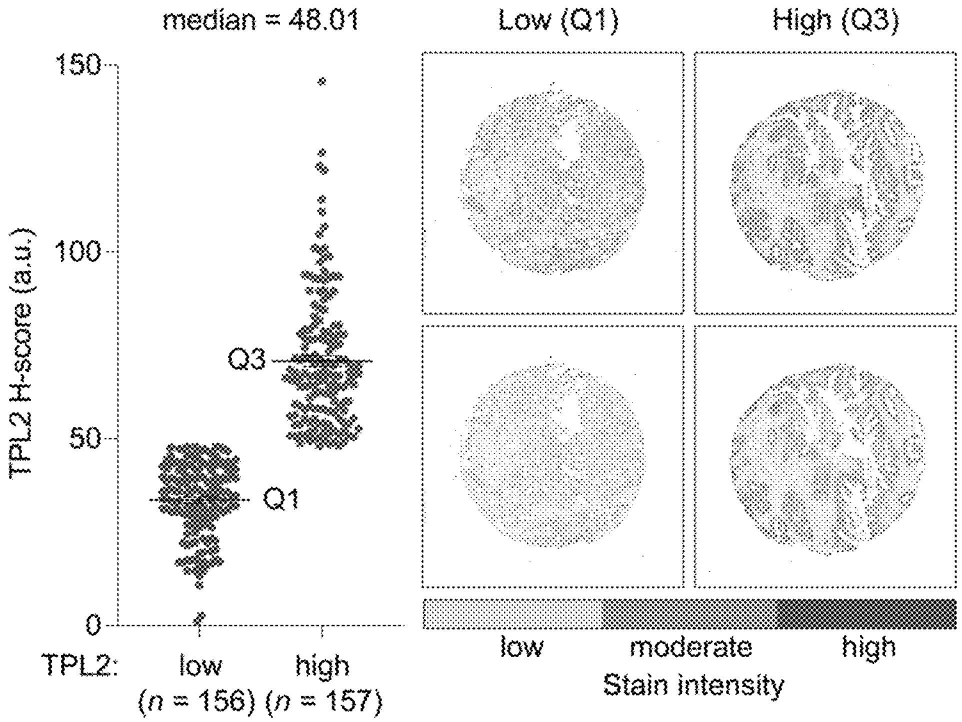
FIG. 14A-FIG. 14C. (A) Scatter plots and representative images (original and with HALO analyzed markup) depicting "high" and "low" TPL2 H-scores for tissue-micro-array (TMA) analysis. Images shown represent Q1 and Q3 quartile H-score by median. (B) Scatter plots and representative images (original and with HALO analyzed markup) depicting "high" and "low" p-IRAK4 H-scores for tissue-microarray (TMA) analysis. Images shown represent Q1 and Q3 quartile H-score by median. (C) Graph depicting MAP3K8 (encoding TPL2) RNA expression in multiple cancers in the TCGA PanCancer Atlas project. Data are arranged by increasing median expression, from left to right. Disease of interest, PDAC, is in red color. P values are from one-way ANOVA with Dunnett's multiple comparison test and are listed for each comparison in TABLE 6. All error bars indicate mean±SEM; **P<0.0001, *P<0.0002, **P<0.0021, *P<0.0332.
Figure 14B:
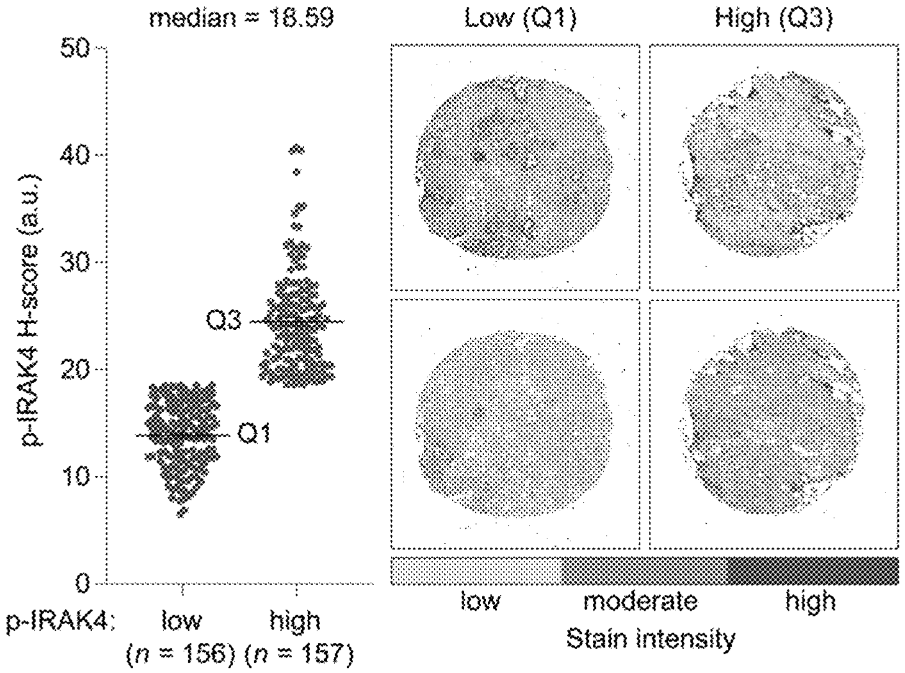
Figure 14C:
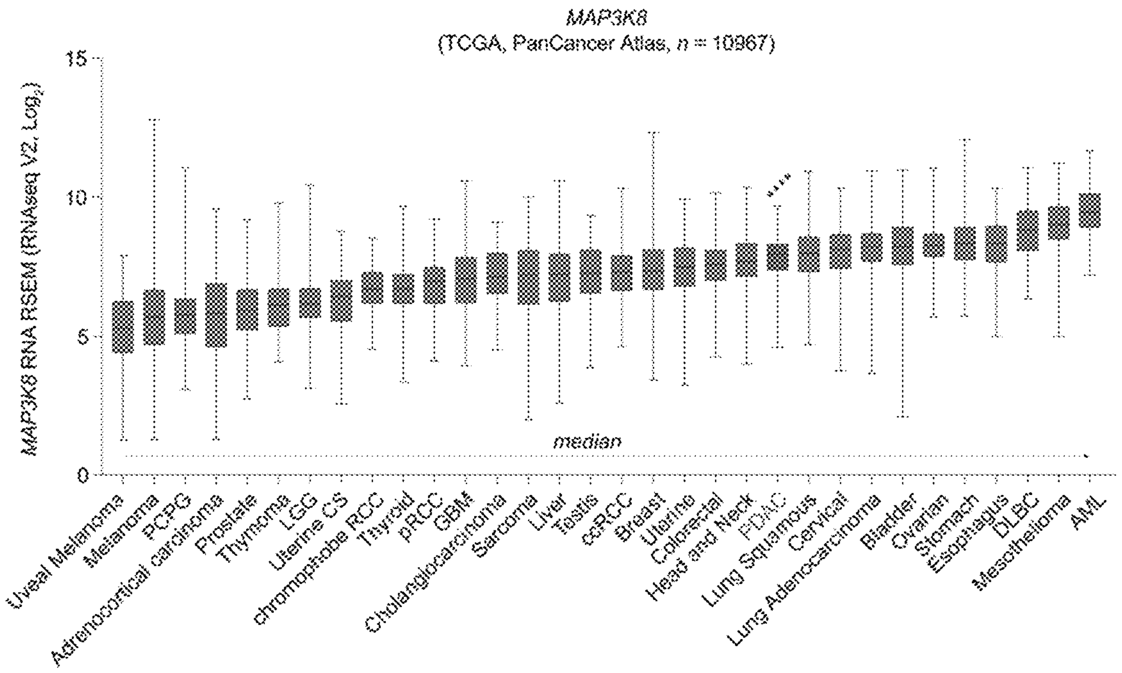

Ablation of Irak4 decreased TPL2 (encoded by MAP3K8) expression in the majority of gene sets, and importantly, low TPL2 expression was closely associated and clustered with low MEK1 expression (see e.g., FIG. 3C and FIG. 13B). These data position TPL2 as the signal transducer between IRAK4 and MEK in PDAC. In human PDAC lines, strong, positive relation was observed between the protein levels of TPL2 and p-ERK (see e.g., FIG. 3D and FIG. 3E) by Western blotting. In human and murine PDAC tumor tissues, IHC analyses showed co-occurrence of p-ERK, TPL2, and p-IRAK4 staining in the neoplastic ductal epithelia, whereas these markers were largely absent in normal ductal epithelia (see e.g., FIG. 3F).

High TPL2 Expression is Poorly Prognostic in PDAC.

Figure 4A:
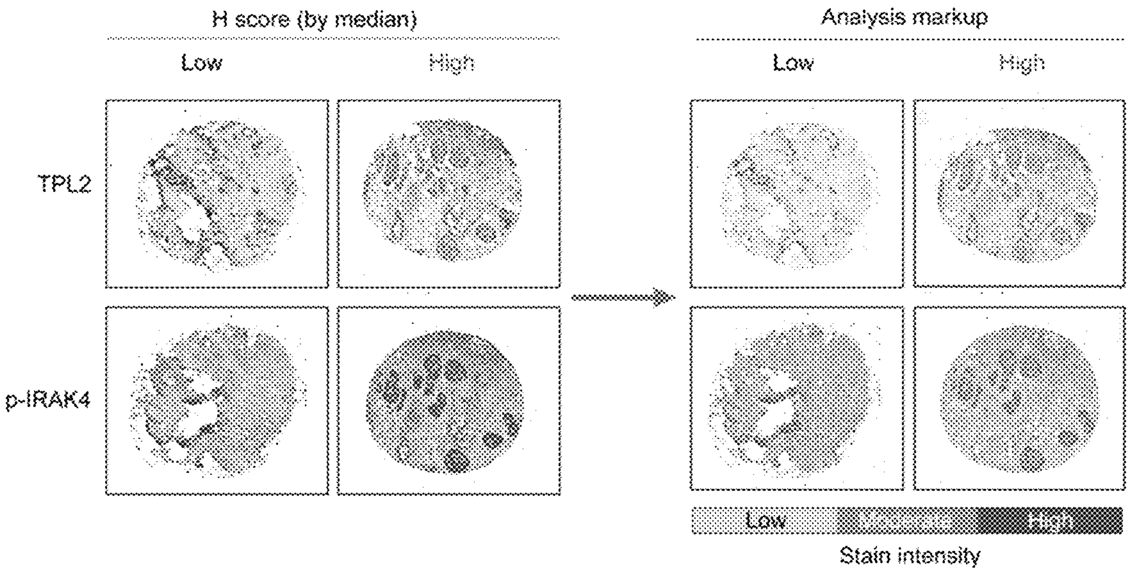
FIG. 4A-FIG. 4G. High TPL2 expression is poorly prognostic in PDAC. (A) IHC images representing high and low staining H-scores for TPL2 and p-IRAK4 with and without HALO analysis markup. H-score=3×(% of strongly stained area)+2×(% of moderately stained area)+1×(% of weakly stained area). (B) Spearman (r) correlation plot of TPL2 and p-IRAK4 H-scores from tissue microarray (TMA) analysis of 313 tissue specimens from 157 PDAC patients, represented in A. (C) Kaplan-Meier plot comparing survival of patients with high vs. low TPL2 protein expression based on analysis of TMA above. Of the patients with survival data, those who died within 1 month of surgery were excluded from the analysis. (D) Graph depicting MAP3K8 (TPL2) expression in normal human pancreas versus PDAC tissue. Data for normal pancreas tissue is from the Genotype-Tissue Expression (GTEx) project and PDAC expression was from the pancreatic adenocarcinoma TCGA PanCancer Atlas study. P values are from unpaired, 2-sided t test. Outliers (5 in normal, 3 in PDAC) were removed by ROUT, Q=0.1%. (E) Graph of overall survival (OS) of TCGA PDAC patients separated into short- and longer-surviving cohorts using median OS of approximately 15.5 months. (F) Graph comparing MAP3K8 mRNA expression in longer-vs. short-surviving patients defined in E. P values are from unpaired, 2-sided t test. All 178 (out of 185) TCGA PDAC samples with mRNA expression data were analyzed. (G) Graph comparing months of OS of patients with high (Z score>1, n=22) versus low (Z score<1, n=28) MAP3K8 expression based on analysis of TCGA Firehose Legacy data set. P values from Kruskal-Wallis test. **P<0.0001; *P<0.0002.
Figure 4B:
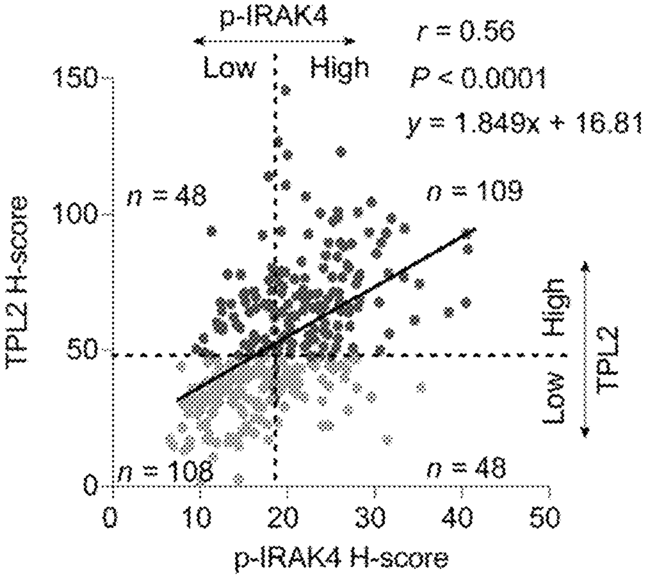
Figure 4C:
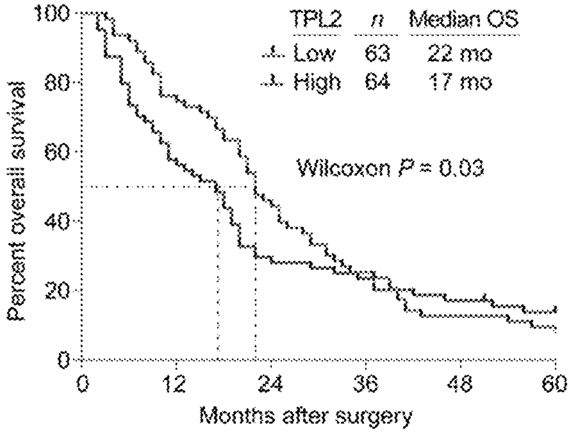
Figure 4D:
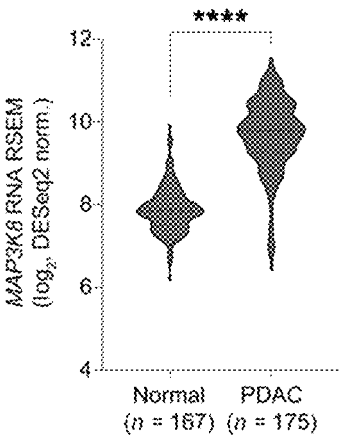

Next, IHC analyses were performed on a panel of 313 PDAC tissue microarray (TMA) specimens and strong, significantly positive correlation of H-score was found, defined by staining area and intensities, between TPL2 and p-IRAK4 ($r=0.56$, $P<0.0001$; see e.g., FIG. 4A, FIG. 4B, FIG. 14A, and FIG. 14B). Notably, high TPL2 staining correlated with poor overall survival in PDAC patients based on Wilcoxon's $P=0.03$, a statistic that gives more weight to early deaths, as typically seen with PDAC patients (see e.g., FIG. 4C). From TCGA and Genotype-Tissue Expression (GTEx) project databases, MAP3K8 mRNA expression was significantly higher in PDAC compared with normal pancreas (see e.g., FIG. 4D) and a majority of other cancer types (see e.g., FIG. 4C and TABLE 6).

TABLE 6

MAP3K8 (TPL2) pan-cancer mRNA expression P-values

| Dunnett's multiple comparisons test | Mean Diff. | 95.00% CI of diff. | Significant? | Summary | Adjusted P Value |
|---|---|---|---|---|---|
| PDAC vs. Adrenocortical carcinoma | 0.4806 | 0.2721 to 0.6890 | Yes | **** | <0.0001 |
| PDAC vs. Bladder | 0.1298 | −0.008270 to 0.2679 | No | ns | 0.0815 |
| PDAC vs. Breast | 0.08398 | −0.04037 to 0.2083 | No | ns | 0.4463 |
| PDAC vs. Cervical | 0.1362 | −0.009685 to 0.2821 | No | ns | 0.0858 |
| PDAC vs. Cholangiocarcinoma | 0.3248 | 0.04444 to 0.6053 | Yes | * | 0.0115 |
| PDAC vs. Colorectal | 0.03366 | −0.09773 to 0.1650 | No | ns | 0.9988 |
| PDAC vs. DLBC | −0.6839 | −0.9335 to −0.4343 | Yes | **** | <0.0001 |
| PDAC vs. Esophagus | −0.09136 | −0.2535 to 0.07076 | No | ns | 0.7085 |
| PDAC vs. GBM | 0.05462 | −0.1127 to 0.2219 | No | ns | 0.9936 |
| PDAC vs. Head and Neck | 0.2036 | 0.06997 to 0.3372 | Yes | *** | 0.0002 |
| PDAC vs. chromophobe RCC | −0.8905 | −1.113 to −0.6681 | Yes | **** | <0.0001 |
| PDAC vs. ccRCC | −0.04327 | −0.1771 to 0.09053 | No | ns | 0.9938 |
| PDAC vs. pRCC | 0.1246 | −0.02233 to 0.2716 | No | ns | 0.1607 |
| PDAC vs. AML | −1.277 | −1.441 to −1.113 | Yes | **** | <0.0001 |
| PDAC vs. LGG | 0.8688 | 0.7351 to 1.002 | Yes | **** | <0.0001 |
| PDAC vs. Liver | 0.8025 | 0.6621 to 0.9429 | Yes | **** | <0.0001 |
| PDAC vs. Lung Adenocarcinoma | 0.1298 | −0.004041 to 0.2636 | No | ns | 0.0643 |
| PDAC vs. Lung Squamous | −0.2042 | −0.3390 to −0.06951 | Yes | *** | 0.0002 |
| PDAC vs. Mesothelioma | 0.0478 | −0.1530 to 0.2486 | No | ns | 0.9989 |
| PDAC vs. Ovarian | 0.2411 | 0.09569 to 0.3864 | Yes | **** | <0.0001 |
| PDAC vs. PCPG | 0.6489 | 0.4861 to 0.8117 | Yes | **** | <0.0001 |
| PDAC vs. Prostate | 0.4648 | 0.3304 to 0.5992 | Yes | **** | <0.0001 |
| PDAC vs. Sarcoma | 0.1332 | −0.01707 to 0.2835 | No | ns | 0.1224 |
| PDAC vs. Melanoma | 0.5222 | 0.3858 to 0.6586 | Yes | **** | <0.0001 |

TABLE 6-continued

| MAP3K8 (TPL2) pan-cancer mRNA expression P-values | | | | | |
|---|---|---|---|---|---|
| Dunnett's multiple comparisons test | Mean Diff. | 95.00% Cl of diff. | Significant? | Summary | Adjusted P Value |
| PDAC vs. Stomach | 0.04626 | −0.09158 to 0.1841 | No | ns | 0.9933 |
| PDAC vs. Testis | 0.7555 | 0.5850 to 0.9261 | Yes | **** | <0.0001 |
| PDAC vs. Thyroid | −0.06449 | −0.1987 to 0.06973 | No | ns | 0.8805 |
| PDAC vs. Thymoma | −0.6417 | −0.8235 to −0.4599 | Yes | **** | <0.0001 |
| PDAC vs. Uterine | 0.2865 | 0.1532 to 0.4197 | Yes | **** | <0.0001 |
| PDAC vs. Uterine CS | 1.067 | 0.8338 to 1.301 | Yes | **** | <0.0001 |
| PDAC vs. Uveal Melanoma | 1.032 | 0.8251 to 1.238 | Yes | **** | <0.0001 |

Figure 4E:
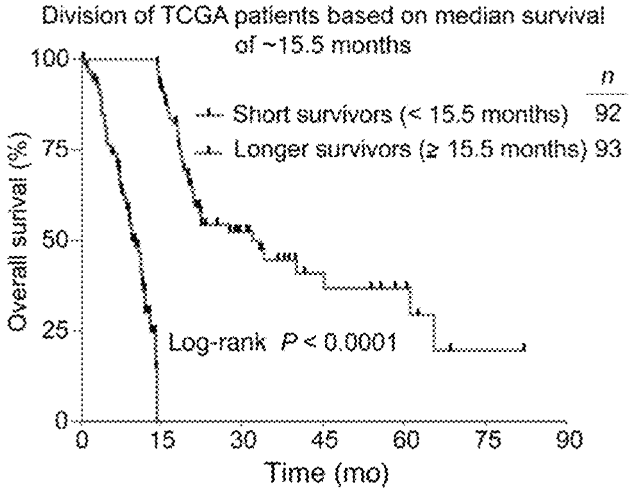
Figure 4F:
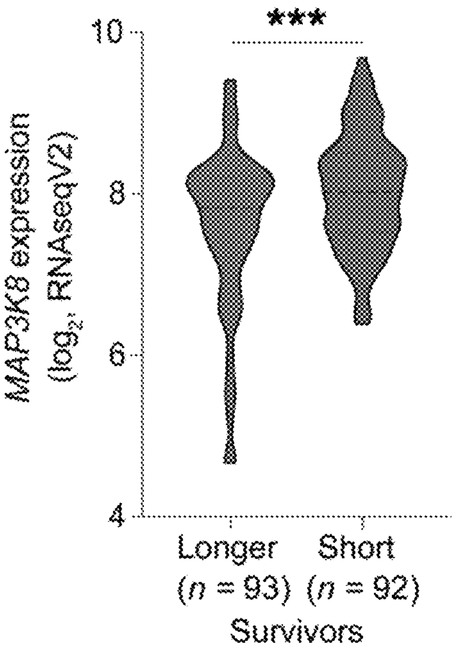
Figure 4G:
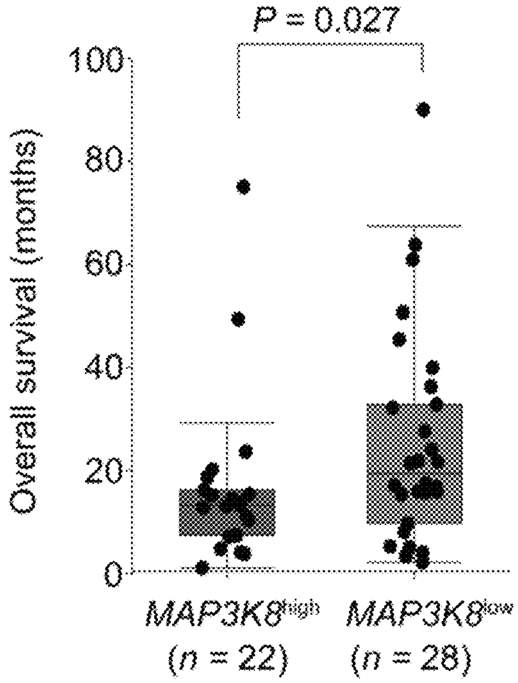

Next, using the median overall survival of TCGA PDAC patients (~15.5 months), patients were divided into 2 groups, short (<15.5 months overall survival, n=92) and longer (≥15.5 months overall survival, n=93) survivors (see e.g., FIG. 4E). The short survivors had significantly higher MAP3K8 expression (see e.g., FIG. 4F). Conversely, high MAP3K8 expression (arbitrarily defined as Z score>1, MAP3K8$^{High}$, n=22) is significantly associated with poorer overall survival compared with low MAP3K8 expression (Z score<1, MAP3Kg$^{Low}$, n=28; see e.g., FIG. 4G). Together, these complementary studies position TPL2 as the intermediate kinase between IRAK4 and MEK and signify its potential as a therapeutic target warranting further investigation.

TPL2 Drives Both MAPK and NF-κB Signaling in PDAC.

Figure 5A:
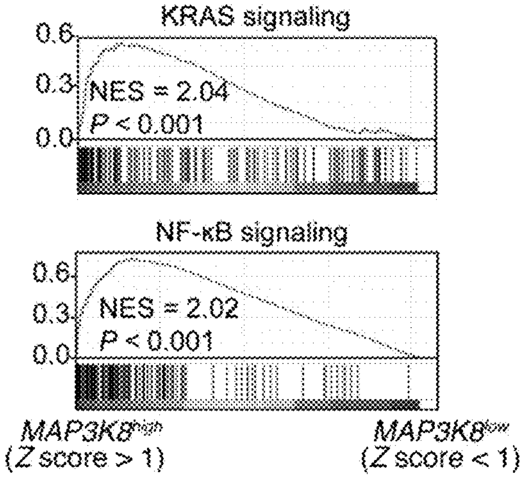
FIG. 5A-FIG. 5K. TPL2 drives both MAPK and NF-κB signaling in PDAC. (A) Gene set enrichment plots for patients with high (Z score>1, n=22) and low (Z score<1, n=28) MAP3K8 (TPL2) expression from TCGA Firehose Legacy study. (B) Immunoblots of KRAS-mutant human PDAC cell lines treated with TPL2 inhibitor (TPL2i) or vehicle (V) for 36 hours in serum-free media. (C) Immunoblots of 293T and 293T-KRAS$^{G12V}$ cells treated with TPL2i for 24 hours in serum-free condition. (D) Immunoblots of Pa01C cells treated with incremental doses of TPL2i. (E) Immunoblots of PDAC cell lines treated with TPL2i. (F) Serum-response element (SRE) reporter assay of HPAC cells treated with TPL2i, BRAFi, MEKi, or ERKi. Data show 3 independent experiments, each done with triplicate samples. (G) Quantification of soft-agar colonies formed by PDAC cell lines treated with TPL2i. Data represent n=3 (n=2 for CFPAC-1) for each cell line. One data point is shown per biological replicate, each consisting of 3 technical replicates. P values from 2-way ANOVA with Dunnett's multiple-comparisons test. (H) Immunoblots of WT or MAP3K8-knockdown HPAC cells. (1) Quantification of HPAC and Pa01C cell proliferation after TPL2 knockdown with shRNA (shMAP3K8). Each data point is the average of 6 replicates. P values by 2-way ANOVA with Dunnett's multiple-comparisons test. (J) Representative crystal violet-stained images of 2D colony formation of TPL2-knockdown HPAC and Pa01C cells. (K) Light microscopic images of organoids formed by HPAC and Pa01C cells with TPL2 knockdown. Scale bars: 100 μm (full images) and 25 μm (insets). Graph on bottom is quantification of number of organoids formed in 3 independent wells. P values by 2-way ANOVA with Dunnett's multiple-comparisons test. All data presented as mean±SEM. **P<0.0001; *P<0.0002; *P<0.0332.
Figure 5B:
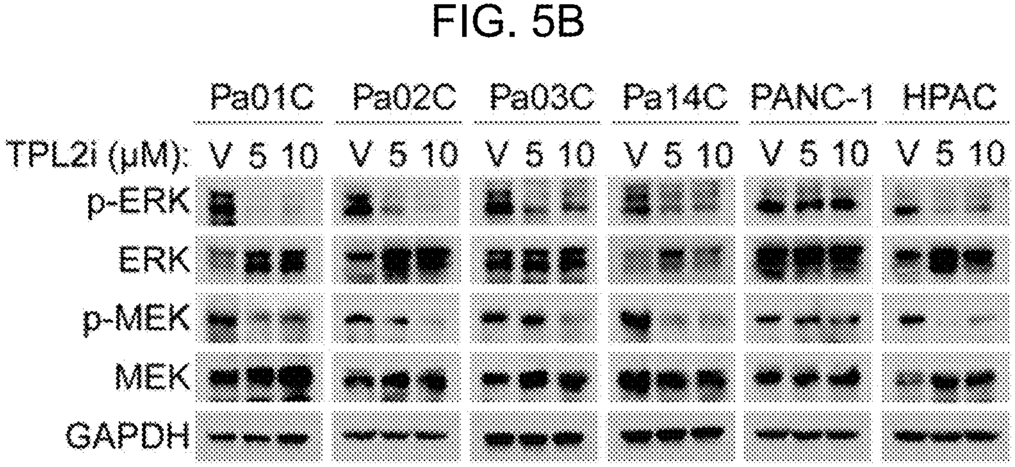
Figure 5C:
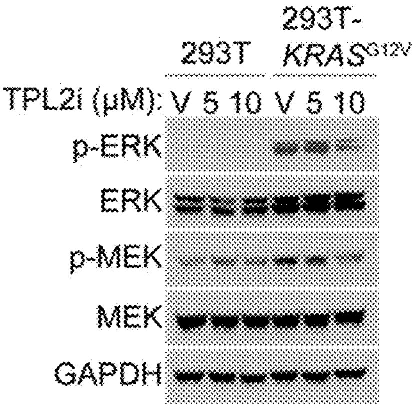
Figure 5D:
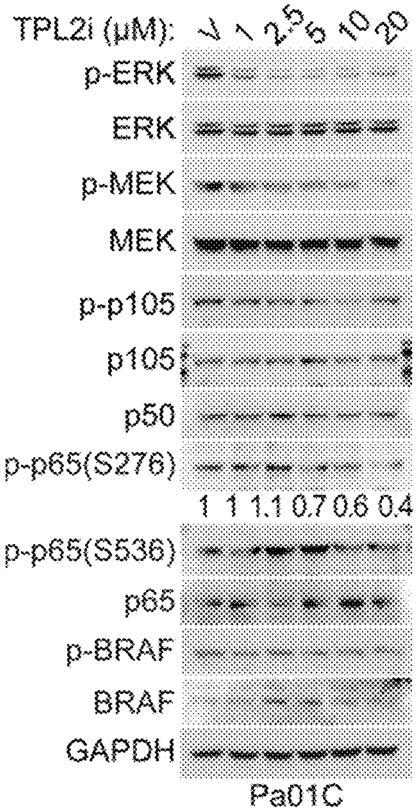
Figure 5E:
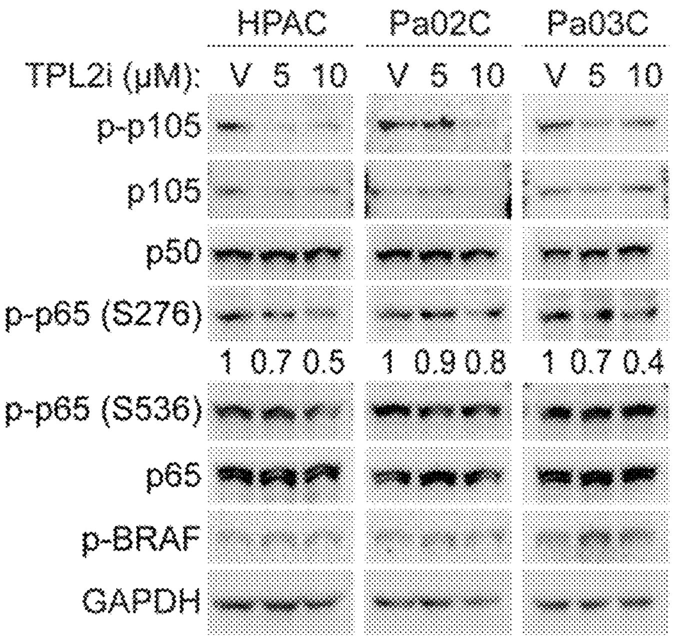
Figure 15A:
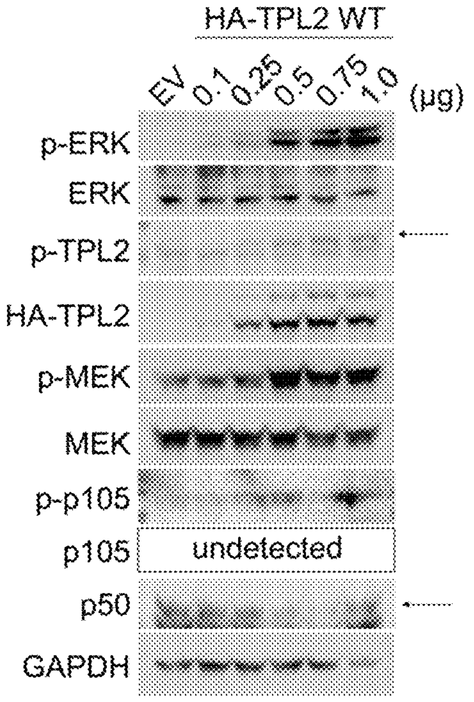
FIG. 15A-FIG. 15F. (A) Immunoblot of 293T cells transfected with 1 μg of empty vector or indicated amounts of plasmid encoding HA epitope-tagged TPL2 WT for 48 hours. (B) Serum-response element (SRE) reporter activity of MIA-PaCa2 cells treated with TPL2i, BRAFi, MEKi or ERKi for 24 hours. Data for TPL2i and ERKi is from three independent experiments each done in technical triplicate. Rest are from one independent experiment. (C) SRE reporter activity of Pa01C cells treated with TPL2i, IKKi (IMD0354), MEKi, and BRAFi. Data for TPL2i and ERKi is from two independent experiments each done in technical triplicate. Rest are from one independent experiment. (D) NF-kB reporter activity of PANC-1 cells treated with serial dilutions from 20 μM of TPL2i, IRAK4i (PF06650833) and MEKi (trametinib) for 18 hours. Data are from three or more independent experiments, each done in technical triplicate. P values from two-way ANOVA and Dunnett's multiple comparison test. (E) Immunoblots of 293T cells transiently transfected with empty vector or MYC epitope-tagged BRAF V600E, and after 16 hours, treated with TPL2i (on left) or IRAK4i (PF06650833; on right) for 24 hours. Experiment with TPL2i was performed twice, IRAK4i was done once. (F) Immunoblots of BxPC-3 cells treated with TPL2i for 16 hours, with or without FBS in media. One representative data of four independent experiments is shown. All error bars indicate mean±SEM; **P<0.0001, *P<0.0002, **P<0.0021, *P<0.0332.

From GSEA analysis found MAP3K8$^{High}$ PDAC samples to be enriched for both KRAS and NF-κB signatures (see e.g., FIG. 5A), mirroring findings with IRAK4 (see e.g., FIG. 2F) and congruous with a prior report which showed that TPL2 can phosphoactivate the p105 NF-κB factor. To determine if TPL2 controls MAPK and NF-κB signaling, KRAS-mutant PDAC cells were treated with 4-[(3-chloro-4-fluorophenyl)amino]-6-[(3-pyridinylmethyl)amino]-1,7-naphthyridine-3-carbonitrile, a selective ATP-competitive small-molecule TPL2i that can suppress LPS-induced TNF-α production in human monocytes. Treatment with TPL2i dose-dependently suppressed p-MEK and p-ERK levels in multiple KRAS-mutant PDAC lines except PANC-1 (see e.g., FIG. 5B), and in 293T cells expressing KRAS$^{G12V}$ (see e.g., FIG. 5C), establishing TPL2 as a contributor to KRAS-induced MAPK activity. Notably, TPL2i dose-dependently blocked p-MEK and p-ERK without affecting p-BRAF (see e.g., FIG. 5D), suggesting that TPL2i does not compromise KRAS-RAF interaction and TPL2 activates MEK independently of RAFs. Apart from MAPK, TPL2i also dose-dependently suppressed p-p105, but this did not lead to increased p50 processing. Notably, TPL2i potently suppressed p-p65 at S276 in 3 out of 4 cell lines, but not S536 (see e.g., FIG. 5D and FIG. 5E), consistent with published studies. Conversely, ectopic expression of TPL2 dose-dependently increased p-p105, p-MEK, and p-ERK levels in 293T cells (see e.g., FIG. 15A). These results show that TPL2 controls both MAPK and NF-κB cascades in PDAC.

Figure 5F:
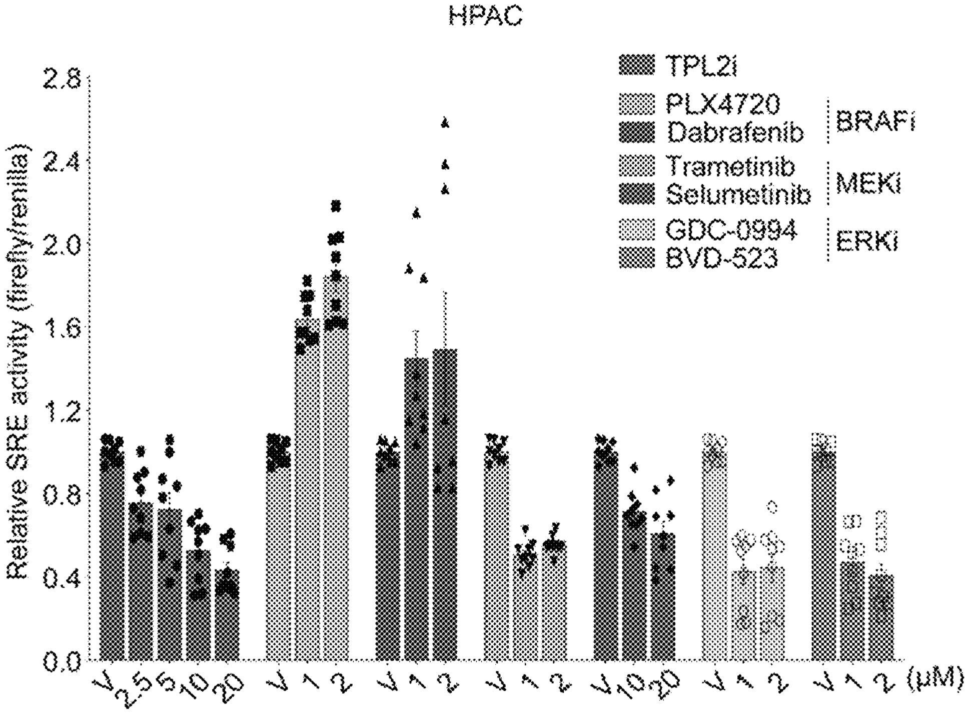
Figure 15B:
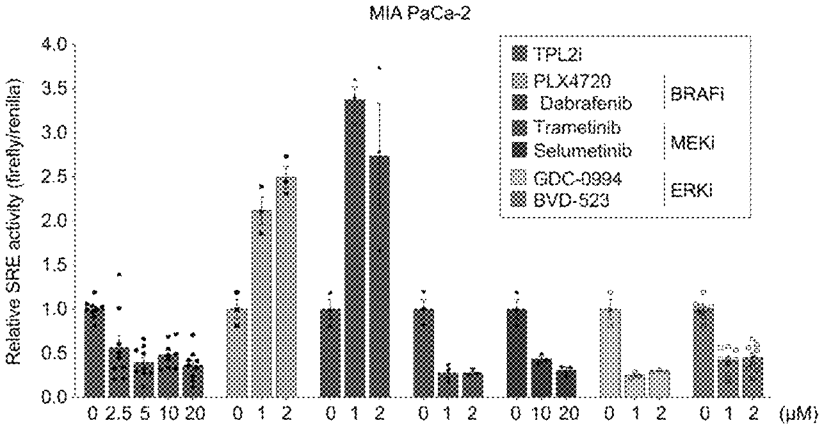
Figure 15C:
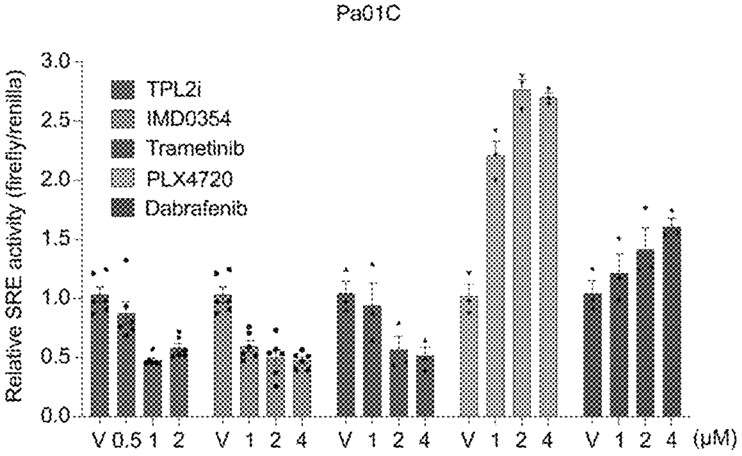
Figure 15D:
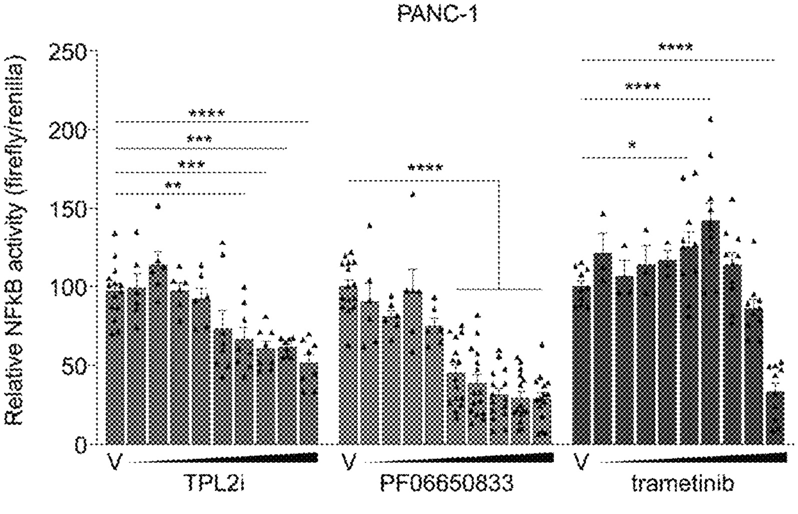
Figure 15E:
Figure 15F:
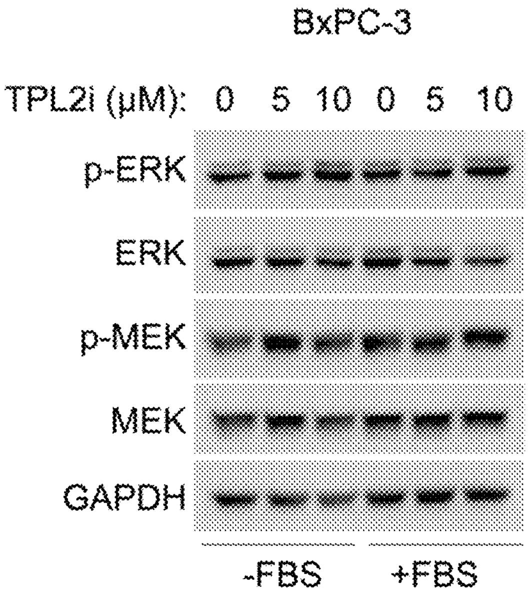

Like the RAF kinases, TPL2 is a MAP3K that activates MEK. However, in RAS-mutant cells, BRAF inhibitors such as PLX-4720 and dabrafenib paradoxically hyperactivate MAPK cascades, which was also observed in KRAS-mutant HPAC, MIA Paca-2, and Pa01C cells expressing an SRE-driven luciferase reporter (see e.g., FIG. 5F, FIG. 15B, and FIG. 15C). In contrast, TPL2i dose-dependently suppressed SRE reporter activity in all 3 cell lines to levels matching those of MEK and ERK inhibitors. Notably, the MEK inhibitor trametinib unexpectedly enhanced NF-κB reporter activity in PDAC cells, perhaps representing a resistance mechanism underlying the lack of clinical efficacy of MEK inhibitors. On the other hand, TPL2i and IRAK4i dose-dependently suppressed both SRE and NF-κB reporter activities in KRAS-mutant PDAC cells (see e.g., FIG. 15D). Notably, neither TPL2i nor IRAK4i suppressed p-MEK and p-ERK in 293T cells transfected with oncogenic BRAF$^{V600E}$ (see e.g., FIG. 15E), or in a BxPc-3 PDAC line that harbors an in-frame gain-of-function BRAF mutation and WT KRAS (see e.g., FIG. 15F), demonstrating IRAK4 and TPL2 as separate activators of MAPK, other than RAFs, downstream of KRAS.

```
BRAF protein sequence:
                                          (SEQ ID NO: 40)
MAALSGGGGGGAEPGQALFNGDMEPEAGAGAGAAASSAADPAIPEEVWNI

KQMIKLTQEHIEALLDKFGGEHNPPSIYLEAYEEYTSKLDALQQREQQLL

ESLGNGTDFSVSSSASMDTVTSSSSSSLSVLPSSLSVFQNPTDVARSNPK

SPQKPIVRVFLPNKQRTVVPARCGVTVRDSLKKALMMRGLIPECCAVYRI

QDGEKKPIGWDTDISWLTGEELHVEVLENVPLTTHNFVRKTFFTLAFCDF

CRKLLFQGFRCQTCGYKFHQRCSTEVPLMCVNYDQLDLLFVSKFFEHHPI

PQEEASLAETALTSGSSPSAPASDSIGPQILTSPSPSKSIPIPQPFRPAD

EDHRNQFGQRDRSSSAPNVHINTIEPVNIDDLIRDQGFRGDGGSTTGLSA

TPPASLPGSLTNVKALQKSPGPQRERKSSSSSEDRNRMKTLGRRDSSDDW

EIPDGQITVGQRIGSGSFGTVYKGKWHGDVAVKMLNVTAPTPQQLQAFKN

EVGVLRKTRHVNILLFMGYSTKPQLAIVTQWCEGSSLYHHLHIIETKFEM

IKLIDIARQTAQGMDYLHAKSIIHRDLKSNNIFLHEDLTVKIGDFGLATV

KSRWSGSHQFEQLSGSILWMAPEVIRMQDKNPYSFQSDVYAFGIVLYELM

TGQLPYSNINNRDQIIFMVGRGYLSPDLSKVRSNCPKAMKRLMAECLKKK

RDERPLFPQILASIELLARSLPKIHRSASEPSLNRAGFQTEDESLYACAS

PKTPIQAGGYGAFPVH
```

Figure 5G:
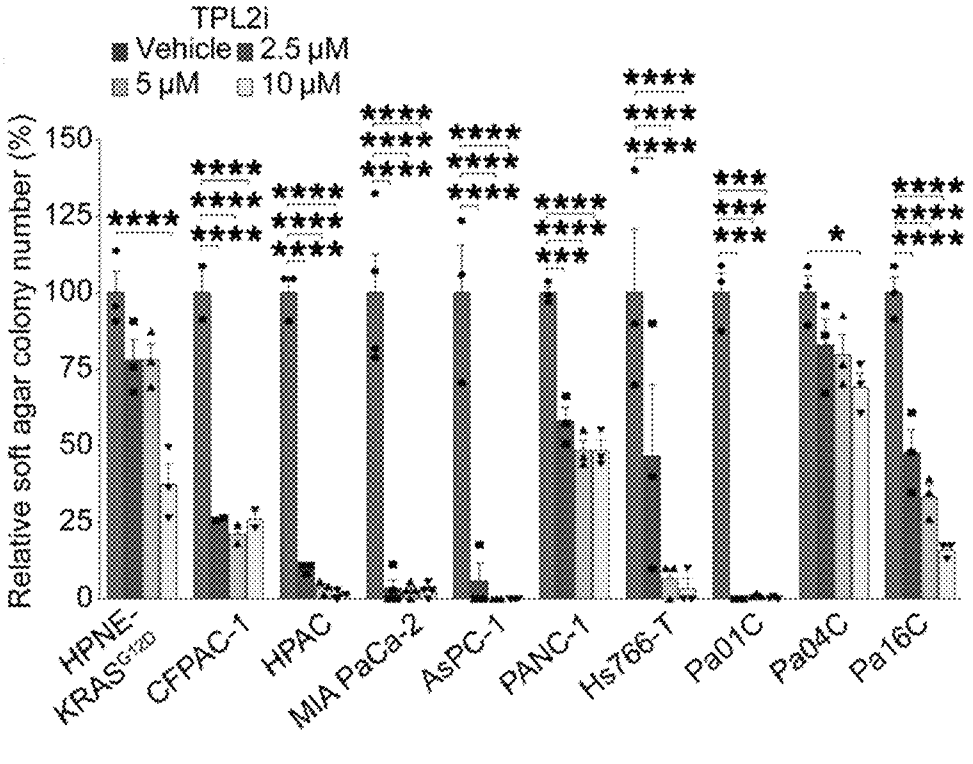
Figure 5H:
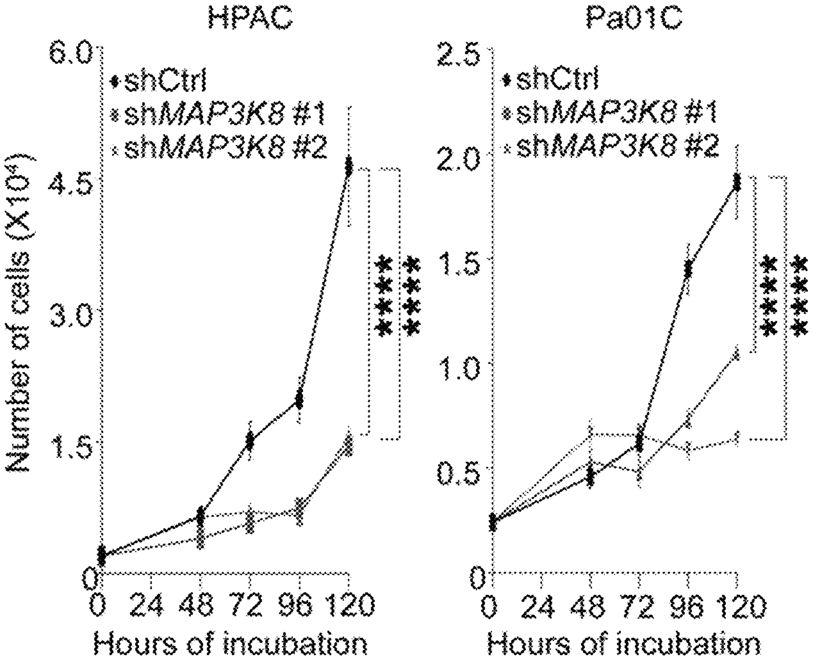
Figure 5I:
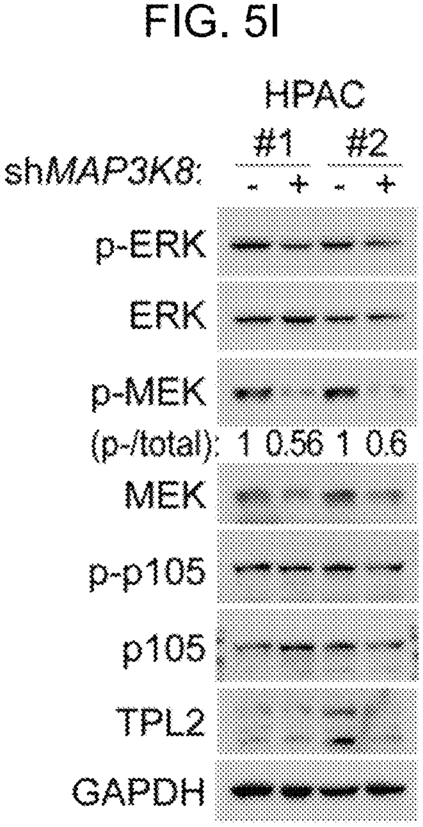
Figure 5J:
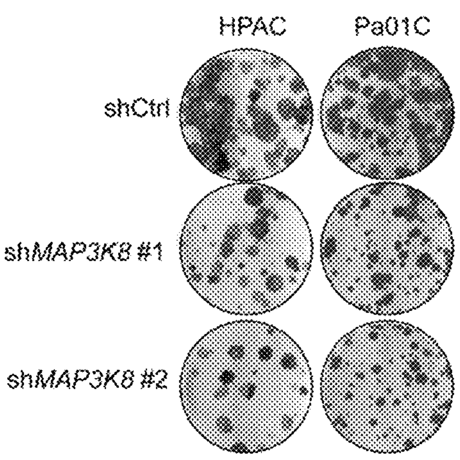
Figure 5K:
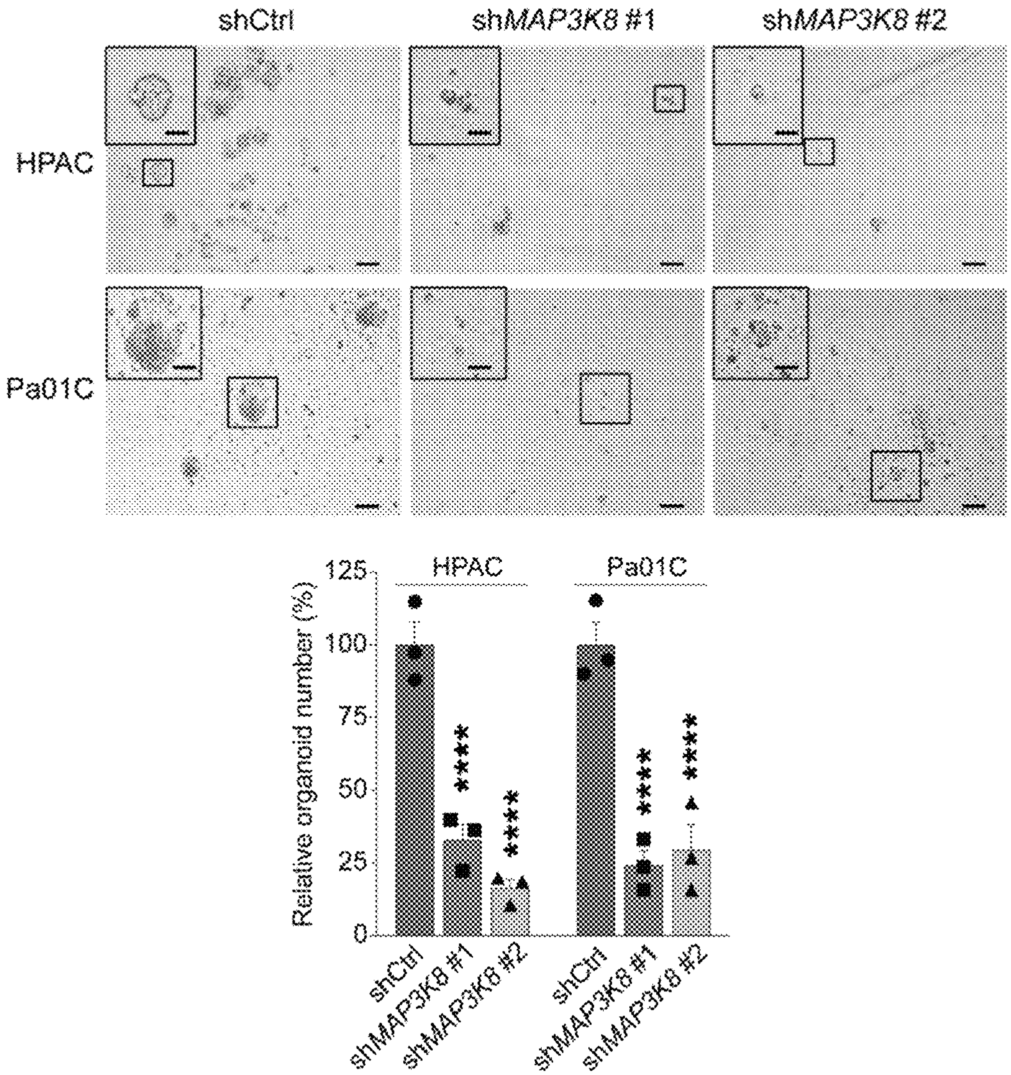
Figure 16A:
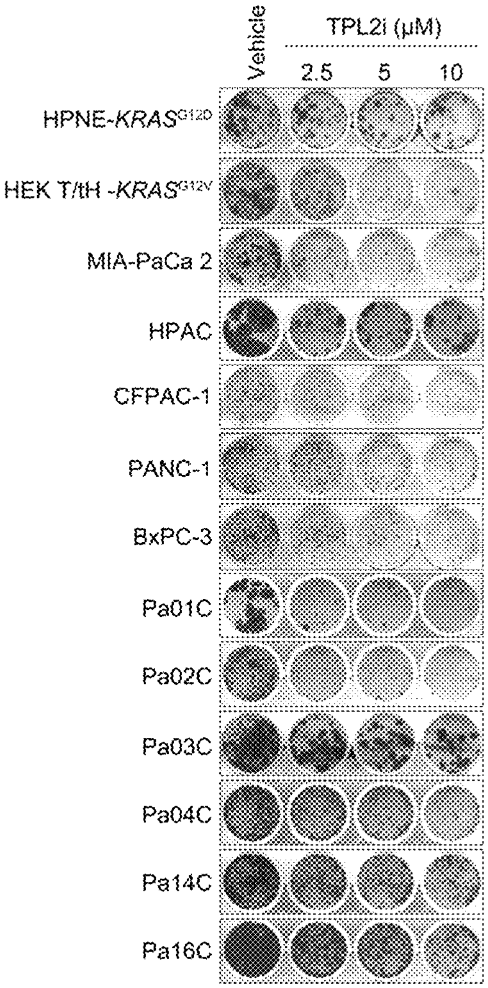
FIG. 16A-FIG. 16B. (A) Images of 2D clonogenic colony formation assays of multiple KRAS mutant cell lines treated with TPL2i. Two independent experiments were performed per cell line. (B) Quantification and representative images depicting soft agar colony formation of HPAC and Pa01C cells stably expressing non-targeting shRNA (shCtrl) or shRNA targeting MAP3K8 (encoding TPL2). Data is from three independent experiments (two for HPAC) each with technical triplicates. Scale bar is 500 μm. P values from two-way ANOVA with Dunnett's multiple comparison test. All error bars are mean±SEM; **P<0.0001, *P<0.0002, **P<0.0021, *P<0.0332.
Figure 16B:
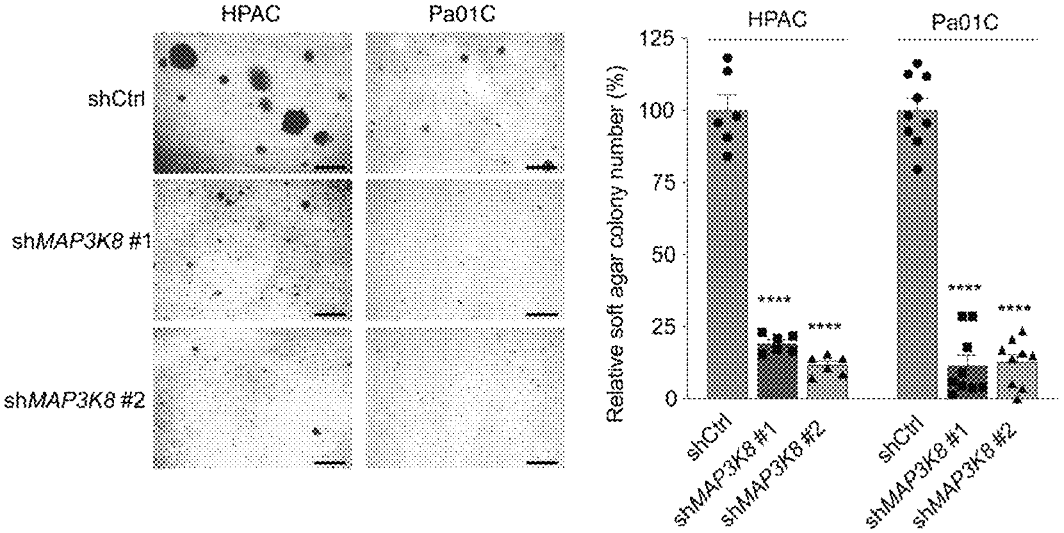

Supporting an essential role of TPL2 in KRAS-induced transformation, TPL2i dose-dependently suppressed 3-dimensional (3D) AI and 2D clonogenic growth of HPNE-KRAS$^{G12D}$ cells, HEKT/tH-KRAS$^{G12V}$ cells, conventional PDAC lines, and PDCLs (see e.g., FIG. 5G and FIG. 16A). Knockdown of TPL2 by shRNA (shMAP3K8) severely impaired HPAC and Pa01C cell proliferation (see e.g., FIG. 5H). The subpopulation that eventually grew again had only partial TPL2 knockdown but displayed reduced p-MEK, p-ERK, and p-p105 levels (see e.g., FIG. 5I) and were markedly impaired in 2D clonogenic growth (see e.g., FIG. 5J), and 3D growth as organoids or soft-agar colonies (see e.g., FIG. 5K and FIG. 16B). Together, these data establish a critical role for TPL2 in PDAC and KRAS signaling via supporting both NF-κB and MAPK pathways.

KRAS Induces Autocrine IL-13 Inflammatory Signaling to Activate IRAK4 and TPL2.

Figure 6A:
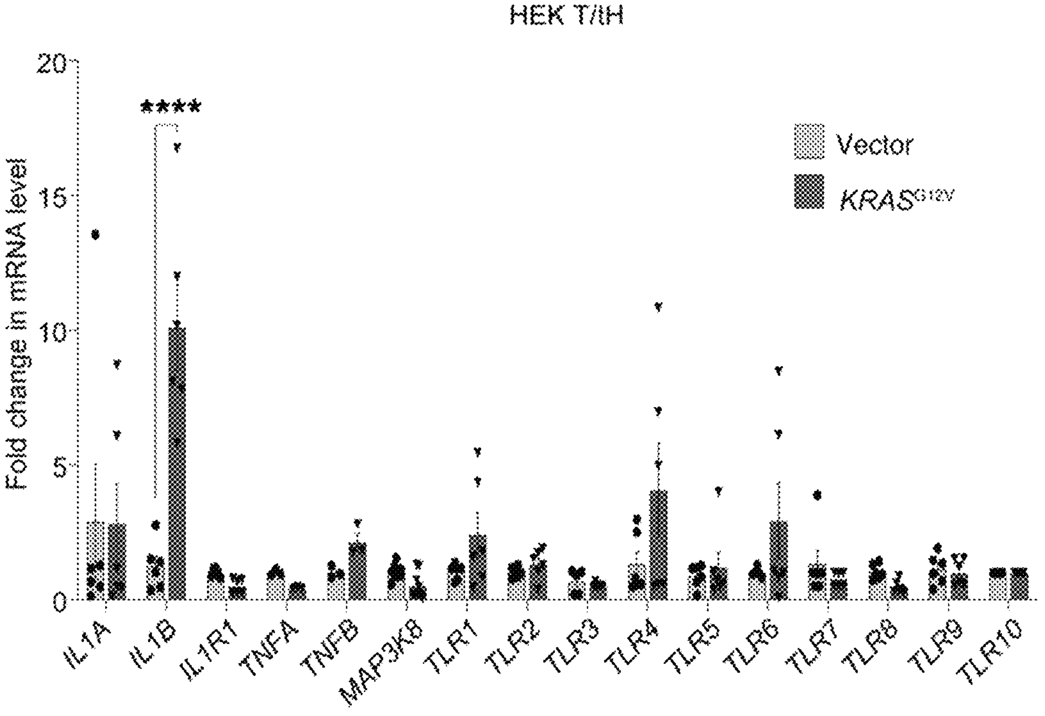
FIG. 6A-FIG. 6H. KRAS induces autocrine IL-1B signaling, which activates IRAK4 and TPL2. (A) qRT-PCR of HEK cells expressing empty vector or KRAS$^{G12V}$. Data show 6 replicates from 2 independent experiments. ****P<0.0001 by 2-way ANOVA with Dunnett's multiple-comparisons test. (B) Heatmap of Hallmark "KRAS signaling up" signature in MAP3K8-high vs. MAP3K8-low patients. IL1B is significantly enriched in MAP3K8$^{High}$ patients, shown also in box-and-whisker plot on right. Significance tested with unpaired, 2-sided t test. (C) Immunoblots of HEK-KRAS$^{G12V}$ cells treated with anti-hIL-1β neutralizing antibody for 24 hours. (D) Immunoblots of HEK cells incubated with conditioned media (CM) from HEK-KRAS$^{G12V}$ cells (called "KRAS$^{G12V}$ CM") and anti-HiI-1β neutralizing antibody. (E) Immunoblots of HEK cells incubated with KRAS$^{G12V}$ CM and TPL2i or vehicle (V) for 16 hours. (F) Immunoblots of HEK and HPAC cells overexpressing HA epitope-tagged WT TPL2 stimulated with 100 ng/ml recombinant hIL-1B for the indicated duration. (G) Immunoblots of HEK cells expressing KRAS$^{G12V}$, HA epitope-tagged WT TPL2, and shIL1R1. (H) Kaplan-Meier curve of PDAC TCGA patients with high vs. low IL1B expression. Follow-up censored at 60 months. All data presented as mean±SEM.
Figure 6B:
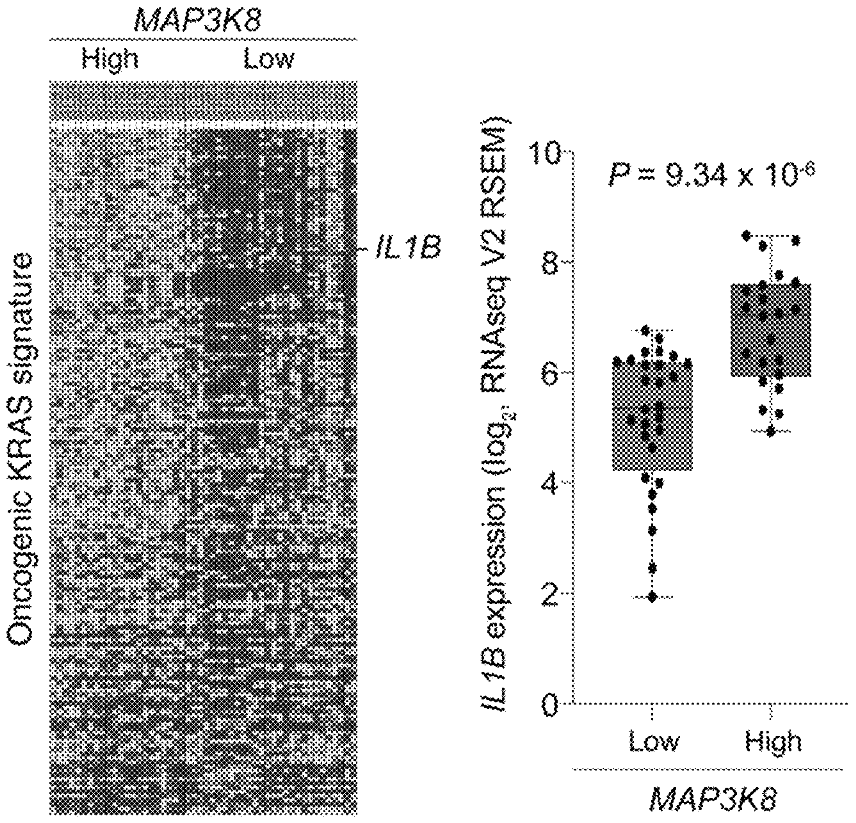
Figure 6C:
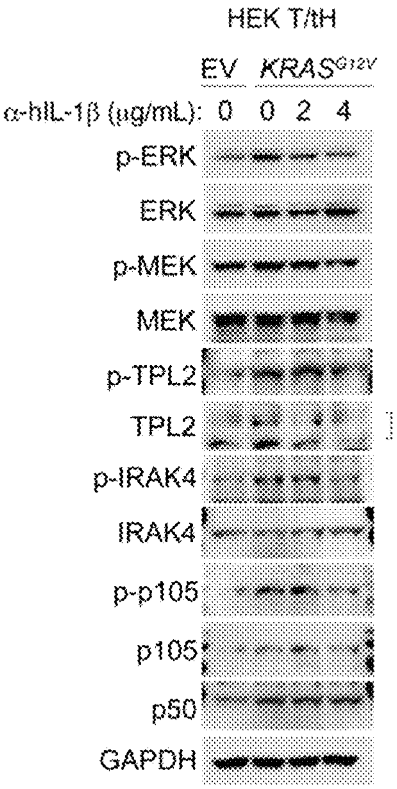
Figure 6D:
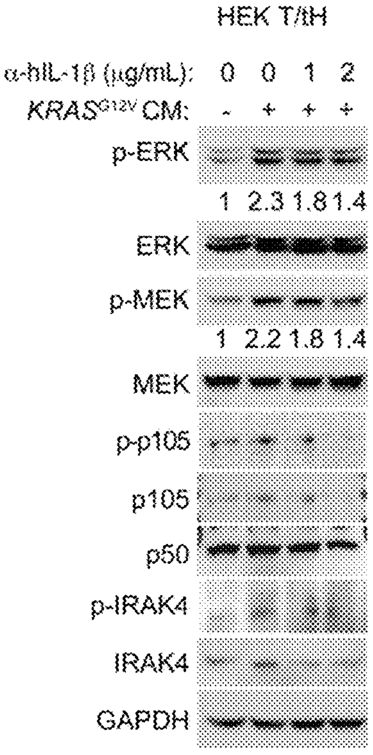
Figure 6E:
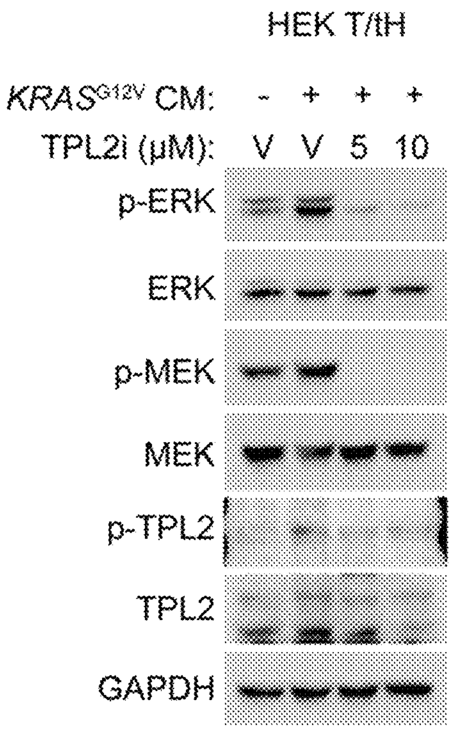
Figure 6F:
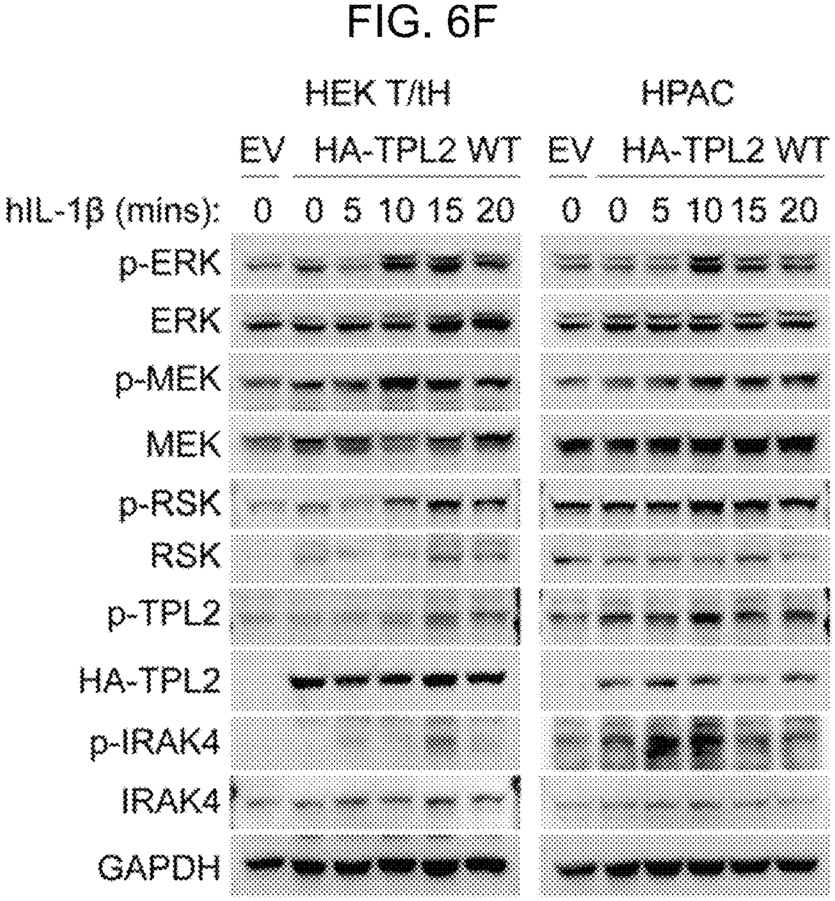
Figure 6G:
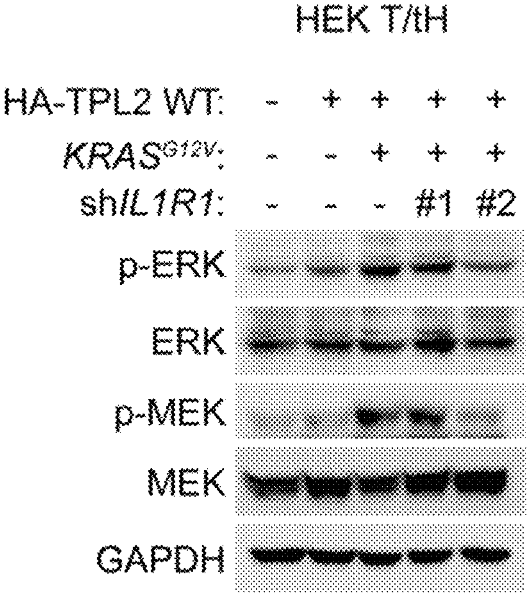
Figure 17A:
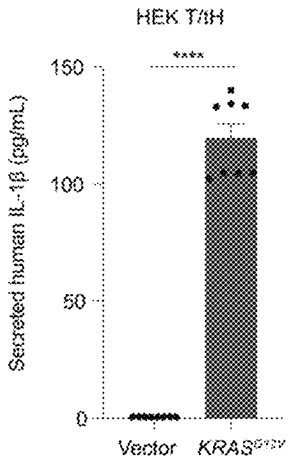
FIG. 17A-FIG. 17G. (A) ELISA for secreted human IL-1B in HEK T/tH cells expressing empty vector or $KRAS^{G12V}$. Data represents two biological replicates, each with four technical replicates. P value from twosided unpaired t-test. (B) Quantification of IL1R1 mRNA level in HEK T/tH $KRAS^{G12V}$ cells after knockdown of IL1R1 (encoding IL-1R1) with shRNA. (C) Immunoblots of WT and IL-1R1 (IL1R1) knock-down HEK T/tH cells stimulated with conditioned media (CM) from HEK T/tH $KRAS^{G12V}$ cells. (D) SRE reporter assay of HPAC cells serum starved for 24 hours and stimulated with serum-free HEK T/tH $KRAS^{G12V}$ CM for 16 hours. Data represent four replicates. P values from two-sided unpaired t-test. (E) Immunoblot of Pa01C cells overexpressing empty vector or HA epitope-tagged TPL2 WT serum starved for 24 hours and then stimulated with 100 ng mL-1 recombinant human IL-1B. (F) Immunoblots of WT and IL-1R1 (IL1R1) knockdown Pa01C cells. (G) IL1B expression by qRT-PCR of HEK vector and HEK-$KRAS^{G12V}$ cells treated with MEKi (trametinib), ERKi (BVD523) and PI3Ki (GDC0941) for 16 hours. Data shows seven replicates from three independent experiments. P values from two-way ANOVA with Dunnett's multiple comparison test. All error bars indicate mean±SEM; **P<0.0001, *P<0.0002, **P<0.0021, *P<0.0332.
Figure 17B:
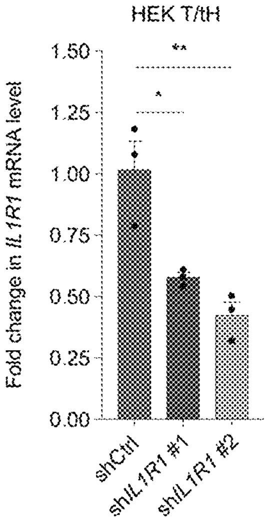
Figure 17C:
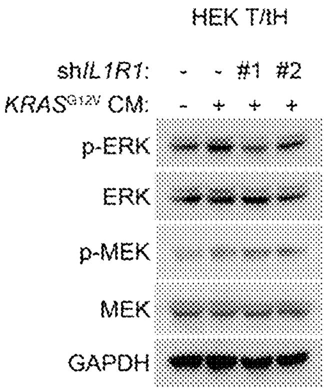
Figure 17D:
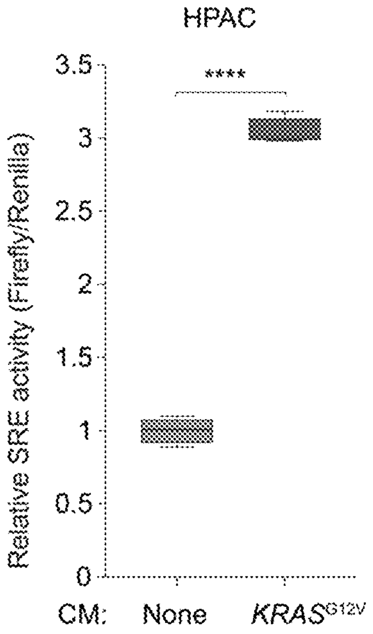
Figure 17E:
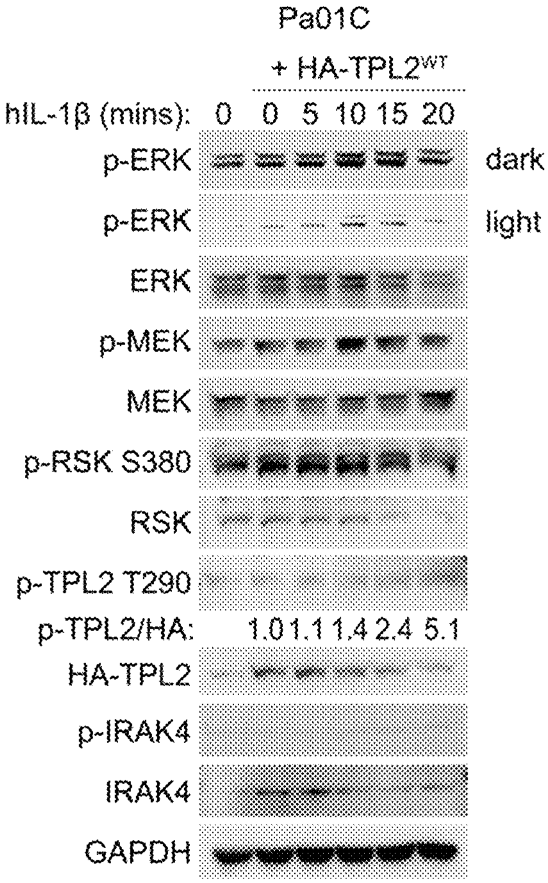
Figure 17F:
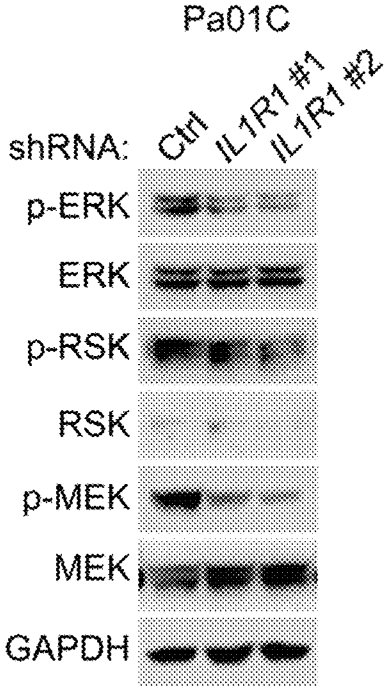

Next, the mechanism by which KRAS activates the IRAK4/TPL2 axis was investigated. IRAK4 and TPL2 are typically activated downstream of IL-1, TNF-α, and TLRs, and not directly by KRAS. On this assumption, the expression of IL-1a/B, TNF-α/B, IL-1R, and all the TLRs was surveyed by qRT-PCR of HEK T/tH cells expressing an empty vector or $KRAS^{G12V}$. Of all 16 targets, only IL1B mRNA was significantly upregulated (by ~10-fold) in $KRAS^{G12V}$-expressing cells compared with vector control (see e.g., FIG. 6A), which was confirmed by IL-1B ELISA of conditioned media (CM) collected from these cells (~120-fold higher in $KRAS^{G12V}$-expressing cells, see e.g., FIG. 17A). Furthermore, analysis of oncogenic KRAS signature showed IL1B expression was significantly higher in $MAP3K8^{High}$ patients (see e.g., FIG. 6B). These results suggest autocrine IL-1B is the driver of IRAK4 and TPL2 activity in KRAS-mutant cells. In support, $KRAS^{G12V}$ expression upregulated p-IRAK4, p-TPL2, p-MEK, and p-ERK levels in HEK T/tH cells, but all were dose-dependently reversed by treatment with a neutralizing anti-human IL-1B (anti-hIL-1B) antibody (see e.g., FIG. 6C). CM collected from HEK-T/tH $KRAS^{G12V}$ cells was able to upregulate p-TPL2, p-IRAK4, p-MEK, and p-ERK levels in HEK T/tH cells, but the effect was blunted with neutralizing anti-hIL-1β antibody (see e.g., FIG. 6D), shRNA knockdown of IL-1R of recipient HEK T/tH cells (see e.g., FIG. 17B and FIG. 17C), and completely blocked by cotreatment with TPL2i (see e.g., FIG. 6E). In support of these data, CM from HEK-T/tH $KRAS^{G12V}$ cells stimulated SRE reporter activity of HPAC cells by approximately 3-fold (see e.g., FIG. 17D) and treatment of HEK T/H, HPAC, and Pa01C cells with recombinant hIL-1B upregulated p-IRAK4, p-TPL2, p-MEK, p-ERK, and p-RSK (see e.g., FIG. 6F and FIG. 17E). Knockdown of IL-1R also blunted upregulation of p-MEK and p-ERK in HEK-T/tH transfected with $KRAS^{G12V}$ or MAP3K8 (TPL2) (see e.g., FIG. 6G), with similar effects observed in KRAS-mutant Pa01C cells (see e.g., FIG. 17F). These data establish autocrine IL-1B/IRAK4/TPL2 signaling as a parallel mechanism, apart from RAF kinases, through which KRAS oncoprotein drives MAPK signaling.

Figure 6H:
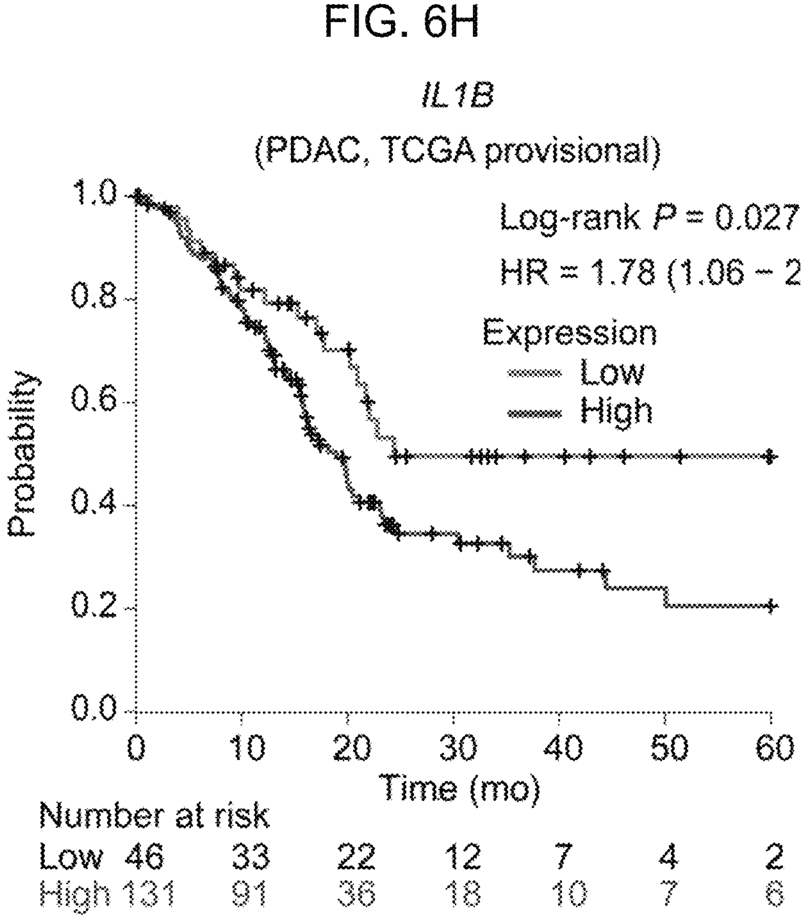
Figure 17G:
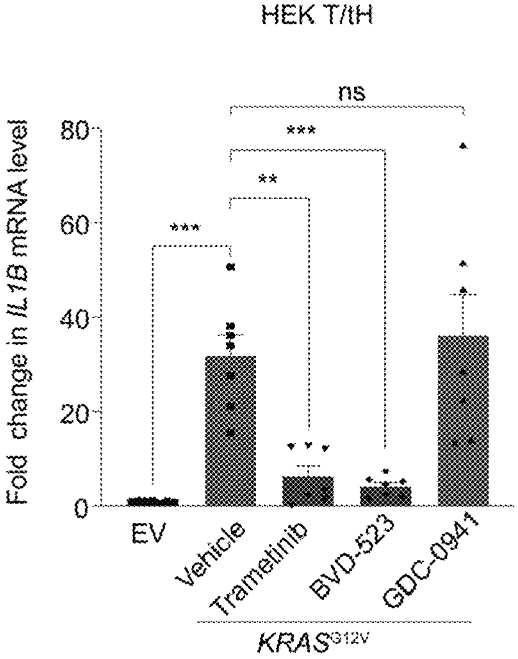
Figure 18A:
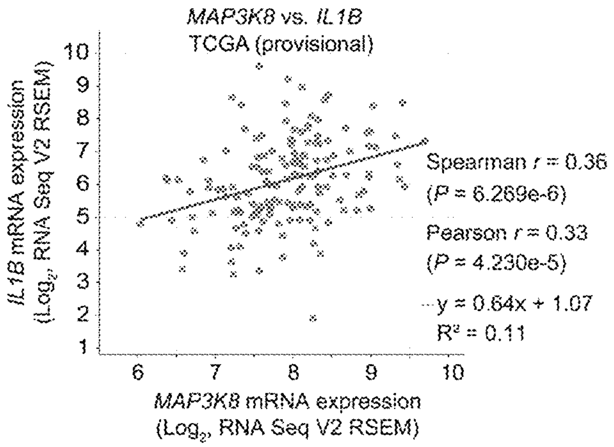
FIG. 18A-FIG. 18E. (A) Scatter plot, linear regression line, and Spearman and Pearson coefficients depicting positive correlation between MAP3K8 (encoding TPL2) and IL1B mRNA expression (in $Log_2$ units) obtained from TCGA database. (B) Scatter plot, linear regression line, and Spearman and Pearson coefficients depicting positive correlation between MAP3K8 and IL1R1 Mrna expression (in $Log_2$ units) obtained from TCGA database. (C) Individual gene set enrichment plots of IL-1 associated gene sets in KP2 Irak4 KO cells. Genes are from the MSigDB and are listed in TABLE 4. (D) Heatmap showing normalized enrichment scores (NES) in KP2 Irak4 KO and Irak4 rescue cells for gene sets in (C). Signatures that were significantly (P<0.05) depleted (blue) or enriched (red) are marked with an asterisk (*). (E) Heatmap showing running enrichment score for MAP3K8 in each gene set in (C) and (D) after Irak4 KO and rescue. #: MAP3K8 is present in the leading edge, indicating that changes in MAP3K8 expression contributed significantly to the enrichment result shown in (C) and (D).
Figure 18B:
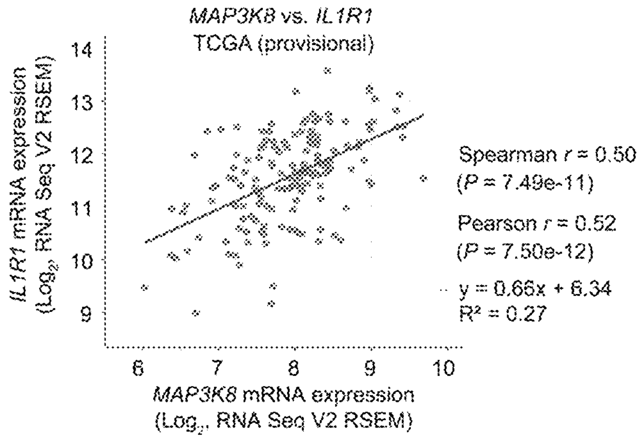
Figure 18C:
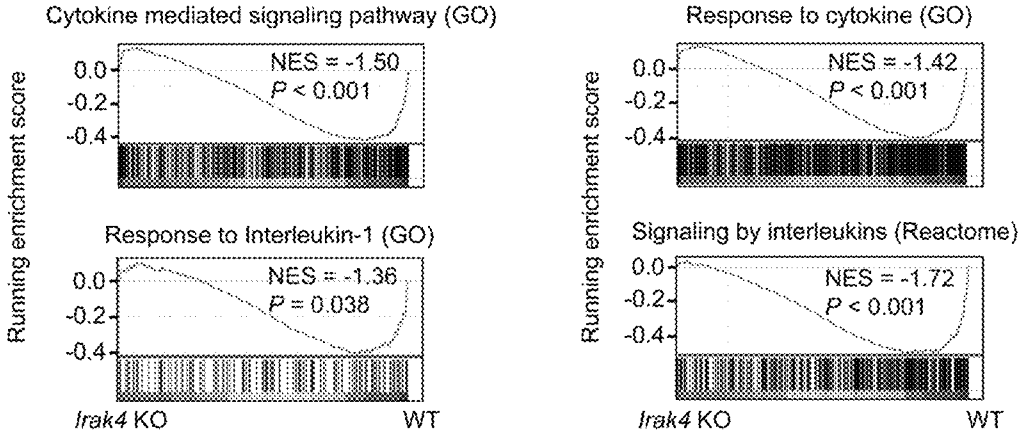
Figure 18D:
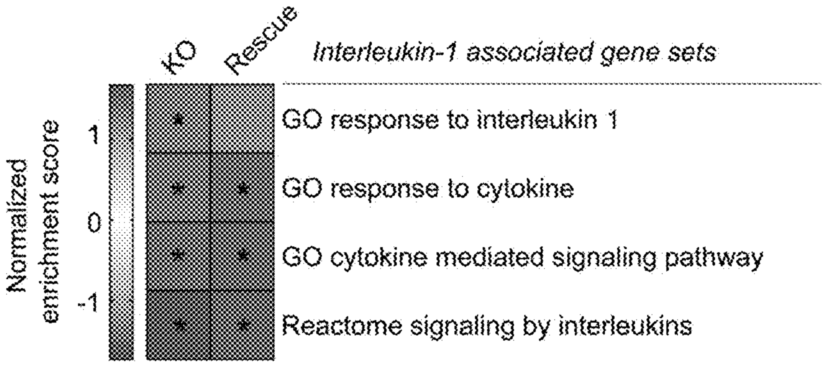
Figure 18E:
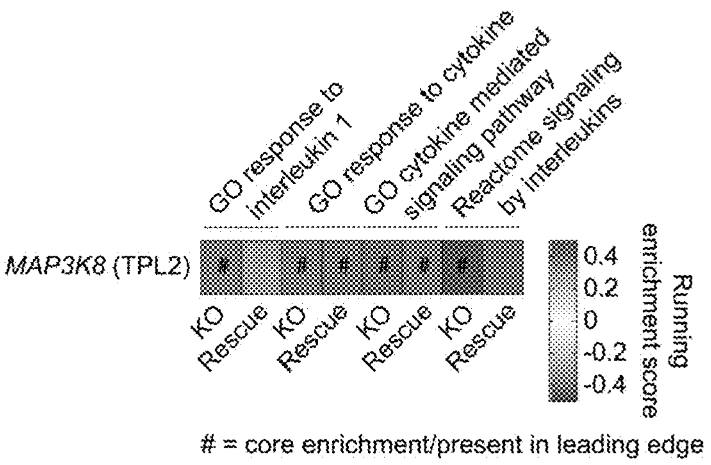

Next, the mechanism by which KRAS promotes IL-1B production was investigated. HEK T/tH $KRAS^{G12V}$ cells were treated with MEK (trametinib), ERK (ulixertinib), or PI3K (GDC-0941) inhibitors and both MEK and ERK inhibitors significantly abrogated IL-1B production, whereas the PI3Ki had no effect (see e.g., FIG. 17G). These data depict a model in which KRAS oncoprotein uses the MAPK effectors to promote IL-1β production and create an autocrine IL-1B-IL-1R-IRAK4-TPL2-MAPK feedforward loop that amplifies MAPK signaling. From TCGA database, elevated IL1B expression associated with poor prognosis in PDAC (see e.g., FIG. 6H). The mRNA level of TPL2 (MAP3K8) moderately (r=0.36) and strongly (r=0.5) positively correlated with IL1B and IL1R1, respectively (see e.g., FIGS. 18A and 18B). In KP2 cells, CRISPR knockout of Irak4 led to downregulation of GO signatures associated with IL-1, and reexpression of Irak4 (rescue) significantly restored these signatures (see e.g., FIG. 18C and FIG. 18D). In these gene sets, TPL2 was present in the leading edge as a core enrichment in an IRAK4-dependent manner (see e.g., FIG. 18E), again signifying its role in IL-1 and cytokine signaling. Together, these data establish autocrine IL-1R/IRAK4/TPL2 signaling as an essential mechanism hijacked by KRAS that should be therapeutically targeted.

TPL2 Inhibition Potentiates Chemotherapy by Curbing MAPK and NF-κB Activation.

Figure 7A:
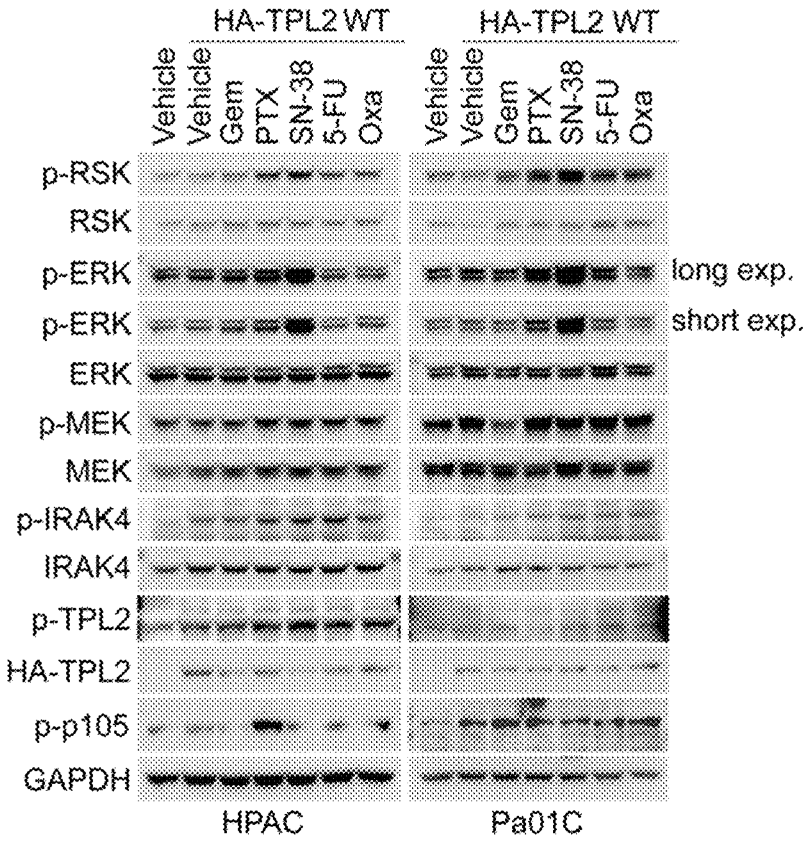
FIG. 7A-FIG. 7H. TPL2 inhibition potentiates chemotherapy by curbing MAPK and NF-κB activation. (A) Immunoblots of 2 PDAC cell lines overexpressing HA epitope-tagged TPL2 WT treated for 16 hours with different chemotherapy agents (10 μM each). (B and C) Quantification of mRNA transcript levels for multiple genes in 3 PDAC cell lines treated with vehicle, gemcitabine-paclitaxel (Gem-PTX), or FIRINOX (10 μM each of 5-FU, SN-38, and oxaliplatin). (D) Duolink proximity ligation assay (PLA) identifying interaction between p-IRAK4 and TLR9 in 3 PDAC cell lines treated with 10 μM SN-38 for 16 hours. Six ×400 magnification fields per condition were analyzed. Scale bars: 10 μm. (E) Immunoblots of 3 PDAC cell lines treated with TPL2i, SN-38, or their combination for 16 hours. FL, full length; V, vehicle. (F) 2D crystal violet clonogenic colony-forming assays of 3 PDAC cell lines treated with TPL2i, SN-38 (2.5 nM, 5 nM, and 10 nM), or their combination in a dose matrix for 3 to 4 weeks. Data show 1 independent experiment out of ≥3 per cell line. (G) Tumor volume curves for patient-derived Pa01C PDAC cells implanted subcutaneously into nude mice followed by treatment with TPL2i, FIRINOX, or combination therapy. Data represent 10 independent tumors (n=10) for each drug treatment group and 8 independent tumors (n=8) for vehicle-treated group. P value from 2-way ANOVA followed by Tukey's multiple-comparisons test. One outlier was removed by Grubb's test, α=0.01. (H) Graph depicting final tumor weight (final pancreas weight −0.1 g i.e., [normal pancreas weight]) after orthoptic injection of murine KI cells and treatment as indicated for 14 days. Images of ex vivo and in vivo tumors detected by ultrasound along with tumor volume are shown on right. P values from 1-way ANOVA with Tukey's multiple-comparisons test. All data presented as mean±SEM. **P<0.0001; *P<0.0002; **P<0.0021; *P<0.0332.
Figure 19A:
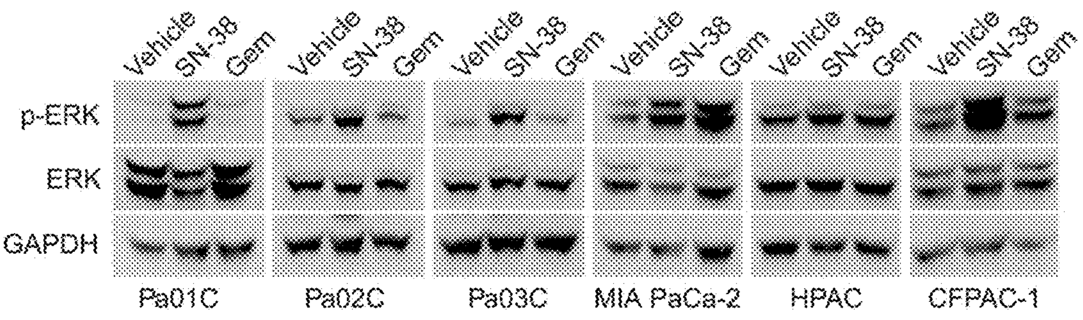
FIG. 19A-FIG. 19G. (A) Immunoblots depicting induction of p-ERK in six PDAC cell lines after 16-hour treatment with chemotherapy agents, SN-38 (10 UM) and gemcitabine (20 μM) in 10% serum DMEM. (B), Scatter plot depicting correlation between mRNA expression of MAP3K8 (encoding TPL2) and TLR9 based on TCGA data. (C) Immunoblot of HPAC cells treated with TPL2i, gemcitabine or the combination for 16 hours in 10% serum DMEM. (D) Quantification of serum-response element (SRE) reporter activity in HPAC cells treated with TPL2i, gemcitabine or the combination for 16 hours in 10% serum DMEM. Data shows six replicates from two independent experiments. P value from two-way ANOVA with Dunnett's multiple comparison test. (E) Immunoblot depicting p-p105 levels in Pa01C cells treated with TPL2i, SN-38 or the combination from same corresponding samples showing in FIG. 7E. (F and G) Flow cytometry scatter plots and bar graph respectively of HPAC cells treated with TPL2i, SN-38 or the combination for 48 hours. Data shows four replicates from two independent experiments. P values from one-way ANOVA with Tukey's multiple comparison test. All error bars indicate mean±SEM; **$P<0.0001$, *$P<0.0002$, **$P<0.0021$, *$P<0.0332$.

Molecularly targeted therapies have been ineffective in treating PDAC patients. Therefore, it is unlikely that TPL2 inhibition or IRAK4 inhibition alone will be clinically effective, and combination regimens will need to be developed. Chemotherapy is currently the only effective treatment modality for PDAC, but treatment response is neither universal nor durable. Stress-induced NF-κB and MAPK survival signaling are among the multiple mechanisms that underlie de novo chemoresistance. To address this, it was examined whether the IRAK4/TPL2 axis contributes to chemotherapy-induced survival and resistance, which will help formulate a rational combinatorial regimen for in vivo testing. PDAC cells were treated with 5 chemotherapeutic agents (gemcitabine, paclitaxel, SN-38, 5-fluorouracil [5-FU], and oxaliplatin) commonly used in patient care. Of these agents, SN-38, an active metabolite of irinotecan, was the most potent in inducing p-ERK, p-MEK, p-RSK, and notably p-TPL2 and p-IRAK4, across multiple PDAC lines (see e.g., FIG. 7A and FIG. 19A), suggesting IRAK4 and TPL2 may contribute to MAPK activation following genotoxic stress. NF-κB was also induced, as evident by an increase in p-p105.

Figure 7B:
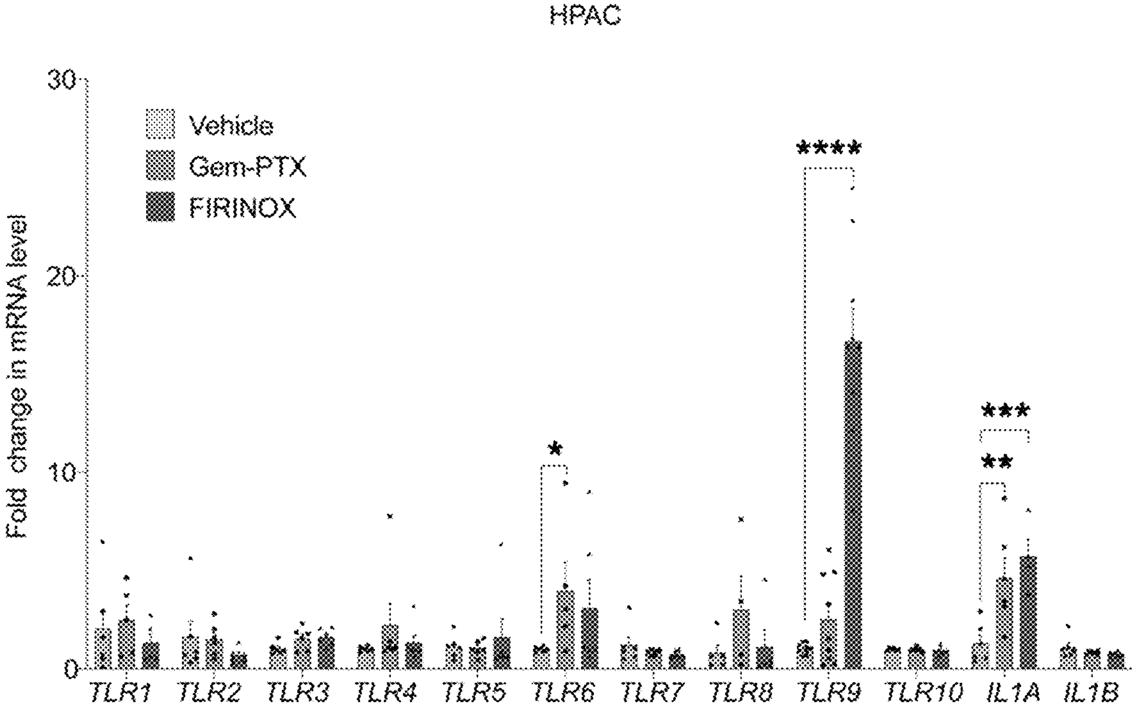
Figure 7C:
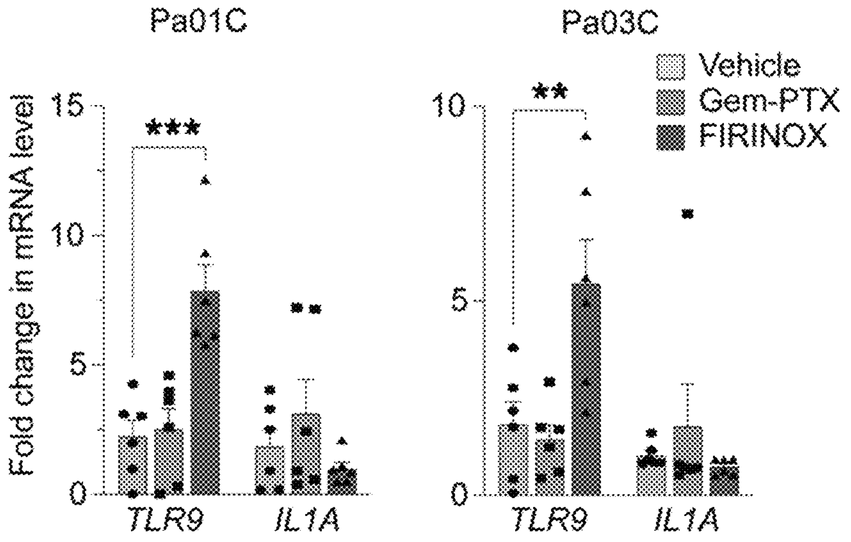
Figure 7D:
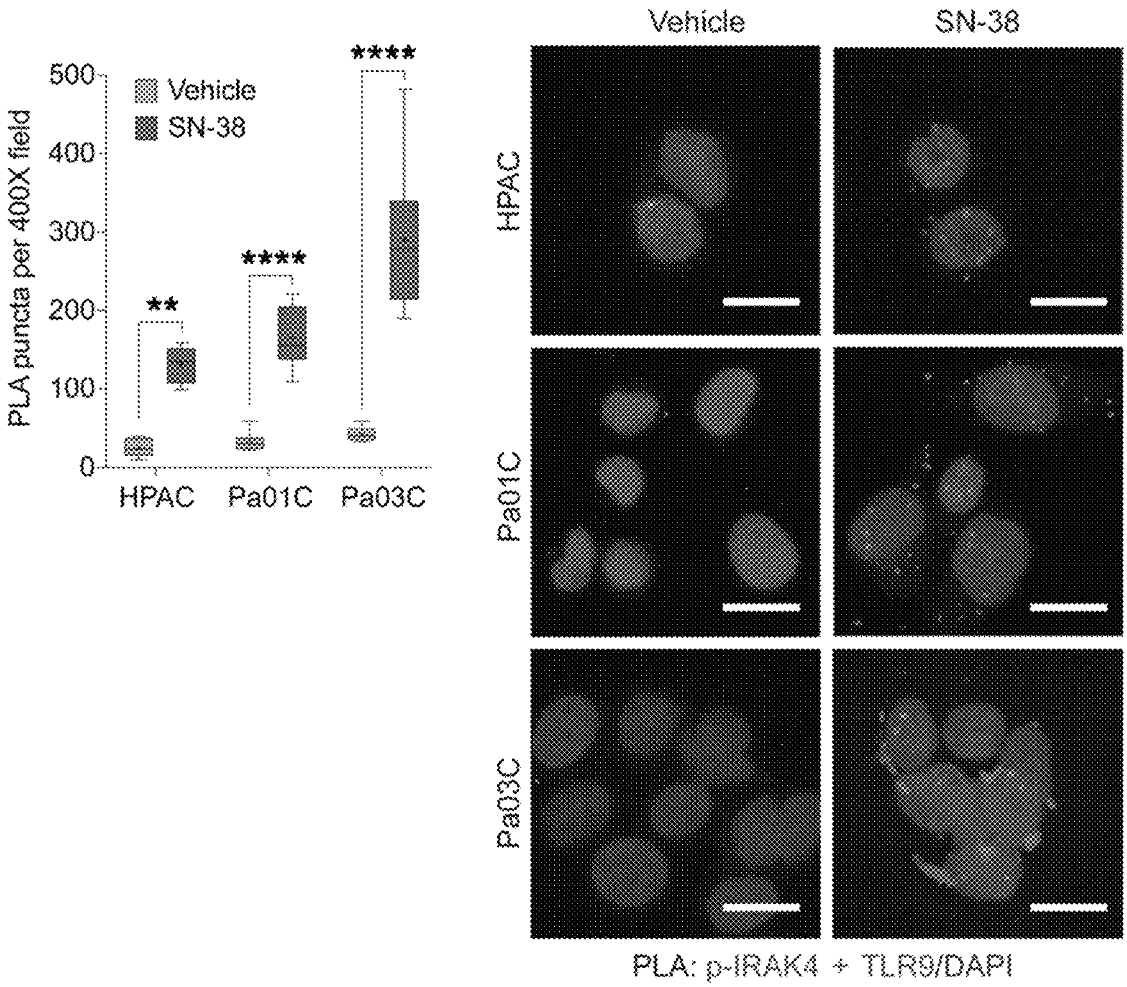
Figure 7E:
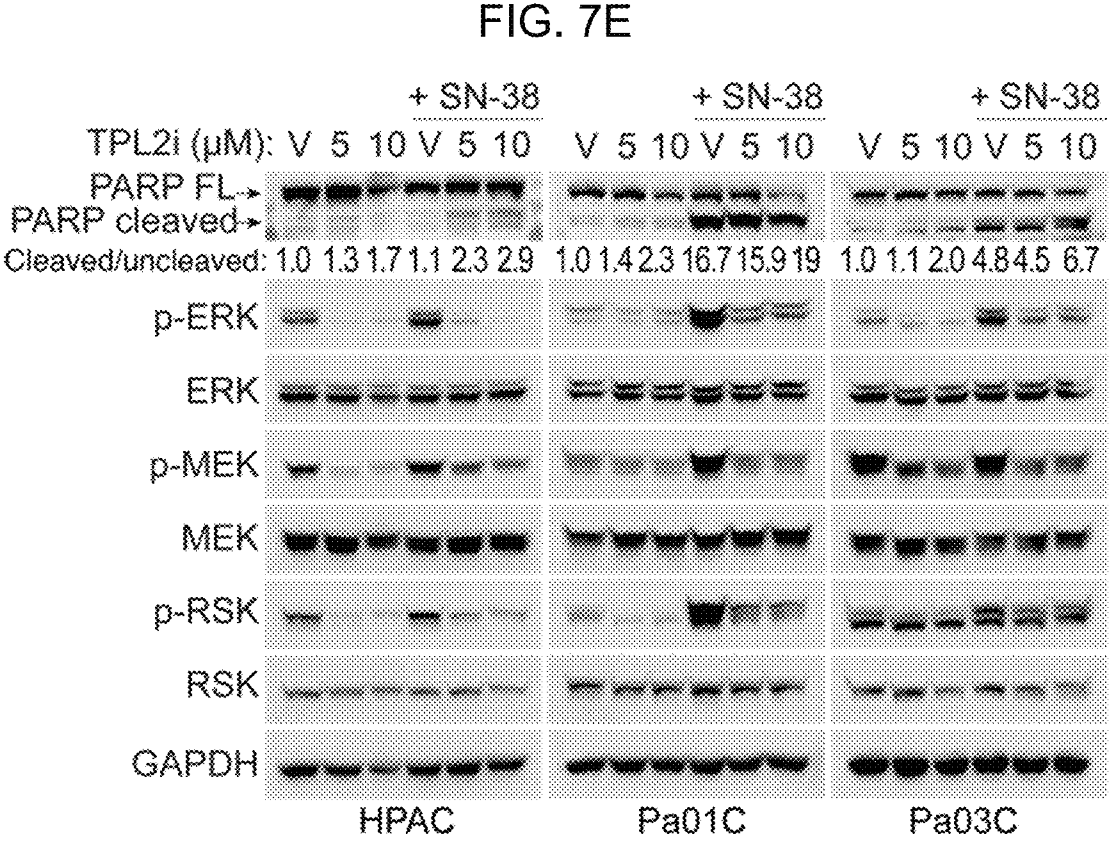
Figure 7F:
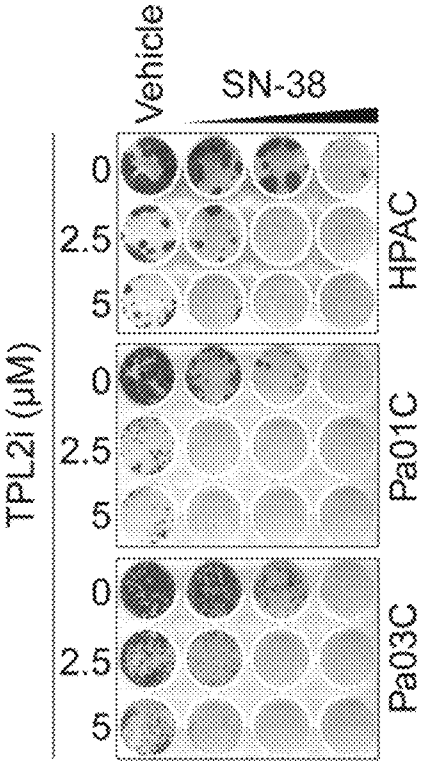
Figure 7G:
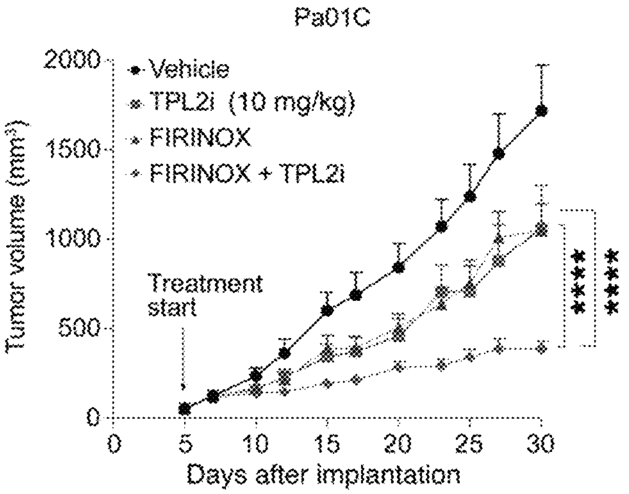
Figure 7H:
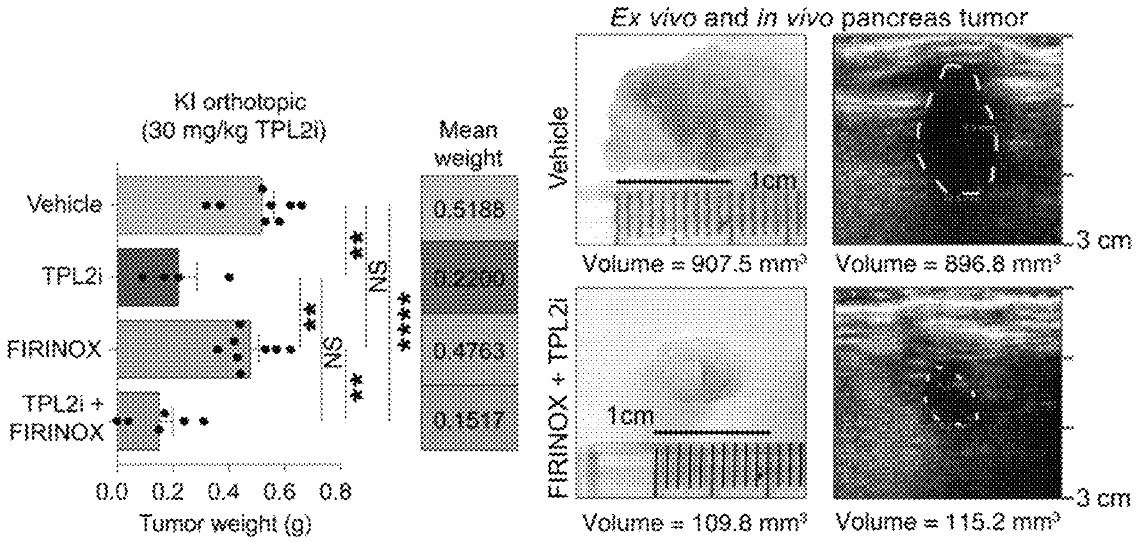
Figure 19B:
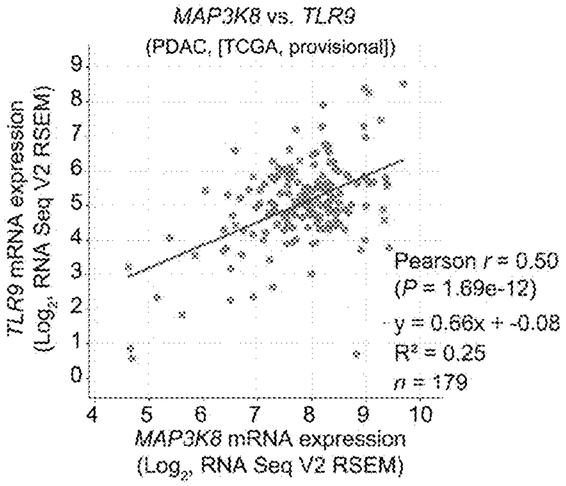
Figure 19C:
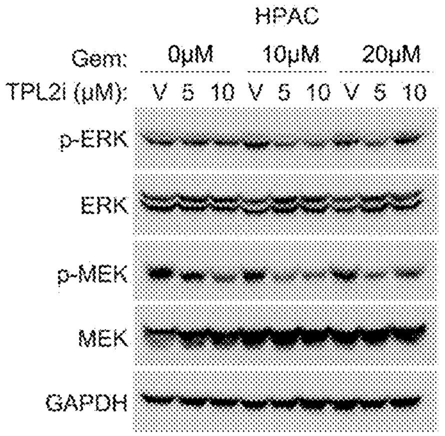
Figure 19D:
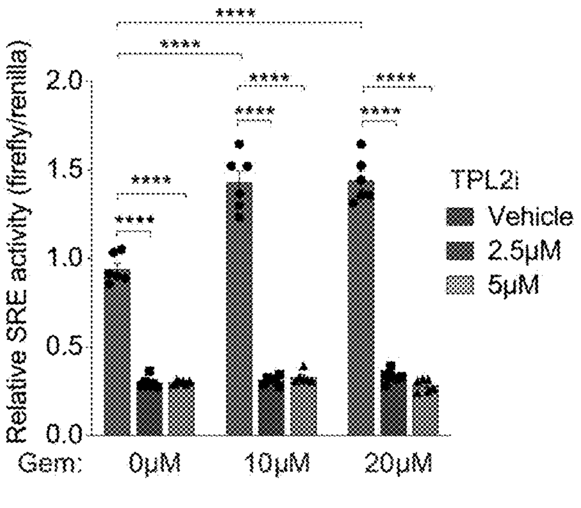
Figure 19E:
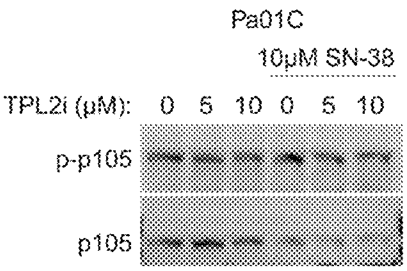
Figure 19F:
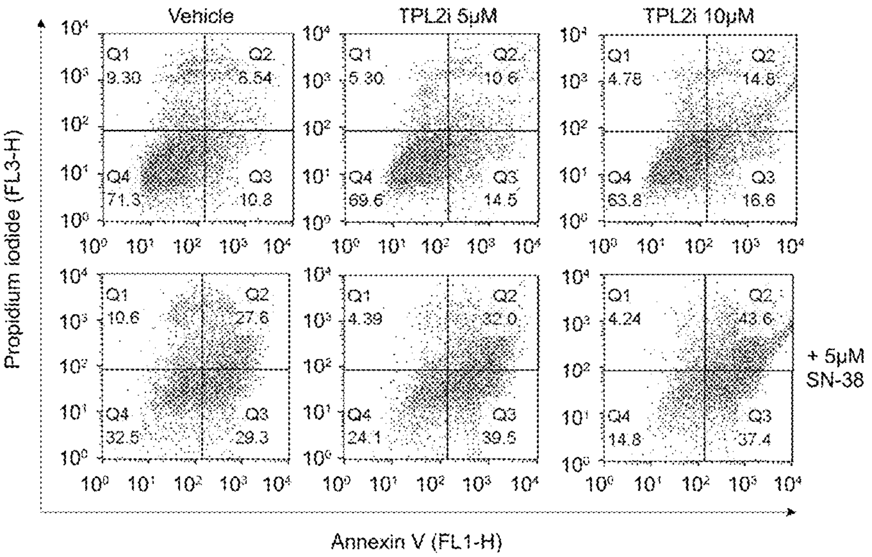
Figure 19G:
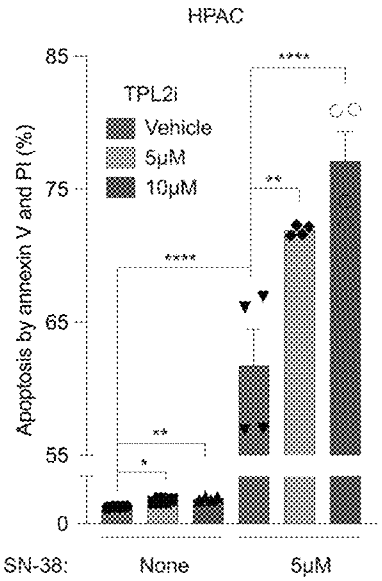
Figure 20A:
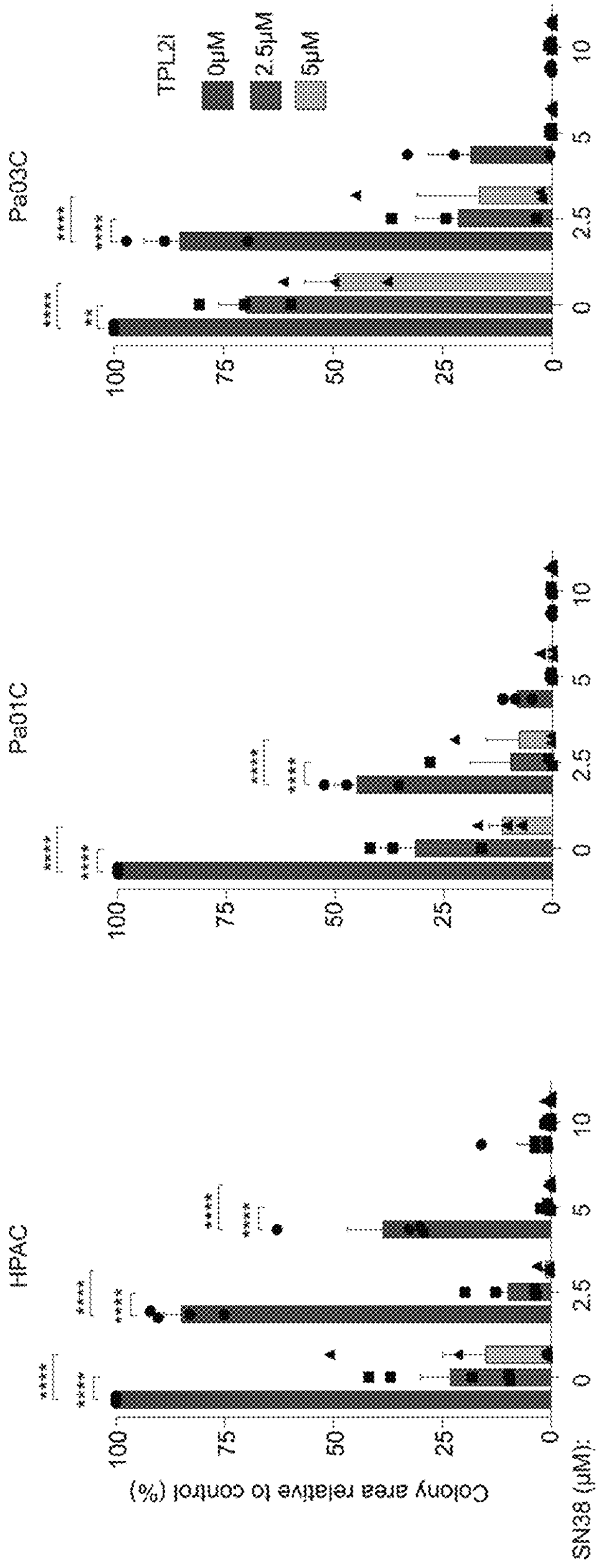
FIG. 20A-FIG. 20E. (A) Quantification of 2D clonogenic colony formation of three PDAC cell line treated with TPL2i, SN-38 or the combination for data shown in FIG. 7F. Data represents n=3 (Pa01C and Pa03C) and n=5 (HPAC) independent experiments. P values from two-way ANOVA with Dunnett's multiple comparison test. (B) Growth inhibition and Loewe additivity excess matrices of TPL2i added to SN-38 for HPAC cells. Darker colors indicate greater cytotoxicity (growth inhibition) and higher synergy scores (Loewe excess). Data shown is compilation of three independent experiments. Concentrations used are stated in method section. (C) Final weight of subcutaneous Pa01C tumors for experiment in FIG. 7G. One outlier was removed by Grubb's, alpha=0.01, and replaced with average value. P value from one-way ANOVA with Holm-Sidak's multiple comparison test. (D) Pictures of all Pa01C subcutaneous tumors isolated from mice treated with vehicle, TPL2i, FIRINOX or combination. Data is from same experiment in (C) and FIG. 7G. (E) Average body weight over time of nude mice for experiments in (C), (D) and FIG. 7G. All error bars indicate mean±SEM; **$P<0.0001$, *$P<0.0002$, **$P<0.0021$, *$P<0.0332$.
Figure 20B:
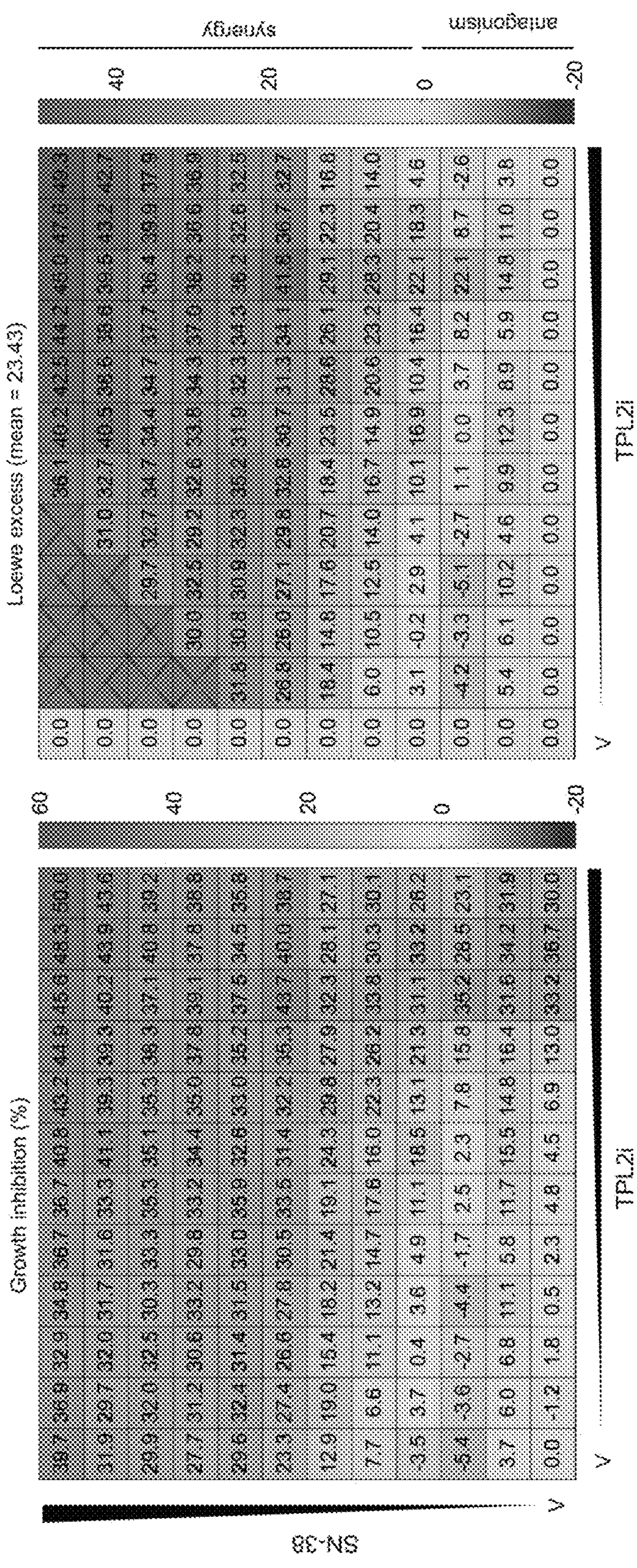
Figure 20C:
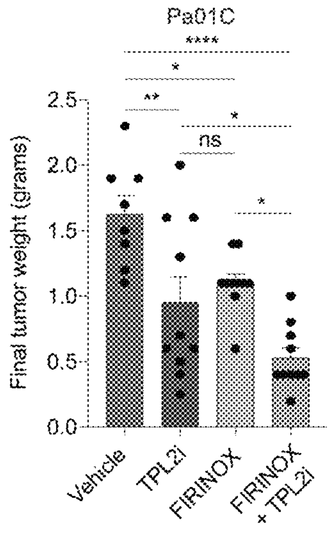
Figure 20D:
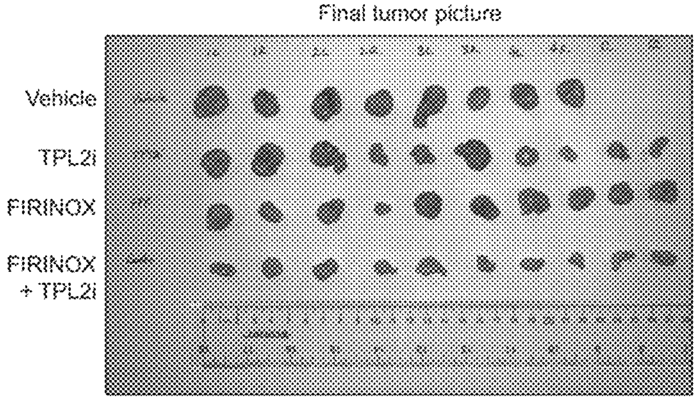
Figure 20E:
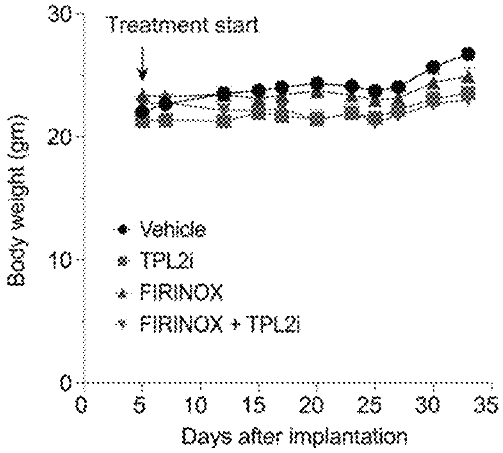

To determine the mechanism that activates these markers, HPAC cells were treated with gemcitabine/paclitaxel or FIRINOX (5-FU/SN-38/oxaliplatin), which mimic clinical regimens, and changes in expression of the TLRs and IL-1a/B were surveyed in HPAC cells. Intriguingly, significantly upregulated expression of TLR6, TLR9, and IL1A, but not IL1B, was observed upon exposure to either chemotherapy (see e.g., FIG. 7B). Survey of 2 other PDCLs, Pa01C and Pa03C, showed TLR9 to be the only gene consistently upregulated following FIRINOX treatment (see e.g., FIG. 7C). Importantly, signaling from TLR9 is transmitted exclusively through IRAK4. Indeed, proximity ligation assay showed markedly increased TLR9 and p-IRAK4 interaction following treatment of 3 different PDAC lines with SN-38 (see e.g., FIG. 7D), suggesting TLR9 to be the driver of IRAK4 and TPL2 upon chemotherapy exposure. Interestingly, analysis of TCGA data also revealed a strong and significant correlation (Pearson r=0.49, $P=2.61\times10^{-12}$) between TLR9 and MAP3K8 (TPL2) mRNA expression in PDAC samples (see e.g., FIG. 19B). Cotreatment with TPL2i significantly attenuated SN-38-induced p-MEK, p-ERK, and p-RSK, and increased poly (ADP-ribose) polymerase (PARP) cleavage in PDAC lines (see e.g., FIG. 7E). Gemcitabine-induced p-MEK and p-ERK levels and SRE activity were also suppressible with TPL2i (see e.g., FIG. 19C and FIG. 19D), suggesting that induction of MAPK activity is not specific to one class of cytotoxic agent. Besides the MAPK cascade, the TPL2i additionally suppressed p-p105 in SN-38-treated Pa01C cells (see e.g., FIG. 19E), making it a more broad-spectrum therapeutic agent than the MEK inhibitor or the ERK inhibitor in curbing chemotherapy-induced survival signaling. PDAC cells cotreated with SN38 and TPL2i showed significantly more apoptosis (see e.g., FIG. 19F and FIG. 19G) by flow cytometric analysis, and completely lost their clonogenicity, an assay that tests emergence of resistant clones (see e.g., FIG. 7F and FIG. 20A). Notably, the combination of TPL2i and SN-38 was synergistic in suppressing PDAC cell growth by the Loewe additivity model (see e.g., FIG. 20B). Accordingly, the combination of TPL2i and FIRINOX was significantly more efficacious in suppressing in vivo subcutaneous growth of Pa01C tumors compared with either treatment alone (see e.g., FIG. 7G, FIG. 20C, and FIG. 20D), and without incurring noticeable toxicities (see e.g., FIG. 20E). TPL2i alone was effective in significantly suppressing growth of orthotopic KI tumors in syngeneic FVB/NJ mice. When combined with FIRINOX, the mean tumor burden was seemingly further reduced, with 2 mice showing no evidence of cancer, although the difference between TPL2i and combo arms did not reach statistical significance probably due to low mouse number per arm (see e.g., FIG. 7H). These results show that targeting TPL2 overcomes genotoxic stress-induced survival signaling and enhances the efficacy of chemotherapy.

MAP3K8 Point Mutations, E188K and R442H, Hyperactivate MAPK and NF-κB Cascades.

Figure 8A:
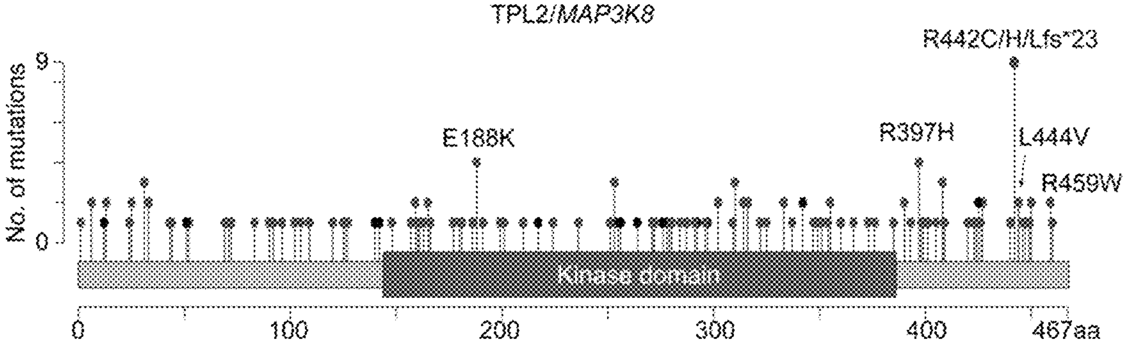
FIG. 8A-FIG. 8E. E188K mutation in MAP3K8/TPL2 is a gain-of-function mutation. (A) Lollipop plot adapted from CBioPortal (as of August 2019) identifying mutations in MAP3K8/TPL2. (B) Immunoblots of 293T cells transfected with empty expression vector (EV, control) or vector encoding HA epitope-tagged WT TPL2 or TPL2 E188K for 48 hours. (C) Relative serum-response element (SRE) activity and NF-κB reporter activity in 293T cells transfected as in B. Data are from 2 independent experiments. ****P<0.0001 by 2-way ANOVA followed by Tukey's multiple-comparisons test. (D) Heatmap representing relative expression in log 2 units of proteins evaluated by reverse-phase protein array (RPPA) of 293T cells transfected with empty vector (EV, control) or vector encoding HA-tagged WT TPL2 or TPL2 E188K in duplicate (n=2) for 48 hours. (E) Relative abundance (in log 2 units) of the top 15 upregulated targets in RPPA shown in D. p-ERK (in bold text) is the top hit and significantly upregulated targets are indicated with P values from 2-way ANOVA with Tukey's multiple-comparisons test. All data presented as mean±SEM.
Figure 21A:
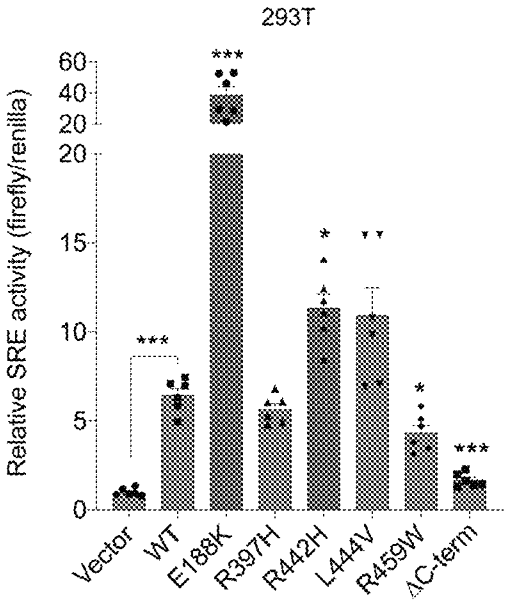
FIG. 21A-FIG. 21C. (A) Relative serum-response element (SRE) activity in 293T cells transfected with empty vector or vector encoding HA epitope-tagged TPL2 (wild-type or mutants) for 48 hours. Data is from two independent experiments, each of technical triplicate. (B) Relative NFKB reporter activity in 293T cells transfected with empty vector or vector encoding HA epitope-tagged TPL2 (wild-type or mutants) for 48 hours. Data is from two independent experiments, each of technical triplicate. (C) Relative viability of Hs695T cells treated with TPL2i for 120 hours. Experiment was done once in technical triplicate P values from one-way ANOVA with Dunnett's multiple comparison test. For (A) and (B) repeated measures one-way ANOVA with Dunnett's multiple comparison test (others vs. WT) was performed. All error bars denote mean±SEM; **$P<0.0001$, *$P<0.0002$, **$P<0.0021$, *$P<0.0332$.
Figure 21B:
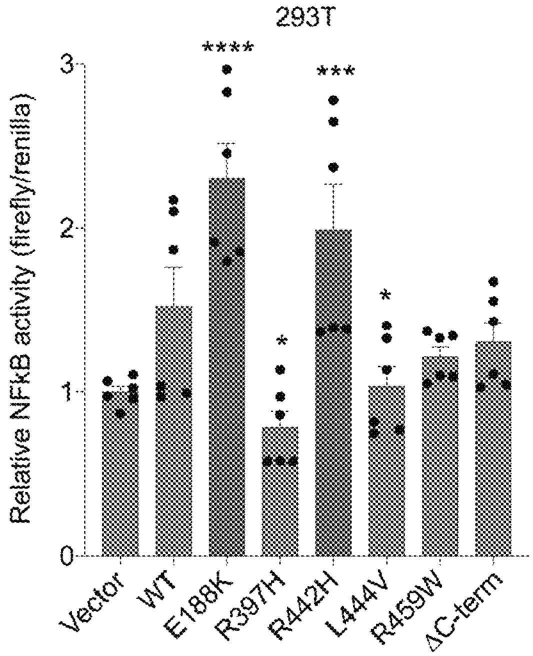

Aside from being summoned by oncogenic RAS and genotoxic stress, TPL2 is also spontaneously activated by genetic mutations. In the basal state, TPL2 protein is bound and inhibited by p105 (NF-κB1) and A20-binding inhibitor of NF-κB (ABIN-2). Activated IKK complex phosphorylates p105 and prompts its proteolysis to p50, which releases TPL2. TPL2 undergoes phosphorylation at residues S400 by IKK and T290 by an unknown kinase to become fully activated, after which it is proteasomally degraded via polyubiquitination at its C-terminus. Therefore, C-terminally truncated TPL2 is more stable and potent in activating the MAPK pathway. Oncogenic truncations and fusions of MAP3K8 are reported in spitzoid melanomas and predict sensitivity to MEK inhibitors in vitro. Besides truncations, from TCGA database several point mutations in MAP3K8 were observed across various non-PDAC cancer types that have not been characterized. Therefore, 5 point mutants that occur with the highest frequency were investigated: E188K, R397H, R442H, L444V, and R459W (see e.g., FIG. 8A). Of these mutants, E188K and R442H to be the most potent in stimulating SRE and NF-κB reporter activities (see e.g., FIG. 21A and FIG. 21B), which were characterized in further detail. The E188K mutation is detected in oligodendroglioma and colon and urothelial carcinoma, whereas R442 can acquire missense (to H or C) or nonsense mutations in colon, ovarian, and gastric cancers, and rhabdoid tumors.

Figure 8B:
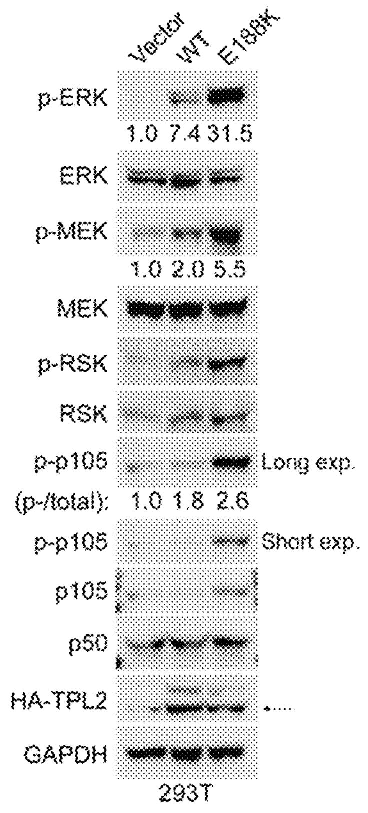
Figure 8C:
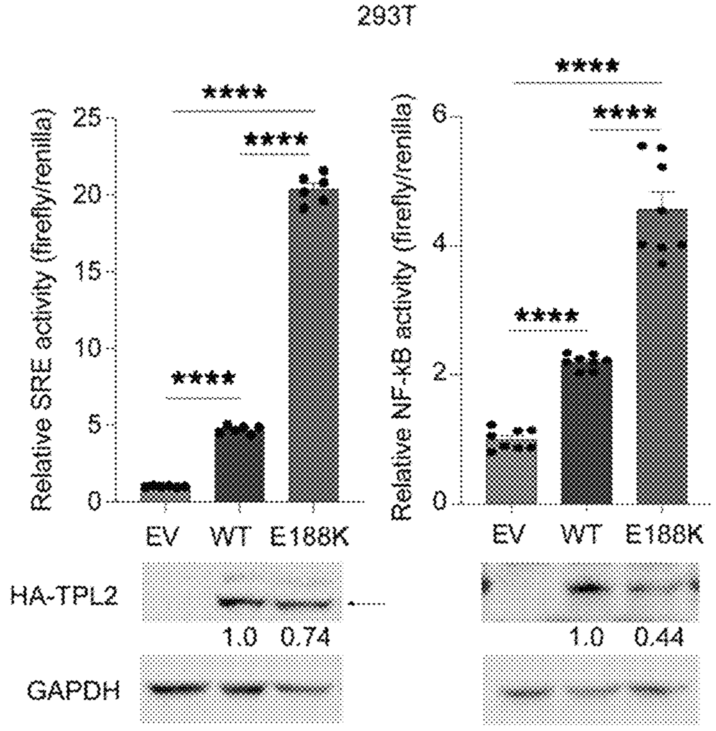
Figure 8D:
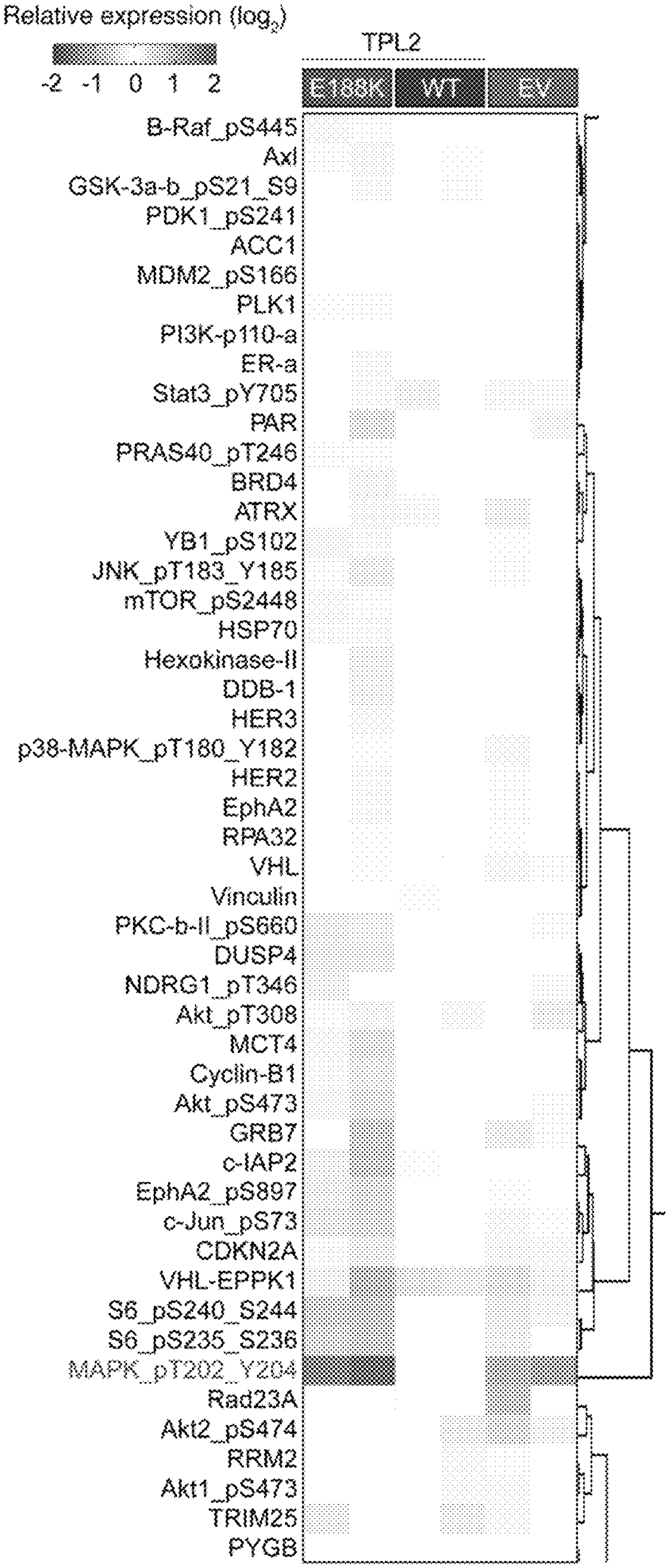
Figure 8E:
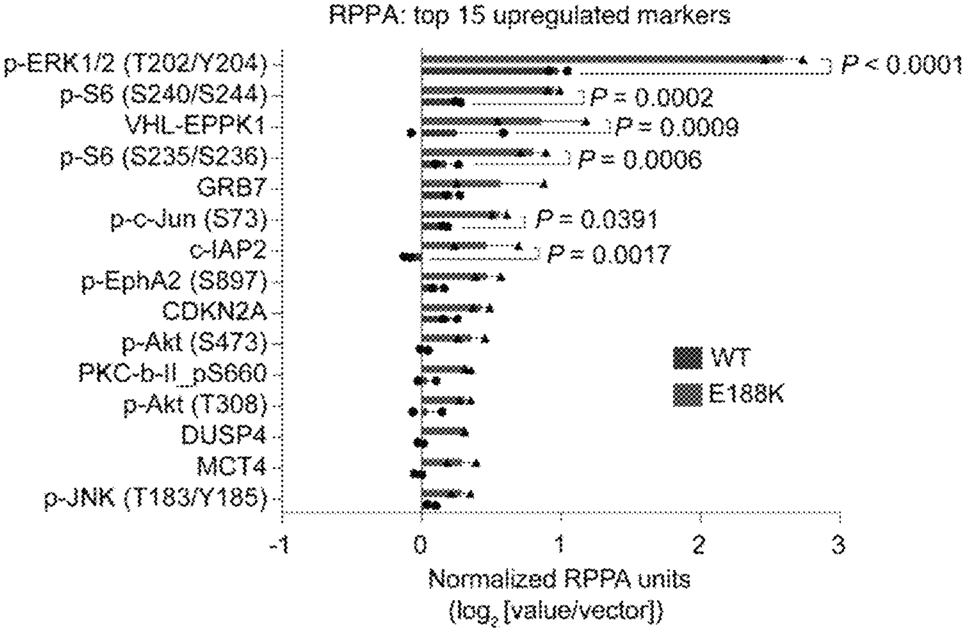

When expressed at the same level as WT, $TPL2^{E188K}$ is markedly more potent in activating MEK, ERK, RSK, and p105 (see e.g., FIG. 8B), as well as inducing SRE and NF-κB reporter activities (see e.g., FIG. 8C) in unperturbed 293T cells, clearly showing this is a gain-of-function mutation. To comprehensively evaluate the impact of the E188K mutation, RPPA analysis was performed on 293T cells ectopically expressing vector, and a roughly equal amount of $TPL2^{WT}$ or $TPL2^{E188K}$ (see e.g., FIG. 8B). Of all 441 markers analyzed, p-ERK is the most differentially upregulated marker in $TPL2^{E188K}$-expressing cells (see e.g., FIG. 8D), validating the findings with immunoblots and reporter assay. Significantly increased p-S6, a known substrate of ERK, and p-c-Jun, which has been described as a TPL2 effector were also observed (see e.g., FIG. 8E). This analysis showed, in a comprehensive and unbiased manner, the MEK/ERK cascade to be the predominant signaling cascade activated by the E188K mutation.

Figure 9A:
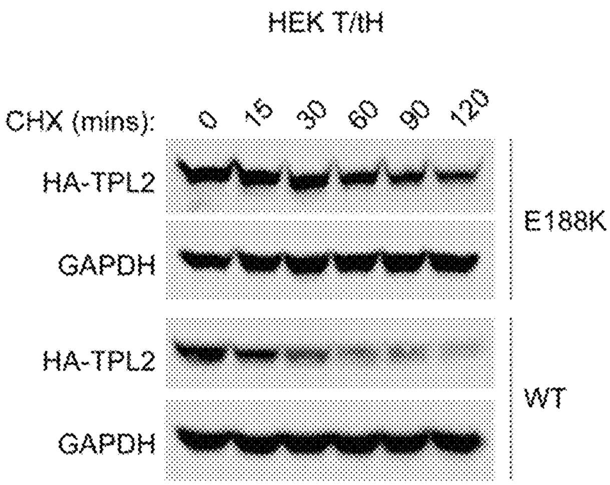
FIG. 9A-FIG. 9F. E188K mutation stabilizes TPL2 protein. (A) Immunoblots of HEK T/tH cells stably expressing HA epitope-tagged WT TPL2 or TPL2 E188K treated with 10 μg/mL cycloheximide (CHX). Table below shows half-life ($t_{1/2}$) of WT TPL2 and TPL2 E188K protein calculated by measuring HA-TPL2 band intensities, normalizing to $t_0$ and performing 1-phase exponential decay. Data represent 1 of 3 independent experiments showing similar results. (B) Immunoprecipitation of HA epitope-tagged WT TPL2 or TPL2 E188K treated with 10 μM MG132 (proteasome inhibitor) and immunoblotted as indicated. (C) Sanger sequencing peaks of MAP3K8 (TPL2) locus in Hs695T. Arrow indicates the naturally occurring missense point mutation responsible for the Glu->Lys substitution at codon 188 (E188K) in TPL2 in the Hs695T cell line. (D) Immunoblot of Hs695T cells treated with TPL2i or vehicle (V) for 24 hours in 10% serum-containing media. (E) Proliferation of Hs695T cells treated with TPL2i. P values from 2-way ANOVA with Dunnett's multiple-comparisons test. (F) Viability of Hs695T cells treated with PLX4032 (BRAFi) alone or in combination with 2 different concentrations of TPL2i. Graph on right depicts $GI_{50}$ of PLX4032 in log 10 units. Data represent 10 replicates from 4 independent experiments. P values are from 1-way ANOVA with Dunnett's multiple-comparisons test. All data presented as mean±SEM. **P<0.0001; *P<0.0002; **P<0.0021.
Figure 9B:
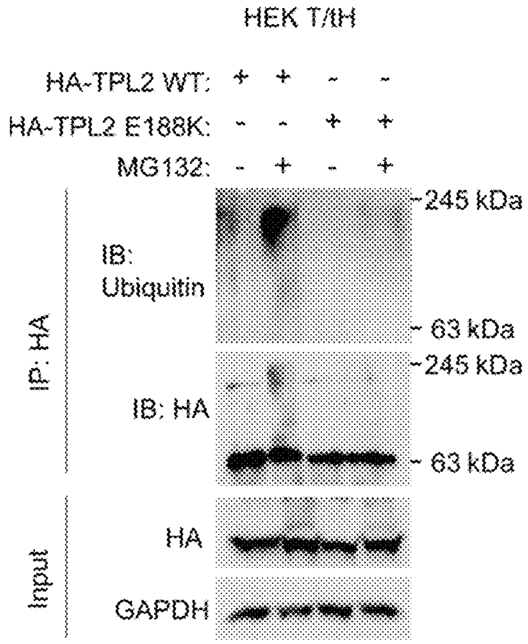
Figure 9C:
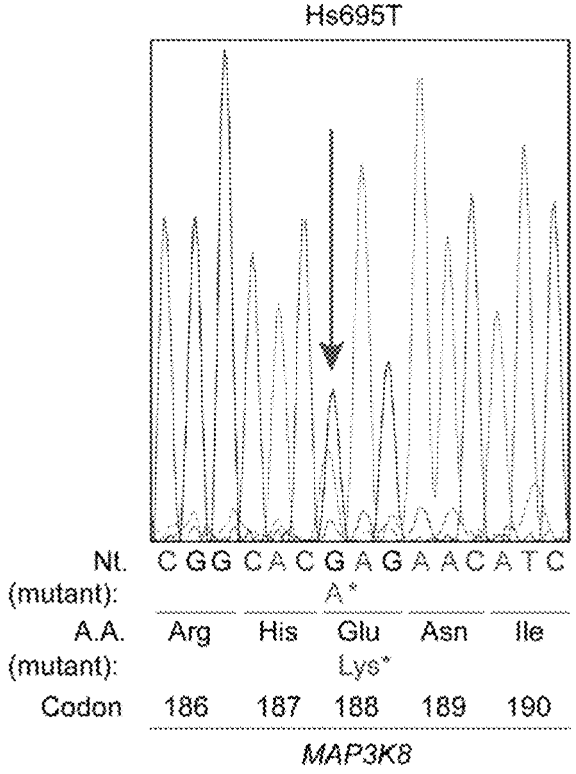
Figure 9D:
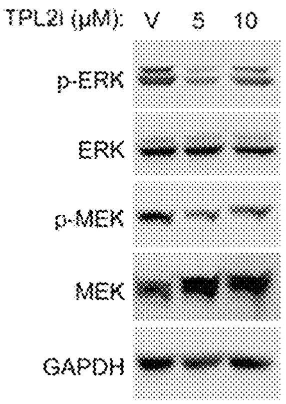
Figure 9E:
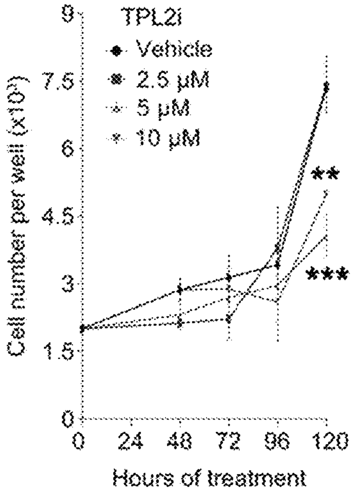
Figure 9F:
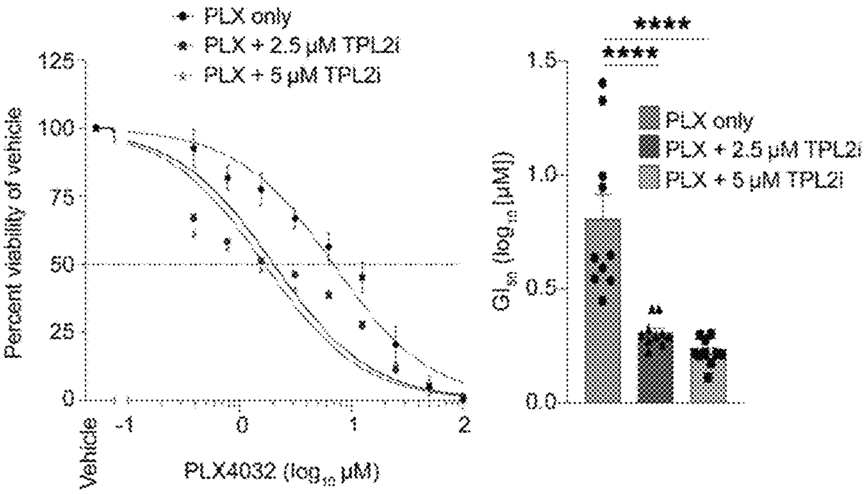
Figure 21C:
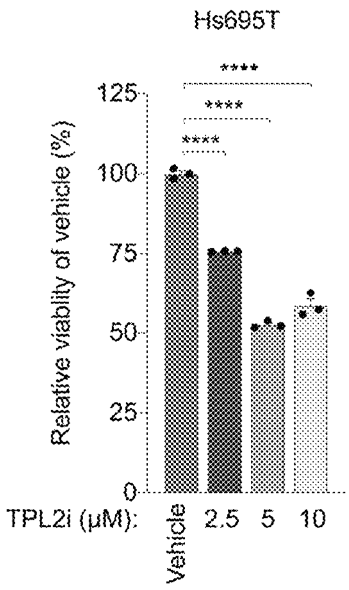

To delineate the molecular mechanism underlying the enhanced kinase activity of $TPL2^{E188K}$, the half-lives of TPL2WT and $TPL2^{E188K}$ were compared in 293T cells treated with a protein synthesis inhibitor, cycloheximide. Surprisingly, the E188K mutation, despite being located within the kinase domain, rendered the TPL2 protein more stable (see e.g., FIG. 9A). Supporting this finding, immunoprecipitation assay showed that the E188K mutation almost completely abolished TPL2 polyubiquitination, a prerequisite for proteasomal degradation (see e.g., FIG. 9B). To evaluate the oncogenicity of $TPL2^{E188K}$, Hs695T, a $BRAF^{V600E}$-mutant melanoma cell line that naturally harbors the $MAP3K8^{E188K}$ mutation was obtained. Sanger sequencing of cDNA from Hs695T confirmed a G->A mutation in codon 188 of MAP3K8, which converts glutamate (GAG) to lysine (AAG) (see e.g., FIG. 9C). Therefore, $TPL2^{E188K}$ may be an oncoprotein driving MAPK activation in this cell line. Supporting this notion, treatment with TPL2i suppressed p-ERK and p-MEK (see e.g., FIG. 9D) as well as in vitro proliferation and viability of Hs695T cells (see e.g., FIG. 9E and FIG. 21C). Importantly, the BRAF inhibitor PLX4032 had a modest growth suppressive effect, but when combined with TPL2i, it significantly lowered ($P<0.0001$) the viability of Hs695T (see e.g., FIG. 9F), indicating that both BRAF and MAP3K8 mutations contribute to MAPK activity in this cell line.

Figure 10A:
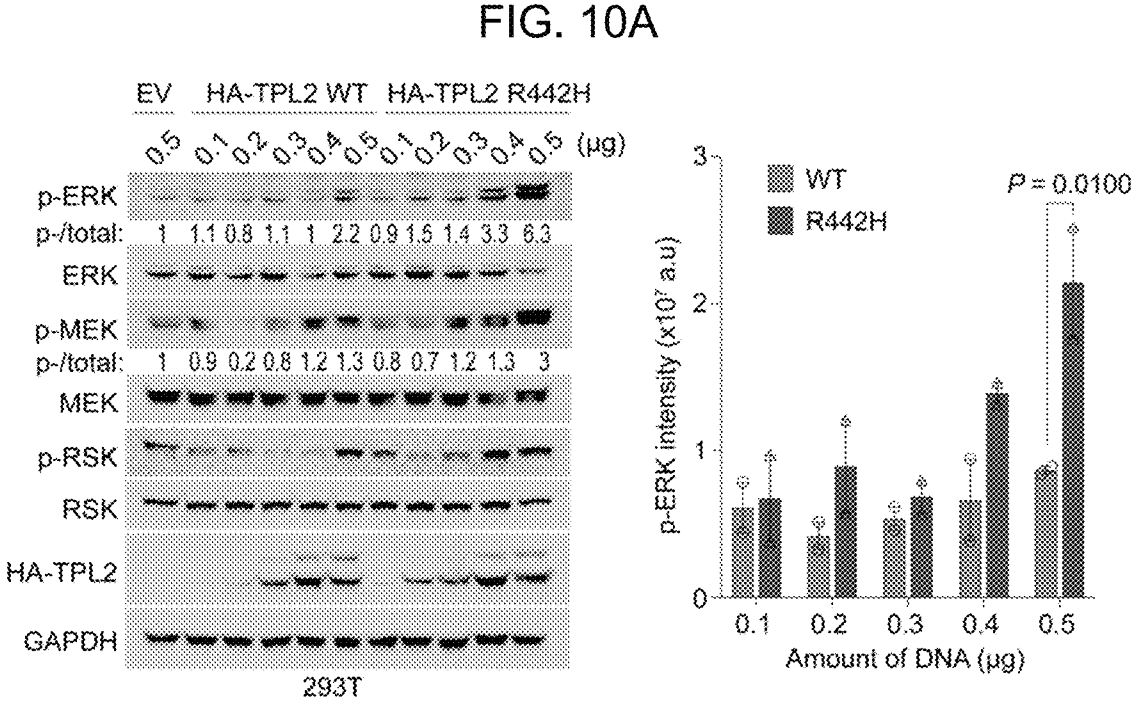
FIG. 10A-FIG. 10H. R442H is a gain-of-function mutation that curtails proteasomal degradation of TPL2. (A) Immunoblots of 293T cells transiently transfected with empty vector (EV), or vector encoding HA epitope-tagged WT TPL2 or TPL2 R442H for 48 hours. On right is quantification of p-ERK band intensities for WT TPL2 and TPL2 R442H samples from immunoblots on left. Data represent 2 independent experiments. P values from 2-way ANOVA with Holm-Sidak multiple-comparisons test. (B) Immunoblots of HEK T/tH cells stably expressing vector encoding WT TPL2 or TPL2 R442H and treated with 10 μg/mL cycloheximide (CHX) for indicated durations. Table states half-life ($t_{1/2}$) of TPL2 WT and mutant proteins calculated by measuring HA-TPL2 band intensities, normalizing to $t_0$ and performing 1-phase exponential decay analysis as shown in graph at the bottom. Experiment was performed 3 times and 1 set of data is shown. (C) Immunoblots of HEK T/tH cells stably expressing empty vector or HA epitope-tagged TPL2 mutants treated with 10 μM MG132 (proteasome inhibitor) for 4 hours. One of 2 or more independent experiments is shown. C-terminally truncated TPL2 (ΔC-term) is used as positive control. Poly-Ub, polyubiquitinated. (D) Immunoblots of IGROV1 cells serum starved for 24 hours and treated with TPL2i for 2 hours. (E) Immunoblots of IGROV1 cells after shRNA-mediated TPL2 depletion. (F and G) Proliferation of IGROV1 cells treated with TPL2i and after shRNA-mediated TPL2 depletion, respectively. P values from 2-way ANOVA with Dunnett's multiple-comparisons test. (H) 3D organoid growth of IGROV1 cells after shRNA-mediated TPL2 depletion and rescue with either WT TPL2 or R442H mutant. Organoids were counted from 4 independent transfected wells per condition. Scale bars: 100 μm. P values from 1-way ANOVA with Dunnett's multiple-comparisons test. All data presented as mean±SEM. **P<0.0001; *P<0.0002; **P<0.0021; *P<0.0332.
Figure 10B:
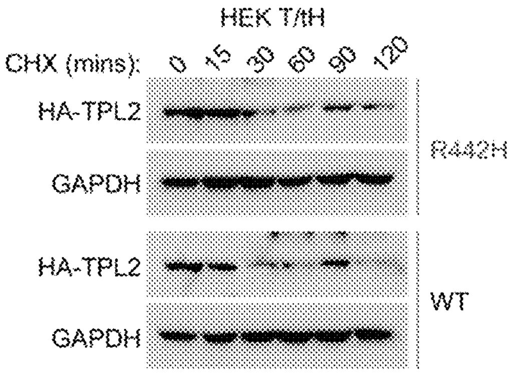
Figure 10B:
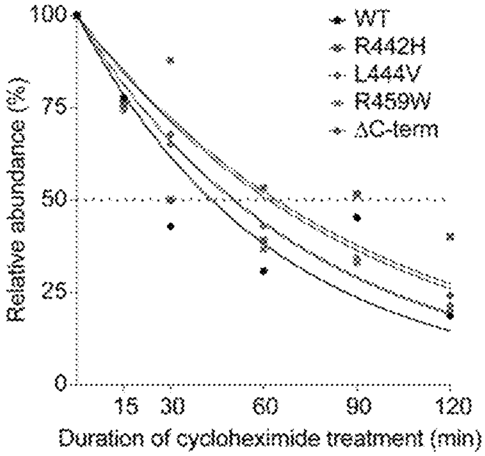
Figure 10C:
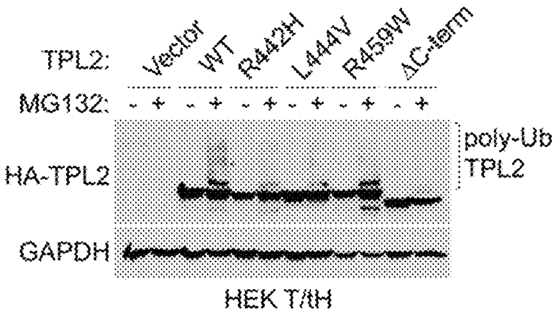
Figure 10D:
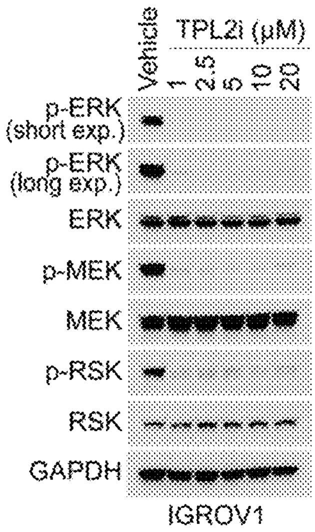
Figure 10E:
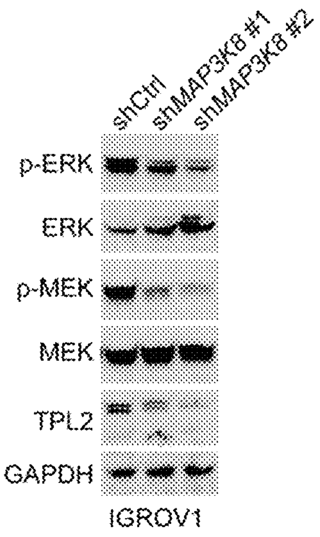
Figure 10F:
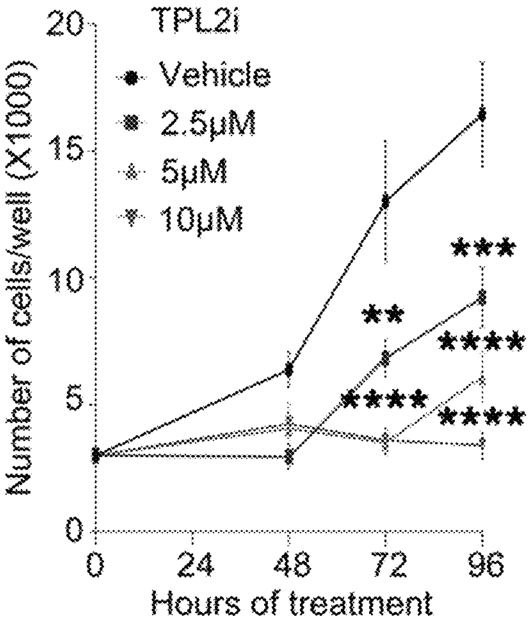
Figure 10G:
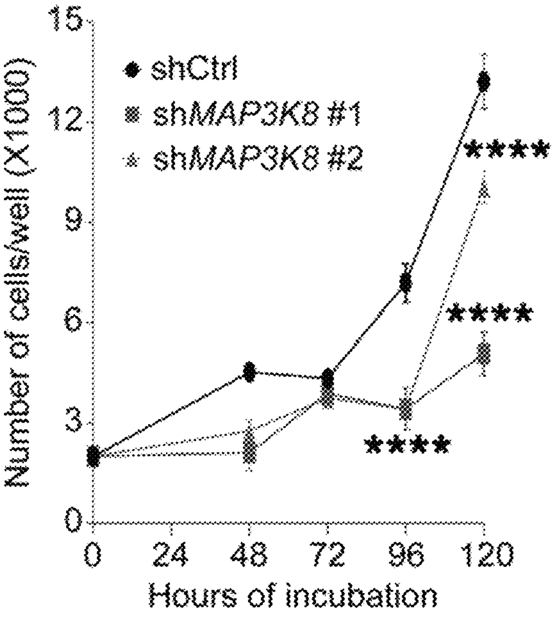
Figure 10H:
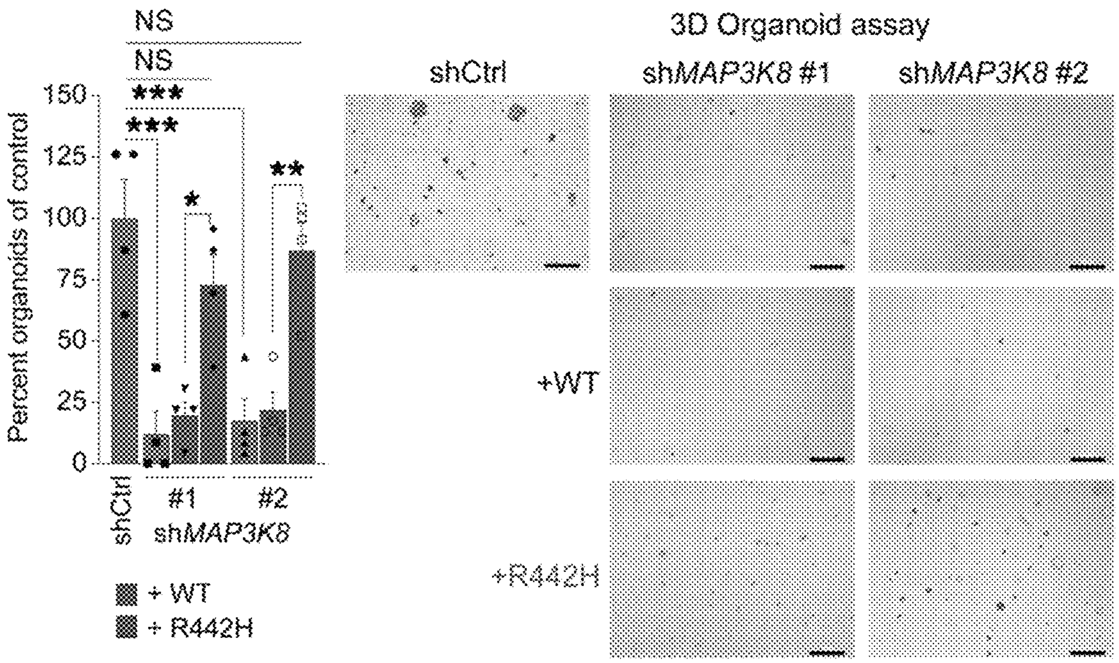
Figure 22A:
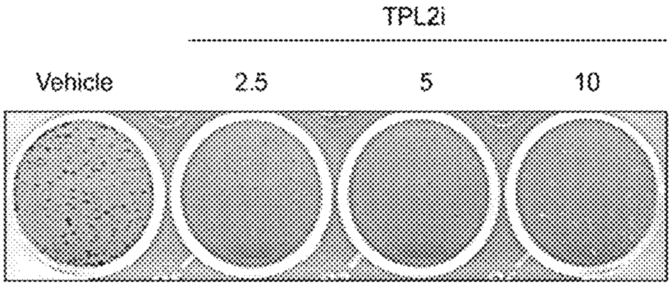
FIG. 22A-FIG. 22D. (A) 2D clonogenic colony formation of IGROV1 cells treated with TPL2i. (B) Relative viability of IGROV1 cells treated with TPL2i for 96 hours. Data is average of nine replicates from two independent experiments. (C) Quantification of soft agar colonies formed by IGROV1 cells after shRNA mediated TPL2 depletion. Data is average of three replicates from a single experiment. Scale bar is 500 μm. (D) Image showing 2D clonogenic growth of IGROV1 cells after TPL2 knockdown as well as restoration of TPL2 expression with TPL2 WT or TPL2 R442H. For (B) and (C), P values from one-way ANOVA with Dunnett's multiple comparison test. All error bars indicate mean±SEM; **$P<0.0001$, *$P<0.0002$, **$P<0.0021$, *$P<0.0332$.
Figure 22B:
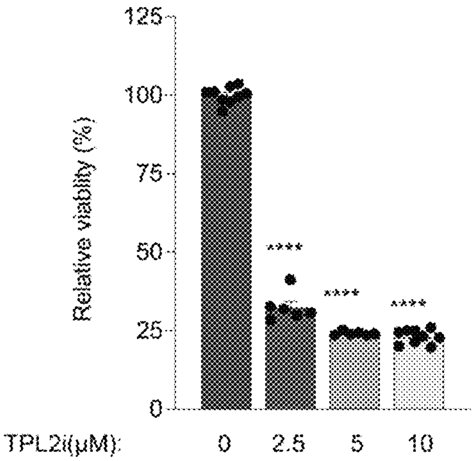
Figure 22C:
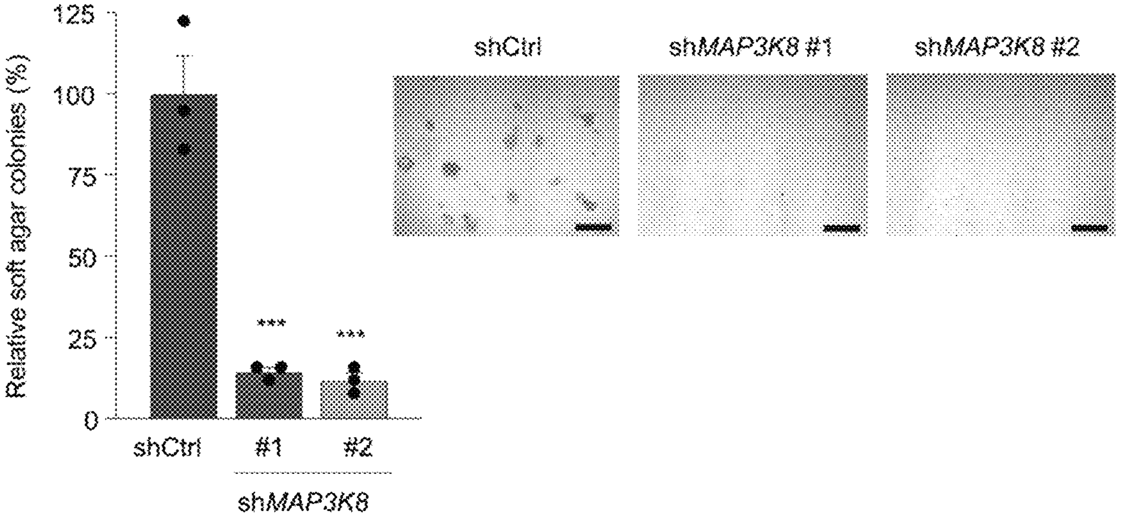
Figure 22D:
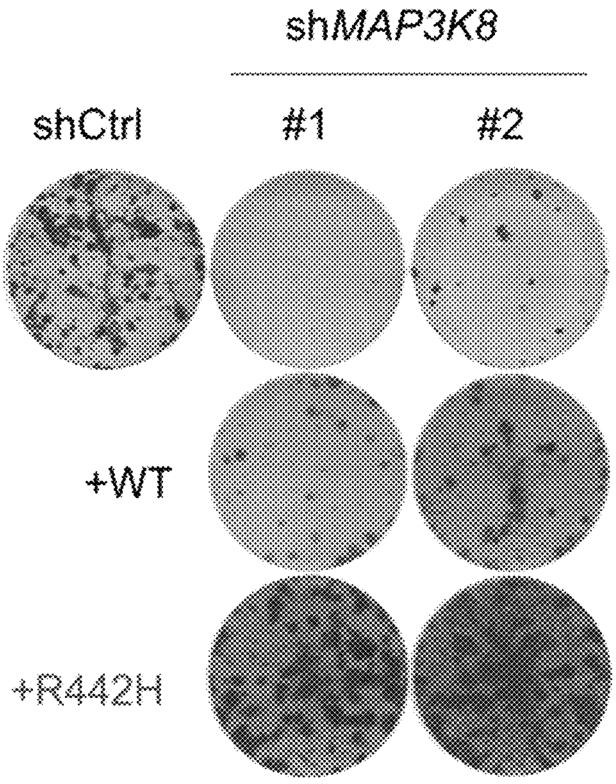

Next the effect of mutation at codon 442 was determined, which resides in the C-terminus, implying disruption of degradation function. The R442H mutant was studied because it is the most common mutation described in TCGA and more potent in inducing SRE and NF-κB reporter activity than WT protein (see e.g., FIG. 21A and FIG. 21B). Compared with $TPL2^{WT}$, $TPL2^{R442H}$ is more potent in activating MEK, ERK, and RSK (see e.g., FIG. 10A) when expressed at equivalent levels. As expected, the stability of $TPL2^{R442H}$ mutant protein was higher than $TPL2^{WT}$ and comparable to C-terminally truncated TPL2 (see e.g., FIG. 10B). Interestingly, other mutations including L444V and R459W also render TPL2 slightly more stable than the WT form, albeit not to the degree imparted by R442H. All these mutations reduce polyubiquitination of TPL2 (see e.g., FIG. 10C), which explains their increased stability. The naturally occurring $MAP3K8^{R442H}$ mutation has been reported in the ovarian cancer cell line IGROV1. Remarkably, short-duration (2 hours) treatment with a very low dose of TPL2i (1 μM) completely blocked p-MEK, p-ERK, and p-RSK in this cell line to undetectable levels even with high exposure time (see e.g., FIG. 10D), suggesting that TPL2 is the dominant driver of MAPK activity in this cell line. In support of this, partial knockdown of TPL2 also reduced MAPK activity in IGROV1 (see e.g., FIG. 10E). Pharmacologic inhibition or silencing of TPL2 significantly decreased the proliferation, colony forming ability, and AI growth of IGROV1 (see e.g., FIG. 10F, FIG. 10G, and FIG. 22A-FIG. 22C), consistent with prior reports. Importantly, while knockdown of TPL2 markedly crippled the ability of IGROV1 to grow into 3D organoids or 2D clones, these growths could only be rescued by reexpression of $TPL2^{R442H}$ but not $TPL2^{WT}$ (see e.g., FIG. 10H and FIG. 22D). Overall, these studies appear to be the first to describe gain-of-function point mutations of MAP3K8 (TPL2) in human cancers, further prompting the need to identify these mutations in clinical practice and develop dedicated TPL2 inhibitors for clinical trials.

Discussion

This study provides broader understanding of the role of IRAK4 and TPL2 in human cancers. Using genetically defined cell lines and PDAC as a disease model, it was shown herein that KRAS oncoprotein uses the MAPK cascade to upregulate IL-1β production, leading to autocrine activation of IRAK4 and TPL2, which feeds back to escalate MAPK activity and additionally the NF-κB cascade. Following genotoxic stress, PDAC cells upregulate TLR9, leading to enhanced utilization of the IRAK4/TPL2 axis to sustain survival. Additionally, characterized herein is what appears to be novel gain-of-function TPL2 mutations that hyperactivate the MAPK and NF-κB pathways.

The malignant feats of RAS oncoproteins result from direct and indirect signaling mechanisms. RAS oncoproteins can directly bind and activate several effectors including the RAF kinases, PI3 kinases, RalGEFs, and Tiam1. Through these pathways, a plethora of inflammatory chemokines and cytokines including IL-6, IL-8, IL-1α/β, and CCL5 are produced, which in an autocrine manner trigger the inflammatory JAK/STAT and NF-κB cascades. These secondary events not only help propagate tumor progression, but also shield cancer cells from therapeutic attacks. For instance, in KRAS-mutant lung cancer, TBK1- and IKK-driven CCL5 and IL-6 can activate the JAK/STAT pathway to confer resistance to MEK inhibitors. In PDAC, STAT3 activation drives resistance to MEK inhibitors. Therefore, autocrine/paracrine cytokine signaling provides equally essential support, in addition to the intrinsic oncogenic events, that help cancer cells adapt and withstand stress. Shown herein is that the autocrine IL-1B-driven IRAK4/TPL2 axis is an essential component of KRAS and MAPK signaling. Because IRAK4 is typically activated by inflammatory receptors IL-1R, TLRs, and TNER, it is most widely studied as the driver of NF-κB activity in immune cells. Strikingly, ablation of IRAK4 completely blocked RAS-induced transformation and tumorigenicity in both epithelial cells and fibroblasts, as well as PDAC cells. These data are in strong agreement with a previous study showing that ablation of IKKB, a key downstream substrate of IRAK4, completely abolished PDAC development in a KRASIInk4a mouse model. The IL-1R antagonist Anakinra is currently being tested in clinical trials in combination with chemotherapy for PDAC. Downstream of IRAK4, revealed herein is TPL2 as a MAP3K that drives MEK/ERK and NF-κB p105 in KRAS-mutant cells independently of the RAF kinases. Therefore, TPL2 is a promising therapeutic target that controls multiple signaling cascades in KRAS-driven cancers.

Aside from enforcing KRAS autocrine signaling, the IRAK4/TPL2 axis is further used following genotoxic stress as a survival mechanism. Induction of MAPK activity is a well-established mechanism that allows cancer cells to endure genotoxic stress. However, MEK inhibitors fail to potentiate chemotherapy in pancreatic cancer, suggesting that targeting MAPK alone is insufficient, or that compensatory escape mechanisms such as enhanced NF-κB activity should be cotargeted. Similarly, in a prostate cancer model, addition of an NF-κB pathway inhibitor significantly potentiates the antitumor effect of MEK inhibitors. Herein, it was found that PDAC cells adapt to chemotherapy by upregulating TLR9, which signals through IRAK4/IKK/TPL2 to activate multiple pathways. Therefore, PDAC cells use different receptors, IL-1R at baseline and TLR9 during genotoxic stress, to engage the same IRAK4/IKK/TPL2 axis for survival. It is important to keep in mind that since the therapeutic spectrum of TPL2i extends beyond MEK/ERK, encompassing the NF-κB, JNK, and p38 cascades, all of which have been implicated in chemoresistance, TPL2 may be a more promising therapeutic target than MEK or ERK when combined with chemotherapy, at least in PDAC. In accordance, pharmacologic TPL2 inhibition completely blocked chemotherapy-induced MAPK and NF-κB activation, resulting in greater apoptosis and tumor suppression in vivo (see e.g., FIG. 19A-FIG. 19G, FIG. 20A-FIG. 20E, and FIG. 23).

This study appears to be the first to report gain-of-function point mutations of TPL2. Overexpression, C-terminal truncations, or fusions of TPL2 have been found in T cell neoplasms, melanoma, ovarian, breast, and lung cancers. These mutations are associated with RAF inhibitor resistance, and can be targeted with MEK inhibitors. Compared with WT protein, the E188K and R442H mutants studied herein are more stable and capable of hyperactivating both MAPK and NF-κB cascades. Furthermore, cancer cell lines naturally harboring these mutations (Hs695T for E188K, and IGROV1 for R442H) are highly sensitive to TPL2 inhibition. Importantly, TPL2i significantly suppressed MAPK activity and proliferation of $BRAF^{V600E}$IMAP3K8$^{E188K}$ double-mutant Hs695T cells, but not in $BRAF^{V600E}$IMAP3K8WT BxPc-3 cells, demonstrating that MAP3K8$^{E188K}$ is oncogenic.

The crystal structure of the C-terminus of TPL2 has not been resolved, and therefore how these mutations conformationally alter the entire protein is unclear. It has been suggested that the C-terminus of TPL2 negatively regulates TPL2 kinase activity via intramolecular interaction with its kinase domain. In addition, the C-terminus of TPL2, upon IKK-dependent phosphorylation of S400 and S443, binds to the 14-3-3 complex that stabilizes TPL2 and increases its kinase activity toward MEK1, possibly by relieving the kinase-inhibitory interaction between the C-terminus and kinase domain. The R442H mutation may impact TPL2 binding with 14-3-3, resulting in the increased stability and increased MEK and ERK activation that was observed herein. On the other hand, R442 is part of a conserved MAPK recognition motif (KRQRSLYIDL) present on TPL2. This raises the possibility that mutation of Arg to His at this residue may alter TPL2's binding affinity and/or specificity for substrates, although detailed additional work may be needed to prove this. The mechanism by which the E188K mutation stabilizes the protein is intriguing, as this residue is located within the kinase domain which is distant from the C-terminal degron. It is possible that this E188K mutation enhances the intrinsic kinase activity in addition to disrupting its degradation, but confirmation of this may need the resolution of the entire TPL2 protein structure. Furthermore, the mechanism including the E3 ligase that governs the degradation of TPL2 is unknown and should be investigated. This is especially important because the PDAC TMA showed p-IRAK4 level to be strongly associated with high TPL2 protein level, which in turn is associated with poor prognosis. Therefore, high IRAK4 activity may protect TPL2 from degradation, although the detailed mechanism remains to be determined. Whether upstream TLR/IL-1R activation is required for the enhanced activity of the E188K or R442H mutant is uncertain. However, this is unlikely because these mutants exhibit markedly enhanced activity in unperturbed 293T cells compared with the WT counterpart. Importantly, both E188K and R442H mutants remain sensitive to the TPL2i that was tested. TPL2i and RAFi cooperate to curb the growth of Hs695T cells that harbor MAP3K8$^{E188K}$ and $BRAF^{V600E}$ mutations, and MAPK activity in IGROV1 ovarian cancer cells that harbor only the MAP3K8R442H mutation is completely abolished by low-dose TPL2i.

Demonstrated herein is the in vivo antitumor efficacy of TPL2i as a single agent and in combination with chemotherapy. Targeting IRAK4 or TPL2 is not expected to have severe side effects and none were observed in mice. Irak4-knockout mice are viable and have normal lifespan but are immunocompromised. Humans with inborn IRAK4 deficiency are susceptible to life-threatening bacterial infection in early infancy, but with proper antibiotic prophylaxis have survived into adolescence and adulthood. The IRAK4 inhibitor CA-4948 is now in clinical trial for patients with refractory hematologic malignancies, and is found to be rather well tolerated, with 23% of patients developing grade 1-2 neutropenia. Similarly, Map3k8-knockout mice do not exhibit obvious phenotypic defects, and have normal bone marrow but are impaired in MEK/ERK activation and TNF-α production following LPS challenge. To date, no TPL2i has been developed and tested in clinical trials. TPL2 is a more versatile kinase that controls multiple oncogenic pathways besides MEK/ERK, and therefore development of a dedicated TPL2i is needed especially for KRAS- or MAP3K8-mutant cancers.

In conclusion, this study comprehensively describes an essential role of IRAK4 and TPL2 in oncogenic RAS signaling, using PDAC as a disease model. Mechanistically, it was shown that the IRAK4/TPL2 axis is differentially engaged in the basal state versus during genotoxic stress by different upstream receptors. It was shown that TPL2 inhibition synergistically sensitizes PDAC to chemotherapy in in vivo models, which is a potentially novel therapeutic strategy. Finally, 2 gain-of-function mutations of MAP3K8 (TPL2) were characterized in melanoma and ovarian cancer, which complement other studies describing overexpression, truncations, or fusion of MAP3K8 (TPL2) as being oncogenic. Overall, this study urges development of dedicated TPL2 is and detection of MAP3K8 (TPL2) mutations for cancer patients.

Methods

Cell Lines

All cell lines including HPNE, HPNE-KRAS$^{G12D}$, HPAC, and Hs695T were obtained from ATCC, which performed its own authentication by short tandem repeat DNA profiling. IGROV1 cells were a gift and originated from the NCI-60 panel (see e.g., Shoemaker (2006) *Nat Rev. Cancer.* 6 (10): 813-823) and not further authenticated. The HEK T/tH cell line was a gift) and previously published (see e.g., Lim et al. (2005) *Cancer Cell.* 7 (6): 533-545). The KP2 cell line was a gift and authenticated by whole-exome sequencing (see e.g., Jiang et al. (2016) *Nat Med.* 22 (8): 851-860). MEFs were isolated from WT or IRAK4-null mice, as described previously (see e.g., Durkin et al. (2013) *Bio Protoc.* 3 (18): e908). The patient-derived cell lines Pa01C, Pa02C, Pa03C, Pa04C, Pa14C, and Pa16C were a gift and have been described previously (see e.g., Jones et al. (2008) *Science.* 321 (5897): 1801-1806). All cell lines were cultured in DMEM supplemented with 10% fetal bovine serum and 1% penicillin/streptomycin except IGROV1 and Hs695T, which were cultured in RPMI-1640 and MEM, respectively, with nonessential amino acids along with other supplements stated above. *Mycoplasma* testing was performed annually using a MycoSEQ Detection kit (Applied Biosystems). All lines were used for fewer than 6 months after receipt or resuscitation from cryopreservation. For all drug treatments, when applicable, a concentration of 0 (zero) is treatment with vehicle, DMSO.

In Vivo Tumorigenesis Assays

For subcutaneous xenograft, approximately 5 million cells per flank were implanted into 6-week-old athymic nude mice (NU/J, Jackson Laboratory). When applicable, treatment with drug compound was initiated when tumors were palpable. FIRINOX (25 mg/kg 5-FU, 17.5 mg/kg irinotecan, and 3.35 mg/kg oxaliplatin) was administered via intraperitoneal injection weekly in 50 μL PBS. TPL2i was administered by intraperitoneal injection at 10 mg/kg in 40 μL DMSO, 5 days per week. Mice in the control group were treated with vehicle. Tumor volume was calculated as width$^2$×(length×0.5). Tumors were measured and mice were weighed 3 days per week. For orthotopic implantation, murine KI PDAC cells were injected into the pancreas of 7-week-old female FVB/NJ mice (Jackson Laboratory), as previously described (see e.g., Kim et al. (2009) *Nat Protoc.* 4 (11): 1670-1680). Six days after implantation, treatment with vehicle, FIRINOX (same dose as above), or TPL2i (30 mg/kg) was initiated for 14 days, at which time all mice were sacrificed. In vivo tumor progression was monitored using ultrasound (VScan, GE Healthcare) with final day representative tumor images shown.

Statistics

All results, when applicable, are expressed as mean±SEM. Statistical analysis was performed using GraphPad Prism v7 or v8 software. Unpaired, 2-tailed (2-sided) Student's t tests were used to compare 2 groups when appropriate. For multiple groups, 1-way or 2-way ANOVA with appropriate post hoc test was used. In instances of systemic/group variation, repeated-measures ANOVA was used. Unadjusted P values less than 0.05 were considered statistically significant. Adjusted P value metrics are stated at end of each figure legend where applicable. Cox proportional hazards models were used to evaluate the relationships between clinical characteristics and overall survival. Kaplan-Meier curve was generated using SAS version 9.4 (SAS Institute) and analyzed by log-rank tests.

Data Availability

RNA sequencing data on KP2 WT, Irak4-knockout and -rescue cells were deposited in NCBI's Gene Expression Omnibus (GEO), accession number GSE148442. Complete, unedited Western blot images are provided herein. All sgRNA and shRNA sequences, and qRT-PCR primers are listed in TABLE 7 and TABLE 8, respectively.

Study Approval

The Washington University PDAC TMA was IRB approved (no. 201404143) and previously published (see e.g., Lim et al. (2017) Oncotarget. 8 (15): 24250-24261). Patient consent was waived per IRB approval. All studies were performed per ethical principles of the Declaration of Helsinki. All animal (mouse) experiments were conducted under IACUC approval (no. 20190138).

Reverse-Phase Protein Array (RPPA)

All lysates were prepared according to sample preparation guidelines provided by MD Anderson Cancer Center (MDACC). HPNE-KRAS$^{G12D}$ were infected with retroviral particles containing AU1-tagged IRAK4 WT or vector control in presence of 8 μg mL-1 polybrene, selected with blasticidin (10 μg mL-1) and RPPA was performed. For drug treatment, IRAK4 overexpressing cells were treated with AS2444697 2 μM or vehicle (DMSO) for 24 hours. For evaluation of TPL2 WT and E188K, 293T cells were transfected in duplicates with Vector (pbabe-puro), TPL2 WT or TPL2 E188K along with equal amount of polyethylenimine. Cells were harvested 48 hrs post-transfection and lysates were prepared and sent for RPPA. For both RPPA experiments, lysates were quantified by Bradford assay (Thermo Scientific), equalized for concentration, and denatured and reduced by adding 4×SDS sample buffer (without bromophenol blue) and boiling for 5 minutes.

Immunoblots and Immunoprecipitations

Standard immunoblotting procedure was followed. Cells were washed twice with ice-cold 1×PBS and lysed with ice-cold triton-X lysis buffer (25 mM Tris, pH 7.4, 150 mM NaCl, 5 mM EDTA, 1% Triton-X) containing 1× protease (10 μg mL-1 leupeptin, 700 ng mL-1 pepstatin, 170 ng mL-1 aprotinin, 1 mM PMSF) and phosphatase (10 mM NaF, 1 mM $Na_3VO_4$, 1 mM $Na_4P_2O^7$, 5 mM Na b-glycerophosphate) inhibitors. Lysates were quantified by Bradford assay (Thermo Scientific), normalized for concentration, and reduced and denatured with 6×SDS sample buffer followed by boiling for 5 minutes. 20-40 μg of protein per sample was resolved by SDS-PAGE, blotted on PVDF membrane and probed with primary antibodies (Cell Signaling Technologies: p-ERK1/2 (#4370), p-MEK1/2 (#9154), ERK1/2 (#4695), MEK1/2 (#8727), p-p105 (#4806), NFS2KB1 p105/p50 (#3035), p-IRAK4 (#11927), IRAK4 (#4363), ubiquitin (#43124), anti-HA (#3724), p-p90RSK (#11989), RSK1/2/3 (#9355), p-TPL2 (#4491), PARP (#9532), p-B-RAF S445 (#2696), BRAF (#9433S). Santa Cruz Biotechnology: GAPDH (#sc-32233), p-p65 S536 (#sc101752). Thermo Fisher Scientific: p-55 TPL2 (#PA5-36635). EMD Millipore: IRAK4 (#07-418). R&D systems: TPL2/MAP3K8 (#MAB4586). Novus Biologicals: anti-AU1 (#NB600-453). Abcam: p-p65 S276 (#ab194726)). Membranes were incubated with appropriate HRP-conjugated secondary antibodies (anti-mouse or anti-rabbit, (1:5000 dilution), Jackson Laboratory) and imaged using chemiluminescent substrate. Additional steps for immunoprecipitation include incubation of soluble fraction lysate with anti-HA magnetic beads (Thermo Scientific cat #88837) overnight at 4° C., washing, and elution using 1×SDS sample buffer and boiling as mentioned in manufacturer's protocol.

(Tocris, cat #5430) TPL2 kinase inhibitor (Tocris #5240), IMD-0354 (Tocris, cat #2611), PF06650833 (Tocris cat #6373), SN-38 (Tocris, cat #2684), BVD-523 (Biomed Valley), GDC-0941 (Selleckchem, cat #S1065), Trametinib (Selleckchem, cat #S2673), Selumetinib (Selleckchem, cat #S1008), PLX-4720 (Selleckchem, cat #S1152), PLX-4032 (Selleckchem, cat #S1267), Dabrafenib (Selleckchem, cat #S2807), GDC-0994 (Selleckchem, cat #S7554), Paclitaxel (Selleckchem, cat #S1150), anti-mouse IL-1b neutralizing antibody (Invivogen, clone 7E3), antihuman IL-1b neutralizing antibody (Invivogen, clone 4H5).

Plasmids pCLXSN-HA-TPL2/COT was a gift from Shao-Cong Sun (Addgene plasmid #27558). HA-TPL2 was subcloned into pBabe expression vector which was utilized for majority of experiments. TPL2 R442H, L444V, R459W and truncated mutants were generated using mutated 3'end reverse PCR primers. TPL2 R397H was were generated by site-directed mutagenesis using Platinum SuperFi Green PCR Master Mix (Invitrogen, cat #12359-010 or 14001011). TPL2 E188K was purchased as a synthetic gene insert and cloned into pBabe vector. All constructs except HA-TPL2 E188K contained KOZAK sequence for robust expression. AU1-tagged IRAK4 WT and IRAK4 KD were expressed in pCMV-puro expression vector. All target sequences for sgRNA and shRNA are listed in TABLE 7.

TABLE 7 shRNA and sgRNA sequences

| Name | Gene | Species | Clone ID | Target Seq |
|---|---|---|---|---|
| shTPL2 #1 | MAP3K8 | human | TRCN0000196518 | GATGAGAATGTGACCTTTAAG (SEQ ID NO: 1) |
| shTPL2 #2 | MAP3K8 | human | TRCN0000381266 | TCTGATGTAATAGACATTATG (SEQ ID NO: 2) |
| shIL-1R #1 | IL-1R1 | human | TRCN0000059260 | GCCAAGAATACACATGGTATA (SEQ ID NO: 3) |
| shIL-1R #2 | IL-1R1 | human | TRCN0000360114 | GTGCTTAATATATCGGAAATT (SEQ ID NO: 4) |
| sgIRAK4 #1 | Irak4 | mouse | n/a | CGGGGGCAAACAGCTCAATC (SEQ ID NO: 5) |
| sgIRAK4 #2 | Irak4 | mouse | n/a | TGGCGACCTTGTGGATCTAC (SEQ ID NO: 6) |

Immunohistochemistry (IHC) and Immunofluorescence (IF)

IHC and IF staining were performed using the following antibodies: p-IRAK4 (T345S) (ABNOVA, A8A8, 1:200), p-ERK (CST, 4370, 1:200) and TPL2 (Sigma-Aldrich, HPA017962, 1:100). For tissue micro-array, entire slides were scanned at 20× magnification using automated Zeiss Axio Scan Z1 Slide Scanner and analysed using HALO software (Indica Labs) TMA module with area quantification v1.0 algorithm to quantify staining area and intensity (weak, moderate, strong). Histology-score (H-score) was computed as (3×strong intensity area %)+(2×moderate intensity area %)+(1×weak intensity area %). Depleted tissue cores were invalidated and excluded from data set and analysis.

Pharmaceutical Compounds

Gemcitabine was purchased from the Siteman Cancer Center Pharmacy. Details of other agents: oxaliplatin (Sigma cat #09512), 5-fluorouracil (Sigma cat #F6627), AS2444697

Lentiviral and Retroviral Production and Transduction

To generate lentivirus, shRNA encoding plasmid (pLKO.1 or Tet-pLKO.1) or sgRNA encoding plasmid (LentiCRISPRv2 or TLCV2) was mixed with packaging plasmids psPAX2 and pMD2.G in 4:2:1 (6 μg: 3 μg: 1.5 μg) ratio in serum free DMEM. Polyethelyneimine (PEI) transfection reagent (42 μL, 4:1 PEI to total DNA ratio) was added, mixture was incubated at room temperature for 20 minutes and added dropwise onto 293TV cells in 100 mm dish. Mediawas replaced with 6 mL fresh 10% FBS DMEM 12-16 hours post-transfection. Virus was collected at 48 hours and 72 hours post-transfection and cleared by 0.45 μM filter. Target cells were transduced with virus in presence of 8 μg mL-1 polybrene (Sigma) for 16 hours before being washed, cultured for 24-48 hours and then selected with 2 μg mL-1 puromycin (Sigma) for 48 hours. After initial selection bout, cells were cultured without puromycin for 48-72 hours after which puromycin was re-added and maintained in culture until cells were used for experiments. Similar procedure was followed for retrovirus production and transduction, except virus was generated by co-transfecting expression vector and packaging plasmid pCL10A1 in 1:1 ratio.

Anchorage Independent Soft Agar Growth Assays

Cells were seeded at 5000-15000 cells in 0.3% noble agar-DMEM suspension per well, in triplicate, in 24 well plate. For drug treatment, compound was added to cell suspension at 1× concentration. Seeded cells were fed with fresh 0.6% agar-DMEM mix once every 7-12 days. In case of drug treatment, compound was added at 2× concentration in 0.6% agar-DMEM mix and applied over existing agar layer (resulting in final drug concentration of 1×) to prevent desiccation and replenish inactive drug compounds. After 3-6 weeks, colonies were counted under microscope and imaged. Colony count was normalized to control and graphed in GraphPad Prism v7/8.

Organoid 3D Assays 48 well plates were coated with 0.6% agar in 10% serum DMEM. Cells were counted, suspended in 1:1 mixture of media and regular Matrigel (Corning), and seeded at 4000-5000 cells (depending on cell line) per well in triplicate or quadruplicate. For IGROV1, TPL2 knockdown cells were transiently transfected with TPL2 WT or TPL2 R442H using XtremeGene9 transfection reagent (Roche) ~24 hours prior to seeding. 10-15 days later, organoids werecounted and imaged. Organoid count was normalized to control and graphed in GraphPad Prism v7/8.

Clonogenic 2D Assays

Cells were seeded at 500-1000 cells per well (6 well plate format) or 200-1000 cells per well (12 well format) in 10% serum media. For drug treatment, compound was added at time of seeding at indicated concentration. Media was replenished as needed over course of incubation. After 3-5 weeks, colonies were fixed with 4% formaldehyde, stained with 0.5% crystal violet and scanned using document scanner. Images were quantified using particle analyzer on ImageJ software and values were normalized to vehicle.

Drug Response and Viability Assays

Cells were seeded at 1500-2500 cells per well in triplicates, in 96 well format. Next day, appropriate inhibitor was added in serial dilution from 1.00×102 μM or indicated single doses. Vehicle (DMSO) was added to match volume of inhibitor used for highest concentration. After 96-120 hours, 5× AlamarBlue® reagent (resazurin sodium salt, Sigma) was added to wells and incubated for 2-4 hours. Fluorescence at 585 nm (excitation 555 nm) was measured by SpectraMax i3 Microplate Reader. Raw values were normalized to vehicle, analyzed and graphed using GraphPad Prism v7/8 software.

Drug Synergy Assays

HPAC cells were plated in 12-by-12 matrix at ~1000 cells per well. Next day, serial dilutions of SN-38 (2 μM to $1.95\times10^{-3}$ μM) and TPL2i (20 μM to $19.5\times10^{-3}$ μM) was added in matrix format. Cells were incubated at 37° C. for 96 hours and viability was measured by AlamarBlue® as described above. Three independent experiments were performed, data was compiled, andsynergy scores by Loewe additivity model were computed using SynergyFinder software, exported and graphed in GraphPad Prism v8.

Cell Proliferation Assays

Cells were seeded in triplicate or quadruplicate at indicated density per well. When applicable, appropriate drug compound was added to cells the next day. Viable cells were counted using trypan blue dye exclusion and BioRad TC20 Automated Cell Counter at each time point.

Enzyme-Linked Immunosorbent Assay (ELISA)

ELISA was performed using BioLegend® Human IL-1b ELISA MAXä Deluxe Set kit (Cat #437004). Cells were cultured in 6 $cm^2$ dish (2 biological replicates in separate dishes) with 2 mL media, starting at ~55% confluency. 0.75 mL fresh media was added to cells 24 hours later. Next, entire 48-hour-old 2.75 mL media supernatant was collected and 50 μL was used for ELISA, performed according to manufacturer's protocol. Final values that were undetected in HEK T/tH cells were reported as the minimum detectable amount of hIL-1b protein (0.5 pg/mL).

Reporter Assays

Cells stably expressing plasmid encoding serum-response-element (SRE) or NFKB promoter driven Firefly luciferase and constitutive *Renilla* luciferase were seeded at equal density per well and treatment was initiated the next day for 16-24 duration. Alternatively, 293T reporter cells were transfected in duplicate or triplicate with 1 μg of appropriate plasmid DNA. Medium was replaced 16-18 hours later and at 48 hours post-transfection reporter activity was measured using Dual-Glo® Luciferase Assay System. Data was acquired using SpectraMax i3Microplate Reader and analysis was performed by calculating ratio of firefly: renilla. Values were normalized to control and graphed using GraphPad Prism v7/8 software.

RNA Sequencing

Samples were prepared according to library kit manufacturer's protocol, indexed, pooled, and sequenced on an Illumina HiSeq. Basecalls and demultiplexing were performed with Illumina's bcl2fastq software and a custom python demultiplexing program with a maximum of one mismatch in the indexing read. RNA-seq reads were then aligned to the Ensembl release top-level assembly with STAR version 2.0.4b1. Gene counts were derived from the number of uniquely aligned unambiguous reads by Subread: featureCount version 1.4.52. Isoform expression of known Ensembl transcripts were estimated with Sailfish version 0.6.133. Sequencing performance was assessed for the total number of aligned reads, total number of uniquely aligned reads, and features detected. The ribosomal fraction, known junction saturation, and read distribution over known gene models were quantified with RSeQC version 2.34. All gene counts were then imported into the R/Bioconductor package EdgeR5 and TMM normalization size factors were calculated to adjust for samples for differences in library size. Ribosomal genes and genes not expressed in the smallest group size minus one samples greater than one count-per-million were excluded from further analysis. The TMM size factors and the matrix of counts were then imported into the R/Bioconductor package Limma6. Weighted likelihoods based on the observed mean-variance relationship of every gene and sample were then calculated for all samples with the voom WithQualityWeights7. The performance of all genes was assessed with plots of the residual standard deviation of every gene to their average log-count with a robustly fitted trend line of the residuals. Differential expression analysis was then performed to analyze for differences between conditions and the results were filtered for only those genes with Benjamini-Hochberg false-discovery rate adjusted p-values less than or equal to 0.05. For each contrast extracted with Limma, global perturbations in known Gene Ontology (GO) terms and KEGG pathways were detected using the R/Bioconductor package GAGE8 to test for changes in expression of the reported log 2 fold-changes reported by Limma in each term versus the background log 2 fold-changes of all genes found outside the respective term. The R/Bioconductor package heatmap39 and Pathview10 was used to display heatmaps or annotated KEGG graphs across groups of samples for each GO term or KEGG pathway (respectively) with a Benjamini-Hochberg false-discovery rate adjusted p-value less than or equal to 0.05.

TCGA Data Analysis

TCGA data was accessed via CBioportal.org and graphs were generated and exported for publication.

Gene Set Enrichment Analysis

Genes in RNAseq differential expression data were ranked by $Log_2$ fold change, and preranked gene set enrichment analysis was performed using ranked lists. Gene sets associated with TPL2, PDAC and IL-1 were downloaded from the Broad Institute Molecular Signature database (MSigDB) and are listed in TABLE 3-TABLE 5. For leading edge analysis, regular (not pre-ranked) gene set enrichment was performed with phenotype permutation in order to preserve gene-to-gene correlation. Ranking metric was set to "difference-of-classes" since expression data was in $Log_2$ units. Otherwise, GSEAv.4 was used for analysis in default format. Data generated was exported and graphed in GraphPad Prism v8 software.

Quantitative (Real-Time) PCR

Total RNA was isolated using RNAzol RT (Sigma), cDNA was generated using High Capacity cDNA reverse transcription kit (Thermo Fisher Scientific, 4368814) and qPCR was performed using SYBR-Green reagent (Applied Biosystems, cat #4309155). Primer sequences are listed in TABLE 8. All experiments were performed in biological duplicates or triplicates (n=2,3).

TABLE 8 qRT-PCR primers

| Name | Gene | Species | Primer sequence |
|---|---|---|---|
| TPL2 forward primer | MAP3K8 | human | GGCCGCAGATGCAATCTTCTTA (SEQ ID NO: 7) |
| TPL2 reverse primer | MAP3K8 | human | TGGCTTTGCAGATACTGCGTT (SEQ ID NO: 8) |
| IL-1 beta forward primer | IL-1 beta | human | CTAAACAGATGAAGTGCTCC (SEQ ID NO: 9) |
| IL-1 beta reverse primer | IL-1 beta | human | GGTCATTCTCCTGGAAGG (SEQ ID NO: 10) |
| IL-1 alpha forward primer | IL-1 alpha | human | CACCTTTTAGCTTCCTGAC (SEQ ID NO: 11) |
| IL-1 alpha reverse primer | IL-1 alpha | human | AATTTCACTGCTTCATCCAG (SEQ ID NO: 12) |
| TNF-alpha forward primer | TNF-alpha | human | GGAGAAGGGTGACCGACTCA (SEQ ID NO: 13) |
| TNF-alpha reverse primer | TNF-alpha | human | CTGCCCAGACTCGGCAA (SEQ ID NO: 14) |
| TNF-beta forward primer | TNF-beta | human | TACACCTCCTCCTTCTGGGG (SEQ ID NO: 15) |
| TNF-beta reverse primer | TNF-beta | human | TCCAATGAGGTGAGCAGCAG (SEQ ID NO: 16) |

TABLE 8-continued qRT-PCR primers

| Name | Gene | Species | Primer sequence |
|---|---|---|---|
| IL-1R1 forward primer | IL-1R1 | human | AGGTAGACGCACCCTCTGAA (SEQ ID NO: 17) |
| IL-1R1 reverse primer | IL-1R1 | human | GCATTTATCAGCCTCCAGAGAAG (SEQ ID NO: 18) |
| TLR1 forward | TLR1 | human | GCCCAAGGAAAAGAGCAAAC (SEQ ID NO: 19) |
| TLR1 reverse | TLR1 | human | AAGCAGCAATATCAACAGGAG (SEQ ID NO: 20) |
| TLR2 forward | TLR2 | human | TCTCCCATTTCCGTCTTTTT (SEQ ID NO: 21) |
| TLR2 reverse | TLR2 | human | GGTCTTGGTGTTCATTATCTTC (SEQ ID NO: 22) |
| TLR3 forward | TLR3 | human | TAAACTGAACCATGCACTCT (SEQ ID NO: 23) |
| TLR3 reverse | TLR3 | human | TATGACGAAAGGCACCTATC (SEQ ID NO: 24) |
| TLR4 forward | TLR4 | human | GAAGCTGGTGGCTGTGGA (SEQ ID NO: 25) |
| TLR4 reverse | TLR4 | human | GATGTAGAACCCGCAAG (SEQ ID NO: 26) |
| TLR5 forward | TLR5 | human | TTGCTCAAACACCTGGACAC (SEQ ID NO: 27) |
| TLR5 reverse | TLR5 | human | CTGCTCACAAGACAAACGAT (SEQ ID NO: 28) |
| TLR6 forward | TLR6 | human | GTGCCATTACGAACTCTA (SEQ ID NO: 29) |
| TLR6 reverse | TLR6 | human | TTGTTGGGAATGCTGTT (SEQ ID NO: 30) |
| TLR7 forward | TLR7 | human | CTGACCACTGTCCCTGAG (SEQ ID NO: 31) |
| TLR7 reverse | TLR7 | human | AACCCACCAGACAAACCA (SEQ ID NO: 32) |
| TLR8 forward | TLR8 | human | AACATCAGCAAGACCCAT (SEQ ID NO: 33) |
| TLR8 reverse | TLR8 | human | GACTCCTTCATTCTCCCT (SEQ ID NO: 34) |
| TLR9 forward | TLR9 | human | CGCCAACGCCCTCAAGACA (SEQ ID NO: 35) |
| TLR9 reverse | TLR9 | human | GGCGCTTACATCTAGTATTTGC (SEQ ID NO: 36) |
| TLR10 forward | TLR10 | human | CTCCCAACTTTGTCCAGAAT (SEQ ID NO: 37) |

TABLE 8-continued

| qRT-PCR primers | | | |
|---|---|---|---|
| Name | Gene | Species | Primer sequence |
| TLR10 reverse | TLR10 | human | GGTGGGAATGCAATAGA AT (SEQ ID NO: 38) |

Flow Cytometry

HPAC cells were stained using Annexin V-FITC and propidium iodide (PI) (BD bioscience #556547) and followed by FACSCalibur (BD bioscience) analysis. The results were further analyzed and quantified by FlowJo software (BD bioscience). Briefly, HPAC cells were plated in the 12-well plates and then treated with TPL2 inhibitor, SN38 or combination for 48 hours. Cells were then trypsinized and washed with PBS twice with centrifugation at 500 g for 5 minutes between each trypsinization and wash. Cells were stained using Annexin V-FITC and PI for 20 minutes on ice and then analyzed by FACSCalibur. After acquiring the data, compensation using non-stain cells, Annexin V-FITC and PI single-stain cells, and gating quantification were performed in FlowJo. The gating area was defined as Q4 (Annexin V− and PI−) containing the main cell population within vehicle cells and the quantitative apoptosis ratio was calculated by adding early apoptosis (Annexin V+ and PI−) and late apoptosis (Annexin V+ and PI+) cells.

Proximity Ligation Assay (PLA)

PLA was performed using Duolink® in situ Red Starter Kit Mouse/Rabbit (DUO92101, Sigma) per manufacturer's protocol. Briefly, cells were seeded on cover slips in 6 well plate at ~50% confluency per well. Next day cells were treated with SN-38 (10 μM) and 16 hours later PLA was performed using p-IRAK4 (ABNOVA) and TLR9 (CST) primary antibodies. Stained cells were imaged using Nikon C2+ fluorescent microscope paired with NIS-Element software. Number of puncta per field was quantitated for six 400× fields per condition using Find Maxima tool in ImageJ software. Data was exported and graphed in GraphPad Prism v8.

What is claimed is:

1. A method of suppressing tumor proliferation or cell growth in a subject having cancer or in cancer cells, the method comprising:

administering a pharmaceutical composition comprising a TPL2 inhibiting agent, wherein the TPL2 inhibiting agent has anti-tumor activity; and wherein the subject has, or the cancer cells are from, a RAS mutant cancer or a TPL2-mutant cancer comprising one or more of TPL2 point mutations selected from E188K, R397H, R442H, R442 frame shift, L444V, and R459W.

2. The method of claim 1, wherein the cancer or the cancer cells further comprise $BRAF^{V600E}$ mutation.

3. The method of claim 1, wherein the cancer comprises cells having $TPL2^{E188K}$ or $TPL2^{R442}$ mutations.

4. The method of claim 1, wherein the cancer comprises cells having $RAF^{V600E}/MAP3K8^{E188K}$ double mutations.

5. The method of claim 1, wherein the cancer is: breast cancer, bladder, colon cancer, rectal cancer, small bowel cancer, endometrial cancer, gastric carcinoma, gastrointestinal carcinoid tumor, gastrointestinal stromal tumor, oligodendroglioma, urothelial carcinoma, head and neck cancer, head and neck squamous cell carcinomas (HNSCC), glioblastoma, hepatocellular carcinoma, lung cancer, lung adenocarcinoma (LAC), small cell lung cancer, non-small lung cancer (NSCLC), melanoma, ovarian cancer, cervical cancer, pancreatic cancer, pancreatic ductal adenocarcinoma (PDAC), biliary tract cancers, prostate carcinoma, acute myelogenous leukemia (AML), non-Hodgkin's lymphoma, T-cell neoplasms, or thyroid carcinoma.

6. The method of claim 1, wherein the TPL2 inhibiting agent is a broader-spectrum therapeutic agent than a MEK inhibiting agent or ERK inhibiting agent.

7. The method of claim 1, wherein the TPL2 inhibiting agent is administered in an amount effective to reduce, block, or inhibit:

MAPK and NF-κB signaling;

chemotherapy-induced MAPK and NF-κB activation, resulting in increased apoptosis and increased tumor suppression;

p-MEK, p-ERK, or p-RSK levels; or crosstalk between IRAK4 and MAPK pathway, compared to the cancer cells not being treated with the TPL2 inhibiting agent.

8. The method of claim 1, wherein the TPL2 inhibiting agent is administered in an amount effective to suppress MAPK activity and proliferation of the cancer or the cancer cells.

9. The method of claim 1, wherein the TPL2 inhibiting agent is administered in an amount effective to sensitize the cancer or the cancer cells to chemotherapy; suppress tumor proliferation or cell growth; increase apoptosis; or increases tumor suppression compared to the cancer cells not being treated with the TPL2 inhibiting agent.

10. The method of claim 1, wherein the TPL2 inhibiting agent targets MEK/ERK or targets cascades implicated in chemoresistance selected from one or more of, NF-κB, JNK, and p38.

11. The method of claim 1, wherein the TPL2 inhibiting agent is an IRAK4 inhibiting agent.

12. The method of claim 1, wherein the TPL2 inhibiting agent is 4-[(3-chloro-4-fluorophenyl)amino]-6-[(3-pyridinylmethyl)amino]-1,7-naphthyridine-3-carbonitrile; Tilpisertib; Emavusertib; Zimlovisertib; a 8-halo-4-(3-chloro-4-fluoro-phenylamino)-6-[(1H-[1,2,3]triazol-4-ylmethyl)-amino]-quinoline-3-carbonitrile, optionally, 8-chloro-4-(3-chloro-4-fluorophenylamino)-6-((1-(1-ethylpiperidin-4-yl)-1H-1,2,3-triazol-4-yl)methylamino) quinoline-3-carbonitrile; Cot inhibitor-1;

or a pharmaceutically acceptable salt thereof, including all tautomers and stereoisomers, and substituted analogs thereof.

13. The method of claim 1, further comprising administering a chemotherapeutic agent or regimen.

14. The method of claim 13, wherein administering the TPL2 inhibiting agent in combination with the chemotherapeutic agent:

synergistically sensitizes the cancer or the cancer cells to chemotherapy;

reduces chemotherapy-induced survival signaling;

suppresses tumor proliferation or cell growth;

increases apoptosis;

reduces clonogenicity (resistant clones);

reduces genotoxic stress-induced survival signaling; or enhances chemotherapy efficacy, compared to either treatment alone.

15. The method of claim 13, wherein the chemotherapeutic agent is selected from one or more of: gemcitabine, a taxane, paclitaxel, docetaxel, irinotecan or metabolite thereof, irinotecan hydrochloride, irinotecan hydrochloride liposome, SN-38, 5-fluorouracil [5-FU], and oxaliplatin.

16. The method of claim 13, wherein the chemotherapeutic agent is selected from a metabolite of irinotecan, SN-38.

17. The method of claim 13, wherein the chemotherapeutic agent is selected from gemcitabine/paclitaxel or FIRINOX (5-FU/SN-38/oxaliplatin).

18. The method of claim 1, further comprising administering:

an IRAK4 inhibiting agent;

an IKK inhibiting agent;

a BRAF inhibiting agent;

a MEK inhibiting agent;
an ERK inhibiting agent;
or
a PI3K inhibiting agent.

19. The method of claim 13, further comprising administering:
an IRAK4 inhibiting agent
an IKK inhibiting agent;
a BRAF inhibiting agent;
a MEK inhibiting agent;
an ERK inhibiting agent;
or
a PI3K inhibiting agent.

20. The method of claim 1, further comprising detecting a gain-of-function TPL2 mutation in a subject.

21. The method of claim 13, further comprising detecting a gain-of-function TPL2 mutation in a subject.

* * * * *

SEQUENCE LISTING

<160> NUMBER OF SEQ ID NOS: 40

<210> SEQ ID NO 1
<211> LENGTH: 21
<212> TYPE: DNA
<213> ORGANISM: Homo sapiens

<400> SEQUENCE: 1
gatgagaatg tgacctttaa g 21

<210> SEQ ID NO 2
<211> LENGTH: 21
<212> TYPE: DNA
<213> ORGANISM: Homo sapiens

<400> SEQUENCE: 2
tctgatgtaa tagacattat g 21

<210> SEQ ID NO 3
<211> LENGTH: 21
<212> TYPE: DNA
<213> ORGANISM: Homo sapiens

<400> SEQUENCE: 3
gccaagaata cacatggtat a 21

<210> SEQ ID NO 4
<211> LENGTH: 21
<212> TYPE: DNA
<213> ORGANISM: Homo sapiens

<400> SEQUENCE: 4
gtgcttaata tatcggaaat t 21

<210> SEQ ID NO 5
<211> LENGTH: 20
<212> TYPE: DNA
<213> ORGANISM: Mus musculus

<400> SEQUENCE: 5
cgggggcaaa cagctcaatc 20

```
<210> SEQ ID NO 6
<211> LENGTH: 20
<212> TYPE: DNA
<213> ORGANISM: Mus musculus

<400> SEQUENCE: 6

tggcgacctt gtggatctac                                                    20

<210> SEQ ID NO 7
<211> LENGTH: 22
<212> TYPE: DNA
<213> ORGANISM: Artificial Sequence
<220> FEATURE:
<223> OTHER INFORMATION: synthetic primer

<400> SEQUENCE: 7

ggccgcagat gcaatcttct ta                                                 22

<210> SEQ ID NO 8
<211> LENGTH: 21
<212> TYPE: DNA
<213> ORGANISM: Artificial Sequence
<220> FEATURE:
<223> OTHER INFORMATION: synthetic primer

<400> SEQUENCE: 8

tggctttgca gatactgcgt t                                                  21

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9

ctaaacagat gaagtgctcc                                                    20

<210> SEQ ID NO 10
<211> LENGTH: 18
<212> TYPE: DNA
<213> ORGANISM: Artificial Sequence
<220> FEATURE:
<223> OTHER INFORMATION: synthetic primer

<400> SEQUENCE: 10

ggtcattctc ctggaagg                                                      18

<210> SEQ ID NO 11
<211> LENGTH: 19
<212> TYPE: DNA
<213> ORGANISM: Artificial Sequence
<220> FEATURE:
<223> OTHER INFORMATION: synthetic primer

<400> SEQUENCE: 11

caccttttag cttcctgac                                                     19

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
```

aatttcactg cttcatccag 20

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
ggagaagggt gaccgactca 20

<210> SEQ ID NO 14
<211> LENGTH: 17
<212> TYPE: DNA
<213> ORGANISM: Artificial Sequence
<220> FEATURE:
<223> OTHER INFORMATION: synthetic primer

<400> SEQUENCE: 14
ctgcccagac tcggcaa 17

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
tacacctcct ccttctgggg 20

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
tccaatgagg tgagcagcag 20

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
aggtagacgc accctctgaa 20

<210> SEQ ID NO 18
<211> LENGTH: 23
<212> TYPE: DNA
<213> ORGANISM: Artificial Sequence
<220> FEATURE:
<223> OTHER INFORMATION: synthetic primer

<400> SEQUENCE: 18
gcatttatca gcctccagag aag 23

<210> SEQ ID NO 19
<211> LENGTH: 20
<212> TYPE: DNA

<213> ORGANISM: Artificial Sequence
<220> FEATURE:
<223> OTHER INFORMATION: synthetic primer

<400> SEQUENCE: 19
gcccaaggaa aagagcaaac 20

<210> SEQ ID NO 20
<211> LENGTH: 21
<212> TYPE: DNA
<213> ORGANISM: Artificial Sequence
<220> FEATURE:
<223> OTHER INFORMATION: synthetic primer

<400> SEQUENCE: 20
aagcagcaat atcaacagga g 21

<210> SEQ ID NO 21
<211> LENGTH: 20
<212> TYPE: DNA
<213> ORGANISM: Artificial Sequence
<220> FEATURE:
<223> OTHER INFORMATION: synthetic primer

<400> SEQUENCE: 21
tctcccattt ccgtcttttt 20

<210> SEQ ID NO 22
<211> LENGTH: 22
<212> TYPE: DNA
<213> ORGANISM: Artificial Sequence
<220> FEATURE:
<223> OTHER INFORMATION: synthetic primer

<400> SEQUENCE: 22
ggtcttggtg ttcattatct tc 22

<210> SEQ ID NO 23
<211> LENGTH: 20
<212> TYPE: DNA
<213> ORGANISM: Artificial Sequence
<220> FEATURE:
<223> OTHER INFORMATION: synthetic primer

<400> SEQUENCE: 23
taaactgaac catgcactct 20

<210> SEQ ID NO 24
<211> LENGTH: 20
<212> TYPE: DNA
<213> ORGANISM: Artificial Sequence
<220> FEATURE:
<223> OTHER INFORMATION: synthetic primer

<400> SEQUENCE: 24
tatgacgaaa ggcacctatc 20

<210> SEQ ID NO 25
<211> LENGTH: 18
<212> TYPE: DNA
<213> ORGANISM: Artificial Sequence
<220> FEATURE:
<223> OTHER INFORMATION: synthetic primer

<400> SEQUENCE: 25
gaagctggtg gctgtgga 18

<210> SEQ ID NO 26
<211> LENGTH: 17
<212> TYPE: DNA
<213> ORGANISM: Artificial Sequence
<220> FEATURE:
<223> OTHER INFORMATION: synthetic primer

<400> SEQUENCE: 26
gatgtagaac ccgcaag 17

<210> SEQ ID NO 27
<211> LENGTH: 20
<212> TYPE: DNA
<213> ORGANISM: Artificial Sequence
<220> FEATURE:
<223> OTHER INFORMATION: synthetic primer

<400> SEQUENCE: 27
ttgctcaaac acctggacac 20

<210> SEQ ID NO 28
<211> LENGTH: 20
<212> TYPE: DNA
<213> ORGANISM: Artificial Sequence
<220> FEATURE:
<223> OTHER INFORMATION: synthetic primer

<400> SEQUENCE: 28
ctgctcacaa gacaaacgat 20

<210> SEQ ID NO 29
<211> LENGTH: 18
<212> TYPE: DNA
<213> ORGANISM: Artificial Sequence
<220> FEATURE:
<223> OTHER INFORMATION: synthetic primer

<400> SEQUENCE: 29
gtgccattac gaactcta 18

<210> SEQ ID NO 30
<211> LENGTH: 17
<212> TYPE: DNA
<213> ORGANISM: Artificial Sequence
<220> FEATURE:
<223> OTHER INFORMATION: synthetic primer

<400> SEQUENCE: 30
ttgttgggaa tgctgtt 17

<210> SEQ ID NO 31
<211> LENGTH: 18
<212> TYPE: DNA
<213> ORGANISM: Artificial Sequence
<220> FEATURE:
<223> OTHER INFORMATION: synthetic primer

<400> SEQUENCE: 31
ctgaccactg tccctgag 18

<210> SEQ ID NO 32
<211> LENGTH: 18
<212> TYPE: DNA
<213> ORGANISM: Artificial Sequence
<220> FEATURE:

<223> OTHER INFORMATION: synthetic primer

<400> SEQUENCE: 32
aacccaccag acaaacca 18

<210> SEQ ID NO 33
<211> LENGTH: 18
<212> TYPE: DNA
<213> ORGANISM: Artificial Sequence
<220> FEATURE:
<223> OTHER INFORMATION: synthetic primer

<400> SEQUENCE: 33
aacatcagca agacccat 18

<210> SEQ ID NO 34
<211> LENGTH: 18
<212> TYPE: DNA
<213> ORGANISM: Artificial Sequence
<220> FEATURE:
<223> OTHER INFORMATION: synthetic primer

<400> SEQUENCE: 34
gactccttca ttctccct 18

<210> SEQ ID NO 35
<211> LENGTH: 19
<212> TYPE: DNA
<213> ORGANISM: Artificial Sequence
<220> FEATURE:
<223> OTHER INFORMATION: synthetic primer

<400> SEQUENCE: 35
cgccaacgcc ctcaagaca 19

<210> SEQ ID NO 36
<211> LENGTH: 22
<212> TYPE: DNA
<213> ORGANISM: Artificial Sequence
<220> FEATURE:
<223> OTHER INFORMATION: synthetic primer

<400> SEQUENCE: 36
ggcgcttaca tctagtattt gc 22

<210> SEQ ID NO 37
<211> LENGTH: 20
<212> TYPE: DNA
<213> ORGANISM: Artificial Sequence
<220> FEATURE:
<223> OTHER INFORMATION: synthetic primer

<400> SEQUENCE: 37
ctcccaactt tgtccagaat 20

<210> SEQ ID NO 38
<211> LENGTH: 19
<212> TYPE: DNA
<213> ORGANISM: Artificial Sequence
<220> FEATURE:
<223> OTHER INFORMATION: synthetic primer

<400> SEQUENCE: 38
ggtgggaatg caatagaat 19

<210> SEQ ID NO 39
<211> LENGTH: 467
<212> TYPE: PRT
<213> ORGANISM: Homo sapiens

<400> SEQUENCE: 39

```
Met Glu Tyr Met Ser Thr Gly Ser Asp Asn Lys Glu Glu Ile Asp Leu
1               5                   10                  15

Leu Ile Lys His Leu Asn Val Ser Asp Val Ile Asp Ile Met Glu Asn
            20                  25                  30

Leu Tyr Ala Ser Glu Glu Pro Ala Val Tyr Glu Pro Ser Leu Met Thr
        35                  40                  45

Met Cys Gln Asp Ser Asn Gln Asn Asp Glu Arg Ser Lys Ser Leu Leu
    50                  55                  60

Leu Ser Gly Gln Glu Val Pro Trp Leu Ser Ser Val Arg Tyr Gly Thr
65                  70                  75                  80

Val Glu Asp Leu Leu Ala Phe Ala Asn His Ile Ser Asn Thr Ala Lys
                85                  90                  95

His Phe Tyr Gly Gln Arg Pro Gln Glu Ser Gly Ile Leu Leu Asn Met
            100                 105                 110

Val Ile Thr Pro Gln Asn Gly Arg Tyr Gln Ile Asp Ser Asp Val Leu
        115                 120                 125

Leu Ile Pro Trp Lys Leu Thr Tyr Arg Asn Ile Gly Ser Asp Phe Ile
    130                 135                 140

Pro Arg Gly Ala Phe Gly Lys Val Tyr Leu Ala Gln Asp Ile Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
            180                 185                 190

Leu Tyr Gly Ala Val Leu Trp Gly Glu Thr Val His Leu Phe Met Glu
        195                 200                 205

Ala Gly Glu Gly Gly Ser Val Leu Glu Lys Leu Glu Ser Cys Gly Pro
    210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255

Ser Asn Ile Val Phe Met Ser Thr Lys Ala Val Leu Val Asp Phe Gly
            260                 265                 270

Leu Ser Val Gln Met Thr Glu Asp Val Tyr Phe Pro Lys Asp Leu Arg
        275                 280                 285

Gly Thr Glu Ile Tyr Met Ser Pro Glu Val Ile Leu Cys Arg Gly His
    290                 295                 300

Ser Thr Lys Ala Asp Ile Tyr Ser Leu Gly Ala Thr Leu Ile His Met
305                 310                 315                 320

Gln Thr Gly Thr Pro Pro Trp Val Lys Arg Tyr Pro Arg Ser Ala Tyr
                325                 330                 335

Pro Ser Tyr Leu Tyr Ile Ile His Lys Gln Ala Pro Pro Leu Glu Asp
            340                 345                 350

Ile Ala Asp Asp Cys Ser Pro Gly Met Arg Glu Leu Ile Glu Ala Ser
        355                 360                 365

Leu Glu Arg Asn Pro Asn His Arg Pro Arg Ala Ala Asp Leu Leu Lys
    370                 375                 380
```

-continued

```
His Glu Ala Leu Asn Pro Pro Arg Glu Asp Gln Pro Arg Cys Gln Ser
385                 390                 395                 400

Leu Asp Ser Ala Leu Leu Glu Arg Lys Arg Leu Leu Ser Arg Lys Glu
                405                 410                 415

Leu Glu Leu Pro Glu Asn Ile Ala Asp Ser Ser Cys Thr Gly Ser Thr
            420                 425                 430

Glu Glu Ser Glu Met Leu Lys Arg Gln Arg Ser Leu Tyr Ile Asp Leu
        435                 440                 445

Gly Ala Leu Ala Gly Tyr Phe Asn Leu Val Arg Gly Pro Pro Thr Leu
    450                 455                 460

Glu Tyr Gly
465


<210> SEQ ID NO 40
<211> LENGTH: 766
<212> TYPE: PRT
<213> ORGANISM: Homo sapiens

<400> SEQUENCE: 40

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285
```

-continued

```
Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700
```

-continued

```
Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765
```